US012653886B2

(12) United States Patent
Schmitt et al.

(10) Patent No.: US 12,653,886 B2
(45) Date of Patent: Jun. 16, 2026

(54) T-CELL IMMUNOTHERAPY SPECIFIC FOR WT-1

(71) Applicant: Fred Hutchinson Cancer Center, Seattle, WA (US)

(72) Inventors: Thomas M. Schmitt, Seattle, WA (US); Aude G. Chapuis, Seattle, WA (US); Philip D. Greenberg, Mercer Island, WA (US)

(73) Assignee: Fred Hutchinson Cancer Center, Seattle, WA (US)

( * ) Notice: Subject to any disclaimer, the term of this patent is extended or adjusted under 35 U.S.C. 154(b) by 1083 days.

(21) Appl. No.: 17/636,314

(22) PCT Filed: Aug. 19, 2020

(86) PCT No.: PCT/US2020/047071
§ 371 (c)(1),
(2) Date: Feb. 17, 2022

(87) PCT Pub. No.: WO2021/034976
PCT Pub. Date: Feb. 25, 2021

(65) Prior Publication Data
US 2022/0409661 A1      Dec. 29, 2022

Related U.S. Application Data

(60) Provisional application No. 62/889,519, filed on Aug. 20, 2019.

(51) Int. Cl.
| | |
|---|---|
| *A61K 40/11* | (2025.01) |
| *A61K 40/32* | (2025.01) |
| *A61K 40/42* | (2025.01) |
| *A61P 35/00* | (2006.01) |
| *C12N 5/0783* | (2010.01) |

(52) U.S. Cl.
CPC .............. *A61K 40/11* (2025.01); *A61K 40/32* (2025.01); *A61K 40/4243* (2025.01); *A61P 35/00* (2018.01); *C12N 5/0636* (2013.01); *C12N 5/0646* (2013.01); *A61K 2239/54* (2023.05)

(58) Field of Classification Search
CPC .... A61K 40/11; A61K 40/4243; A61K 40/32; A61P 35/00
See application file for complete search history.

(56) References Cited

U.S. PATENT DOCUMENTS

| | | | |
|---|---|---|---|
| 5,283,173 A | 2/1994 | Fields et al. | |
| 5,420,032 A | 5/1995 | Marshall et al. | |
| 5,468,614 A | 11/1995 | Fields et al. | |
| 6,833,252 B1 | 12/2004 | Dujon et al. | |
| 7,342,092 B2 | 3/2008 | Sugiyama | |
| 7,608,685 B1 | 10/2009 | Sugiyama et al. | |
| 7,622,119 B2 | 11/2009 | Sugiyama | |

| | | | |
|---|---|---|---|
| 7,951,783 B2 * | 5/2011 | Stauss ................ | A61K 40/4243 |
| | | | 435/325 |
| 8,119,772 B2 | 2/2012 | Yang et al. | |
| 8,697,359 B1 | 4/2014 | Zhang | |
| 9,574,000 B2 | 2/2017 | Langermann et al. | |
| 11,390,921 B2 * | 7/2022 | Milla ................. | A61K 40/4243 |
| 2004/0002092 A1 | 1/2004 | Arnould et al. | |
| 2004/0087025 A1 | 5/2004 | June et al. | |
| 2006/0078552 A1 | 4/2006 | Arnould et al. | |
| 2006/0153826 A1 | 7/2006 | Arnould et al. | |
| 2006/0206949 A1 | 9/2006 | Arnould et al. | |
| 2007/0117128 A1 | 5/2007 | Smith et al. | |
| 2011/0189141 A1 | 8/2011 | Kieback et al. | |
| 2011/0243972 A1 | 10/2011 | Jaffee | |
| 2011/0301073 A1 | 12/2011 | Gregory et al. | |
| 2014/0068797 A1 | 3/2014 | Doudna et al. | |
| 2014/0186843 A1 | 7/2014 | Zhang et al. | |
| 2019/0085081 A1 | 3/2019 | Bicknell et al. | |

FOREIGN PATENT DOCUMENTS

| | | |
|---|---|---|
| WO | WO 9709433 A1 | 3/1997 |
| WO | WO 2005056595 A2 | 6/2005 |
| WO | WO 2010084158 A1 | 7/2010 |
| WO | WO 2013025779 A1 | 2/2013 |
| WO | WO 2015071474 A2 | 5/2015 |
| WO | WO 2015077615 A1 | 5/2015 |
| WO | WO 2016022400 A1 | 2/2016 |
| WO | WO 2016040724 A1 | 3/2016 |
| WO | WO 2016054638 A1 | 4/2016 |
| WO | WO 2016134333 A1 | 8/2016 |
| WO | WO 2016141357 A1 | 9/2016 |
| WO | WO 2017021526 A1 | 2/2017 |

(Continued)

OTHER PUBLICATIONS

Xue et al. (Haematologica. Jan. 2010;95(1):126-34. doi: 10.3324/haematol.2009.006486. Epub Aug. 13, 2009.) (Year: 2009).*

Altschul et al., "Gapped BLAST and PSI-BLAST: a new generation of protein database search programs," *Nucleic Acids Research* 25(17):3389-3402, 1997. (14 pages).

Argast et al., "I-PpoI and I-CreI Homing Site Sequence Degeneracy Determined by Random Mutagenesis and Sequential in Vitro Enrichment," *J. Mol. Biol.* 280:345-353, 1998. (9 pages).

Ashouri et al., "Endogenous Nur77 Is a Specific Indicator of Antigen Receptor Signaling in Human T and B Cells," *The Journal of Immunology* 198(2):657-668, Jan. 15, 2017. (13 pages).

Ashworth et al., "Computational redesign of endonuclease DNA binding and cleavage specificity," *Nature* 441(7093):656-659, Jun. 1, 2006 (NIH Public Access Author Manuscript, available in PMC Dec. 9, 2010) (11 pages).

(Continued)

*Primary Examiner* — Fereydoun G Sajjadi
*Assistant Examiner* — Joel D Levin
(74) *Attorney, Agent, or Firm* — Seed IP Law Group LLP

(57) ABSTRACT

The present disclosure provides binding proteins specific for human Wilms tumor protein 1 (WT-1) epitopes, as well as host cells that express the binding proteins. Also provided are polynucleotides that encode a binding protein and vectors that comprise a polynucleotide. Related methods and uses of the presently disclosed compositions are provided for treating diseases or disorders associated with WT-1 expression, such as various cancers.

32 Claims, 13 Drawing Sheets
Specification includes a Sequence Listing.

(56) References Cited

FOREIGN PATENT DOCUMENTS

| WO | WO 2017059084 A1 | 4/2017 |
| WO | WO 2017112944 A1 | 6/2017 |
| WO | WO 2018058002 A1 | 3/2018 |
| WO | WO 2018197492 A1 | 11/2018 |
| WO | WO 2019178427 A1 | 9/2019 |

OTHER PUBLICATIONS

Belfort et al., "Homing endonucleases: keeping the house in order," *Nucleic Acids Research* 25(17):3379-3388, 1997. (10 pages).

Betts et al., "The Functional Profile of Primary Human Antiviral CD8+ T Cell Effector Activity Is Dictated by Cognate Peptide Concentration," *The Journal of Immunology* 172:6407-6417, 2004. (12 pages).

Cavallo et al., "2011: the immune hallmarks of cancer," *Cancer Immunol Immunother* 60:319-326, 2011. (8 pages).

Cawthon et al., "Peptide Requirement for CTL Activation Reflects the Sensitivity to CD3 Engagement: Correlation with CD8αβ Versus CD8αα Expression," *The Journal of Immunology* 167:2577-2584, 2001. (9 pages).

Chapuis et al., "T Cell Receptor Gene Therapy Targeting WT1 Prevents Acute Myeloid Leukemia Relapse Post-Transplant," *Nature Medicine* 25(7):1064-1072, Jul. 2019 (HHS Public Access Author Manuscript, available in PMC Jan. 2, 20205). (36 pages).

Chapuis et al., "Transferred melanoma-specific CD8+ T cells persist, mediate tumor regression, and acquire central memory phenotype," *PNAS* 109(12):4592-4597, Mar. 20, 2012. (6 pages).

Chapuis et al., "Transferred WT1-reactive CD8+ T cells can mediate antileukemic activity and persist in post-transplant patients," *Sci Transl Med* 5(174):174ra27, Feb. 27, 2013 (NIH Public Access Author manuscript, available in PMC Jun. 11, 2013) (25 pages).

Cheever et al., "The Prioritization of Cancer Antigens: A National Cancer Institute Pilot Project for the Acceleration of Translational Research," *Clin. Cancer Res.* 15(17):5323-5337, Sep. 1, 2009. (15 pages).

Chen et al., "Oncology Meets Immunology: The Cancer-Immunity Cycle," *Immunity* 39:1-10, Jul. 25, 2013. (10 pages).

Chevalier et al., "Design, Activity, and Structure of a Highly Specific Artificial Endonuclease," *Molecular Cell* 10:895-905, Oct. 2002. (11 pages).

Chothia et al., "The outline structure of the T-cell αβ receptor," *The EMBO Journal* 7(12):3745-3755, 1988. (11 pages).

Cohen et al., "Enhanced Antitumor Activity of T Cells Engineered to Express T-Cell Receptors with a Second Disulfide Bond," *Cancer Research* 67(8):3898-3903, Apr. 15, 2007. (6 pages).

Cole et al., "CD8: Adhesion Molecule, Co-Receptor and Immuno-Modulator," *Cellular & Molecular Immunology* 1(2):81-88, Apr. 2004. (8 pages).

Cole et al., "The molecular determinants of CD8 co-receptor function," *Immunology* 137:139-148, Jul. 18, 2012. (10 pages).

Coosemans et al., "Wilms' tumor gene 1 immunotherapy in pelvic gynecological malignancies," *Expert Rev. Clin. Immunol.* 10(6):705-711, 2014. (8 pages).

Dangaj et al., "Novel Recombinant Human B7-H4 Antibodies Overcome Tumoral Immune Escape to Potentiate T-Cell Antitumor Responses," *Cancer Res* 73(15):4820-4829, Aug. 1, 2013. (10 pages).

Desjarlais et al., "Use of a zinc-finger consensus sequence framework and specificity rules to design specific DNA binding proteins," *Proc. Natl. Acad. Sci. USA* 90:2256-2260, Mar. 1993. (5 pages).

Di Stasi et al., "Inducible Apoptosis as a Safety Switch for Adoptive Cell Therapy," *The New England Journal of Medicine* 365(18):1673-1683, Nov. 3, 2011. (11 pages).

Dossett et al., "Adoptive Immunotherapy of Disseminated Leukemia With TCR-transduced, CD8+ T Cells Expressing a Known Endogenous TCR," *Molecular Therapy* 17(4):742-749, Apr. 2009. (8 pages).

Dudley et al., "Adoptive Cell Therapy for Patients With Metastatic Melanoma: Evaluation of Intensive Myeloablative Chemoradiation Preparative Regimens," *Journal of Clinical Oncology* 26(32):5233-5239, Nov. 10, 2008. (7 pages).

Dujon et al., "Mobile introns: definition of terms and recommended nomenclature," *Gene* 82:115-118, 1989. (4 pages).

Dunbar et al., "ANARCI: antigen receptor numbering and receptor classification," *Bioinformatics* 32(2):298-300, 2016 [Advance Access published Sep. 30, 2015]. (3 pages).

Engels et al., "Retroviral Vectors for High-Level Transgene Expression in T Lymphocytes," *Human Gene Therapy* 14:1155-1168, Aug. 10, 2003 [Published online Jun. 25, 2003]. (14 pages).

Epinat et al., "A novel engineered meganuclease induces homologous recombination in yeast and mammalian cells," *Nucleic Acids Research* 31(11):2952-2962, 2003. (11 pages).

Fehse et al., "CD34 Splice Variant: An Attractive Marker for Selection of Gene-Modified Cells," *Molecular Therapy* 1(5):448-456, May 2000. (9 pages).

Floros et al., "Anticancer Cytokines: Biology and Clinical Effects of IFN-α2, IL-2, IL-15, IL-21, and IL-12," *Semin Oncol.* 42(4):539-548, Aug. 2015. (HHS Public Access, Author Manuscript, available in PMC Aug. 1, 2016) (17 pages).

Frecha et al., "Advances in the Field of Lentivector-based Transduction of T and B Lymphocytes for Gene Therapy," *Molecular Therapy* 18(10):1748-1757, Oct. 2010 [Published online Aug. 24, 2010]. (10 pages).

Gaiger et al., "WT1-specific Serum Antibodies in Patients with Leukemia," *Clinical Cancer Research* 7 (Suppl.):761s-765s, Mar. 2001. (5 pages).

Gao et al., "Molecular interactions of coreceptor CD8 and MCH class I: the molecular basis for functional coordination with the T-cell receptor," *Immunology Today* 21(12):630-636, Dec. 2000. (7 pages).

Gimble et al., "Substrate Recognition and Induced DNA Distortion by the PI-SceI Endonuclease, an Enzyme Generated by Protein Splicing," *J. Mol. Biol.* 263:163-180, 1996. (18 pages).

Govers et al., "T cell receptor gene therapy: strategies for optimizing transgenic TCR pairing," *Trends in Molecular Medicine* 16(2):77-87, 2010. (11 pages).

Green et al., "Mitichondria and Apoptosis," *Science* 281:1309-1312, Aug. 28, 1998. (4 pages).

Hanahan et al., "Hallmarks of Cancer: The Next Generation," *Cell* 144:646-674, Mar. 4, 2011. (29 pages).

Hanahan et al., "The Hallmarks of Cancer," *Cell* 100:57-70, Jan. 7, 2000. (14 pages).

Harris et al., "Adoptive T Cell Therapies: A Comparison of T Cell Receptors and Chimeric Antigen Receptors," *Trends in Pharmacological Sciences* 37(3):220-230, Mar. 2016. (11 pages).

Heemskerk et al., "Redirection of antileukemic reactivity of peripheral T lymphocytes using gene transfer of minor histocompatibility antigen HA-2-specific T-cell receptor complexes expressing a conserved alpha joining region," *Blood* 102(10):3530-3540, Nov. 15, 2003. (11 pages).

Ho et al., "In vitro methods for generating CD8+ T-cell clones for immunotherapy from the naïve repertoire," *Journal of Immunological Methods* 310:40-52, 2006. (13 pages).

Howie et al., "High-throughput pairing of T cell receptor α and β sequences," *Science Translational Medicine* 7(301):301ra131, Aug. 19, 2015. (12 pages).

Hylander et al., "Expression of Wilms tumor gene (WT1) in epithelial ovarian cancer," *Gynecologic Oncology* 101:12-17, 2006. (6 pages).

IMGT, "IMGT Repertoire (IG and TR)," retrieved at URL=imgt.org/IMGTrepertoire/LocusGenes/listIG_TR/TR/human/Hu_TRgroup.html, last updated Sep. 22, 2023. (1 page).

Inoue et al., "WTI as a New Prognostic Factor and a New Marker for the Detection of Minimal Residual Disease in Acute Leukemia," *Blood* 84(9):3071-3079, Nov. 1, 1994. (9 pages).

International Search Report and Written Opinion, mailed Sep. 14, 2020, for International Application No. PCT/US2020/021916. (25 pages).

International Search Report, dated Feb. 3, 2021, for International Patent Application No. PCT/US2020/047071. (8 pages).

(56) References Cited

OTHER PUBLICATIONS

Jaigirdar et al., "A high avidity WT1 reactive T cell receptor mediates recognition of peptide and processed antigen but not naturally occurring WT1 positive tumor cells," *J. Immunother.* *39*(3):105-116, Apr. 2016. (HHS Public Access, Author Manuscript, available in PMC Apr. 1, 2017) (26 pages).

Jasin, "Genetic manipulation of genomes with rare-cutting endonucleases," *TIG 12*(6):224-228, Jun. 1996. (5 pages).

Jinek et al., "A programmable dual RNA-guided DNA endonuclease in adaptive bacterial immunity," *Science 337*(6096):816-821, Aug. 17, 2012. (HHMI Public Access, Author Manuscript, available in PMC Dec. 7, 2018) (14 pages).

Jores et al., "Resolution of hypervariable regions in T-cell receptor β chains by a modified Wu-Kabat index of amino acid diversity," *Proc. Natl. Acad. Sci. USA 87*:9138-9142, Dec. 1990. (5 pages).

Kalos et al., "T Cells with Chimeric Antigen Receptors Have Potent Antitumor Effects and Can Establish Memory in Patients with Advanced Leukemia," *Sci. Transl. Med. 3*(95):95ra73, Aug. 10, 2011 (NIH Public Access, Author Manuscript, available in PMC Aug. 10, 2012) (21 pages).

Kennedy et al., "Multiple roles for CD4+ T cells in anti-tumor immune responses," *Immunological Reviews 222*:129-144, Apr. 2008. (16 pages).

Kieback et al., "A safeguard eliminates T cell receptor gene-modified autoreactive T cells after adoptive transfer," *PNAS 105*(2):623-628, Jan. 15, 2008. (6 pages).

Kochenderfer et al., "Eradication of B-lineage cells and regression of lymphoma in a patient treated with autologous T cells genetically engineered to recognize CD19," *Blood 116*(20):4099-4102, Nov. 18, 2010. (4 pages).

Krisky et al., "Development of herpes simplex virus replicationdefective multigene vectors for combination gene therapy applications," *Gene Therapy 5*:1517-1530, Nov. 1998. (14 pages).

Kuball et al., "Facilitating matched pairing and expression of TCR chains introduced into human T cells," *Blood 109*(6):2331-2338, Mar. 15, 2007. (8 pages).

Kyrgidis et al., "Melanoma: Stem cells, sun exposure and hallmarks for carcinogenesis, molecular concepts and future clinical implications," *Journal of Carcinogenesis 9*(3):1-15, Apr. 1, 2010. (15 pages).

Langenkamp et al., "T cell priming by dendritic cells: thresholds for proliferation, differentiation and death and intraclonal functional diversification," *Eur. J. Immunol. 32*:2046-2054, 2002. (9 pages).

Leen et al., "Improving T Cell Therapy for Cancer" *Annu. Rev. Immunol. 25*:243-265, 2007. (26 pages).

Lefranc et al., "IMGT unique numbering for immunoglobulin and T cell receptor variable domains and Ig superfamily V-like domains," *Developmental and Comparative Immunology 27*:55-77, 2003. (23 pages).

Liebl et al., "Transfer of *Brevibacterium divaricatum* DSM 20297$^T$, "*Brevibacterium flavum*" DSM 20411, "*Brevibacterium lactofermentum*" DSM 20412 and DSM 1412, and *Corynebacterium lilium* DSM 20137$^T$ to *Corynebacterium glutamicum* and Their Distinction by rRNA Gene Restriction Patterns," *International Journal of Systematic Bacteriology 41*(2):255-260, Apr. 1991. (6 pages).

Liu et al., "Selective inhibition of IDO1 effectively regulates mediators of antitumor immunity," *Blood 115*(17):3520-3530, Apr. 29, 2010. (11 pages).

Luescher et al., "CD8 modulation of T-cell antigen receptor-ligand interactions on living cytotoxic T lymphocytes," *Nature 373*:353-356, Jan. 26, 1995. (4 pages).

Mautino et al., "Abstract 491: NLG919, a novel indoleamine-2,3-dioxygenase (IDO)-pathway inhibitor drug candidate for cancer therapy," *Proceedings: AACR 104th Annual Meeting 2013, American Association for Cancer Research*, Washington, DC, Apr. 6-10, 2013, *Cancer Res. 73*(8 Suppl): Abstract nr 491. (4 pages).

Mavilio et al., "Peripheral Blood Lymphocytes as Target Cells of Retroviral Vector-Mediated Gene Transfer," *Blood 83*(7):1988-1997, Apr. 1, 1994. (10 pages).

Menssen et al., "Presence of Wilms' tumor gene (wt1) transcripts and the WT1 nuclear protein in the majority of human acute leukemias," *Leukemia 9*:1060-1067, 1995. (8 pages).

Morgan et al., "Cancer Regression in Patients After Transfer of Genetically Engineered Lymphocytes," *Science 314*(5796):126-129, Oct. 6, 2006. (NIH Public Access, Author Manuscript, available in PMC Mar. 12, 2008) (10 pages).

Nakanishi et al., "CTL mobilization to virus-infected tissue requires CD4+ T cell help," *Nature 462*(7272):510-513, Nov. 26, 2009 (HHS Public Access Author Manuscript, available in PMC May 26, 2010). (12 pages).

Nakatsuka et al., "Immunohistochemical detection of WT1 protein in a variety of cancer cells," *Modern Pathology 19*:804-814, 2006. (11 pages).

Ogawa et al., "The usefulness of monitoring WT1 gene transcripts for the prediction and management of relapse following allogeneic stem cell transplantation in acute type leukemia," *Blood 101*(5): 1698-1704, Mar. 1, 2003. (7 pages).

Oji et al., "Expression of the Wilms' Tumor Gene WT1 in Solid Tumors and Its Involvement in Tumor Cell Growth," *Jpn. J. Cancer Res. 90*:194-204, Feb. 1999. (11 pages).

Oji et al., "Overexpression of the Wilms' Tumor Gene WT1 in De Novo Lung Cancers," *Int. J. Cancer 100*:297-303, 2002. (7 pages).

Pâques et al., "Meganucleases and DNA Double-Strand Break-Induced Recombination: Perspectives for Gene Therapy," *Current Gene Therapy 7*(1):49-66, 2007. (18 pages).

Pardoll, "The blockade of immune checkpoints in cancer immunotherapy," *Nature Reviews Cancer 12*:252-264, Apr. 2012. (13 pages).

Park et al., "Cancer Stem Cell-Directed Therapies: Recent Data From the Laboratory and Clinic," *Molecular Therapy 17*(2):219-230, Feb. 2009. (12 pages).

Penix et al., "Two Essential Regulatory Elements in the Human Interferon ? Promoter Confer Activation Specific Expression in T Cells," *The Journal of Experimental Medicine 178*:1483-1496, Nov. 1993. (14 pages).

Perler et al., "Protein splicing elements: inteins and exteins—a definition of terms and recommended nomenclature," *Nucleic Acids Research 22*(7):1125-1127, 1994. (3 pages).

Philip et al., "A highly compact epitope-based marker/suicide gene for easier and safer T-cell therapy," *Blood 124*(8):1277-1287, Aug. 21, 2014. (11 pages).

Pittet et al., "α3 Domain Mutants of Peptide/MHC Class I Multimers Allow the Selective Isolation of High Avidity Tumor-Reactive CD8 T Cells," *The Journal of Immunology 171*:1844-1849, 2003. (7 pagse).

Porter et al., "Chimeric Antigen Receptor-Modified T Cells in Chronic Lymphoid Leukemia," *The New England Journal of Medicine 365*(8):725-733, Aug. 25, 2011. (9 pages).

Porteus et al., "Gene targeting using zinc finger nucleases," *Nature Biotechnology 23*(8):967-973, Aug. 2005. (7 pages).

Ren et al., "Multiplex genome editing to generate universal CAR T cells resistant to PD1 inhibition," *Clin Cancer Res 23*(9):2255-2266, May 1, 2017. (HHS Public Access, Author Manuscript, available in PMC May 1, 2018) (21 pages).

Richman et al., "Display, engineering, and applications of antigen-specific T cell receptors," *Biomolecular Engineering 24*:361-373, Oct. 2007. (13 pages).

Robbins et al., "Tumor Regression in Patients With Metastatic Synovial Cell Sarcoma and Melanoma Using Genetically Engineered Lymphocytes Reactive With NY-ESO-1," *Journal of Clinical Oncology 29*(7):917-924, Mar. 1, 2011. (8 pages).

Robins et al., "Comprehensive assessment of T-cell receptor β-chain diversity in αβ T cells," *Blood 114*(19):4099-4107, Nov. 5, 2009. (9 pages).

Robins et al., "Overlap and effective size of the human CD8+ T-cell receptor repertoire," *Sci. Transl. Med. 2*(47):47ra64, Sep. 1, 2010. (NIH Public Access, Author Manuscript, available in PMC Nov. 9, 2011) (9 pages).

Robins et al., "Ultra-sensitive detection of rare T cell clones," *J. Immunol. Methods 375*(0):14-19, Jan. 31, 2012. (NIH Public Access, Author Manuscript, available in PMC Jul. 24, 2013) (9 pages).

(56)  References Cited

OTHER PUBLICATIONS

Sadelain et al., "The basic principles of chimeric antigen receptor (CAR) design," *Cancer Discov.* 3(4):388-398, Apr. 2013 (NIH Public Access Author Manuscript, available in PMC Apr. 2, 2014). (21 pages).

Salter et al., "Impaired assembly and transport of HLA-A and -B antigens in a mutant TxB cell hybrid," *The EMBO Journal* 5(5):943-949, 1986. (7 pages).

Scatchard et al., "The Attractions of Proteins for Small Molecules and Ions," *Annals of the New York Academy of Sciences* 51(4):660-672, May 1949. (13 pages).

Schmied et al., "Analysis of the functional $WT_1$-specific T-cell repertoire in healthy donors reveals a discrepancy between $CD4^+$ and $CD8^+$ memory formation," *Immunology* 145:558-569, 2015. (12 pages).

Schmitt et al., "Generation of TCRs of higher affinity by antigen-driven differentiation of progenitor T cells in vitro," *Nat. Biotechnol.* 35(12):1188-1195, Dec. 2017. (HHS Public Access, Author Manuscript, available in PMC May 6, 2018) (with Supplementary Material). (21 pages).

Schmitt et al., "T Cell Receptor Gene Therapy for Cancer," *Human Gene Therapy* 20:1240-1248, Nov. 2009. (9 pages).

Scholten et al., "Codon modification of T cell receptors allows enhanced functional expression in transgenic human T cells," *Clinical Immunology* 119:135-145, 2006. (11 pages).

Seeliger et al., "Boosting antibody developability through rational sequence optimization," *mAbs* 7(3):505-515, May 1, 2015. (12 pages).

Stone et al., "A novel T cell receptor single-chain signaling complex mediates antigen-specific T cell activity and tumor control," *Cancer Immunol. Immunother.* 63(11): 1163-1176, Nov. 2014 (NIH Public Access Author Manuscript, available in PMC Nov. 1, 2015). (23 pages).

Stone et al., "Role of T cell receptor affinity in the efficacy and specificity of adoptive T cell therapies," *Frontiers in Immunology* 4:244, Aug. 21, 2013. (16 pages).

Straathof et al., "An inducible caspase 9 safety switch for T-cell therapy," *Blood* 105(11):4247-4254, Jun. 1, 2005. (8 pages).

Stromnes et al., "Abrogation of SHP-1 in tumor-specific T cells improves efficacy of adoptive immunotherapy by enhancing the effector function and accumulation of short-lived effector T cells in vivo," *J. Immunol.* 189(4):1812-1825, Aug. 15, 2012. (NIH Public Access, Author Manuscript, available in PMC Aug. 15, 2013) (31 pages).

Sussman et al., "Isolation and Characterization of New Homing Endonuclease Specificites at Individual Target Site Positions," *J. Mol. Biol.* 342:31-41, 2004. (11 pages).

Terentis et al., "The Selenazal Drug Ebselen Potently Inhibits Indoleamine 2,3-Dioxygenase by Targeting Enzyme Cysteine Residues," *Biochemistry* 49(3):591-600, 2010. (10 pages).

Thompson et al., "cis-Acting Sequences Required for Inducible Interleukin-2 Enhancer Function Bind a Novel Ets-Related Protein, Elf-1," *Molecular and Cellular Biology* 12(3):1043-1053, Mar. 1992. (11 pages).

Till et al., "Adoptive immunotherapy for indolent non-Hodgkin lymphoma and mantle cell lymphoma using genetically modified autologous CD20-specific T cells," *Blood* 112(6):2261-2271, Sep. 15, 2008. (11 pages).

Todd et al., "Transcription of the Interleukin 4 Gene Is Regulated by Multiple Promoter Elements," *J. Exp. Med.* 177:1663-1674, Jun. 1993. (12 pages).

Torikai et al., "A foundation for universal T-cell based immunotherapy: T cells engineeredto express a CD 19-specific chimeric-antigen-receptor and eliminate expression of endogenous TCR," *Blood* 119(24):5697-5705, Jun. 14, 2012. (10 pages).

Torikai et al., "Genetic editing of HLA expression in hematopoietic stem cells to broaden their human application," Nature Scientific Reports 6:21757, Feb. 23, 2016. (11 pages).

Torikai et al., "Toward eliminating HLA class I expression to generate universal cells from allogeneic donors," *Blood* 122(8):1341-1349, Aug. 22, 2013. (9 pages).

Tsuta et al., "Comparison of Different Clones (WT49 Versus 6F-H2) of WT-1 Antibodies for Immunohistochemical Diagnosis of Malignant Pleural Mesothelioma," *Appl. Immunohistochem. Mol. Morphol.* 17(2):126-130, Mar. 2009. (5 pages).

Udyavar et al., "Subtle Affinity-Enhancing Mutations in a Myelin Oligodendrocyte Glycoprotein-Specific TCR Alter Specificity and Generate New Self-Reactivity," *The Journal of Immunology* 182(7):4439-4447, Apr. 1, 2009. (10 pages).

Verhoeyen et al., "Chapter 8: Lentiviral Vector Gene Transfer into Human T Cells," *Methods in Molecular Biology, Methods and Protocols* 506:97-114, 2009. (18 pages).

Viola et al., "T Cell Activation Determined by T Cell Receptor No. and Tunable Thresholds," *Science* 273:104-106, Jul. 5, 1996. (3 pages).

Wälchli et al., "A Practical Approach to T-Cell Receptor Cloning and Expression," *PLoS ONE* 6(11):e27930, Nov. 21, 2011. (11 pages).

Walseng et al., "A TCR-based Chimeric Antigen Receptor," Nature Scientific Reports 7:10713, Sep. 6, 2017. (10 pages).

Walseng et al., "Soluble T-Cell Receptors Produced in Human Cells for Targeted Delivery," *PLoS ONE* 10(4):e0119559, Apr. 13, 2015. (15 pages).

Wang et al., "A transgene-encoded cell surface polypeptide for selection, in vivo tracking, and ablation of engineered cells," *Blood* 118(5):1255-1263, Aug. 4, 2011. (9 pages).

Wang et al., "Optimizing Adoptive Polyclonal T Cell Immunotherapy of Lymphomas, Using a Chimeric T Cell Receptor Possessing CD28 and CD137 Costimulatory Domains," *Human Gene Therapy* 18:712-725, Aug. 2007. (16 pages).

Warren et al., "Exhaustive T-cell repertoire sequencing of human peripheral blood samples reveals signatures of antigen selection and a directly measured repertoire size of at least 1 million clonotypes," *Genome Research* 21:790-797, 2011. (8 pages).

Wilson, "Analyzing Biomolecular Interactions," *Science* 295(5562):2103-2105, Mar. 15, 2002. (3 pages).

Wolfe et al., "Analysis of Zinc Fingers Optimized via Phage Display: Evaluating the Utility of a Recognition Code," *J. Mol. Biol.* 285:1917-1934, 1999. (18 pages).

Wolff et al., "Monoclonal Antibody Homodimers: Enhanced Anti-tumor Activity in Nude Mice," *Cancer Research* 53:2560-2565, Jun. 1, 1993. (6 pages).

Xie et al., "sgRNAcas9: A Software Package for Designing CRISPR sgRNA and Evaluating Potential Off-Target Cleavage Sites," *PLoS ONE* 9(6):e100448, Jun. 23, 2014. (9 pages).

Zhao et al., "High-Affinity TCRs Generated by Phage Display Provide CD4+ T Cells with the Ability to Recognize and Kill Tumor Cell Lines," *The Journal of Immunology* 179(9):5845-5854, Nov. 1, 2007. (11 pages).

Zhao et al., "Primary Human Lymphocytes Transduced with NY-ESO-1 Antigen-SpecificTCR Genes Recognize and Kill Diverse Human Tumor Cell Lines," *The Journal of Immunology* 174(7):4415-4423, Apr. 1, 2005. (10 pages).

Zhou et al., "Improving the Safety of T Cell Therapies using an Inducible Caspase-9 Gene," *Exp Hematol* 44(11):1013-1019, Nov. 2016. (HHS Public Access, Author Manuscript, available in PMC Nov. 1, 2017) (14 pages).

* cited by examiner

1

T-CELL IMMUNOTHERAPY SPECIFIC FOR WT-1

STATEMENT OF GOVERNMENT INTEREST

This invention was made with government support under CA018029 awarded by the National Institutes of Health. The government has certain rights in the invention.

STATEMENT REGARDING SEQUENCE LISTING

The Sequence Listing associated with this application is provided in text format in lieu of a paper copy, and is hereby incorporated by reference into the specification. The name of the text file containing the Sequence Listing is 360056_473USPC_SEQUENCE_LISTING. The text file is 109 KB, was created on Feb. 14, 2022, and is being submitted electronically via EFS-Web.

BACKGROUND

T cell receptor (TCR) gene therapy is an emerging treatment approach designed to overcome obstacles associated with conventional T cell adoptive immunotherapy, such as the extensive time and labor required to isolate, characterize, and expand tumor antigen-specific T cells (Schmitt et al., *Hum. Gene Ther.* 20:1240, 2009). Another hurdle is that most identified tumor antigens that can be targeted by T cell immunotherapy are over-expressed self-proteins, so high affinity T cells specific for these antigens are generally eliminated during thymic selection, and are rare or non-existent in the peripheral repertoire.

Strategies have been considered for enhancing the affinity of TCRs intended for use in TCR gene therapy (e.g., Udyavar et al., *J. Immunol.* 182:4439, 2009; Zhao et al., *J. Immunol.* 179:5845, 2007; Richman and Kranz, *Biomol. Eng.* 24:361, 2007).

A precondition for targeted T-cell therapy achieving a maximal clinical effect that would be accompanied by minimal immunological toxicity involves identifying disease-associated antigens with high expression in and presentation by, for example, a malignant cell compartment, but without significant expression in normal tissue. For example, several acute myeloid leukemia (AML) associated antigens have been described, and Wilms tumor protein 1 (WT-1) has been shown to be expressed in the leukemia stem cell (LSC) compartment of the majority of AML patients at levels significantly higher than in physiological hematopoietic stem cells (HSCs). WT-1 has been targeted in clinical trials both with adoptive T-cell transfer and peptide vaccination (see, e.g., U.S. Pat. Nos. 7,342,092; 7,608,685; 7,622,119). In addition, WT-1 expression has been reported to be a marker of minimal residual disease because increased transcript levels in patients with AML in morphologic remission were predictive of overt clinical relapse (Inoue et al., *Blood* 84:3071, 1994; Ogawa et al., *Blood* 101:1698, 2003).

Since WT-1 is an intracellular (usually nuclear) protein, immunotherapies targeting WT-1 have used cellular approaches aimed at generating WT-1-specific CD8$^+$ cytotoxic T lymphocyte (CTL) responses that recognize peptides presented on the cell surface by MHC class I molecules. For induction of a CTL response, intracellular proteins are usually degraded by the proteasome or endo/lysosomes, with the resulting peptide fragments binding to MHC class I or class II molecules. These peptide-MHC complexes are displayed on the cell surface where they are bound by T cells via the peptide-MHC-TCR interaction. Peptides derived from the WT-1 protein can theoretically be used in a vaccine in humans to induce human leukocyte antigen (HLA)-restricted cytotoxic CD8$^+$ T cells that are capable of killing tumor cells. However, because WT-1 is a self-protein, immunization may only elicit responses by T cells with low affinity TCRs. In addition, antibodies against WT-1 are detectable in patients with hematopoietic malignancies and solid tumors, which show that WT-1 can be a highly immunogenic antigen (Gaiger et al., *Clin. Cancer Res.* 7 (Suppl. 3):761, 2001).

Clearly there is a need for alternative gene therapies for use as highly specific, WT-1 targeted immunotherapies directed against various cancers, such as leukemia and tumors. The presently disclosed embodiments address this need and provide other related advantages.

BRIEF SUMMARY

The present disclosure provides, according to certain embodiments, binding proteins that are capable of binding to a RMFPNAPYL (SEQ ID NO:94):human leukocyte antigen (HLA) complex, wherein the binding proteins comprise (a) a T cell receptor (TCR) α chain variable (Vα) domain comprising the CDR3 amino acid sequence (CDR3α) according to any one of SEQ ID NOs.:19, 22, 25, or 28, or a variant thereof, and a TCR β chain variable (Vβ) domain, wherein the Vβ optionally comprises or consists of an amino acid sequence having at least 90% (e.g., 90%, 91%, 92%, 93%, 94%, 95%, 96%, 97%, 98%, 99%, or more) identity to the amino acid sequence set forth in any one of SEQ ID NOs.:5-8 or 13-16; (b) a TCR Vβ domain comprising the CDR3 amino acid sequence (CDR3β) according to any one of SEQ ID NOs.:31, 34, 37, or 40, or a variant thereof, and a TCR Vα domain, wherein the Vα optionally comprises or consists of an amino acid sequence having at least 90% identity to the amino acid sequence set forth in any one of SEQ ID NOs.: 1-4 or 9-12; or (c) a TCR Vα domain of (a), and a TCR Vβ domain of (b).

In certain embodiments, a binding protein is capable of binding to a RMFPNAPYL (SEQ ID NO.:94):human leukocyte antigen (HLA) complex with an IFNγ production pEC$_{50}$ of 4.0, 4.5, 5.0, 5.1, 5.2, 5.3, 5.4, 5.5, 5.6, 5.7, 5.8, 5.9, 6.0, 6.1, 6.2, 6.3, 6.4, 6.5, or higher (e.g., an immune cell (such as, for example, a T cell, a NK-T cell, or a NK cell) comprising the binding protein has a SEQ ID NO.:94:HLA IFNγ production pEC$_{50}$ of 4.0, 4.5, 5.0, 5.1, 5.2, 5.3, 5.4, 5.5, 5.6, 5.7, 5.8, 5.9, 6.0, 6.1, 6.2, 6.3, 6.4, 6.5, or higher).

In certain embodiments, the HLA comprises HLA-A*0201.

In certain embodiments, the binding protein is human, humanized, or chimeric.

In any of the herein disclosed embodiments, a binding protein is capable of binding to a RMFPNAPYL (SEQ ID NO.:94):human leukocyte antigen (HLA) complex, wherein the binding protein comprises a TCR Vβ domain and a TCR Vα domain, wherein: (i) the Vβ domain comprises or consists of an amino acid sequence having at least 90% identity (e.g., 90%, 91%, 92%, 93%, 94%, 95%, 96%, 97%, 98%, 99%, or more) to the amino acid sequence of any one of SEQ ID NOs.: 5-8 or 13-16; and/or (ii) the Vα domain comprises or consists of an amino acid sequence having at least 90% identity to the amino acid sequence of any one of SEQ ID NOs.:1-4 or 9-12.

In certain embodiments, the encoded binding protein is a TCR, a CAR, or a scTCR.

Also provided herein modified immune cells that comprise a heterologous polynucleotide that encodes a binding protein as disclosed herein. In certain embodiments, the immune cell comprises a T cell, a NK cell, a NK-T cell, or any combination thereof. In certain embodiments, an immune cell encoding a binding protein as disclosed herein is activated in the presence of a peptide according to SEQ ID NO.:94 (e.g., comprised in a peptide:HLA complex). In certain embodiments, an immune cell encoding a binding protein as disclosed herein is capable of killing a target cell expressing a SEQ ID NO: 94:HLA complex.

Also provided are isolated polynucleotides that encode a binding protein according to the present disclosure. In certain embodiments, the encoded binding protein comprises: (i) the amino acid sequence set forth in any one of SEQ ID NOs.: 19, 22, 25, 28, 31, 34, 37, or 40; (ii) the amino acid sequence set forth in any one of SEQ ID NOs.: 17, 20, 23, 26, 29, 32, 35, or 38; (iii) the amino acid sequence set forth in any one of SEQ ID NOs.: 18, 21, 24, 27, 30, 33, 36, or 39; (iv) an amino acid sequence comprising, consisting of, or having at least 90% (e.g., 90%, 91%, 92%, 93%, 94%, 95%, 96%, 97%, 98%, 99%, or 100%) identity to the amino acid sequence set forth in any one of SEQ ID NOs: 1-4 or 9-12; (v) an amino acid sequence comprising, consisting of, or having at least 90% identity to the amino acid sequence set forth in any one of SEQ ID NOs: 5-8 or 13-16; (vi) an amino acid sequence comprising, consisting of, or having at least 90% identity to the amino acid sequence set forth in any one of SEQ ID NOs.: 46-53; (vii) an amino acid sequence comprising, consisting of, or having at least 90% identity to the amino acid sequence set forth in any one of SEQ ID NOs.: 54-61; or (viii) any combination of (i)-(vii).

In certain embodiments, the polynucleotide comprises or consists of a polynucleotide having at least 75% (e.g., 75%, 80%, 85%, 90%, 91%, 92%, 93%, 94%, 95%, 96%, 97%, 98%, 99% or 100%) identity to the nucleotide sequence set forth in any one of SEQ ID NOs.: 62-81. In certain embodiments, the polynucleotide is codon-optimized for expression in a host cell, such an immune cell (e.g., human T cell).

Vectors that contain a polynucleotide as described herein are also provided, as well as compositions that comprise a presently disclosed modified cell, binding protein, polynucleotide, and/or vector.

Also provided are methods for treating a subject having a disease or disorder associated with WT-1 expression or activity, wherein the methods comprise administering to the subject an effective amount of a modified immune cell, binding protein, polynucleotide, or vector as disclosed herein.

In certain embodiments, the disease or disorder is a hematological malignancy or a solid cancer. For example, the hematological malignancy to be treated may be acute lymphoblastic leukemia (ALL), acute lymphocytic leukemia, acute myelocytic leukemia, acute myeloid leukemia (AML, including refractory and relapsed AML, and including acute myeloblastic leukemia, acute promyelocytic leukemia, acute myelocytic leukemia, acute myelomonocytic leukemia (e.g., with or without eosinophilia), acute monocytic leukemia, acute erythroid leukemia, and acute megakaryoblastic leukemia), chronic myelogenous leukemia (CML), chronic myelocytic leukemia, chronic eosinophilic leukemia (CEL), myelodysplastic syndrome (MDS), non-Hodgkin's lymphoma (NHL), or multiple myeloma (MM, including refractory and relapsed MM). Exemplary solid cancer to be treated may be biliary cancer, bladder cancer, bone and soft tissue carcinoma, brain tumor, breast cancer, breast carcinoma, cervical cancer, colon cancer, colorectal adenocarcinoma, colorectal cancer, desmoid tumor, embryonal cancer, endometrial cancer, esophageal cancer, gastric cancer, gastric adenocarcinoma, glioblastoma multiforme, glioblastoma, melanoma, diffuse peritoneal mesothelioma, malignant pleural mesothelioma, glioma, astrocytoma, gynecological tumor, head and neck squamous cell carcinoma, hepatic cancer, hepatocellular carcinoma, lung cancer, non small-cell lung cancer, malignant melanoma, osteosarcoma, ovarian cancer (e.g., epithelial ovarian cancer, ovarian carcinoma), fallopian tube cancer, endometrial carcinoma, pancreatic cancer, pancreatic ductal adenocarcinoma, primary astrocytic tumor, primary thyroid cancer, prostate cancer, renal cancer, renal cell carcinoma, rhabdomyosarcoma, skin cancer, soft tissue sarcoma, osteogenic sarcoma, testicular germ-cell tumor, urothelial cancer, uterine sarcoma, uterine carcinosarcoma, or uterine cancer.

These and other aspects and embodiments of the present disclosure will be further understood upon reference to the following detailed description and attached drawings. All of the U.S. patents, U.S. patent application publications, U.S. patent applications, foreign patents, foreign patent applications and non-patent publications referred to in this specification and/or listed in the Application Data Sheet are incorporated herein by reference in their entirety, as if each was incorporated individually. Aspects and embodiments of the disclosure can be modified, if necessary, to employ concepts of the various patents, applications and publications to provide yet further embodiments.

DETAILED DESCRIPTION

Figure 1:
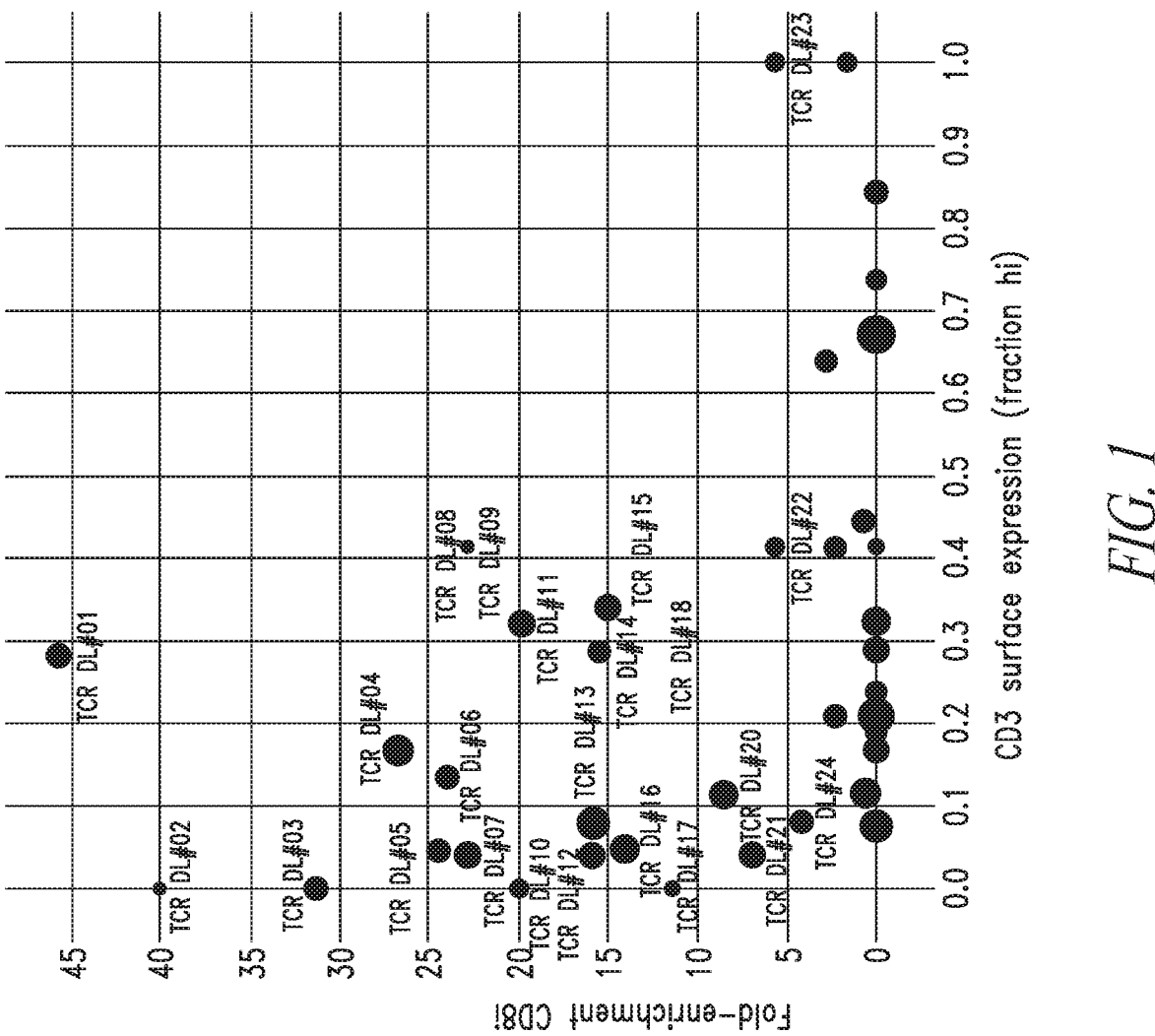
FIG. 1 shows identification of WT-1-specific T cell lines. Briefly, WT-1-specific polyclonal T cell lines (CD8+) obtained from 4 healthy donors were cultured with peptide-pulsed autologous dendritic cells, stained with CD8-independent (CD8i) WT-1 peptide/HLA-A tetramer, and sorted for high tetramer staining cells. Twenty-four (24) WT-1-specific clonotypes were identified. TCR repertoire analysis was performed by sequencing. The fold-enrichment of each clonotype within the sorted versus unsorted populations (y-axis) and the CD3 surface expression (x-axis) of each clonotype are shown.

In certain aspects, the present disclosure provides binding protein (e.g., TCRs, CARs, scTCRs) having specificity for WT-1 peptide antigen associated with a major histocompatibility complex (MHC) (e.g., human leukocyte antigen (HLA)), polynucleotides that encode a binding protein, vectors, modified immune cells that encode and/or express the binding proteins, and related compositions. The presently disclosed WT-1 specific compositions are useful in, for example, adoptive immunotherapy to treat cancer. By way of background, most tumor targets for T cell-based immunotherapies are self-antigens since tumors arise from previously normal tissue. For example, such tumor-associated antigens (TAAs) may be expressed at high levels in a cancer cell, but may not be expressed or may be minimally expressed in other cells. During T cell development in the thymus, T cells that bind weakly to self-antigens are allowed to survive in the thymus, which can undergo further development to increase specificity against foreign invaders, while T cells that bind strongly to self-antigens are eliminated by the immune system since such cells would mount an undesirable autoimmune response. Hence, T cells are sorted by their relative ability to bind to antigens to prepare the immune system to respond against a foreign invader (i.e., recognition of non-self-antigen) while at the same time preventing an autoimmune response (i.e., recognition of self-antigen). This tolerance mechanism limits naturally occurring T cells that can recognize tumor (self) antigens with high affinity and, therefore, eliminates the T cells that would effectively eliminate tumor cells. Consequently, isolating T cells having high affinity TCRs specific for tumor antigens is difficult because such cells are essentially eliminated by the immune system.

An advantage of the instant disclosure is to provide a binding protein specific for a WT-1 peptide, wherein the binding protein is capable of binding to a WT-1 (SEQ ID NO.:94):HLA (e.g., HLA-A*0201) complex. In certain embodiments, the binding protein is capable of binding to the WT-1 independent or in the absence of CD8, is capable of more efficiently associating with a CD3 protein as compared to an endogenous TCR, is capable of initiating a signal to a host cell expressing the binding protein to produce a cytokine, or any combination thereof. In certain embodiments, a binding protein is capable of binding to a RMFPNAPYL (SEQ ID NO: 94):HLA complex with an IFNγ production $pEC_{50}$ of 4.0, 4.5, 5.0, 5.1, 5.2, 5.3, 5.4, 5.5, 5.6, 5.7, 5.8, 5.9, 6.0, 6.1, 6.2, 6.3, 6.4, 6.5, or higher; and/or wherein the binding protein is capable of binding to a RMFPNAPYL (SEQ ID NO.: 94):HLA complex with a higher IFNγ production $pEC_{50}$ as compared to a TCR comprising an α-chain amino acid sequence of SEQ ID NO: 82 and a β-chain amino acid sequence of SEQ ID NO: 83.

The compositions and methods described herein will in certain embodiments have therapeutic utility for the treatment of diseases and conditions associated with WT-1 expression (e.g., detectable WT-1 expression at a level that is greater in magnitude, in a statistically significant manner, than the level of WT-1 expression that is detectable in a normal or disease-free cell). Such diseases include various diseases and disorders, such as hematological malignancies and solid cancers. Non-limiting examples of these and related uses are described herein and include in vitro, ex vivo and in vivo stimulation of WT-1 antigen-specific T-cell responses, such as by the use of recombinant immune cells, such as T cells, encoding and/or expressing a heterologous binding protein specific for a WT-1 peptide (e.g., RMFPNAPYL, SEQ ID NO.: 94).

Prior to setting forth this disclosure in more detail, it may be helpful to an understanding thereof to provide definitions of certain terms to be used herein. Additional definitions are set forth throughout this disclosure.

In the present description, any concentration range, percentage range, ratio range, or integer range is to be understood to include the value of any integer within the recited range and, when appropriate, fractions thereof (such as one tenth and one hundredth of an integer), unless otherwise indicated. Also, any number range recited herein relating to any physical feature, such as polymer subunits, size or thickness, are to be understood to include any integer within the recited range, unless otherwise indicated. As used herein, the term "about" means±20% of the indicated range, value, or structure, unless otherwise indicated. It should be understood that the terms "a" and "an" as used herein refer to "one or more" of the enumerated components. The use of the alternative (e.g., "or") should be understood to mean either one, both, or any combination thereof of the alternatives. As used herein, the terms "include," "have" and "comprise" are used synonymously, which terms and variants thereof are intended to be construed as non-limiting.

In addition, it should be understood that the individual compounds, or groups of compounds, derived from the various combinations of the structures and substituents described herein, are disclosed by the present application to the same extent as if each compound or group of compounds was set forth individually. Thus, selection of particular structures or particular substituents is within the scope of the present disclosure.

The term "consisting essentially of" is not equivalent to "comprising", and refers to the specified materials or steps, or to those that do not materially affect the basic characteristics of a claimed invention. For example, a protein domain, region, or module (e.g., a binding domain, hinge region, linker module) or a protein (which may have one or more domains, regions, or modules) "consists essentially of" a particular amino acid sequence when the amino acid sequence of a domain, region, module, or protein includes extensions, deletions, mutations, or a combination thereof (e.g., amino acids at the amino- or carboxy-terminus or between domains) that, in combination, contribute to at most 20% (e.g., at most 15%, 10%, 8%, 6%, 5%, 4%, 3%, 2% or 1%) of the length of a domain, region, module, or protein and do not substantially affect (i.e., do not reduce the activity by more than 50%, such as no more than 40%, 30%, 25%, 20%, 15%, 10%, 5%, or 1%) the activity of the domain(s), region(s), module(s), or protein (e.g., the target binding affinity of a binding protein).

As used herein, the term "host" refers to a cell (e.g., T cell) or microorganism targeted for genetic modification with a heterologous or exogenous nucleic acid molecule to produce a polypeptide of interest (e.g., enhanced affinity anti-WT-1 TCR). In certain embodiments, a host cell may optionally already possess or be modified to include other genetic modifications that confer desired properties related or unrelated to biosynthesis of the heterologous or exogenous protein (e.g., inclusion of a detectable marker; deleted, altered or truncated endogenous TCR; increased co-stimulatory factor expression). In certain embodiments, a host cell is a human hematopoietic progenitor cell transduced with heterologous or exogenous nucleic acid molecule encoding a TCRα chain specific for a WT-1 antigen peptide.

As used herein, an "immune system cell" means any cell of the immune system that originate from a hematopoietic stem cell in the bone marrow, which gives rise to two major lineages, a myeloid progenitor cell (which give rise to myeloid cells such as monocytes, macrophages, dendritic cells, megakaryocytes and granulocytes) and a lymphoid progenitor cell (which give rise to lymphoid cells such as T cells, B cells and natural killer (NK) cells). Exemplary immune system cells include a CD4+ T cell, a CD8+ T cell, a CD4− CD8− double negative T cell, a γδ T cell, a natural killer cell, and a dendritic cell. Macrophages and dendritic cells may be referred to as "antigen presenting cells" or "APCs," which are specialized cells that can activate T cells when a major histocompatibility complex (MHC) receptor on the surface of the APC interacts with a TCR on the surface of a T cell. In certain embodiments, an immune system cell is a human immune system cell.

As used herein, a "hematopoietic progenitor cell" is a cell that can be derived from hematopoietic stem cells or fetal tissue and is capable of further differentiation into mature cells types (e.g., immune system cells). Exemplary hematopoietic progenitor cells include those with a CD24$^{Lo}$ Lin− CD117+ phenotype or those found in the thymus (referred to as progenitor thymocytes).

"Major histocompatibility complex" (MHC) refers to glycoproteins that deliver peptide antigens to a cell surface. MHC class I molecules are heterodimers having a membrane spanning α chain (with three α domains) and a non-covalently associated β2 microglobulin. MHC class II molecules are composed of two transmembrane glycoproteins, α and β, both of which span the membrane. Each chain has two domains. MHC class I molecules deliver peptides originating in the cytosol to the cell surface, where a peptide:MHC complex is recognized by CD8+ T cells. MHC class II molecules deliver peptides originating in the vesicular system to the cell surface, where they are recognized by CD4+ T cells. Human MHC are referred to as human leukocyte antigen (HLA).

A "T cell" is an immune system cell that matures in the thymus and produces T cell receptors (TCRs). T cells can be naïve (not exposed to antigen; increased expression of CD62L, CCR7, CD28, CD3, CD127, and CD45RA, and decreased expression of CD45RO as compared to T$_{CM}$), memory T cells (T$_M$) (antigen-experienced and long-lived), and effector cells (antigen-experienced, cytotoxic). T$_M$ can be further divided into subsets of central memory T cells (T$_{CM}$, increased expression of CD62L, CCR7, CD28, CD127, CD45RO, and CD95, and decreased expression of CD54RA as compared to naïve T cells), stem cell memory T cells, and effector memory T cells (TEM, decreased expression of CD62L, CCR7, CD28, CD45RA, and increased expression of CD127 as compared to naïve T cells or T$_{CM}$). Effector T cells (T$_E$) refers to a antigen-experienced CD8+ cytotoxic T lymphocytes that has decreased expression of CD62L, CCR7, CD28, and are positive for granzyme and perforin as compared to T$_{CM}$.

"T cell receptor" (TCR) refers to an immunoglobulin superfamily member (having a variable binding domain, a constant domain, a transmembrane region, and a short cytoplasmic tail; see, e.g., Janeway et al., *Immunobiology: The Immune System in Health and Disease*, 3$^{rd}$ Ed., Current Biology Publications, p. 4:33, 1997) capable of specifically binding to an antigen peptide bound to a MHC receptor. A TCR can be found on the surface of a cell or in soluble form and generally is comprised of a heterodimer having α and β chains (also known as TCRα and TCRβ, respectively), or γ and δ chains (also known as TCRγ and TCRδ, respectively). Like other immunoglobulins (e.g., antibodies), the extracellular portion of TCR chains (e.g., α-chain, β-chain) contain two immunoglobulin domains, a variable domain (e.g., α-chain variable domain or V$_α$, β-chain variable domain or V$_β$; typically amino acids 1 to 116 based on Kabat numbering Kabat et al., "Sequences of Proteins of Immunological Interest, US Dept. Health and Human Services, Public Health Service National Institutes of Health, 1991, 5$^{th}$ ed.) at the N-terminus, and one constant domain (e.g., α-chain constant domain or C$_α$, typically amino acids 117 to 259 based on Kabat, β-chain constant domain or C$_β$, typically amino acids 117 to 295 based on Kabat) adjacent to the cell membrane. Also like other immunoglobulins, the variable domains contain complementary determining regions (CDRs) separated by framework regions (FRs) (see, e.g., Jores et al., *Proc. Nat'l Acad. Sci. U.S.A.* 87:9138, 1990; Chothia et al., *EMBO J.* 7:3745, 1988; see also Lefranc et al., *Dev. Comp. Immunol.* 27:55, 2003). In certain embodiments, a TCR is found on the surface of T cells (or T lymphocytes) and associates with the CD3 complex. The source of a TCR as used in the present disclosure may be from various animal species, such as a human, mouse, rat, rabbit or other mammal.

The term "variable region" or "variable domain" refers to the domain of an immunoglobulin superfamily binding protein (e.g., a TCR α-chain or β-chain (or γ chain and δ chain for γδ TCRs)) that is involved in binding of the immunoglobulin superfamily binding protein (e.g., TCR) to antigen. In the case of a TCR, the variable domains of the α chain and β chain (Vα and Vβ, respectively) generally have similar structures, with each domain comprising four conserved framework regions (FRs) and three CDRs. The Vα domain is encoded by two separate DNA segments, the variable gene segment and the joining gene segment (V-J); the Vβ domain is encoded by three separate DNA segments, the variable gene segment, the diversity gene segment, and the joining gene segment (V-D-J). A single Vα or Vβ domain, or a functional fragment or portion thereof, may be sufficient to confer antigen-binding specificity. Furthermore, TCRs that bind a particular antigen may be isolated using a Vα or Vβ domain from a TCR that binds the antigen to screen a library of complementary Vα or Vβ domains, respectively.

The terms "complementarity determining region," and "CDR," are synonymous with "hypervariable region" or "HVR," and are known in the art to refer to sequences of amino acids within immunoglobulin (e.g., TCR) variable regions, which confer antigen specificity and/or binding affinity and are separated from one another by framework regions. In general, there are three CDRs in each TCR α-chain variable region (αCDR1, αCDR2, αCDR3) and three CDRs in each TCR β-chain variable region (βCDR1, βCDR2, βCDR3). In TCRs, CDR3 is thought to be the main CDR responsible for recognizing processed antigen. Typically, CDR1 and CDR2 mainly interact with the MHC.

CDR1 and CDR2 are encoded within the variable gene segment of a TCR variable region-coding sequence, whereas CDR3 is encoded by the region spanning the variable and joining segments for Vα, or the region spanning variable, diversity, and joining segments for Vβ. Thus, if the identity of the variable gene segment of a Vα or Vβ is known, the sequences of their corresponding CDR1 and CDR2 can be deduced. Compared with CDR1 and CDR2, CDR3 is typically significantly more diverse because of the addition and loss of nucleotides during the recombination process.

TCR variable domain sequences can be aligned to a numbering scheme (e.g., IMGT, Kabat, Chothia, Enhanced Chothia, Contact, and Aho), allowing equivalent residue positions to be annotated and for different molecules to be compared using, for example, ANARCI software tool (2016, Bioinformatics 15:298-300). A numbering scheme provides a standardized delineation of framework regions and CDRs in the TCR variable domains. Accordingly, it will be understood that a CDR from a TCR Vα or Vβ region or domain may have a particular sequence according to a particular numbering scheme, and may have a slightly shorter, longer, or shifted (e.g., partially overlapping) sequence according to a different numbering scheme. In certain presently disclosed embodiments, CDRs are determined using the IMGT numbering scheme; for example, using IMGT V-Quest (imgt.org/IMGTindexN-QUEST.php).

"CD3" is known in the art as a multi-protein complex of six chains (see, Abbas and Lichtman, 2003; Janeway et al., p 172 and 178, 1999). In mammals, the complex comprises a CD3γ chain, a CD3δ chain, two CD3ε chains, and a homodimer of CD3ζ chains. The CD3γ, CD3δ, and CD3ε chains are highly related cell surface proteins of the immunoglobulin superfamily containing a single immunoglobulin domain. The transmembrane regions of the CD3γ, CD3δ, and CD3ε chains are negatively charged, which is a characteristic that is thought to allow these chains to associate with positively charged regions of T cell receptor chains. The intracellular tails of the CD3γ, CD3δ, and CD3ε chains each contain a single conserved motif known as an immunoreceptor tyrosine-based activation motif or ITAM, whereas each CD3ζ chain has three. Without wishing to be bound by theory, it is believed that ITAMs are important for the signaling capacity of a TCR complex. CD3 as used in the present disclosure may be from various animal species, including human, mouse, rat, or other mammals.

As used herein, "TCR complex" refers to a complex formed by the association of CD3 with TCR. For example, a TCR complex can be composed of a CD3γ chain, a CD3δ chain, two CD3ε chains, a homodimer of CD3ζ chains, a TCRα chain, and a TCRβ chain. Alternatively, a TCR complex can be composed of a CD3γ chain, a CD3δ chain, two CD3ε chains, a homodimer of CD3ζ chains, a TCRγ chain, and a TCRδ chain.

A "component of a TCR complex," as used herein, refers to a TCR chain (i.e., TCRα, TCRβ, TCRγ or TCRδ), a CD3 chain (i.e., CD3γ, CD3δ, CD3ε or CD3ζ), or a complex formed by two or more TCR chains or CD3 chains (e.g., a complex of TCRα and TCRβ, a complex of TCRγ and TCRδ, a complex of CD3ε and CD3δ, a complex of CD3γ and CD3ε, or a sub-TCR complex of TCRα, TCRβ, CD3γ, CD3δ, and two CD3ε chains).

As used herein, the term "CD8 co-receptor" or "CD8" means the cell surface glycoprotein CD8, which can be expressed by T cells as a homodimer comprising two CD8a chains, or as a heterodimer comprising an α chain and a β chain. The CD8 co-receptor is believed to assist in the function of cytotoxic T cells (CD8$^+$) and functions through signaling via its cytoplasmic tyrosine phosphorylation pathway (Gao and Jakobsen, *Immunol. Today* 21:630-636, 2000; Cole and Gao, *Cell. Mol. Immunol.* 1:81-88, 2004). In particular, and without wishing to be bound by theory, it is believed that the CD8 co-receptor binds to an MHC-I protein complex expressed on the surface of an antigen-expressing cell, and that this binding in the context of TCR:antigen-MHC binding initiates or assists in a T cell signaling pathway that produces an immune response (e.g., transcription and expression of cytokines, calcium secretion, cytolytic activity, or the like) against the antigen-expressing cell. In humans, eight (8) different CD8 beta chain isoforms are known ("M1"-"M8"; see UniProtKB identifiers P10966-1, 2, 3, 4, 6, 7, 8, and 9); of these, isoforms 1, 2, 4, and 5 are thought to associate with the cell membrane in nature, while isoforms 3, 6, 7, and 8 are believed to associate with extracellular regions or be secreted. Also in humans, three CD8 alpha chain isoforms are known (see UniProtKB identifiers P01732-1, 2, and 3).

"CD4" refers to an immunoglobulin co-receptor glycoprotein that assists the TCR in communicating with antigen-presenting cells (see, Campbell & Reece, *Biology* 909 (Benjamin Cummings, Sixth Ed., 2002); UniProtKB P01730). CD4 is found on the surface of immune cells such as T helper cells, monocytes, macrophages, and dendritic cells, and typically includes four immunoglobulin domains (D1(comprising an Ig-like V-type domain), D2, D3, and D4 (respectively comprising Ig-like C2-type domains 1, 2, and 3)) that are expressed at the cell surface. During antigen presentation, CD4 is recruited, along with the TCR complex, to bind to different regions of the MHCII molecule (CD4 binds MHCII β2, while the TCR complex binds MHCII α1/β1). Without wishing to be bound by theory, it is believed that close proximity to the TCR complex allows CD4-associated kinase molecules to phosphorylate the immunoreceptor tyrosine activation motifs (ITAMs) present on the cytoplasmic domains of CD3. This activity is thought to amplify the signal generated by the activated TCR in order to produce various types of T helper cells.

A "binding domain" (also referred to as a "binding region" or "binding moiety"), as used herein, refers to a peptide, oligopeptide, polypeptide, or protein that possesses the ability to specifically and non-covalently associate, unite, or combine with a target (e.g., WT-1 or WT-1 peptide: MHC complex). A binding domain includes any naturally occurring, synthetic, semi-synthetic, or recombinantly produced binding partner for a biological molecule, a molecular complex (i.e., complex comprising two or more biological molecules), or other target of interest. Exemplary binding domains include single chain immunoglobulin variable regions (e.g., scTCR, scFv), receptor ectodomains, ligands (e.g., cytokines, chemokines), or synthetic polypeptides selected for the specific ability to bind to a biological molecule, a molecular complex or other target of interest.

As used herein, "specifically binds" or "specific for" refers to an association or union of a binding protein (e.g., TCR receptor) or a binding domain (or fusion protein thereof) to a target molecule with an affinity or $K_a$ (i.e., an equilibrium association constant of a particular binding interaction with units of 1/M) equal to or greater than $10^5$ $M^{-1}$ (which equals the ratio of the on-rate $[k_{on}]$ to the off-rate $[k_{off}]$ for this association reaction), while not significantly associating or uniting with any other molecules or components in a sample. Binding proteins or binding domains (or fusion proteins thereof) may be classified as "high affinity" binding proteins or binding domains (or fusion proteins thereof) or as "low affinity" binding proteins or binding domains (or fusion proteins thereof). "High affinity" binding proteins or binding domains refer to those binding proteins or binding domains having a $K_a$ of at least $10^7$ $M^{-1}$, at least $10^8$ $M^{-1}$, at least $10^9$ $M^{-1}$, at least $10^{10}$ $M^{-1}$, at least $10^{11}$ $M^{-1}$, at least $10^{12}$ $M^{-1}$, or at least $10^{13}$ $M^{-1}$. "Low affinity" binding proteins or binding domains refer to those binding proteins or binding domains having a $K_a$ of up to $10^7$ $M^{-1}$, up to $10^6$ $M^{-1}$, up to $10^5$ $M^{-1}$. Alternatively, affinity may be defined as an equilibrium dissociation constant ($K_d$) of a particular binding interaction with units of M (e.g., $10^{-5}$ M to $10^{-13}$ M).

In certain embodiments, a receptor or binding domain may have "enhanced affinity," which refers to a selected or engineered receptors or binding domain with stronger binding to a target antigen than a wild type (or parent) binding domain. For example, enhanced affinity may be due to a $K_a$ (equilibrium association constant) for the target antigen that is higher than the wild type binding domain, due to a $K_d$ (dissociation constant) for the target antigen that is less than that of the wild type binding domain, due to an off-rate ($k_{off}$) for the target antigen that is less than that of the wild type binding domain, or a combination thereof. In certain embodiments, enhanced affinity TCRs may be codon optimized to enhance expression in a particular host cell, such as T cells (Scholten et al., *Clin. Immunol.* 119:135, 2006).

The term "functional avidity" refers to a biological measure or activation threshold of an in vitro immune cell (e.g., T cell, NK cell, NK-T cell) response to a given concentration of a ligand, wherein the biological measures can include cytokine production (e.g., IFNγ production, IL-2 production, etc.), cytotoxic activity, activation, and proliferation. For example, T cells that biologically (immunologically) respond in vitro to a low antigen dose by producing cytokines, being cytotoxic, expressing an activation marker, or proliferating are considered to have high functional avidity, while T cells having lower functional avidity require higher amounts of antigen before an immune response, similar to the high-avidity T cells, is elicited. It will be understood that functional avidity is different from affinity and avidity. Affinity refers to the strength of any given bond between a binding protein and its antigen/ligand. Some binding proteins are multivalent and bind to multiple antigens—in this case, the strength of the overall connection is the avidity.

Numerous correlations exist between the functional avidity and the effectiveness of an immune response. Some ex vivo studies have shown that distinct T cell functions (e.g., proliferation, cytokines production, etc.) can be triggered at different thresholds (see, e.g., Betts et al., *J. Immunol.* 172:6407, 2004; Langenkamp et al., *Eur. J. Immunol.* 32:2046, 2002). Factors that can affect functional avidity include (a) the affinity of a TCR for the pMHC-complex, that is, the strength of the interaction between the TCR and pMHC (Cawthon et al., *J. Immunol.* 167:2577, 2001), (b) expression levels of the TCR and the CD4 or CD8 co-receptors, and (c) the distribution and composition of signaling molecules (Viola and Lanzavecchia, *Science* 273: 104, 1996), as well as expression levels of molecules that attenuate T cell function and TCR signaling.

The concentration of antigen needed to induce a half-maximum response between the baseline and maximum response after a specified exposure time is referred to as the "half maximal effective concentration" or "$EC_{50}$". The $EC_{50}$ value is generally presented as a molar (moles/liter) amount, but it is often converted into a logarithmic value as follows $-\log_{10}(EC_{50})$ (see, e.g., FIG. 4(C)). For example, if the $EC_{50}$ equals 1 μM ($10^{-6}$ M), the $\log_{10}(EC_{50})$ value is −6. Another value used is $pEC_{50}$, which is defined as the negative logarithm of the $EC_{50}$ ($-\log_{10}(EC_{50})$). In the above example, the $EC_{50}$ equaling 1 μM has a pEC50 value of 6. In certain embodiments, the functional avidity of a binding protein of this disclosure will be a measure of its ability to promote IFNγ production by immune cells (e.g., T cells, NK-T cells, NK cells), which can be measured using assays known in the art and/or described herein. "High functional avidity" TCRs or binding domains thereof refer to those TCRs or binding domains thereof having a $EC_{50}$ of at least $10^{-4}$ M, at least about $10^{-5}$ M, or at least about $10^{-6}$ M.

In some embodiments, a $pEC_{50}$ is used to describe the amount of peptide antigen required for 50% of immune cells to express the activation marker Nur77.

A variety of assays are known for identifying binding domains of the present disclosure that specifically bind a particular target, as well as determining binding domain or fusion protein affinities, such as Western blot, ELISA, analytical ultracentrifugation, spectroscopy and surface plasmon resonance (Biacore®) analysis (see, e.g., Scatchard et al., *Ann. N.Y. Acad. Sci.* 51:660, 1949; Wilson, Science 295:2103, 2002; Wolff et al., *Cancer Res.* 53:2560, 1993; and U.S. Pat. Nos. 5,283,173, 5,468,614, or the equivalent), and peptide:MHC tetramer staining.

The term "WT-1-specific immunoglobulin superfamily binding protein" or "WT-1-specific binding protein" refers in certain embodiments to a protein or polypeptide of the present disclosure that specifically binds to WT-1 or a peptide thereof, optionally in complex with a HLA molecule. The term "WT-1 binding domain" or "WT-1 binding fragment" refer to a domain or portion of a WT-1-specific binding protein responsible for the specific WT-1 binding. A WT-1-specific binding domain alone (i.e., without any other portion of a WT-1-specific binding protein) can be soluble. Exemplary WT-1-specific binding domains include those from a WT-1-specific TCR, such as can be found in a TCR or a scTCR (e.g., single chain αβTCR proteins such as Vα-L-Vβ, Vβ-L-Vα, Vα-Ca-L-Vα, or Vα-L-Vβ-Cβ, wherein Vα and Vβ are TCRα and β variable domains respectively, Cα and Cβ are TCRα and β constant domains, respectively, and L is a linker) and scFv fragments as described herein, which can be derived from an anti-WT-1 TCR or antibody.

"WT-1 antigen" or "WT-1 peptide antigen" refer to a naturally or synthetically produced portion of a WT-1 protein ranging in length from about 7 amino acids to about 15 amino acids, which can form a complex with a MHC (e.g., HLA) molecule and such a complex can bind with a TCR specific for a WT-1 peptide:MHC (e.g., HLA) complex. Principles of antigen processing by antigen presenting cells (APC) (such as dendritic cells, macrophages, lymphocytes or other cell types), and of antigen presentation by APC to T cells, including major histocompatibility complex (MHC)-restricted presentation between immunocompatible (e.g., sharing at least one allelic form of an MHC gene that is relevant for antigen presentation) APC and T cells, are well established (see, e.g., Murphy, Janeway's Immunobiology (8$^{th}$ Ed.) 2011 Garland Science, NY; chapters 6, 9 and 16). For example, processed antigen peptides originating in the cytosol (e.g., tumor antigen, intracellular pathogen) are generally from about 7 amino acids to about 11 amino acids in length and will associate with class I MHC molecules, whereas peptides processed in the vesicular system (e.g., bacterial, viral) will vary in length from about 10 amino acids to about 25 amino acids and associate with class II MHC molecules. Since WT-1 is an internal host protein, WT-1 antigen peptides will be presented in the context of class I WIC. In particular embodiments, a WT-1 peptide is RMFPNAPYL (SEQ ID NO.:94), which is known to associate with human class I HLA (and, more specifically, associates with allele HLA-A*201).

A "linker" refers to an amino acid sequence that connects two proteins, polypeptides, peptides, domains, regions, or motifs and may provide a spacer function compatible with interaction of the two sub-binding domains so that the resulting polypeptide retains a specific binding affinity (e.g., scTCR) to a target molecule or retains signaling activity (e.g., TCR complex). In certain embodiments, a linker is comprised of about two to about 35 amino acids, for instance, or about four to about 20 amino acids or about eight to about 15 amino acids or about 15 to about 25 amino acids.

As used herein, "fusion protein" refers to a protein that, in a single chain, has at least two distinct domains or motifs, wherein the domains or motifs are not naturally found together in a protein. A polynucleotide encoding a fusion protein may be constructed using PCR, recombinantly engineered, or the like, or such fusion proteins can be synthesized. A fusion protein may further contain other components, such as a tag, a linker, or a transduction marker. In certain embodiments, a fusion protein expressed or produced by a host cell (e.g., an immune cell, such as, for example, a T cell) locates to the cell surface, where the fusion protein is anchored to the cell membrane (e.g., via a transmembrane component or domain) and comprises an extracellular component (e.g., capable of associating with a MEW molecule) and an intracellular component (e.g., containing a signaling domain, effector domain, co-stimulatory domain or portions or combinations thereof).

"Junction amino acids" or "junction amino acid residues" refer to one or more (e.g., about 2-10) amino acid residues between two adjacent motifs, regions or domains of a polypeptide, such as, for example, between a binding domain and an adjacent constant domain or between a TCR chain and an adjacent self-cleaving peptide. Junction amino acids may result from the construct design of a fusion protein (e.g., amino acid residues resulting from the use of a restriction enzyme site during the construction of a nucleic acid molecule encoding a fusion protein).

An "altered domain" or "altered protein" refers to a motif, region, domain, peptide, polypeptide, or protein with a sequence identity to a wild type motif, region, domain, peptide, polypeptide, or protein (e.g., a wild type TCRα chain, TCRβ chain, TCRα constant domain, TCRβ constant domain) of at least 85% (e.g., 85%, 86%, 87%, 88%, 89%, 90%, 91%, 92%, 93%, 94%, 95%, 96%, 97%, 98%, 99%, or 99.5%).

As used herein, "nucleic acid" or "nucleic acid molecule" or "polynucleotide" refers to any of deoxyribonucleic acid (DNA), ribonucleic acid (RNA), oligonucleotides, fragments generated, for example, by the polymerase chain reaction (PCR) or by in vitro translation, and fragments generated by any of ligation, scission, endonuclease action, or exonuclease action. In certain embodiments, the polynucleotides of the present disclosure are produced by PCR. Polynucleotides may be composed of monomers that are naturally occurring nucleotides (such as deoxyribonucleotides and ribonucleotides), analogs of naturally occurring nucleotides (e.g., α-enantiomeric forms of naturally-occurring nucleotides), or a combination of both. Modified nucleotides can have modifications in or replacement of sugar moieties, or pyrimidine or purine base moieties. Nucleic acid monomers can be linked by phosphodiester bonds or analogs of such linkages. Analogs of phosphodiester linkages include phosphorothioate, phosphorodithioate, phosphoroselenoate, phosphorodiselenoate, phosphoroanilothioate, phosphoranilidate, phosphoramidate, and the like. Polynucleotides can be either single stranded or double stranded.

The term "isolated" means that the material is removed from its original environment (e.g., the natural environment if it is naturally occurring). For example, a naturally occurring nucleic acid or polypeptide present in a living animal is not isolated, but the same nucleic acid or polypeptide, separated from some or all of the co-existing materials in the natural system, is isolated. Such nucleic acid could be part of a vector and/or such nucleic acid or polypeptide could be part of a composition (e.g., a cell lysate), and still be isolated in that such vector or composition is not part of the natural environment for the nucleic acid or polypeptide. The term "gene" means the segment of DNA involved in producing a polypeptide chain; it includes regions preceding and following the coding region "leader and trailer" as well as intervening sequences (introns) between individual coding segments (exons).

Any host cell, binding protein, polynucleotide, or vector of the present disclosure can be "isolated".

As used herein, the terms "recombinant", "engineered", and "modified" refer to a cell, microorganism, nucleic acid molecule, or vector that has been modified by introduction of an exogenous nucleic acid molecule, or refers to a cell or microorganism that has been altered such that expression of an endogenous nucleic acid molecule or gene is controlled, deregulated or constitutive, where such alterations or modifications may be introduced by genetic engineering. Genetic alterations may include, for example, modifications introducing nucleic acid molecules (which may include an expression control element, such as a promoter) encoding one or more proteins or enzymes, or other nucleic acid molecule additions, deletions, substitutions, or other functional disruption of or addition to a cell's genetic material. Exemplary modifications include those in coding regions or functional fragments thereof of heterologous or homologous polypeptides from a reference or parent molecule.

As used herein, "mutation" refers to a change in the sequence of a nucleic acid molecule or polypeptide molecule as compared to a reference or wild-type nucleic acid molecule or polypeptide molecule, respectively. A mutation can result in several different types of change in sequence, including substitution, insertion or deletion of nucleotide(s) or amino acid(s). In certain embodiments, a mutation is a substitution of one or three codons or amino acids, a deletion of one to about 5 codons or amino acids, or a combination thereof.

A "conservative substitution" is recognized in the art as a substitution of one amino acid for another amino acid that has similar properties. Exemplary conservative substitutions are well known in the art (see, e.g., WO 97/09433 at page 10; Lehninger, Biochemistry, $2^{nd}$ Edition; Worth Publishers, Inc. NY, NY, pp. 71-77, 1975; Lewin, Genes IV, Oxford University Press, NY and Cell Press, Cambridge, MA, p. 8, 1990). A variety of criteria known to persons skilled in the art indicate whether an amino acid that is substituted at a particular position in a peptide or polypeptide is conservative (or similar). For example, a similar amino acid or a conservative amino acid substitution is one in which an amino acid residue is replaced with an amino acid residue having a similar side chain. Similar amino acids may be included in the following categories: amino acids with basic side chains (e.g., lysine, arginine, histidine); amino acids with acidic side chains (e.g., aspartic acid, glutamic acid); amino acids with uncharged polar side chains (e.g., glycine, asparagine, glutamine, serine, threonine, tyrosine, cysteine, histidine); amino acids with nonpolar side chains (e.g., alanine, valine, leucine, isoleucine, proline, phenylalanine, methionine, tryptophan); amino acids with beta-branched side chains (e.g., threonine, valine, isoleucine), and amino acids with aromatic side chains (e.g., tyrosine, phenylalanine, tryptophan). Proline, which is considered more difficult to classify, shares properties with amino acids that have aliphatic side chains (e.g., leucine, valine, isoleucine, and alanine). In certain circumstances, substitution of glutamine for glutamic acid or asparagine for aspartic acid may be considered a similar substitution in that glutamine and asparagine are amide derivatives of glutamic acid and aspartic acid, respectively. As understood in the art "similarity" between two polypeptides is determined by comparing the amino acid sequence and conserved amino acid substitutes thereto of the polypeptide to the sequence of a second polypeptide (e.g., using GENEWORKS, Align, the BLAST algorithm, or other algorithms described herein and practiced in the art).

In certain embodiments, proteins (e.g., binding proteins) according to the present disclosure comprise a variant sequence as compared to a reference sequence (e.g., a variant TCR CDR as compared to a reference TCR CDR disclosed herein). Variant proteins, peptides, polypeptides, and amino acid sequences of the present disclosure can, in certain embodiments, comprise one or more conservative substitutions relative to a reference amino acid sequence. Variants of polynucleotides and polypeptides of this disclosure are also contemplated. Variant nucleic acid molecules or polypeptides are at least 70%, 75%, 80%, 85%, 90%, and are preferably at least 90%, 91%, 92%, 93%, 94%, 95%, 96%, 97%, 98%, 99%, or 99.9% identical to a defined or reference polynucleotide or polypeptide (respectively) as described herein, or that, for a polynucleotide, hybridize to a reference polynucleotide under stringent hybridization conditions of 0.015M sodium chloride, 0.0015M sodium citrate at about 65-68° C. or 0.015M sodium chloride, 0.0015M sodium citrate, and 50% formamide at about 42° C. Nucleic acid molecule variants retain the capacity to encode a binding protein or a binding domain thereof having a functionality described herein, such as specifically binding a target molecule. For additional details and explanation of stringency of hybridization reactions, see Ausubel, F. M. (1995), Current Protocols in Molecular Biology. John Wiley & Sons, Inc. Moreover, the person skilled in the art may follow the instructions given in the manual Boehringer Mannheim GmbH (1993) The DIG System Users Guide for Filter Hybridization, Boehringer Mannheim GmbH, Mannheim, Germany and in Liebl, W., Ehrmann, M., Ludwig, W., and Schleifer, K. H. (1991) International Journal of Systematic Bacteriology 41: 255-260 on how to identify DNA sequences by means of hybridization.

Variants can also refer to fragments (e.g., a portion resulting from truncation, cleavage, or the like) of a defined or reference sequence, and fragments can be of any length shorter than the length of the defined or reference sequence. As used herein, a "functional portion" or "functional fragment" refers to a polypeptide or polynucleotide that comprises only a domain, portion or fragment of a parent or reference compound, and the polypeptide or encoded polypeptide retains at least 50% activity associated with the domain, portion or fragment of the parent or reference compound, preferably at least 55%, 60%, 70%, 75%, 80%, 85%, 90%, 95%, 96%, 97%, 98%, 99%, 99.9%, or 100% level of activity of the parent polypeptide, or provides a biological benefit (e.g., effector function). A "functional portion" or "functional fragment" of a polypeptide or encoded polypeptide of this disclosure has "similar binding" or "similar activity" when the functional portion or fragment displays no more than a 50% reduction in performance in a selected assay as compared to the parent or reference polypeptide (preferably no more than 20% or 10%, or no more than a log difference as compared to the parent or reference with regard to affinity), such as an assay for measuring binding affinity or measuring effector function (e.g., cytokine release). In certain embodiments, a functional portion refers to a "signaling portion" of an effector molecule, effector domain, costimulatory molecule, or costimulatory domain.

In certain embodiments, a variant binding protein or a portion (e.g., binding domain) or fragment thereof can comprise one or more amino acid substitutions relative to a parent or reference binding protein or domain, wherein the one or more amino acid substitutions remove, change, or attenuate, a potential undesired feature or characteristic, if present in the parent or reference binding domain or protein; e.g., an amino acid sequence that is potentially immunogenic, or an amino acid sequence that may provide an undesired glycosylation site, an undesired deamidation site, an undesired oxidation site, an undesired isomerization site, or a reduction in thermodynamic stability, or that may result in mis-pairing or mis-folding in a binding protein (e.g., unpaired cysteine residues in close proximity). Amino acid sequences, patterns, and motifs that may provide for an undesired feature or characteristic are known (see, e.g., Seeliger et al., *mAbs* 7(3): 505-515 (2015)).

In certain embodiments, an amino acid substitution comprises a substitution to remove a somatic mutation, such as, for example, a reversion to a germline-encoded amino acid. For example, in certain embodiments, a variant of a reference CDR amino acid sequence, or of a TCR variable domain sequence or TCR constant region sequence, comprises a substitution to remove or attenuate a potential undesired feature or characteristic. It will be understood that such variants are selected so as not to compromise, or substantially compromise, a desired function (e.g., binding specificity and/or affinity for a WT-1 antigen:HLA complex).

The term "construct" refers to any polynucleotide that contains a recombinant nucleic acid. A construct may be present in a vector (e.g., a bacterial vector, a viral vector) or may be integrated into a genome. A "vector" is a nucleic acid molecule that is capable of transporting another nucleic acid. Vectors may be, for example, plasmids, cosmids, viruses, a RNA vector or a linear or circular DNA or RNA molecule that may include chromosomal, non-chromosomal, semi-synthetic or synthetic nucleic acids. Exemplary vectors are those capable of autonomous replication (episomal vector) or expression of nucleic acids to which they are linked (expression vectors).

Viral vectors include retrovirus, adenovirus, parvovirus (e.g., adeno-associated viruses), coronavirus, negative strand RNA viruses such as ortho-myxovirus (e.g., influenza virus), rhabdovirus (e.g., rabies and vesicular stomatitis virus), paramyxovirus (e.g., measles and Sendai), positive strand RNA viruses such as picornavirus and alphavirus, and double-stranded DNA viruses including adenovirus, herpesvirus (e.g., Herpes Simplex virus types 1 and 2, Epstein-Barr virus, cytomegalovirus), and poxvirus (e.g., vaccinia, fowlpox and canarypox). Other viruses include Norwalk virus, togavirus, flavivirus, reoviruses, papovavirus, hepadnavirus, and hepatitis virus, for example. Examples of retroviruses include avian leukosis-sarcoma, mammalian C-type, B-type viruses, D type viruses, HTLV-BLV group, lentivirus, spumavirus (Coffin, J. M., Retroviridae: The viruses and their replication, In Fundamental Virology, Third Edition, B. N. Fields et al., Eds., Lippincott-Raven Publishers, Philadelphia, 1996).

"Lentiviral vector," as used herein, means HIV-based lentiviral vectors for gene delivery, which can be integrative or non-integrative, have relatively large packaging capacity, and can transduce a range of different cell types. Lentiviral vectors are usually generated following transient transfection of three (packaging, envelope and transfer) or more plasmids into producer cells. Like HIV, lentiviral vectors enter the target cell through the interaction of viral surface glycoproteins with receptors on the cell surface. On entry, the viral RNA undergoes reverse transcription, which is mediated by the viral reverse transcriptase complex. The product of reverse transcription is a double-stranded linear viral DNA, which is the substrate for viral integration into the DNA of infected cells.

The term "operably-linked" refers to the association of two or more nucleic acid molecules on a single nucleic acid fragment so that the function of one is affected by the other. For example, a promoter is operably-linked with a coding sequence when it is capable of affecting the expression of that coding sequence (i.e., the coding sequence is under the transcriptional control of the promoter). "Unlinked" means that the associated genetic elements are not closely associated with one another and the function of one does not affect the other.

As used herein, "expression vector" refers to a DNA construct containing a nucleic acid molecule that is operably-linked to a suitable control sequence capable of effecting the expression of the nucleic acid molecule in a suitable host. Such control sequences include a promoter to effect transcription, an optional operator sequence to control such transcription, a sequence encoding suitable mRNA ribosome binding sites, and sequences which control termination of transcription and translation. The vector may be a plasmid, a phage particle, a virus, or simply a potential genomic insert. Once transformed into a suitable host, the vector may replicate and function independently of the host genome, or may, in some instances, integrate into the genome itself. In the present specification, "plasmid," "expression plasmid," "virus" and "vector" are often used interchangeably.

The term "expression", as used herein, refers to the process by which a polypeptide is produced based on the nucleic acid sequence of a gene. The process includes both transcription and translation.

The term "introduced" in the context of inserting a nucleic acid sequence into a cell, means "transfection", or "transformation" or "transduction" and includes reference to the incorporation of a nucleic acid sequence into a eukaryotic or prokaryotic cell wherein the nucleic acid molecule may be incorporated into the genome of a cell (e.g., chromosome, plasmid, plastid, or mitochondrial DNA), converted into an autonomous replicon, or transiently expressed (e.g., transfected mRNA).

As used herein, "heterologous" or "exogenous" nucleic acid molecule, construct or sequence refers to a nucleic acid molecule or portion of a nucleic acid molecule that is not native to a host cell, but may be homologous to a nucleic acid molecule or portion of a nucleic acid molecule from the host cell. The source of the heterologous or exogenous nucleic acid molecule, construct or sequence may be from a different genus or species. In certain embodiments, a heterologous or exogenous nucleic acid molecule is added (i.e., not endogenous or native) to a host cell or host genome by, for example, conjugation, transformation, transfection, electroporation, or the like, wherein the added molecule may integrate into the host genome or exist as extra-chromosomal genetic material (e.g., as a plasmid or other form of self-replicating vector), and may be present in multiple copies. In addition, "heterologous" refers to a non-native enzyme, protein or other activity encoded by an exogenous nucleic acid molecule introduced into the host cell, even if the host cell encodes a homologous protein or activity. Moreover, a cell comprising a "modification" or a "heterologous" polynucleotide or binding protein includes progeny of that cell, regardless of whether the progeny were themselves transduced, transfected, or otherwise manipulated or changed.

As described herein, more than one heterologous or exogenous nucleic acid molecule can be introduced into a host cell as separate nucleic acid molecules, as a plurality of individually controlled genes, as a polycistronic nucleic acid molecule, as a single nucleic acid molecule encoding a fusion protein, or any combination thereof. For example, as disclosed herein, a host cell can be modified to express two or more heterologous or exogenous nucleic acid molecules encoding desired TCR specific for a WT-1 antigen peptide (e.g., TCRα and TCRβ). When two or more exogenous nucleic acid molecules are introduced into a host cell, it is understood that the two more exogenous nucleic acid molecules can be introduced as a single nucleic acid molecule (e.g., on a single vector), on separate vectors, integrated into the host chromosome at a single site or multiple sites. The number of referenced heterologous nucleic acid molecules or protein activities refers to the number of encoding nucleic acid molecules or the number of protein activities, not the number of separate nucleic acid molecules introduced into a host cell. Exogenous nucleic acid molecules (e.g., encoding a binding protein or a CD8 co-receptor of the present disclosure) can also be introduced into the genome of a host cell by gene-editing techniques, e.g., using a CRISPR-Cas system, a meganuclease, or the like.

As used herein, the term "endogenous" or "native" refers to a gene, protein, or activity that is normally present in a host cell. Moreover, a gene, protein or activity that is mutated, overexpressed, shuffled, duplicated or otherwise altered as compared to a parent gene, protein or activity is still considered to be endogenous or native to that particular host cell. For example, an endogenous control sequence from a first gene (e.g., promoter, translational attenuation sequences) may be used to alter or regulate expression of a second native gene or nucleic acid molecule, wherein the expression or regulation of the second native gene or nucleic acid molecule differs from normal expression or regulation in a parent cell.

The term "homologous" or "homolog" refers to a molecule or activity found in or derived from a host cell, species or strain. For example, a heterologous or exogenous nucleic acid molecule may be homologous to a native host cell gene, and may optionally have an altered expression level, a different sequence, an altered activity, or any combination thereof.

"Sequence identity," as used herein, refers to the percentage of amino acid residues in one sequence that are identical with the amino acid residues in another reference polypeptide sequence after aligning the sequences and introducing gaps, if necessary, to achieve the maximum percent sequence identity, and not considering any conservative substitutions as part of the sequence identity. The percentage sequence identity values can be generated using the NCBI BLAST2.0 software as defined by Altschul et al. (1997) "Gapped BLAST and PSI-BLAST: a new generation of protein database search programs", Nucleic Acids Res. 25:3389-3402, with the parameters set to default values.

As understood in the art, "similarity" between two polypeptides is determined by comparing the amino acid sequence and conserved amino acid substitutes thereto of the polypeptide to the sequence of a second polypeptide (e.g., using GENEWORKS™ Align, Clustal™, the BLAST algorithm, or the like).

As used herein, "hyperproliferative disorder" refers to excessive growth or proliferation as compared to a normal or undiseased cell. Exemplary hyperproliferative disorders include tumors, cancers, neoplastic tissue, carcinoma, pre-malignant cells, as well as non-neoplastic or non-malignant hyperproliferative disorders (e.g., adenoma, fibroma, lipoma, leiomyoma, hemangioma, restenosis, as well as autoimmune diseases such as rheumatoid arthritis, osteoarthritis, psoriasis, inflammatory bowel disease, or the like). Certain diseases that involve abnormal or excessive growth that occurs more slowly than in the context of a hyperproliferative disease can be referred to as "proliferative diseases", and include certain tumors, cancers, neoplastic tissue, carcinoma, sarcoma, malignant cells, pre malignant cells, as well as non-neoplastic or non-malignant disorders. Binding Proteins Specific for WT-1 Antigen Peptides In certain embodiments, the instant disclosure provides a binding protein, comprising (a) a T cell receptor (TCR) a chain variable (Vα) domain comprising a CDR3 amino acid sequence (CDR3a) according to any one of SEQ ID NOs: 19, 22, 25, or 28, or a variant thereof, and a TCR Vβ domain; (b) a TCR Vβ domain comprising a CDR3 amino acid sequence (CDR3β) according to any one of SEQ ID NOs: 31, 34, 37, or 40, or a variant thereof, and a TCR Vα domain; or (c) a TCR Vα domain of (a), and a TCR Vβ domain of (b), wherein the binding protein is capable of binding to a RMFPNAPYL (SEQ ID NO.: 94):human leukocyte antigen (HLA) complex wherein, optionally, the HLA comprises HLA-A*0201.

In certain embodiments, the binding protein is capable of binding to a RMFPNAPYL (SEQ ID NO.: 94):HLA complex with an IFNγ production $pEC_{50}$ of 4.0, 4.5, 5.0, 5.1, 5.2, 5.3, 5.4, 5.5, 5.6, 5.7, 5.8, 5.9, 6.0, 6.1, 6.2, 6.3, 6.4, 6.5, or higher.

In certain embodiments, the Vβ domain of (a), (b), or (c) comprises or consists of an amino acid sequence having at least 90% (e.g., 90%, 91%, 92%, 93%, 94%, 95%, 96%, 97%, 98%, or 99%) identity to the amino acid sequence set forth in any one of SEQ ID NOs: 5-8 or 13-16, and/or the Vα domain of (a), (b), or (c) comprises or consists of any amino acid sequence having at least 90% identity to the amino acid sequence set forth in any one of SEQ ID NOs: 1-4 or 9-12.

In certain embodiments, the CDR3β comprises or consists of the amino acid sequence set forth in SEQ ID NO: 31 and the CDR3a comprises or consists of the amino acid sequence set forth in SEQ ID NO: 19. In certain embodiments, the CDR3β comprises or consists of the amino acid sequence set forth in SEQ ID NO: 34, and the CDR3a comprises or consists of the amino acid sequence set forth in SEQ ID NO: 22. In certain embodiments, the CDR3β comprises or consists of the amino acid sequence set forth in SEQ ID NO: 37, and the CDR3a comprises or consists of the amino acid sequence set forth in SEQ ID NO: 25. In certain embodiments, the CDR3β comprises or consists of the amino acid sequence set forth in SEQ ID NO: 40, and the CDR3a comprises or consists of the amino acid sequence set forth in SEQ ID NO: 28.

In certain embodiments, the binding protein comprises a Vα domain comprising a CDR1α, a CDR2α, and a CDR3α, and a Vβ domain comprising a CDR1β, a CDR2β, and a CDR3β.

In certain embodiments, the Vβ domain comprises the CDR1β amino acid sequence of any one of SEQ ID NOs: 29, 32, 35, or 38, or a variant thereof, and/or the CDR2β amino acid sequence of any one of SEQ ID NOs: 30, 33, 36, or 39, or a variant thereof. In certain embodiments, the Vα domain comprises the CDR1a amino acid sequence of any one of SEQ ID NOs: 17, 20, 23, or 26, or a variant thereof, and/or the CDR2α amino acid sequence of any one of SEQ ID NOs: 18, 21, 24, or 27, or a variant thereof.

In particular embodiments, the TCR Vα and Vβ domains comprise, respectively, CDR1α, CDR2α, CDR3α, and CDR1β, CDR2β, CDR3β and amino acid sequences of: (i) SEQ ID NOs.:26-28 and 38-40, respectively; (ii) SEQ ID NOs.:23, 27, 28, and 38-40, respectively; (iii) SEQ ID NOs.: 17-19 and 29-31, respectively; (iv) SEQ ID NOs.: 20-22 and 32-34, respectively; or (v) SEQ ID NOs.: 23-25 and 35-37, respectively.

In any of the presently disclosed embodiments, the binding protein binds to a WT-1 peptide:HLA-A*201 complex. In any of the presently disclosed embodiments, the binding protein is capable of binding to a WT-1 peptide:HLA complex on a cell surface independent of CD8 or in the absence of CD8.

In certain embodiments, a binding protein as described herein includes variant polypeptide species that have one or more amino acid substitutions, insertions, or deletions in the amino acid sequence relative to the sequences of SEQ ID NOS:1-61 as presented herein. In certain embodiments, a substitution is or comprises a conservative substitution. Conservative substitutions of amino acids are well known and may occur naturally or may be introduced when the binding protein is recombinantly produced. Amino acid substitutions, deletions, and additions may be introduced into a protein using mutagenesis methods known in the art (see, e.g., Sambrook et al., *Molecular Cloning: A Laboratory Manual,* 3d ed., Cold Spring Harbor Laboratory Press, N Y, 2001). Oligonucleotide-directed site-specific (or segment specific) mutagenesis procedures may be employed to provide an altered polynucleotide that has particular codons altered according to the substitution, deletion, or insertion desired. Alternatively, random or saturation mutagenesis techniques, such as alanine scanning mutagenesis, error prone polymerase chain reaction mutagenesis, and oligonucleotide-directed mutagenesis may be used to prepare immunogen polypeptide variants (see, e.g., Sambrook et al., supra).

In certain embodiments, species (or variants) of a particular binding protein specific for WT-1 may include a protein that has at least 85%, 86%, 87%, 88%, 89%, 90%, 91%, 92%, 93%, 94%, 95%, 96%, 97%, 98%, or 99% amino acid sequence identity to any of the exemplary amino acid sequences disclosed herein (e.g., SEQ ID NOs.:1-61).

In certain embodiments, a binding protein is provided that comprises a Vβ domain having at least 90% (e.g., 90%, 91%, 92%, 93%, 94%, 95%, 96%, 97%, 98%, 99%, or 100%) sequence identity to an amino acid sequence as set forth in any one of SEQ ID NOs.: 1-4 or 9-12, and/or a Vα domain having at least 90% sequence identity to an amino acid sequence as set forth in any one of SEQ ID NOs.: 5-8 or 13-16, wherein the binding protein is capable of binding to a RMFPNAPYL (SEQ ID NO:94):HLA complex. In further embodiments, any one or more of the β or α CDR amino acid sequences as provided herein can be present in the Vβ domain and/or the Vα domain, respectively.

In certain embodiments, the binding protein comprises a Vβ domain comprising or consisting of an amino acid sequence having at least 90% identity to any one of SEQ ID NOs.: 5-8 or 13-16, and/or a Vα domain comprising or consisting of an amino acid sequence having at least 90% identity to any one of SEQ ID NOs.: 1-4 or 9-12, provided that (a) at least three or four of the CDRs have no mutations, (b) the CDRs that do have mutations have only up to two amino acid substitutions, up to a contiguous five amino acid deletion, or a combination thereof, and (c) the binding protein retains its ability to bind to a RMFPNAPYL (SEQ ID NO:94):HLA complex, optionally with an IFNγ production $pEC_{50}$ of 4.0, 4.5, 5.0, 5.1, 5.2, 5.3, 5.4, 5.5, 5.6, 5.7, 5.8, 5.9, 6.0, 6.1, 6.2, 6.3, 6.4, 6.5, or higher.

In certain embodiments, a binding protein comprises a TCR variable domain comprising an amino acid sequence encoded by a human TCR V, D, and/or J allele. By way of background, during lymphocyte development, Vα exons are assembled from different variable and joining gene segments (V-J), and Vβ exons are assembled from different variable, diversity, and joining gene segments (V-D-J). The TCRα chromosomal locus has 70-80 variable gene segments and 61 joining gene segments. The TCRβ chromosomal locus has 52 variable gene segments, and two separate clusters of each containing a single diversity gene segment, together with six or seven joining gene segments. Functional Vα and Vβ gene exons are generated by the recombination of a variable gene segment with a joining gene segment for Vα, and a variable gene segment with a diversity gene segment and a joining gene segment for Vβ. Nucleotide and amino acid sequences according to TCR gene segments of various alleles are known in the art and are can be found on the ImMunoGeneTics website; for example, at imgt.org/IMGTrepertoire/LocusGenes/listIG_TR/TR/human/Hu_TRgroup.html.

It will be understood that while a polynucleotide encoding a binding protein can comprise a same nucleotide sequence according to a TCR gene segment as disclosed herein, any nucleotide sequence that encodes the amino acid sequence of the gene segment may be used within the context of the present disclosure.

In certain embodiments, the binding protein comprises a Vβ domain comprising (i) an amino acid sequence according to a TRBJ02-03 gene segment; and/or (ii) an amino acid sequence according to a TRBV06-05 gene segment, an amino acid sequence according to a TRBV07-09 gene segment, or an amino acid sequence according to a TRBV20-01 gene segment. In certain embodiments, the binding protein comprises a Vα domain comprising (i) an amino acid sequence according to a TRAJ43 gene segment; and/or (ii) an amino acid sequence according to a TRAV20-02 gene segment; an amino acid sequence encoded by a TRAV38DV08 gene segment; or an amino acid sequence according to a TRAV38-01 gene segment. In related embodiments, the Vβ domain comprises an amino acid sequence according to a TRBJ02-03 gene segment and the Vα domain comprises an amino acid sequence according to a TRAJ43 gene segment; the Vβ domain comprises an amino acid sequence according to TRBV06-05 gene segment and the Vα domain comprises an amino acid sequence according to a TRAV20-02 gene segment; the Vβ domain comprises an amino acid sequence according to TRBV07-09 gene segment and the Vα domain comprises an amino acid sequence according to a TRAV38DV08 gene segment; or the Vβ domain comprises an amino acid sequence according to a TRBV20-01 gene segment and the Vα domain comprises an amino acid sequence according to a TRAV38-01 gene segment.

In the aforementioned embodiments, the amino acid sequence according to a TRA or TRB gene segment is 5, 6, 7, 8, 9, 10, 15, 20, 25, 30, 35, 40, 45, 50, 55, 60, 65, 70, 75, 80, 85, 90, 95, 100, 105, 110, 115, 120, 125, 130, 135, 140, 145, or 150 amino acids in length, and including any length of amino acids between these exemplary lengths (e.g., 11, 12, 13, 14 amino acids, or the like).

In certain embodiments, a binding protein is provided that is capable of binding to a RMFPNAPYL (SEQ ID NO.:94): HLA complex, wherein the binding protein comprises a TCR Vα domain and a TCR Vβ domain. In certain embodiments, the Vα domain comprises or consists of the amino acid sequence set forth in SEQ ID NO.: 1 or 9 and the Vβ domain comprises or consists of the amino acid sequence set forth in SEQ ID NO.: 5 or 13. In certain embodiments, the Vα domain comprises or consists of the amino acid sequence set forth in SEQ ID NO.: 2 or 10 and the Vβ domain comprises or consists of the amino acid sequence set forth in SEQ ID NO.: 6 or 14. In certain embodiments, the Vα domain comprises or consists of the amino acid sequence set forth in SEQ ID NO.: 3 or 11 and the Vβ domain comprises or consists of the amino acid sequence set forth in SEQ ID NO.: 7 or 15. In certain embodiments, the Vα domain comprises or consists of the amino acid sequence set forth in SEQ ID NO.: 4 or 12 and the Vβ domain comprises or consists of the amino acid sequence set forth in SEQ ID NO.: 8 or 16.

In any of the presently disclosed embodiments, a binding protein can comprise an α-chain constant domain (Cα) or a fragment thereof and/or a β-chain constant domain (Cβ) or a fragment or portion thereof. In certain embodiments, the Cα comprises or consists of an amino acid sequence having at least 90% (e.g., 90%, 91%, 92%, 93%, 94%, 95%, 96%, 97%, 98%, 99% or 100%) sequence identity to any one of SEQ ID NOs.:41-44. In certain embodiments, the Cβ comprises or consists of an amino acid sequence having at least 90% sequence identity to SEQ ID NO:45.

In further embodiments, a TCR Cβ comprises a cysteine amino acid in place of a native serine at amino acid position 57 (e.g., GV(S→C)TD) and a TCR Cα comprises a cysteine amino acid in place of a native threonine at amino acid position 48 (e.g., DK(T→C)VL; see, e.g., Cohen et al., *Cancer Res.* 67(8):3898-3903 (2007)).

In certain embodiments, the binding protein is a T cell receptor (TCR), a chimeric antigen receptor or an antigen-binding fragment of a TCR, any of which can be chimeric, humanized or human. In further embodiments, an antigen-binding fragment of the TCR comprises a single chain TCR (scTCR) or a chimeric antigen receptor (CAR).

"Chimeric antigen receptor" (CAR) refers to a fusion protein that is engineered to contain two or more naturally occurring amino acid sequences linked together in a way that does not occur naturally or does not occur naturally in a host cell, which fusion protein can function as a receptor when present on a surface of a cell. CARs can include an extracellular portion comprising an antigen-binding domain (e.g., obtained or derived from an immunoglobulin or immunoglobulin-like molecule, such as a TCR binding domain derived or obtained from a TCR specific for a cancer antigen, a scFv derived or obtained from an antibody, or an antigen-binding domain derived or obtained from a killer immunoreceptor from an NK cell) linked to a transmembrane domain and one or more intracellular signaling domains (optionally containing co-stimulatory domain(s)) (see, e.g., Sadelain et al., *Cancer Discov.,* 3(4):388 (2013); see also Harris and Kranz, *Trends Pharmacol. Sci.,* 37(3): 220 (2016), Stone et al., *Cancer Immunol. Immunother.,* 63(11):1163 (2014), and Walseng et al., *Scientific Reports* 7:10713 (2017), which CAR constructs and methods of making the same are incorporated by reference herein). CARs of the present disclosure that specifically bind to a WT-1 antigen (e.g., in the context of a peptide:HLA complex) comprise a TCR Vα domain and a Vβ domain, or a functional fragment or portion thereof.

In certain embodiments, a WT-1 specific binding protein is a TCR. In related embodiments, the binding protein (a) comprises a TCR α-chain having at least 90% (e.g., 90%, 91%, 92%, 93%, 94%, 95%, 96%, 97%, 98%, 99% or 100%) identity to, comprising, or consisting of the amino acid sequence as set forth in SEQ ID NO: 50 or 46, and a TCR β-chain having at least 90% identity to, comprising, or consisting of the amino acid sequence set forth in SEQ ID NO: 58 or 54; (b) comprises a TCR α-chain having at least 90% identity to, comprising, or consisting of the amino acid sequence set forth in SEQ ID NO: 51 or 47, and a TCR β-chain having at least 90% identity to, comprising, or consisting of the amino acid sequence set forth in SEQ ID NO: 59 or 55; (c) comprises a TCR α-chain having at least 90% identity to, comprising, or consisting of the amino acid sequence set forth in SEQ ID NO: 52 or 48, and a TCR β-chain having at least 90% identity to, comprising, or consisting of the amino acid sequence set forth in SEQ ID NO: 60 or 56; or (d) comprises a TCR α-chain having at least 90% identity to, comprising, or consisting of the amino acid sequence set forth in SEQ ID NO:53 or 49, and a TCR β-chain having at least 90% identity to, comprising, or consisting of the amino acid sequence set forth in SEQ ID NO: 61 or 57.

In certain embodiments, the binding protein comprises a fusion protein comprising (i) an extracellular component comprising a binding domain that comprises a T cell receptor (TCR) α chain variable (Vα) domain and a T cell receptor (TCR) β chain variable (Vβ) domain, wherein the Vα domain comprises the CDR3 amino acid sequence (CDR3α) according to any one of SEQ ID NOs: 19, 22, 25, or 28, or a variant thereof, and the TCR Vβ domain comprises the CDR3 amino acid sequence (CDR3β) according to any one of SEQ ID NOs: 31, 34, 37, or 40, or a variant thereof; (ii) an intracellular component; and (iii) a transmembrane component disposed between the extracellular component and the intracellular component. In certain embodiments, the fusion protein is a CAR.

In certain embodiments, the binding protein comprises a fusion protein comprising (i) an extracellular component comprising a binding domain that specifically binds to a RMFPNAPYL (SEQ ID NO:94) peptide:HLA complex, wherein the binding domain comprises a T cell receptor (TCR) a chain variable (Vα) domain and a T cell receptor (TCR) β chain variable (Vβ) domain, wherein the Vα domain comprises or consists of an amino acid sequence having at least 90% identity to any one of SEQ ID NOs: 1, 2, 3, 4, 9, 10, 11, or 12, or a variant thereof, and the Vβ domain comprises or consists of an amino acid sequence having at least 90% identity to any one of SEQ ID NOs: 5, 6, 7, 8, 13, 14, 15, or 16, or a variant thereof, optionally provided that: (a) at least three or four of the CDRs have no mutations, (b) the CDRs that do have mutations have only up to two amino acid substitutions, up to a contiguous five amino acid deletion, or a combination thereof; and (c) the fusion protein retains its ability to bind to a RMFPNAPYL (SEQ ID NO:94):HLA complex; (ii) an intracellular component; and (iii) a transmembrane component disposed between the extracellular component and the intracellular component.

It will be understood that any of the presently disclosed binding domains, including the exemplary CDR and variable domain sequences and variants thereof, can be comprised in a fusion protein according to the present disclosure.

In any of the embodiments described herein, an encoded polypeptide of this disclosure can comprise a "signal peptide" (also known as a leader sequence, leader peptide, or transit peptide). Signal peptides target newly synthesized polypeptides to their appropriate location inside or outside the cell. Amino acid sequences of exemplary proteins or polypeptides of the present disclosure that comprise a signal peptide are provided in, for example, SEQ ID NOs.:1-8, 46-49, and 54-57. A signal peptide may be removed from the polypeptide during or once localization or secretion is completed. Polypeptides that have a signal peptide are referred to herein as a "pre-protein" and polypeptides having their signal peptide removed are referred to herein as "mature" proteins or polypeptides. In any of the herein disclosed embodiments, a binding protein or fusion protein comprises, or is, a mature protein, or is or comprises a pre-protein. Amino acid sequences of exemplary mature proteins or polypeptides of the present disclosure are provided in SEQ ID NOs.:9-16, 50-53, and 58-61.

In certain embodiments, a binding protein of the present disclosure comprises one or more junction amino acids.

In certain embodiments, a binding protein comprises a linker. In certain embodiments, a linker is comprised of about two to about 35 amino acids, for instance, or about four to about 20 amino acids or about eight to about 15 amino acids or about 15 to about 25 amino acids. Exemplary linkers include glycine-serine linkers (e.g., SEQ ID NOs.:95 and 96).

In certain embodiments, there is provided a composition comprising a WT-specific binding protein according to any one of the aforementioned embodiments and a pharmaceutically acceptable carrier, diluent, or excipient.

In certain embodiments, a WT-1-specific binding protein is provided in soluble form (see, e.g., Walseng et al., PLoS One doi:10.1371/journal.pone.0119559 (2015)), and can optionally be conjugated to a cytotoxic agent and/or a detectable agent. Methods useful for isolating and purifying recombinantly produced soluble TCR, by way of example, may include obtaining supernatants from suitable host cell/vector systems that secrete the recombinant soluble TCR into culture media and then concentrating the media using a commercially available filter. Following concentration, the concentrate may be applied to a single suitable purification matrix or to a series of suitable matrices, such as an affinity matrix or an ion exchange resin. One or more reverse phase HPLC steps may be employed to further purify a recombinant polypeptide. These purification methods may also be employed when isolating an immunogen from its natural environment. Methods for large scale production of one or more of the isolated/recombinant soluble TCR described herein include batch cell culture, which is monitored and controlled to maintain appropriate culture conditions. Purification of the soluble TCR may be performed according to methods described herein and known in the art and that comport with laws and guidelines of domestic and foreign regulatory agencies.

In certain embodiments, nucleic acid molecules encoding a binding protein specific for WT-1 are used to transfect/transduce a host cell (e.g., T cells) for use in adoptive transfer therapy. Advances in TCR sequencing have been described (e.g., Robins et al., 2009 *Blood* 114:4099; Robins et al., 2010 *Sci. Translat. Med.* 2:47ra64, PMID: 20811043; Robins et al. 2011 (September 10)*J. Imm. Meth. Epub ahead of print, PMID:* 21945395; Warren et al., 2011 *Genome Res.* 21:790) and may be employed in the course of practicing the embodiments according to the present disclosure. Similarly, methods for transfecting/transducing T-cells with desired nucleic acids have been described (e.g., US 2004/0087025) as have adoptive transfer procedures using T-cells of desired antigen-specificity (e.g., Schmitt et al., *Hum. Gen.* 20:1240, 2009; Dossett et al., Mol. Ther. 17:742, 2009; Till et al., *Blood* 112:2261, 2008; Wang et al., *Hum. Gene Ther.* 18:712, 2007; Kuball et al., *Blood* 109:2331, 2007; US 2011/0243972; US2011/0189141; Leen et al., *Ann. Rev. Immunol.* 25:243, 2007), such that adaptation of these methodologies to the presently disclosed embodiments is contemplated, based on the teachings herein, including those directed to enhanced affinity TCRs specific for WT-1 peptide antigen RMFPNAPYL (SEQ ID NO.:94) complexed with an HLA.

In certain embodiments, WT-1-specific binding proteins or domains as described herein, may expressed by a host T cell and can be functionally characterized according to any of a large number of art accepted methodologies for assaying T cell activity, including determination of T cell binding, activation or induction and also including determination of T cell responses that are antigen-specific. In certain embodiments, the binding protein is capable of promoting an antigen-specific T cell response against human WT-1 in a class I HLA-restricted manner. In further embodiments, the class I HLA-restricted response is transporter-associated with antigen processing (TAP)-independent. In certain embodiments, the antigen-specific T cell response comprises at least one of a CD4$^+$ helper T lymphocyte (Th) response and a CD8$^+$ cytotoxic T lymphocyte (CTL) response. In related embodiments, the CTL response is directed against a WT-1-overexpressing cell. Further examples of methodologies for assaying T cell activity include determination of T cell proliferation, T cell cytokine release, antigen-specific T cell stimulation, MHC restricted T cell stimulation, CTL activity (e.g., by detecting $^{51}$Cr release from pre-loaded target cells), changes in T cell phenotypic marker expression, and other measures of T-cell functions. Procedures for performing these and similar assays are may be found, for example, in Lefkovits (*Immunology Methods Manual: The Comprehensive Sourcebook of Techniques,* 1998). See also *Current Protocols in Immunology*; Weir, *Handbook of Experimental Immunology*, Blackwell Scientific, Boston, MA (1986); Mishell and Shigii (eds.) *Selected Methods in Cellular Immunology*, Freeman Publishing, San Francisco, CA (1979); Green and Reed, *Science* 281:1309 (1998) and references cited therein).

"MHC-peptide tetramer staining" refers to an assay used to detect antigen-specific T cells, which features a tetramer of MHC molecules, each comprising an identical peptide having an amino acid sequence that is cognate (e.g., identical or related to) at least one antigen (e.g., WT-1), wherein the complex is capable of binding T cell receptors specific for the cognate antigen. Each of the MHC molecules may be tagged with a biotin molecule. Biotinylated MHC/peptides are tetramerized by the addition of streptavidin, which can be fluorescently labeled. The tetramer may be detected by flow cytometry via the fluorescent label. In certain embodiments, an MHC-peptide tetramer assay is used to detect or select enhanced affinity TCRs of the instant disclosure.

Levels of cytokines may be determined according to methods described herein and practiced in the art, including for example, ELISA, ELISPOT, intracellular cytokine staining, and flow cytometry and combinations thereof (e.g., intracellular cytokine staining and flow cytometry). Immune cell proliferation and clonal expansion resulting from an antigen-specific elicitation or stimulation of an immune response may be determined by isolating lymphocytes, such as circulating lymphocytes in samples of peripheral blood cells or cells from lymph nodes, stimulating the cells with antigen, and measuring cytokine production, cell proliferation and/or cell viability, such as by incorporation of tritiated thymidine or non-radioactive assays, such as MTT assays and the like. The effect of an immunogen described herein on the balance between a Th1 immune response and a Th2 immune response may be examined, for example, by determining levels of Th1 cytokines, such as IFN-γ, IL-12, IL-2, and TNF-0, and Type 2 cytokines, such as IL-4, IL-5, IL-9, IL-10, and IL-13.

Polynucleotides and Vectors

Also provided are polynucleotides (e.g., isolated polynucleotides) that encode a binding protein or a fragment or portion thereof according to the present disclosure. Isolated or recombinant polynucleotides encoding binding proteins specific for WT-1 as described herein may be produced and prepared according to various methods and techniques of the molecular biology or polypeptide purification arts.

In certain embodiments, a polynucleotide is codon optimized for efficient expression in a target host cell. Codon optimization can be performed using known techniques and tools, e.g., using the GenScript® OptimumGene™ tool; GeneArt® GeneOptimizer™ (Sigma), or the like. Codon-optimized sequences include sequences that are partially codon-optimized (i.e., at least one codon is optimized for expression in the host cell) and those that are fully codon-optimized. Codon optimization for expression in certain immune host cells is disclosed in, for example, Scholten et al., *Clin. Immunol.* 119:135, 2006.

As one of skill in the art will recognize, a polynucleotide may refer to a single- or a double-stranded DNA, cDNA or RNA in any form, and may include a positive and a negative strand of the nucleic acid which complement each other, including anti-sense DNA, cDNA and RNA. Also included are siRNA, microRNA, RNA-DNA hybrids, ribozymes, and other various naturally occurring or synthetic forms of DNA or RNA.

In some embodiments, a polynucleotide encoding a binding protein of the present disclosure comprises a polynucleotide having at least 75% identity (e.g., 75%, 80%, 81%, 82%, 83%, 84%, 85%, 86%, 87%, 88%, 89%, 90%, 91%, 92%, 93%, 94%, 95%, 96%, 97%, 98%, 99%, or 100%) to the polynucleotide sequence set forth in any one of SEQ ID NOs:62-81.

In certain embodiments, the polynucleotide encoding a binding protein comprises (i) a TCRβ chain-encoding polynucleotide having at least 75% identity to the polynucleotide sequence set forth in SEQ ID NO: 74, and a TCRα chain-encoding polynucleotide having at least 75% identity to the polynucleotide sequence set forth in SEQ ID NO: 66; (ii) TCRβ chain-encoding a polynucleotide having at least 75% identity to the polynucleotide sequence set forth in SEQ ID NO: 75, and a TCRα chain-encoding polynucleotide having at least 75% identity to the polynucleotide sequence set forth in SEQ ID NO: 67; (iii) a TCRβ chain-encoding polynucleotide having at least 75% identity to the polynucleotide sequence set forth in SEQ ID NO: 76, and a TCRα chain-encoding polynucleotide having at least 75% identity to the polynucleotide sequence set forth in SEQ ID NO: 68; or (iv) a TCRβ chain-encoding polynucleotide having at least 75% identity to the polynucleotide sequence set forth in SEQ ID NO: 77, and a TCRα chain-encoding polynucleotide having at least 75% identity to the polynucleotide sequence set forth in SEQ ID NO: 69.

In some embodiments, a single polynucleotide encodes a binding protein as described herein, or, alternatively, the binding protein may be encoded by more than one polynucleotide. In other words, components or portions of a binding protein may be encoded by two or more polynucleotides, which may be contained on a single nucleic acid molecule or may be contained on two or more nucleic acid molecules.

In certain embodiments, a polynucleotide encoding two or more components or portions of a binding protein of the present disclosure comprises the two or more coding sequences operatively associated in a single open reading frame. Such an arrangement can advantageously allow coordinated expression of desired gene products, such as, for example, contemporaneous expression of alpha- and beta-chains of a TCR, such that they are produced in about a 1:1 ratio. In certain embodiments, two or more substituent gene products of a binding protein of this disclosure, such as a TCR (e.g., alpha- and beta-chains) or CAR, are expressed as separate molecules and associate post-translationally. In further embodiments, two or more substituent gene products of a binding protein of this disclosure are expressed as a single polypeptide with the parts separated by a cleavable or removable segment. For instance, self-cleaving peptides useful for expression of separable polypeptides encoded by a single polynucleotide or vector are known in the art and include, for example, a Porcine teschovirus-1 2A (P2A-1) peptide, a Porcine teschovirus-2 2A (P2A-2) peptide, a Thosea asigna virus 2A (T2A) peptide, an Equine rhinitis A virus (ERAV) 2A (E2A) peptide, and a Foot-and-Mouth disease virus 2A (F2A) peptide. Exemplary nucleotide and amino acid sequences of self-cleaving peptides are provided in SEQ ID NOs: 84-93. In certain embodiments, the polynucleotide encoding a self-cleaving peptide comprises or consists of a polynucleotide sequence having at least 75% identity to the polynucleotide sequence set forth in any one of SEQ ID NOs: 89-93. In certain embodiments, the encoded self-cleaving peptide comprises or consists of an amino acid sequence having at least 90% (e.g., 90%, 91%, 92%, 93%, 94%, 95%, 96%, 97%, 98%, 99%, or 100%) identity to the amino acid sequence set forth in any one of SEQ ID NOs: 84-88.

It will be understood that various arrangements of polynucleotides encoding two polypeptides of interest separated by a self-cleaving peptide (e.g., β-chain-encoding polynucleotide-self-cleaving peptide-α-chain-encoding polynucleotide; α-chain-encoding polynucleotide-self-cleaving peptide-β-chain-encoding polynucleotide) are contemplated.

Accordingly, in some embodiments, the polynucleotide encoding a binding protein has a structure comprising or having 5'-end to 3'-end of (TCRβ domain (e.g., chain)-encoding polynucleotide)-(self-cleaving peptide-encoding polynucleotide)-(TCRα domain (e.g., chain)-encoding polynucleotide).

In certain embodiments, the polynucleotide encoding a binding protein comprises or consists of a polynucleotide sequence having at least 75% (e.g., 75%, 80%, 81%, 82%, 83%, 84%, 85%, 86%, 87%, 88%, 89%, 90%, 91%, 92%, 93%, 94%, 95%, 96%, 97%, 98%, 99%, or more) identity to the polynucleotide sequence set forth in any one of SEQ ID NOs: 78-81. In certain embodiments, the polynucleotide comprises a polynucleotide sequence comprising or consisting of the polynucleotide sequence set forth in any one of SEQ ID NOs: 78-81.

In further aspects, there is provided an isolated polynucleotide encoding a binding protein wherein the encoded binding protein is capable of binding to a RMFPNAPYL (SEQ ID NO.:94):HLA complex and comprises a TCR Vα domain and a TCR Vβ domain that comprise: (i) the amino acid sequence set forth in any one of SEQ ID NOs: 19, 22, 25, 28, 31, 34, 37, or 40; (ii) the amino acid sequence set forth in any one of SEQ ID NOs: 17, 20, 23, 26, 29, 32, 35, or 38; (iii) the amino acid sequence set forth in any one of SEQ ID NOs: 18, 21, 24, 27, 30, 33, 36, or 39; (iv) an amino acid sequence comprising, consisting of, or having at least 90% (e.g., 90%, 91%, 92%, 93%, 94%, 95%, 96%, 97%, 98%, 99%, or 100%) identity to the amino acid sequence set forth in any one of SEQ ID NOs: 1-4 or 9-12; (v) an amino acid sequence comprising, consisting of, or having at least 90% identity to the amino acid sequence set forth in any one of SEQ ID NOs: 5-8 or 13-16; (vi) an amino acid sequence comprising, consisting of, or having at least 90% identity to the amino acid sequence set forth in any one of SEQ ID NOs: 46-53; (vii) an amino acid sequence comprising, consisting of, or having at least 90% identity to the amino acid sequence set forth in any one of SEQ ID NOs: 54-61; or (viii) any combination of (i)-(vii).

In further embodiments, an encoded binding protein is expressed as part of a transgene construct that encodes, and/or a modified immune cell can encode: one or more additional accessory protein, such as a safety switch protein; a tag, a selection marker; a CD8 co-receptor β-chain; a CD8 co-receptor α-chain or both; or any combination thereof. Polynucleotides and transgene constructs useful for encoding and expressing binding proteins and accessory components (e.g., one or more of a safety switch protein, a selection marker, CD8 co-receptor β-chain, or a CD8 co-receptor α-chain) are described in PCT publication no. WO 2018/058002, the polynucleotides, transgene constructs, and accessory components, including the nucleotide and amino acid sequences of which, are hereby incorporated by reference. It will be understood that any or all of a binding protein of the present disclosure, a safety switch protein, a tag, a selection marker, a CD8 co-receptor β-chain, or a CD8 co-receptor α-chain may be encoded by a single nucleic acid molecule or may be encoded by polynucleotide sequences that are, or are present on, separate nucleic acid molecules.

Exemplary safety switch proteins include, for example, a truncated EGF receptor polypeptide (huEGFRt) that is devoid of extracellular N-terminal ligand binding domains and intracellular receptor tyrosine kinase activity, but that retains its native amino acid sequence, has type I transmembrane cell surface localization, and has a conformationally intact binding epitope for pharmaceutical-grade anti-EGFR monoclonal antibody, cetuximab (Erbitux) tEGF receptor (tEGFr; Wang et al., *Blood* 118:1255-1263, 2011); a caspase polypeptide (e.g., iCasp9; Straathof et al., *Blood* 105:4247-4254, 2005; Di Stasi et al., *N. Engl. J. Med.* 365:1673-1683, 2011; Zhou and Brenner, *Exp. Hematol.* pii:S0301-472X (16)30513-6. doi:10.1016/j.exphem.2016.07.011), RQR8 (Philip et al., *Blood* 124:1277-1287, 2014); a 10-amino-acid tag derived from the human c-myc protein (Myc) (Kieback et al., *Proc. Natl. Acad. Sci. USA* 105:623-628, 2008); and a marker/safety switch polypeptide, such as RQR (CD20+ CD34; Philip et al., 2014).

Other accessory components useful for modified immune cells of the present disclosure comprise a tag or selection marker that allows the cells to be identified, sorted, isolated, enriched, or tracked. For example, marked immune cells having desired characteristics (e.g., an antigen-specific TCR and a safety switch protein) can be sorted away from unmarked cells in a sample and more efficiently activated and expanded for inclusion in a product of desired purity.

As used herein, the term "selection marker" comprises a nucleic acid construct (and the encoded gene product) that confers an identifiable change to a cell permitting detection and positive selection of immune cells transduced with a polynucleotide comprising a selection marker. RQR is a selection marker that comprises a major extracellular loop of CD20 and two minimal CD34 binding sites. In some embodiments, an RQR-encoding polynucleotide comprises a polynucleotide that encodes the 16-amino-acid CD34 minimal epitope. In some embodiments, the CD34 minimal epitope is incorporated at the amino terminal position of a CD8 co-receptor stalk domain (Q8). In further embodiments, the CD34 minimal binding site sequence can be combined with a target epitope for CD20 to form a compact marker/suicide gene for T cells (RQR8) (Philip et al., 2014, incorporated by reference herein). This construct allows for the selection of immune cells expressing the construct, with for example, CD34 specific antibody bound to magnetic beads (Miltenyi) and that utilizes clinically accepted pharmaceutical antibody, rituximab, that allows for the selective deletion of a transgene expressing engineered T cell (Philip et al., 2014).

Further exemplary selection markers also include several truncated type I transmembrane proteins normally not expressed on T cells: the truncated low-affinity nerve growth factor, truncated CD19, and truncated CD34 (see for example, Di Stasi et al., *N. Engl. J. Med.* 365:1673-1683, 2011; Mavilio et al., *Blood* 83:1988-1997, 1994; Fehse et al., *Mol. Ther.* 1:448-456, 2000; each incorporated herein in their entirety). A useful feature of CD19 and CD34 is the availability of the off-the-shelf Miltenyi CliniMACs™ selection system that can target these markers for clinical-grade sorting. However, CD19 and CD34 are relatively large surface proteins that may tax the vector packaging capacity and transcriptional efficiency of an integrating vector. Surface markers containing the extracellular, non-signaling domains or various proteins (e.g., CD19, CD34, LNGFR) also can be employed. Any selection marker may be employed and should be acceptable for Good Manufacturing Practices. In certain embodiments, selection markers are expressed with a polynucleotide that encodes a gene product of interest (e.g., a binding protein of the present disclosure, such as a TCR or CAR). Further examples of selection markers include, for example, reporters such as GFP, EGFP, β-gal or chloramphenicol acetyltransferase (CAT). In certain embodiments, a selection marker, such as, for example, CD34 is expressed by a cell and the CD34 can be used to select enrich for, or isolate (e.g., by immunomagnetic selection) the transduced cells of interest for use in the methods described herein. As used herein, a CD34 marker is distinguished from an anti-CD34 antibody, or, for example, a scFv, TCR, or other antigen recognition moiety that binds to CD34.

In certain embodiments, a selection marker comprises an RQR polypeptide, a truncated low-affinity nerve growth factor (tNGFR), a truncated CD19 (tCD19), a truncated CD34 (tCD34), or any combination thereof.

By way of background, inclusion of CD4$^+$ T cells in an immunotherapy cell product can provide antigen-induced IL-2 secretion and augment persistence and function of introduced cytotoxic CD8$^+$ T cells (see, e.g., Kennedy et al., Immunol. Rev. 222:129 (2008); Nakanishi et al., Nature 462(7272):510 (2009)). In certain circumstances, a class I restricted TCR in CD4$^+$ T cells may require the transfer of a CD8 co-receptor to enhance sensitivity of the TCR to class I HLA peptide complexes. CD4 co-receptors differ in structure to CD8 and have been shown to be ineffective substitutes for CD8 co-receptors (see, e.g., Stone & Kranz, *Front. Immunol.* 4:244 (2013); see also Cole et al., *Immunology* 137(2):139 (2012). Thus, another accessory protein for use in the compositions and methods of this disclosure comprises a CD8 co-receptor or component thereof.

Engineered immune cells comprising a heterologous polynucleotide encoding a binding protein of the present disclosure may, in certain embodiments, further comprise a heterologous polynucleotide encoding a CD8 co-receptor protein, or a beta-chain or alpha-chain component thereof.

An encoded CD8 co-receptor includes, in some embodiments, an α-chain or a fragment or variant thereof. An amino acid sequence of the human CD8 co-receptor α-chain precursor is known and is provided at, for example, UniProtKB—P30433 (see also UniProtKB—P31783; -P10732; and -P10731).

An encoded CD8 co-receptor includes, in some embodiments, a β-chain or a fragment or variant thereof. An amino acid sequence of the human CD8 co-receptor β-chain precursor is known and is provided at, for example, UniProtKB-P10966 (see also UniProtKB-Q9UQ56; -E9PD41; Q8TD28; and -P30434; and -P05541). Without wishing to be bound by theory, it is believed that distance from the host cell surface is important for RQR polypeptides to function as selection markers/safety switches (Philip et al., 2010 (supra)). In some embodiments, the encoded RQR polypeptide is contained in a β-chain, an α-chain, or both, or a fragment or variant of either or both, of the encoded CD8 co-receptor. In specific embodiments, a modified immune cell comprises a heterologous polynucleotide encoding iCasp9 and a heterologous polynucleotide encoding a recombinant CD8 co-receptor protein that comprises a β-chain containing a RQR polypeptide and further comprises a CD8 α-chain.

An isolated polynucleotide of this disclosure may further comprise a polynucleotide encoding a safety switch protein, a selection marker, a CD8 co-receptor beta chain, or a CD8 co-receptor alpha chain as disclosed herein, or may comprise a polynucleotide encoding any combination thereof.

In certain embodiments, a modified immune cell of the present disclosure further comprises: (i) a heterologous polynucleotide encoding a polypeptide that comprises an extracellular portion of a CD8 co-receptor α chain, wherein, optionally, the encoded polypeptide is or comprises a CD8 co-receptor α chain; (ii) a heterologous polynucleotide encoding a polypeptide that comprises an extracellular portion of a CD8 co-receptor β chain, wherein, optionally, the encoded polypeptide is or comprises a CD8 co-receptor β chain; or (iii) the polynucleotide of (i) and the polynucleotide of (ii), wherein, optionally, the host cell comprises a CD4+ T cell, a CD8+ T cell, or both.

In further embodiments, the modified immune cell comprises: (a) the heterologous polynucleotide encoding a polypeptide comprising an extracellular portion of a CD8 co-receptor α chain wherein, optionally, the encoded polypeptide is or comprises a CD8 co-receptor α chain; (b) the heterologous polynucleotide encoding a polypeptide comprising an extracellular portion of a CD8 co-receptor β chain, wherein, optionally, the encoded polypeptide is or comprises a CD8 co-receptor β chain; and (c) a polynucleotide encoding a self-cleaving peptide disposed between the polynucleotide of (a) and the polynucleotide of (b).

In some embodiments, a polynucleotide encoding a binding protein further comprises a polynucleotide that encodes a selection marker.

Standard techniques may be used for recombinant DNA, peptide and oligonucleotide synthesis, immunoassays and tissue culture and transformation (e.g., electroporation, lipofection). Enzymatic reactions and purification techniques may be performed according to manufacturer's specifications or as commonly accomplished in the art or as described herein. These and related techniques and procedures may be generally performed according to conventional methods well-known in the art and as described in various general and more specific references in microbiology, molecular biology, biochemistry, molecular genetics, cell biology, virology and immunology techniques that are cited and discussed throughout the present specification. See, e.g., Sambrook, et al., *Molecular Cloning: A Laboratory Manual*, 3d ed., Cold Spring Harbor Laboratory Press, Cold Spring Harbor, N.Y.; *Current Protocols in Molecular Biology* (John Wiley and Sons, updated July 2008); *Short Protocols in Molecular Biology: A Compendium of Methods from Current Protocols in Molecular Biology*, Greene Pub. Associates and Wiley-Interscience; Glover, *DNA Cloning: A Practical Approach*, vol. I & II (IRL Press, Oxford Univ. Press USA, 1985); *Current Protocols in Immunology* (Edited by: John E. Coligan, Ada M. Kruisbeek, David H. Margulies, Ethan M. Shevach, Warren Strober 2001 John Wiley & Sons, NY, NY); *Real-Time PCR: Current Technology and Applications*, Edited by Julie Logan, Kirstin Edwards and Nick Saunders, 2009, Caister Academic Press, Norfolk, UK; Anand, *Techniques for the Analysis of Complex Genomes*, (Academic Press, New York, 1992); Guthrie and Fink, *Guide to Yeast Genetics and Molecular Biology* (Academic Press, New York, 1991); *Oligonucleotide Synthesis* (N. Gait, Ed., 1984); *Nucleic Acid Hybridization* (B. Hames & S. Higgins, Eds., 1985); *Transcription and Translation* (B. Hames & S. Higgins, Eds., 1984); *Animal Cell Culture* (R. Freshney, Ed., 1986); Perbal, *A Practical Guide to Molecular Cloning* (1984); *Next-Generation Genome Sequencing* (Janitz, 2008 Wiley-VCH); *PCR Protocols (Methods in Molecular Biology)* (Park, Ed., 3$^{rd}$ Edition, 2010 Humana Press); *Immobilized Cells And Enzymes* (IRL Press, 1986); the treatise, *Methods In Enzymology* (Academic Press, Inc., N.Y.); *Gene Transfer Vectors For Mammalian Cells* (J. H. Miller and M. P. Calos eds., 1987, Cold Spring Harbor Laboratory); Harlow and Lane, *Antibodies*, (Cold Spring Harbor Laboratory Press, Cold Spring Harbor, N.Y., 1998); *Immunochemical Methods In Cell And Molecular Biology* (Mayer and Walker, eds., Academic Press, London, 1987); *Handbook Of Experimental Immunology*, Volumes I-IV (D.

M. Weir and C C Blackwell, eds., 1986); Roitt, *Essential Immunology*, 6th Edition, (Blackwell Scientific Publications, Oxford, 1988); *Embryonic Stem Cells: Methods and Protocols* (Methods in Molecular Biology) (Kurstad Turksen, Ed., 2002); *Embryonic Stem Cell Protocols: Volume I: Isolation and Characterization* (Methods in Molecular Biology) (Kurstad Turksen, Ed., 2006); *Embryonic Stem Cell Protocols: Volume II: Differentiation Models* (Methods in Molecular Biology) (Kurstad Turksen, Ed., 2006); *Human Embryonic Stem Cell Protocols* (Methods in Molecular Biology) (Kursad Turksen Ed., 2006); *Mesenchymal Stem Cells: Methods and Protocols* (Methods in Molecular Biology) (Darwin J. Prockop, Donald G. Phinney, and Bruce A. Bunnell Eds., 2008); *Hematopoietic Stem Cell Protocols* (Methods in Molecular Medicine) (Christopher A. Klug, and Craig T. Jordan Eds., 2001); *Hematopoietic Stem Cell Protocols* (Methods in Molecular Biology) (Kevin D. Bunting Ed., 2008) *Neural Stem Cells: Methods and Protocols* (Methods in Molecular Biology) (Leslie P. Weiner Ed., 2008).

Certain embodiments include a polynucleotide contained in a vector. One of skill in the art can readily ascertain suitable vectors for use with certain embodiments disclosed herein. A typical vector may comprise a polynucleotide capable of transporting another nucleic acid to which it has been linked, or which is capable of replication in a host organism. Some examples of vectors include plasmids, viral vectors, cosmids, and others. Some vectors may be capable of autonomous replication in a host cell into which they are introduced (e.g. bacterial vectors having a bacterial origin of replication and episomal mammalian vectors), whereas other vectors may be integrated into the genome of a host cell upon introduction into the host cell and thereby replicate along with the host genome. Additionally, some vectors are capable of directing the expression of genes to which they are operatively linked. According to related embodiments, it is further understood that, if one or more agents (e.g., polynucleotides encoding binding proteins specific for WT-1, or variants thereof, as described herein) is co-administered to a subject, that each agent may reside in separate or the same vectors, and multiple vectors (each containing a different agent the same agent) may be introduced to a cell or cell population or administered to a subject.

In certain embodiments, polynucleotides of the present disclosure may be operatively linked to certain elements of a vector. For example, polynucleotide sequences that are needed to effect the expression and processing of coding sequences to which they are ligated may be operatively linked. Expression control sequences may include appropriate transcription initiation, termination, promoter and enhancer sequences; efficient RNA processing signals such as splicing and polyadenylation signals; sequences that stabilize cytoplasmic mRNA; sequences that enhance translation efficiency (i.e. Kozak consensus sequences); sequences that enhance protein stability; and possibly sequences that enhance protein secretion. Expression control sequences may be operatively linked if they are contiguous with the gene of interest and expression control sequences that act in trans or at a distance to control the gene of interest.

In certain embodiments, the vector comprises a plasmid vector or a viral vector (e.g., a vector selected from lentiviral vector or a γ-retroviral vector). Viral vectors include retrovirus, adenovirus, parvovirus (e.g., adeno-associated viruses), coronavirus, negative strand RNA viruses such as ortho-myxovirus (e.g., influenza virus), rhabdovirus (e.g., rabies and vesicular stomatitis virus), paramyxovirus (e.g., measles and Sendai), positive strand RNA viruses such as picornavirus and alphavirus, and double-stranded DNA viruses including adenovirus, herpesvirus (e.g., Herpes Simplex virus types 1 and 2, Epstein-Barr virus, cytomegalovirus), and poxvirus (e.g., vaccinia, fowlpox and canarypox). Other viruses include Norwalk virus, togavirus, flavivirus, reoviruses, papovavirus, hepadnavirus, and hepatitis virus, for example. Examples of retroviruses include avian leukosis-sarcoma, mammalian C-type, B-type viruses, D type viruses, HTLV-BLV group, lentivirus, and spumavirus (Coffin, J. M., Retroviridae: The viruses and their replication, In Fundamental Virology, Third Edition, B. N. Fields et al., Eds., Lippincott-Raven Publishers, Philadelphia, 1996).

"Retroviruses" are viruses having an RNA genome, which is reverse-transcribed into DNA using a reverse transcriptase enzyme, the reverse-transcribed DNA is then incorporated into the host cell genome. "Gammaretrovirus" refers to a genus of the retroviridae family. Examples of gammaretroviruses include mouse stem cell virus, murine leukemia virus, feline leukemia virus, feline sarcoma virus, and avian reticuloendotheliosis viruses. "Lentiviral vector," as used herein, means HIV-based lentiviral vectors for gene delivery, which can be integrative or non-integrative, have relatively large packaging capacity, and can transduce a range of different cell types. Lentiviral vectors are usually generated following transient transfection of three (packaging, envelope and transfer) or more plasmids into producer cells. Like HIV, lentiviral vectors enter the target cell through the interaction of viral surface glycoproteins with receptors on the cell surface. On entry, the viral RNA undergoes reverse transcription, which is mediated by the viral reverse transcriptase complex. The product of reverse transcription is a double-stranded linear viral DNA, which is the substrate for viral integration into the DNA of infected cells.

In certain embodiments, the viral vector can be a gammaretrovirus, e.g., Moloney murine leukemia virus (MLV)-derived vectors. In other embodiments, the viral vector can be a more complex retrovirus-derived vector, e.g., a lentivirus-derived vector. HIV-1-derived vectors belong to this category. Other examples include lentivirus vectors derived from HIV-2, FIV, equine infectious anemia virus, SIV, and Maedi-Visna virus (ovine lentivirus). Methods of using retroviral and lentiviral viral vectors and packaging cells for transducing mammalian host cells with viral particles containing TCR or CAR transgenes are known in the art and have been previous described, for example, in: U.S. Pat. No. 8,119,772; Walchli et al., PLoS One 6:327930, 2011; Zhao et al., J. Immunol. 174:4415, 2005; Engels et al., Hum. Gene Ther. 14:1155, 2003; Frecha et al., Mol. Ther. 18:1748, 2010; and Verhoeyen et al., Methods Mol. Biol. 506:97, 2009. Retroviral and lentiviral vector constructs and expression systems are also commercially available. Other viral vectors also can be used for polynucleotide delivery including DNA viral vectors, including, for example adenovirus-based vectors and adeno-associated virus (AAV)-based vectors; vectors derived from herpes simplex viruses (HSVs), including amplicon vectors, replication-defective HSV and attenuated HSV (Krisky et al., Gene Ther. 5:1517, 1998).

Other vectors developed for gene therapy uses can also be used with the compositions and methods of this disclosure. Such vectors include those derived from baculoviruses and α-viruses. (Jolly, D J. 1999. Emerging Viral Vectors. pp 209-40 in Friedmann T. ed. The Development of Human Gene Therapy. New York: Cold Spring Harbor Lab), or plasmid vectors (such as Sleeping Beauty or other transposon vectors).

When a viral vector genome comprises a plurality of polynucleotides to be expressed in a host cell as separate transcripts, the viral vector may also comprise additional sequences between the two (or more) transcripts allowing for bicistronic or multicistronic expression. Examples of such sequences used in viral vectors include internal ribosome entry sites (IRES), furin cleavage sites, viral 2A peptide, or any combination thereof.

In certain embodiments, a vector is capable of delivering the polynucleotide or transgene construct to a host cell (e.g., a hematopoietic progenitor cell or a human immune system cell). In specific embodiments, a vector is capable of delivering a polynucleotide or transgene construct to human immune system cell, such as, for example, a CD4+ T cell, a CD8+ T cell, a CD4− CD8− double negative T cell, a stem cell memory T cell, a γδ T cell, a natural killer cell, a dendritic cell, or any combination thereof. In further embodiments, a vector is capable of delivering a transgene construct to a naïve T cell, a central memory T cell, an effector memory T cell, or any combination thereof. In some embodiments, a vector that encodes a polynucleotide or transgene construct of the present disclosure may further comprise a polynucleotide that encodes a nuclease that can be used to perform a chromosomal knockout in a host cell (e.g., a CRISPR-Cas endonuclease or another endonuclease as disclosed herein) or that can be used to deliver a therapeutic polynucleotide or transgene or portion thereof to a host cell in a gene therapy replacement or gene repair therapy. Alternatively, a nuclease used for a chromosomal knockout or a gene replacement or gene repair therapy can be delivered to a host cell independent of a vector that encodes a polynucleotide or transgene construct of this disclosure.

Host Cells

Also provided herein are host cells that comprise a heterologous polynucleotide of the present disclosure (e.g., encoding any presently disclosed binding protein or fusion protein and optionally encoding one or more additional proteins, such as a selection marker a self-cleaving peptide, a CD8 co-receptor polypeptide, or any combination thereof) and/or express any binding protein as disclosed herein. Such a host cell may be generated by, for example, transfection or transduction with a vector of the present disclosure, and/or by gene-editing.

In some embodiments, a host cell comprises an immune system cell, which may be any human immune system cell, such as those exemplary immune system cells described herein. In certain embodiments, the host cell comprises a T cell, a NK cell, a NK-T cell, or any combination thereof. In further embodiments, the T cell comprises a CD8$^+$ T cell, a CD4$^+$ T cell, or both.

Accordingly, in particular embodiments, a modified immune cell comprises a heterologous polynucleotide that encodes a binding protein according to the present disclosure, wherein the encoded binding protein is capable of binding to a RMFPNAPYL (SEQ ID NO.:94):human leukocyte antigen (HLA) complex.

In certain embodiments, the encoded binding protein is capable of binding to the SEQ ID NO.:94:HLA complex with an IFNγ production pEC$_{50}$ of 4.0, 4.5, 5.0, 5.1, 5.2, 5.3, 5.4, 5.5, 5.6, 5.7, 5.8, 5.9, 6.0, 6.1, 6.2, 6.3, 6.4, 6.5, or higher.

In certain embodiments, the peptide:HLA complex comprises a peptide:HLA-A*201 complex.

In any of the presently disclosed embodiments, 50% or more of the modified immune cells in a population produce interferon-gamma (IFN-γ) when the population of the modified immune cells is co-cultured for 4 hours with antigen-presenting cells (e.g., T2 cells, Jurkat cells, dendritic cells, expressing an HLA such as HLA-A*0201) pulsed with a peptide comprising or consisting of the amino acid sequence RMFPNAPYL (SEQ ID NO.:94) at a peptide concentration of $10^{-4}$ μM, or $10^{-5}$ μM, or $10^{-6}$ μM in the co-culture. In certain embodiments, 10%, 15%, 20%, 25%, 30%, 35%, 40%, 45%, 50%, or more of the modified immune cells in a population are Nur77$^+$ (i.e., express Nur77) when the population of the modified immune cells is co-cultured with antigen-presenting cells (also called "target cells" in some contexts) pulsed with a peptide comprising or consisting of the amino acid sequence RMFPNAPYL (SEQ ID NO.:94) at a peptide concentration of about $10^{-2}$ μM in the co-culture, wherein the antigen-presenting cells express optionally comprise T2 cells, Jurkat cells, or both, and are optionally HLA-A*0201+.

In some embodiments, 10%, 15%, 20%, or more of the modified immune cells in the population are Nur77$^+$ when the population of the modified immune cells is co-cultured with antigen-presenting cells pulsed with a peptide comprising or consisting of the amino acid sequence RMFPNAPYL (SEQ ID NO.:94) at a peptide concentration of $10^{-3}$ μM in the co-culture.

In some embodiments, a binding protein has a Nur77 expression pEC50 (SEQ ID NO.:94:HLA, such as HLA-A*0201) of 1.0, 1.1, 1.2, 1.3, 1.4, 1.4, 1.5, 1.6, 1.7, 1.8, 1.9, 2.0, 2.1, 2.2, 2.3, 2.4, 2.5, 2.6, or more.

In any of the presently disclosed embodiments, a modified immune cell is capable of killing at least 11%, 12%, 13%, 14%, 15%, 20%, 25%, or more of the HLA-A*0201$^+$ MDA-MB-468 cells in a sample when the modified immune cell and the MDA-MB-468 cells are present in the sample at a ratio of 30:1. In certain embodiments, the modified immune cell is capable of killing 10% or more of HLA-A*0201$^+$ MDA-MB-468 cells in a sample when the modified immune cell and the MDA-MB-468 cells are present in the sample at a ratio of 10:1. In certain embodiments, the modified immune cell is capable of killing about 5% or more of HLA-A*0201$^+$ MDA-MB-468 cells in a sample when the modified immune cell and the MDA-MB-468 cells are present in the sample at a ratio of 1:1.

In any of the presently disclosed embodiments, killing can be measured using a 4 hr co-culture assay, optionally using labeled chromium (e.g., $^{51}$Cr), as described herein.

In certain embodiments, a modified immune cell is capable of killing 21%, 22%, 23%, 24%, 25%, or more of the Panc1 cells in a sample when the modified immune cell and the Panc1 cells are present at a ratio of 30:1. In further embodiments, a modified immune cell is capable of killing 10%, 15%, or more of the Panc1 cells in a sample when the modified immune cell and the Panc1 cells are present at a ratio of 10:1. In further embodiments, a modified immune cell is capable of killing 10%, 15% or more of the Panc1 cells in a sample when the modified immune cell and the Panc1 cells are present at a ratio of 9:1, 8:1, 7:1, 6:1, or 5:1.

In certain embodiments, a modified immune cell: has increased killing activity against HLA-A*0201$^+$ MDA-MB-468 cells and/or against Panc1 cells in a 4-hour co-culture, and/or has improved IFN-γ production in a 4-hour co-culture with peptide-pulsed target cells, and/or further reduces proliferation of Panc-1 cancer cells (e.g., over 60, 75, 100, 125, 150, or more hours, as measured using an IncuCyte assay, at an 8:1 effector:target cell ratio), as compared to a reference immune cell comprising a polynucleotide that encodes a T cell receptor comprising a TCRα chain having the amino acid sequence set forth in SEQ ID NO: 82 and a TCRβ chain having the amino acid sequence set forth in SEQ ID NO: 83.

In some embodiments, a modified immune cell of the present disclosure prevents or substantially prevents growth and/or proliferation of Panc-1 cancer cells for over 50, 100, 150 hours, or more, wherein, optionally, the modified immune cell and the Panc-1 cancer cells are present at a 8:1 effector:target cell ratio.

In any of the presently disclosed embodiments, killing can be measured using a 4 hr co-culture assay, optionally using labeled chromium (e.g., $^{51}$Cr), as described herein.

It will be understood that a "reference" immune cell is of a same immune cell type and is phenotypically identical or substantially identical to the subject modified immune cell, with the exception of the encoded binding protein. For example, for a modified CD8+ human T cell, a reference immune cell is a CD8+ human T cell, and can be, for example, from the same source or donor as the modified immune cell.

In any of the aforementioned embodiments, an encoded binding protein can be a TCR, a CAR, or a scTCR. In any of the aforementioned embodiments, an encoded binding protein is capable of binding to a WT-1 peptide (SEQ ID NO.:94):HLA complex on a cell surface independent of CD8 or in the absence of CD8.

In any of the presently disclosed embodiments, a binding protein expressed by a modified immune cell can comprise a TCR, a single-chain TCR (scTCR), a chimeric antigen receptor (CAR), or any combination thereof.

Any suitable immune cell may be modified to include a heterologous polynucleotide encoding a binding protein of this disclosure, including, for example, a T cell, a NK cell, a NK-T cell, a macrophage, a monocyte, or a dendritic cell. In some embodiments, a modified immune cell comprises a CD4$^+$ T cell, a CD8$^+$ T cell, or both. In some embodiments, a modified immune cell comprises a CD4-CD8– double negative T cell or a γδ T cell. In some embodiments, the T cell is a naïve T cell, a central memory T cell, an effector memory T cell, or any combination thereof. Methods for transfecting/transducing T cells with desired nucleic acids have been described (e.g., U.S. Patent Application Pub. No. US 2004/0087025) as have adoptive transfer procedures using T cells of desired target-specificity (e.g., Schmitt et al., *Hum. Gen.* 20:1240, 2009; Dossett et al., *Mol. Ther.* 17:742, 2009; Till et al., *Blood* 112:2261, 2008; Wang et al., *Hum. Gene Ther.* 18:712, 2007; Kuball et al., *Blood* 109:2331, 2007; US 2011/0243972; US 2011/0189141; Leen et al., *Ann. Rev. Immunol.* 25:243, 2007), such that adaptation of these methodologies to the presently disclosed embodiments is contemplated, based on the teachings herein.

Any appropriate method can be used to transfect or transduce the cells, for example, the T cells, or to administer the polynucleotides or compositions of the present methods. Known methods for delivering polynucleotides to host cells include, for example, use of cationic polymers, lipid-like molecules, and certain commercial products such as, for example, IN-VIVO-JET PEI. Other methods include ex vivo transduction, injection, electroporation, DEAE-dextran, sonication loading, liposome-mediated transfection, receptor-mediated transduction, microprojectile bombardment, transposon-mediated transfer, and the like. Still further methods of transfecting or transducing host cells employ vectors, described in further detail herein. In certain embodiments, a host cell is gene-edited to comprise in its genome a polynucleotide that encodes a binding protein (or other protein or polypeptide) as provided herein.

In any of the foregoing embodiments, a modified immune cell may modified to reduce or eliminate expression (e.g., by a chromosomal gene knockout as described herein) of one or more endogenous genes that encode a polypeptide involved in immune signaling or other related activities, and/or to comprise a heterologous polynucleotide as provided herein. Exemplary gene knockouts include those that encode PD-1, LAG-3, CTLA4, TIM3, an HLA molecule, a TCR molecule, or the like. Without wishing to be bound by theory, certain endogenously expressed immune cell proteins may be recognized as foreign by an allogeneic host receiving the modified immune cells, which may result in elimination of the modified immune cells (e.g., an HLA allele), or may downregulate the immune activity of the modified immune cells (e.g., PD-1, LAG-3, CTLA4), or may interfere with the binding activity of a heterologously expressed binding protein of the present disclosure (e.g., an endogenous TCR of a modified T cell that binds a non-WT-1 antigen and may interferes with the modified immune cell binding a cell that expresses WT-1 antigen), or may compete for expression with a heterologous binding protein.

Accordingly, decreasing or eliminating expression or activity of such endogenous genes or proteins can improve the activity, tolerance, expression of a binding protein, or persistence of the modified immune cells in an autologous or allogeneic host setting, and may allow for universal administration of the cells (e.g., to any recipient regardless of HLA type). In certain embodiments, a modified immune cell is a donor cell (e.g., allogeneic) or an autologous cell. In certain embodiments, a modified immune cell of this disclosure comprises a chromosomal gene knockout of one or more of a gene that encodes PD-1, LAG-3, CTLA4, TIM3, TIGIT, an HLA component (e.g., a gene that encodes an α1 macroglobulin, an α2 macroglobulin, an α3 macroglobulin, a β1 microglobulin, or a β2 microglobulin), or a TCR component (e.g., a gene that encodes a TCR variable region or a TCR constant region) (see, e.g., Torikai et al., *Nature Sci. Rep.* 6:21757 (2016); Torikai et al., *Blood* 119(24):5697 (2012); and Torikai et al., *Blood* 122(8):1341 (2013), the gene-editing techniques, compositions, and adoptive cell therapies of which are herein incorporated by reference in their entirety).

As used herein, the term "chromosomal gene knockout" refers to a genetic alteration or introduced inhibitory agent in a host cell that prevents (e.g., reduces, delays, suppresses, or abrogates) production, by the host cell, of a functionally active endogenous polypeptide product. Alterations resulting in a chromosomal gene knockout can include, for example, introduced nonsense mutations (including the formation of premature stop codons), missense mutations, gene deletion, and strand breaks, as well as the heterologous expression of inhibitory nucleic acid molecules that inhibit endogenous gene expression in the host cell.

In certain embodiments, a chromosomal gene knock-out or gene knock-in is made by chromosomal editing of a host cell. Chromosomal editing can be performed using, for example, endonucleases. As used herein "endonuclease" refers to an enzyme capable of catalyzing cleavage of a phosphodiester bond within a polynucleotide chain. In certain embodiments, an endonuclease is capable of cleaving a targeted gene thereby inactivating or "knocking out" the targeted gene. An endonuclease may be a naturally occurring, recombinant, genetically modified, or fusion endonuclease. The nucleic acid strand breaks caused by the endonuclease are commonly repaired through the distinct mechanisms of homologous recombination or non-homologous end joining (NHEJ). During homologous recombination, a donor nucleic acid molecule may be used for a donor gene "knock-in", for target gene "knock-out", and optionally to inactivate a target gene through a donor gene knock in or target gene knock out event. NHEJ is an error-prone repair process that often results in changes to the DNA sequence at the site of the cleavage, e.g., a substitution, deletion, or addition of at least one nucleotide. NHEJ may be used to "knock-out" a target gene. Examples of endonucleases include zinc finger nucleases, TALE-nucleases, CRISPR-Cas nucleases, meganucleases, and megaTALs.

As used herein, a "zinc finger nuclease" (ZFN) refers to a fusion protein comprising a zinc finger DNA-binding domain fused to a non-specific DNA cleavage domain, such as a FokI endonuclease. Each zinc finger motif of about 30 amino acids binds to about 3 base pairs of DNA, and amino acids at certain residues can be changed to alter triplet sequence specificity (see, e.g., Desjarlais et al., *Proc. Natl. Acad. Sci.* 90:2256-2260, 1993; Wolfe et al., *J. Mol. Biol.* 285:1917-1934, 1999). Multiple zinc finger motifs can be linked in tandem to create binding specificity to desired DNA sequences, such as regions having a length ranging from about 9 to about 18 base pairs. By way of background, ZFNs mediate genome editing by catalyzing the formation of a site-specific DNA double strand break (DSB) in the genome, and targeted integration of a transgene comprising flanking sequences homologous to the genome at the site of DSB is facilitated by homology directed repair. Alternatively, a DSB generated by a ZFN can result in knock out of target gene via repair by non-homologous end joining (NHEJ), which is an error-prone cellular repair pathway that results in the insertion or deletion of nucleotides at the cleavage site. In certain embodiments, a gene knockout comprises an insertion, a deletion, a mutation or a combination thereof, made using a ZFN molecule.

As used herein, a "transcription activator-like effector nuclease" (TALEN) refers to a fusion protein comprising a TALE DNA-binding domain and a DNA cleavage domain, such as a FokI endonuclease. A "TALE DNA binding domain" or "TALE" is composed of one or more TALE repeat domains/units, each generally having a highly conserved 33-35 amino acid sequence with divergent 12th and 13th amino acids. The TALE repeat domains are involved in binding of the TALE to a target DNA sequence. The divergent amino acid residues, referred to as the Repeat Variable Diresidue (RVD), correlate with specific nucleotide recognition. The natural (canonical) code for DNA recognition of these TALEs has been determined such that an HD (histine-aspartic acid) sequence at positions 12 and 13 of the TALE leads to the TALE binding to cytosine (C), NG (asparagine-glycine) binds to a T nucleotide, NI (asparagine-isoleucine) to A, NN (asparagine-asparagine) binds to a G or A nucleotide, and NG (asparagine-glycine) binds to a T nucleotide. Non-canonical (atypical) RVDs are also known (see, e.g., U.S. Patent Publication No. US 2011/0301073, which atypical RVDs are incorporated by reference herein in their entirety). TALENs can be used to direct site-specific double-strand breaks (DSB) in the genome of T cells. Non-homologous end joining (NHEJ) ligates DNA from both sides of a double-strand break in which there is little or no sequence overlap for annealing, thereby introducing errors that knock out gene expression. Alternatively, homology directed repair can introduce a transgene at the site of DSB providing homologous flanking sequences are present in the transgene. In certain embodiments, a gene knockout comprises an insertion, a deletion, a mutation or a combination thereof, and made using a TALEN molecule.

As used herein, a "clustered regularly interspaced short palindromic repeats/Cas" (CRISPR/Cas) nuclease system refers to a system that employs a CRISPR RNA (crRNA)-guided Cas nuclease to recognize target sites within a genome (known as protospacers) via base-pairing complementarity and then to cleave the DNA if a short, conserved protospacer associated motif (PAM) immediately follows 3' of the complementary target sequence. CRISPR/Cas systems are classified into three types (i.e., type I, type II, and type III) based on the sequence and structure of the Cas nucleases. The crRNA-guided surveillance complexes in types I and III need multiple Cas subunits. Type II system, the most studied, comprises at least three components: an RNA-guided Cas9 nuclease, a crRNA, and a trans-acting crRNA (tracrRNA). The tracrRNA comprises a duplex forming region. A crRNA and a tracrRNA form a duplex that is capable of interacting with a Cas9 nuclease and guiding the Cas9/crRNA:tracrRNA complex to a specific site on the target DNA via Watson-Crick base-pairing between the spacer on the crRNA and the protospacer on the target DNA upstream from a PAM. Cas9 nuclease cleaves a double-stranded break within a region defined by the crRNA spacer. Repair by NHEJ results in insertions and/or deletions which disrupt expression of the targeted locus. Alternatively, a transgene with homologous flanking sequences can be introduced at the site of DSB via homology directed repair. The crRNA and tracrRNA can be engineered into a single guide RNA (sgRNA or gRNA) (see, e.g., Jinek et al., *Science* 337: 816-21, 2012). Further, the region of the guide RNA complementary to the target site can be altered or programed to target a desired sequence (Xie et al., *PLOS One* 9:e100448, 2014; U.S. Pat. Appl. Pub. No. US 2014/0068797, U.S. Pat. Appl. Pub. No. US 2014/0186843; U.S. Pat. No. 8,697,359, and PCT Publication No. WO 2015/071474; each of which is incorporated by reference). In certain embodiments, a gene knockout comprises an insertion, a deletion, a mutation or a combination thereof, and made using a CRISPR/Cas nuclease system.

Exemplary gRNA sequences and methods of using the same to knock out endogenous genes that encode immune cell proteins include those described in Ren et al., *Clin. Cancer Res.* 23(9):2255-2266 (2017), the gRNAs, Cas9 DNAs, vectors, and gene knockout techniques of which are hereby incorporated by reference in their entirety.

Alternative Cas nucleases may be used, including but not limited to, Cas 12, Cas 13, and Cas 14 nucleases, and variants thereof. For example, Cas nucleases disclosed in WO 2019/178427, which is hereby incorporated by reference in its entirety (including the Cas nucleases, CRISPR-Cas systems, and related methods disclosed therein), may be utilized.

As used herein, a "meganuclease," also referred to as a "homing endonuclease," refers to an endodeoxyribonuclease characterized by a large recognition site (double stranded DNA sequences of about 12 to about 40 base pairs). Meganucleases can be divided into five families based on sequence and structure motifs: LAGLIDADG (SEQ ID NO: 97), GIY-YIG (SEQ ID NO:98), HNH, His-Cys box and PD-(D/E)XK (SEQ ID NO:99). Exemplary meganucleases include I-SceI, I-CeuI, PI-PspI, PI-Sce, I-SceIV, I-CsmI, I-PanI, I-SceII, I-PpoI, I-SceIII, I-CreI, I-TevI, I-TevII and I-TevIII, whose recognition sequences are known (see, e.g., U.S. Pat. Nos. 5,420,032 and 6,833,252; Belfort et al., *Nucleic Acids Res.* 25:3379-3388, 1997; Dujon et al., *Gene* 82:115-118, 1989; Perler et al., *Nucleic Acids Res.* 22:1125-1127, 1994; Jasin, *Trends Genet.* 12:224-228, 1996; Gimble et al., *J. Mol. Biol.* 263:163-180, 1996; Argast et al., *J. Mol. Biol.* 280:345-353, 1998).

In certain embodiments, naturally occurring meganucleases may be used to promote site-specific genome modification of a target selected from PD-1, LAG3, TIM3, CTLA4, TIGIT, an HLA-encoding gene, or a TCR component-encoding gene. In other embodiments, an engineered meganuclease having a novel binding specificity for a target gene is used for site-specific genome modification (see, e.g., Porteus et al., *Nat. Biotechnol.* 23:967-73, 2005; Sussman et al., *J. Mol. Biol.* 342:31-41, 2004; Epinat et al., *Nucleic Acids Res.* 31:2952-62, 2003; Chevalier et al., *Molec. Cell* 10:895-905, 2002; Ashworth et al., *Nature* 441:656-659, 2006; Paques et al., *Curr. Gene Ther.* 7:49-66, 2007; U.S. Patent Publication Nos. US 2007/0117128; US 2006/0206949; US 2006/0153826; US 2006/0078552; and US 2004/0002092). In further embodiments, a chromosomal gene knockout is generated using a homing endonuclease that has been modified with modular DNA binding domains of TALENs to make a fusion protein known as a megaTAL. MegaTALs can be utilized to not only knock-out one or more target genes, but to also introduce (knock in) heterologous or exogenous polynucleotides when used in combination with an exogenous donor template encoding a polypeptide of interest.

In certain embodiments, a chromosomal gene knockout comprises an inhibitory nucleic acid molecule that is introduced into a host cell (e.g., an immune cell) comprising a heterologous polynucleotide encoding an antigen-specific receptor that specifically binds to a tumor associated antigen, wherein the inhibitory nucleic acid molecule encodes a target-specific inhibitor and wherein the encoded target-specific inhibitor inhibits endogenous gene expression (i.e., of PD-1, TIM3, LAG3, CTLA4, TIGIT, an HLA component, or a TCR component, or any combination thereof) in the host immune cell.

A chromosomal gene knockout can be confirmed directly by DNA sequencing of the host immune cell following use of the knockout procedure or agent. Chromosomal gene knockouts can also be inferred from the absence of gene expression (e.g., the absence of an mRNA or polypeptide product encoded by the gene) following the knockout.

Any of the foregoing gene-editing techniques can be used to introduce a polynucleotide of the present disclosure (e.g., encoding a binding protein and/or a CD8 co-receptor polypeptide) into a host cell genome. In some embodiments, a heterologous polynucleotide is introduced into a locus encoding an endogenous TCR component, HLA component, PD-1, LAG-3, CTLA4, TIM3, or TIGIT, or a safe harbor locus such as Rosa26, AAVS1, CCR5, or the like. In certain embodiments, a heterologous polynucleotide encoding a binding protein and/or encoding a CD8 co-receptor polypeptide is introduced into a host cell TRAC locus. In further embodiments, a chromosomal knockout of a host cell TRBC locus is introduced.

Accordingly, in certain embodiments, a host cell (e.g., modified immune cell) is provided that comprises, in an endogenous TRAC locus, a heterologous polynucleotide encoding a binding protein of the present disclosure, a CD8 co-receptor of the present disclosure, or both. In further embodiments, the host cell comprises a chromosomal knockout of an endogenous TRBC locus.

In another aspect, compositions are provided herein that comprise a modified immune cell of the present disclosure (and/or a polynucleotide, vector, or binding protein) and a pharmaceutically acceptable carrier, diluent, or excipient.

Also provided herein are unit doses that comprise an effective amount of a modified immune cell or of a composition comprising the modified immune cell. In certain embodiments, a unit dose comprises (i) a composition comprising at least about 30%, at least about 40%, at least about 50%, at least about 60%, at least about 70%, at least about 80%, at least about 85%, at least about 90%, or at least about 95% modified CD4+ T cells, combined with (ii) a composition comprising at least about 30%, at least about 40%, at least about 50%, at least about 60%, at least about 70%, at least about 80%, at least about 85%, at least about 90%, or at least about 95% modified CD8+ T cells, in about a 1:1 ratio, wherein the unit dose contains a reduced amount or substantially no naïve T cells (i.e., has less than about 50%, less than about 40%, less than about 30%, less than about 20%, less than about 10%, less than about 5%, or less then about 1% the population of naïve T cells present in a unit dose as compared to a patient sample having a comparable number of PBMCs).

In some embodiments, a unit dose comprises (i) a composition comprising at least about 50% modified CD4+ T cells, combined with (ii) a composition comprising at least about 50% modified CD8+ T cells, in about a 1:1 ratio, wherein the unit dose contains a reduced amount or substantially no naïve T cells. In further embodiments, a unit dose comprises (i) a composition comprising at least about 60% modified CD4+ T cells, combined with (ii) a composition comprising at least about 60% modified CD8+ T cells, in about a 1:1 ratio, wherein the unit dose contains a reduced amount or substantially no naïve T cells. In still further embodiments, a unit dose comprises (i) a composition comprising at least about 70% modified CD4+ T cells, combined with (ii) a composition comprising at least about 70% modified CD8+ T cells, in about a 1:1 ratio, wherein the unit dose contains a reduced amount or substantially no naïve T cells. In some embodiments, a unit dose comprises (i) a composition comprising at least about 80% modified CD4+ T cells, combined with (ii) a composition comprising at least about 80% modified CD8+ T cells, in about a 1:1 ratio, wherein the unit dose contains a reduced amount or substantially no naïve T cells. In some embodiments, a unit dose comprises (i) a composition comprising at least about 85% modified CD4+ T cells, combined with (ii) a composition comprising at least about 85% modified CD8+ T cells, in about a 1:1 ratio, wherein the unit dose contains a reduced amount or substantially no naïve T cells. In some embodiments, a unit dose comprises (i) a composition comprising at least about 90% modified CD4+ T cells, combined with (ii) a composition comprising at least about 90% modified CD8+ T cells, in about a 1:1 ratio, wherein the unit dose contains a reduced amount or substantially no naïve T cells.

It will be appreciated that a unit dose of the present disclosure may comprise a modified immune cell as described herein (i.e., expressing a binding protein specific for a WT-1 antigen according to SEQ ID NO:94) and a modified immune cell expressing a binding protein specific for a different antigen (e.g., a different WT-1 antigen (e.g., comprising SEQ ID NO.:100), or an antigen from a different protein or target, such as, for example, BCMA, CD3, CEACAM6, c-Met, EGFR, EGFRvIII, ErbB2, ErbB3, ErbB4, EphA2, IGF1R, GD2, O-acetyl GD2, O-acetyl GD3, GHRHR, GHR, FLT1, KDR, FLT4, CD44v6, CD151, CA125, CEA, CTLA-4, GITR, BTLA, TGFBR2, TGFBR1, IL6R, gp130, Lewis A, Lewis Y, TNFR1, TNFR2, PD1, PD-L1, PD-L2, HVEM, MAGE-A (e.g., including MAGE-A1, MAGE-A3, and MAGE-A4), mesothelin, NY-ESO-1, PSMA, RANK, ROR1, TNFRSF4, CD40, CD137, TWEAK-R, HLA, tumor- or pathogen-associated peptide bound to HLA, hTERT peptide bound to HLA, tyrosinase peptide bound to HLA, KRAS peptide bound to HLA, LTβR, LIFRβ, LRP5, MUC1, OSMRβ, TCRα, TCRβ, CD19, CD20, CD22, CD25, CD28, CD30, CD33, CD52, CD56, CD79a, CD79b, CD80, CD81, CD86, CD123, CD171, CD276, B7H4, TLR7, TLR9, PTCH1, HA1-H, Robo1, α-fetoprotein (AFP), Frizzled, OX40, PRAIVIE, BRAF, Core Binding Factor, MR-1 (Crowther et al., Nature Immunol. 21:175-185 (2020)), and SSX-2, or the like). For example, a unit dose can comprise modified CD8$^+$ T cells expressing a binding protein that specifically binds to a WT-1:HLA complex and modified CD4$^+$ T cells (and/or modified CD8+ T cells) expressing a binding protein (e.g., a CAR) that specifically binds to a CD19 antigen.

In any of the embodiments described herein, a unit dose comprises equal, or approximately equal, numbers of engineered CD45RA$^-$ CD3$^+$ CD8$^+$ and modified CD45RA$^-$ CD3$^+$ CD4$^+$ TM cells.

In some embodiments, a composition is provided that comprises (i) a modified immune cell as disclosed herein and further comprises (ii) an immune cell comprising a polynucleotide that encodes a binding protein that comprises a TCR Vα and a TCR and is capable of specifically binding to a VLDFAPPGA (SEQ ID NO.:100):HLA complex, wherein, optionally, the HLA comprises HLA-A*0201, and wherein, optionally, the modified immune cell of (i) and the immune cell of (ii) are each independently selected from a T cell, a NK cell, and NK-T cell.

In certain further embodiments, the binding protein of the immune cell in (ii) comprises: (a) CDR1α, CDR2α, CDR3α, CDR1β, CDR2β, and CDR3β amino acid sequences of SEQ ID NOs.:101-103 and 105-107, respectively, and wherein, optionally, (1) the Vα has at least 90% identity to, comprises, or consists of the amino acid sequence set forth in SEQ ID NO.:104 and/or (2) the Vβ has at least 90% identity to, comprises, or consists of the amino acid sequence set forth in SEQ ID NO.:108; (b) CDR1α, CDR2α, CDR3α, CDR1β, CDR2β, and CDR3β amino acid sequences of SEQ ID NOs.:109-110 and 113-115, respectively, and wherein, optionally, (1) the Vα has at least 90% (e.g., 90%, 91%, 92%, 93%, 94%, 95%, 96%, 97%, 98%, 99%, or 100%) identity to, comprises, or consists of the amino acid sequence set forth in SEQ ID NO.:112 and/or (2) the Vβ has at least 90% identity to, comprises, or consists of the amino acid sequence set forth in SEQ ID NO.:116; or (c) CDR1α, CDR2α, CDR3α, CDR1β, CDR2β, and CDR3β amino acid sequences of SEQ ID NOs.:117-119 and 121-123, respectively, and wherein, optionally, (1) the Vα has at least 90% identity to, comprises, or consists of the amino acid sequence set forth in SEQ ID NO.:120 and/or (2) the Vβ has at least 90% identity to, comprises, or consists of the amino acid sequence set forth in SEQ ID NO.:124.

Uses

In certain aspects, the instant disclosure is directed to methods for treating a disease or disorder associated with WT-1 expression by administering to human subject in need thereof an effective amount of a binding protein, polynucleotide, vector, cell, or composition according to any presently disclosed embodiments.

"Treat" or "treatment" or "ameliorate" refers to medical management of a disease, disorder, or condition of a subject (e.g., a human or a non-human mammal, such as a primate, horse, cat, dog, goat, mouse, or rat). Therapeutic or prophylactic/preventive benefit includes improved clinical outcome; lessening or alleviation of symptoms associated with a disease; decreased occurrence of symptoms; improved quality of life; longer disease-free status; diminishment of extent of disease, stabilization of disease state; delay of disease progression; remission; survival; prolonged survival; or any combination thereof.

A "therapeutically effective amount" or "effective amount", as used herein, refers to an amount of modified immune cells sufficient to result in a therapeutic effect, including improved clinical outcome; lessening or alleviation of symptoms associated with a disease; decreased occurrence of symptoms; improved quality of life; longer disease-free status; diminishment of extent of disease, stabilization of disease state; delay of disease progression; remission; survival; or prolonged survival in a statistically significant manner.

As used herein, "statistically significant" refers to a p value of 0.050 or less when calculated using the Students t-test and indicates that it is unlikely that a particular event or result being measured has arisen by chance.

Subjects that can be treated according to methods of the present disclosure are, in general, human and other primate subjects, such as monkeys and apes for veterinary medicine and/or research purposes. Mice or rats can also be used for research purposes. In any of the aforementioned embodiments, the subject may be a human subject. The subject can be male or female and can be any suitable age, including infant, juvenile, adolescent, adult, and geriatric subjects. Cells according to the present disclosure may be administered in a manner appropriate to the disease, condition, or disorder to be treated as determined by persons skilled in the medical art. In any of the above embodiments, a modified immune cell or unit dose as described herein is administered intravenously, intraperitoneally, intratumorally, into the bone marrow, into a lymph node, or into the cerebrospinal fluid so as to encounter target cells (e.g., leukemia cells). An appropriate dose, suitable duration, and frequency of administration of the compositions will be determined by such factors as a condition of the patient; size, type, and severity of the disease, condition, or disorder; the particular form of the active ingredient; and the method of administration.

When referring to an individual active ingredient or a cell expressing a single active ingredient, administered alone, a therapeutically effective amount refers to the effects of that ingredient or cell expressing that ingredient alone. When referring to a combination, a therapeutically effective amount refers to the combined amounts of active ingredients or combined adjunctive active ingredient with a cell expressing an active ingredient that results in a therapeutic effect, whether administered serially or simultaneously. A combination may also be a cell expressing more than one active ingredient.

As used herein, the term "adoptive immune therapy" or "adoptive immunotherapy" refers to administration of naturally occurring or genetically engineered, disease- or antigen-specific immune cells (e.g., T cells). Adoptive cellular immunotherapy may be autologous (immune cells are from the recipient), allogeneic (immune cells are from a donor of the same species) or syngeneic (immune cells are from a donor genetically identical to the recipient).

A condition associated with WT-1 expression includes any disorder or condition in which underactivity, overactivity or improper activity of a WT-1 cellular or molecular event is present, and typically results from unusually high (with statistical significance) levels of WT-1 expression in afflicted cells (e.g., leukemic cells), relative to normal cells. A subject having such a disorder or condition would benefit from treatment with a composition or method of the presently described embodiments. Some conditions associated with WT-1 overexpression thus may include acute as well as chronic disorders and diseases, such as those pathological conditions that predispose the subject to a particular disorder.

Diseases and disorders associated with WT-1 expression include the presence of dysplastic, cancerous and/or trans-formed cells in the subject, including, for example neoplastic, tumor, non-contact inhibited or oncogenically transformed cells, or the like (e.g., solid cancers; hematologic cancers including lymphomas and leukemias, such as acute myeloid leukemia, chronic myeloid leukemia, etc.), which are known in the art and for which criteria for diagnosis and classification are established (e.g., Hanahan and Weinberg, 2011 Cell 144:646; Hanahan and Weinberg 2000 Cell 100: 57; Cavallo et al., 2011 Canc. Immunol. Immunother. 60:319; Kyrigideis et al., 2010 J. Carcinog. 9:3). In certain embodiments, such cancer cells may be cells of acute myeloid leukemia, B-cell lymphoblastic leukemia, T-cell lymphoblastic leukemia, or myeloma, including cancer stem cells that are capable of initiating and serially transplanting any of these types of cancer (see, e.g., see Park et al. 2009 Molec. Therap. 17:219). According to certain embodiments, virtually any type of cancer that is characterized by WT-1 overexpression may be treated through the use of compositions and methods disclosed herein, including hematological cancers (e.g., leukemia including acute myeloid leukemia (AML), T or B cell lymphomas, myeloma, and others). Furthermore, "cancer" may refer to any accelerated proliferation of cells, including solid tumors, ascites tumors, blood or lymph or other malignancies; connective tissue malignancies; metastatic disease; minimal residual disease following transplantation of organs or stem cells; multi-drug resistant cancers, primary or secondary malignancies, angiogenesis related to malignancy, or other forms of cancer. Also contemplated within the presently disclosed embodiments are specific embodiments wherein only one of the above types of disease is included, or where specific conditions may be excluded regardless of whether or not they are characterized by WT-1 overexpression.

Some examples of conditions associated with WT-1 overexpression include hyperproliferative disorders and proliferative disorders in a subject including tumors, neoplasms, cancer, malignancy, etc. In addition to activated or proliferating cells, a hyperproliferative or proliferative disorder may also include an aberration or dysregulation of cell death processes, whether by necrosis or apoptosis. Such aberration of cell death processes may be associated with a variety of conditions, including cancer (including primary, secondary malignancies as well as metastasis), or other conditions.

In certain embodiments, presently methods are useful for treating a hematological malignancy or a solid cancer. Exemplary hematological malignancies include acute lymphoblastic leukemia (ALL), acute lymphocytic leukemia, acute myelocytic leukemia, acute myeloid leukemia (AML, including refractory and relapsed AML, and including acute myeloblastic leukemia, acute promyelocitic leukemia, acute myelocytic leukemia, acute myelomonocytic leukemia (e.g., with or without eosinophilia), acute monocytic leukemia, acute erythroid leukemia, and acute megakaryoblastic leukemia), chronic myelogenous leukemia (CML), chronic myelocytic leukemia, chronic eosinophilic leukemia (CEL), myelodysplastic syndrome (MDS), non-Hodgkin's lymphoma (NHL), or multiple myeloma (MM, including refractory and relapsed MM).

In certain embodiments, presently disclosed methods are useful for treating a solid cancer, such as biliary cancer, bladder cancer, bone and soft tissue carcinoma, brain tumor, breast cancer, breast carcinoma, cervical cancer, colon cancer, colorectal adenocarcinoma, colorectal cancer, desmoid tumor, embryonal cancer, endometrial cancer, esophageal cancer, gastric cancer, gastric adenocarcinoma, glioblastoma multiforme, glioblastoma, melanoma, diffuse peritoneal mesothelioma, malignant pleural mesothelioma, glioma, astrocytoma, gynecological tumor, head and neck squamous cell carcinoma, hepatic cancer, hepatocellular carcinoma, lung cancer, non small-cell lung cancer, malignant melanoma, osteosarcoma, ovarian cancer (e.g., epithelial ovarian cancer, ovarian carcinoma), fallopian tube cancer, endometrial carcinoma, pancreatic cancer, pancreatic ductal adenocarcinoma, primary astrocytic tumor, primary thyroid cancer, prostate cancer, renal cancer, renal cell carcinoma, rhabdomyosarcoma, skin cancer, soft tissue sarcoma, osteogenic sarcoma, testicular germ-cell tumor, urothelial cancer, uterine sarcoma, uterine carcinosarcoma, or uterine cancer.

Also provided are pharmaceutical compositions that comprise a binding protein, polynucleotide, vector, host cell, and/or modified immune cell (optionally in combination with an immune cell encoding a binding protein that is capable of binding to a SEQ ID NO.:100:HLA complex) for use according to any of the methods described herein. Pharmaceutical compositions may be administered in a manner appropriate to the disease or condition to be treated (or prevented) as determined by persons skilled in the medical art. An appropriate dose and a suitable duration and frequency of administration of the compositions will be determined by such factors as the health condition of the patient, size of the patient (i.e., weight, mass, or body area), the type and severity of the patient's condition, the particular form of the active ingredient, and the method of administration. In general, an appropriate dose and treatment regimen provide the composition(s) in an amount sufficient to provide therapeutic and/or prophylactic benefit (such as described herein, including an improved clinical outcome, such as more frequent complete or partial remissions, or longer disease-free and/or overall survival, or a lessening of symptom severity).

An effective amount of a pharmaceutical composition refers to an amount sufficient, at dosages and for periods of time needed, to achieve the desired clinical results or beneficial treatment, as described herein. An effective amount may be delivered in one or more administrations. If the administration is to a subject already known or confirmed to have a disease or disease-state, the term "therapeutic amount" may be used in reference to treatment, whereas "prophylactically effective amount" may be used to describe administrating an effective amount to a subject that is susceptible or at risk of developing a disease or disease-state (e.g., recurrence) as a preventative course.

In certain embodiments, a method comprises administering a modified immune cell as provided herein to a subject who has received, is receiving, or will receive an immune cell comprising a polynucleotide that encodes a binding protein that comprises a TCR Vα and a TCR Vβ and is capable of specifically binding to a VLDFAPPGA (SEQ ID NO.:100):HLA complex, wherein, optionally, the HLA comprises HLA-A*0201, and wherein, optionally, the modified immune cell and the immune cell are each independently selected from a T cell, a NK cell, and NK-T cell. In certain embodiments, the binding protein that is capable of specifically binding to the VLDFAPPGA (SEQ ID NO.:100):HLA complex comprises: (a) CDR1α, CDR2α, CDR3α, CDR1β, CDR2β, and CDR3β amino acid sequences of SEQ ID NOs.:101-103 and 105-107, respectively, and wherein, optionally, (1) the Vα has at least 90% identity to, comprises, or consists of the amino acid sequence set forth in SEQ ID NO.:104 and/or (2) the Vβ has at least 90% identity to, comprises, or consists of the amino acid sequence set forth in SEQ ID NO.:108;

(b) CDR1α, CDR2α, CDR3α, CDR1β, CDR2β, and CDR3β amino acid sequences of SEQ ID NOs.:109-110 and 113-115, respectively, and wherein, optionally, (1) the Vα has at least 90% identity to, comprises, or consists of the amino acid sequence set forth in SEQ ID NO.:112 and/or (2) the Vβ has at least 90% identity to, comprises, or consists of the amino acid sequence set forth in SEQ ID NO.:116; or (c) CDR1α, CDR2α, CDR3α, CDR1β, CDR2β, and CDR3β amino acid sequences of SEQ ID NOs.:117-119 and 121-123, respectively, and wherein, optionally, (1) the Vα has at least 90% identity to, comprises, or consists of the amino acid sequence set forth in SEQ ID NO.:120 and/or (2) the Vβ has at least 90% identity to, comprises, or consists of the amino acid sequence set forth in SEQ ID NO.:124.

In general, an appropriate dosage and treatment regimen provides the active molecules or cells in an amount sufficient to provide a benefit. Such a response can be monitored by establishing an improved clinical outcome (e.g., more frequent remissions, complete or partial, or longer disease-free survival) in treated subjects as compared to non-treated subjects. Increases in preexisting immune responses to a tumor protein generally correlate with an improved clinical outcome. Such immune responses may generally be evaluated using standard proliferation, cytotoxicity or cytokine assays, which are routine in the art and may be performed using samples obtained from a subject before and after treatment.

For prophylactic use, a dose should be sufficient to prevent, delay the onset of, or diminish the severity of a disease associated with disease or disorder. Prophylactic benefit of the compositions administered according to the methods described herein can be determined by performing pre-clinical (including in vitro and in vivo animal studies) and clinical studies and analyzing data obtained therefrom by appropriate statistical, biological, and clinical methods and techniques, all of which can readily be practiced by a person skilled in the art.

Certain methods of treatment or prevention contemplated herein include administering a host cell (which may be autologous, allogeneic or syngeneic) comprising a desired nucleic acid molecule as described herein that is stably integrated into the chromosome of the cell, or is present as an extrachromosomal nucleic acid molecule. For example, such a cellular composition may be generated ex vivo using autologous, allogeneic or syngeneic immune system cells (e.g., T cells, antigen-presenting cells, natural killer cells) in order to administer a desired, WT-1-targeted T-cell composition to a subject as an adoptive immunotherapy. In certain embodiments, the immune cell is a CD4$^+$ T cell, a CD8$^+$ T cell, a CD4$^-$CD8$^-$ double negative T cell, a γδ T cell, a natural killer cell, a dendritic cell, or any combination thereof. In further embodiments, the immune cell is a naïve T cell, a central memory T cell, an effector memory T cell, or any combination thereof.

The amount of cells in a composition or unit dose is at least one cell (for example, one modified CD8$^+$ T cell subpopulation (e.g., optionally comprising memory and/or naïve CD8$^+$ T cells); one modified CD4$^+$ T cell subpopulation (e.g., optionally comprising memory and/or naïve CD4$^+$ T cells)) or is more typically greater than 10$^2$ cells, for example, up to 10$^4$, up to 10$^5$, up to 10$^6$, up to 10$^7$, up to 10$^8$, up to 10$^9$, up to 10$^{10}$, or up to 10$^{11}$ cells. In certain embodiments, the cells are administered in a range from about 10$^4$ to about 10$^{11}$ cells/m$^2$, preferably in a range of about 10$^5$ to about 10$^9$ cells/m$^2$. In some embodiments, an administered dose comprises up to about 3.3×10$^5$ cells/kg. In some embodiments, an administered dose comprises up to about 1×10$^6$ cells/kg. In some embodiments, an administered dose comprises up to about 3.3×10$^6$ cells/kg. In some embodiments, an administered dose comprises up to about $1 \times 10^7$ cells/kg. In certain embodiments, a modified immune cell is administered to a subject at a dose comprising up to about $5 \times 10^4$ cells/kg, $5 \times 10^5$ cells/kg, $5 \times 10^6$ cells/kg, or up to about $5 \times 10^7$ cells/kg. In certain embodiments, a modified immune cell is administered to a subject at a dose comprising at least about $5 \times 10^4$ cells/kg, $5 \times 10^5$ cells/kg, $5 \times 10^6$ cells/kg, or up to about $5 \times 10^7$ cells/kg. The number of cells will depend upon the ultimate use for which the composition is intended as well the type of cells included therein. For example, cells modified to contain a binding protein will comprise a cell population containing at least 30%, 35%, 40%, 45%, 50%, 55%, 60%, 65%, 70%, 75%, 80%, 85%, 90%, 95% or more of such cells. For uses provided herein, cells are generally in a volume of a liter or less, 500 mls or less, 250 mls or less, or 100 mls or less. In embodiments, the density of the desired cells is typically greater than $10^4$ cells/ml and generally is greater than $10^7$ cells/ml, generally $10^8$ cells/ml or greater. The cells may be administered as a single infusion or in multiple infusions over a range of time. A clinically relevant number of immune cells can be apportioned into multiple infusions that cumulatively equal or exceed $10^6$, $10^7$, $10^8$, $10^9$, $10^{10}$, or $10^{11}$ cells. In certain embodiments, a unit dose of the modified immune cells can be co-administered with (e.g., simultaneously or contemporaneously with) hematopoietic stem cells from an allogeneic donor. In some embodiments, one or more of the modified immune cells comprised in the unit dose is autologous to the subject.

The pharmaceutical compositions described herein may be presented in unit-dose or multi-dose containers, such as sealed ampoules or vials. Such containers may be frozen to preserve the stability of the formulation until use. In certain embodiments, a unit dose comprises a recombinant host cell as described herein at a dose of about $10^4$ cells/m² to about $10^{11}$ cells/m². The development of suitable dosing and treatment regimens for using the particular compositions described herein in a variety of treatment regimens, including e.g., parenteral or intravenous administration or formulation.

In certain embodiments, a pharmaceutical composition that comprises a modified immune cell as disclosed herein further comprises a pharmaceutically acceptable carrier, diluent, or excipient. The term "pharmaceutically acceptable excipient or carrier" or "physiologically acceptable excipient or carrier" refer to biologically compatible vehicles, e.g., physiological saline, which are described in greater detail herein, that are suitable for administration to a human or other non-human mammalian subject and generally recognized as safe or not causing a serious adverse event.

Suitable excipients include water, saline, dextrose, glycerol, or the like and combinations thereof. In embodiments, compositions comprising fusion proteins or host cells as disclosed herein further comprise a suitable infusion media. Suitable infusion media can be any isotonic medium formulation, typically normal saline, Normosol R (Abbott) or Plasma-Lyte A (Baxter), 5% dextrose in water, Ringer's lactate can be utilized. An infusion medium can be supplemented with human serum albumin or other human serum components.

If the subject composition is administered parenterally, the composition may also include sterile aqueous or oleaginous solution or suspension. Suitable non-toxic parenterally acceptable diluents or solvents include water, Ringer's solution, isotonic salt solution, 1,3-butanediol, ethanol, propylene glycol or polyethylene glycols in mixtures with water. Aqueous solutions or suspensions may further comprise one or more buffering agents, such as sodium acetate, sodium citrate, sodium borate or sodium tartrate. Of course, any material used in preparing any dosage unit formulation should be pharmaceutically pure and substantially non-toxic in the amounts employed. In addition, the active compounds may be incorporated into sustained-release preparation and formulations. Dosage unit form, as used herein, refers to physically discrete units suited as unitary dosages for the subject to be treated; each unit may contain a predetermined quantity of recombinant cells or active compound calculated to produce the desired therapeutic effect in association with an appropriate pharmaceutical carrier.

As used herein, administration of a composition or therapy refers to delivering the same to a subject, regardless of the route or mode of delivery. Administration may be effected continuously or intermittently, and parenterally. Administration may be for treating a subject already confirmed as having a recognized condition, disease or disease state, or for treating a subject susceptible to or at risk of developing such a condition, disease or disease state. Co-administration with an adjunctive therapy may include simultaneous and/or sequential delivery of multiple agents in any order and on any dosing schedule (e.g., modified immune cells with one or more cytokines; immunosuppressive therapy such as calcineurin inhibitors, corticosteroids, microtubule inhibitors, low dose of a mycophenolic acid prodrug, or any combination thereof).

In certain embodiments, a plurality of doses of a modified immune cell or binding protein as described herein is administered to the subject, which may be administered at intervals between administrations of about two to about four weeks. In further embodiments, a cytokine is administered sequentially, provided that the subject was administered the modified immune cell at least three or four times before cytokine administration. In certain embodiments, the cytokine is administered subcutaneously (e.g., IL-2, IL-15, IL-21). In still further embodiments, the subject being treated is further receiving immunosuppressive therapy, such as calcineurin inhibitors, corticosteroids, microtubule inhibitors, low dose of a mycophenolic acid prodrug, or any combination thereof.

Treatment or prevention methods of this disclosure may be administered to a subject as part of a treatment course or regimen, which may comprise additional treatments prior to, or after, administration of the instantly disclosed unit doses, cells, or compositions. For example, in certain embodiments, a subject receiving a unit dose of the modified immune cell is receiving or had previously received a hematopoietic cell transplant (HCT; including myeloablative and non-myeloablative HCT). In some embodiments, the modified immune cell may be administered at least two to at least three months after the non-myeloablative hematopoietic cell transplant. Techniques and regimens for performing HCT are known in the art and can comprise transplantation of any suitable donor cell, such as a cell derived from umbilical cord blood, bone marrow, or peripheral blood, a hematopoietic stem cell, a mobilized stem cell, or a cell from amniotic fluid. Accordingly, in certain embodiments, a modified immune cell of the present disclosure can be administered with or shortly after hematopoietic stem cells in a modified HCT therapy. In some embodiments, the HCT comprises a donor hematopoeitic cell comprising a chromosomal knockout of a gene that encodes an HLA component, a chromosomal knockout of a gene that encodes a TCR component, or both.

In some embodiments, the subject receiving the modified immune cell or binding protein has previously received lymphodepleting chemotherapy. In further embodiments, the lymphodepleting chemotherapy comprises cyclophosph-amide, fludarabine, anti-thymocyte globulin, or a combina-tion thereof.

In certain embodiments, the subject has previously received therapy for AML, or is at-risk for developing or progressing AML.

Methods according to this disclosure may further include administering one or more additional agents to treat the disease or disorder in a combination therapy. In some embodiments, the method further comprises administering a modified immune cell or binding protein with (concurrently, simultaneously, or sequentially) an immune checkpoint inhibitor. In some embodiments, the method comprises administering a modified immune cell with an agonist of a stimulatory immune checkpoint agent. In further embodi-ments, a combination therapy comprises administering a modified immune cell with a secondary therapy, such as a chemotherapeutic agent, a radiation therapy, a surgery, an antibody, or any combination thereof.

As used herein, the term "immune suppression agent" or "immunosuppression agent" refers to one or more cells, proteins, molecules, compounds or complexes providing inhibitory signals to assist in controlling or suppressing an immune response. For example, immune suppression agents include those molecules that partially or totally block immune stimulation; decrease, prevent or delay immune activation; or increase, activate, or up regulate immune suppression. Exemplary immunosuppression agents to target (e.g., with an immune checkpoint inhibitor) include PD-1, PD-L1, PD-L2, LAG3, CTLA4, B7-H3, B7-H4, CD244/ 2B4, HVEM, BTLA, CD160, TIM3, GALS, KIR, PVR1G (CD112R), PVRL2, adenosine, A2aR, immunosuppressive cytokines (e.g., IL-10, IL-4, IL-1RA, IL-35), IDO, arginase, VISTA, TIGIT, LAIR1, CEACAM-1, CEACAM-3, CEACAM-5, Treg cells, or any combination thereof.

An immune suppression agent inhibitor (also referred to as an immune checkpoint inhibitor) may be a compound, an antibody, an antibody fragment or fusion polypeptide (e.g., Fc fusion, such as CTLA4-Fc or LAG3-Fc), an antisense molecule, a ribozyme or RNAi molecule, or a low molecular weight organic molecule. In any of the embodiments dis-closed herein, a method may comprise a modified immune cell or binding protein with one or more inhibitor of any one of the following immune suppression components, singly or in any combination.

In certain embodiments, a modified immune cell or bind-ing protein is used in combination with a PD-1 inhibitor, for example a PD-1-specific antibody or binding fragment thereof, such as pidilizumab, nivolumab, pembrolizumab, MEDI0680 (formerly AMP-514), AMP-224, BMS-936558 or any combination thereof. In further embodiments, a modified immune cell or binding protein of the present disclosure is used in combination with a PD-L1 specific antibody or binding fragment thereof, such as BMS-936559, durvalumab (MEDI4736), atezolizumab (RG7446), ave-lumab (MSB0010718C), MPDL3280A, or any combination thereof.

In certain embodiments, a modified immune cell or bind-ing protein of the present disclosure is used in combination with a LAG3 inhibitor, such as LAG525, IMP321, IMP701, 9H12, BMS-986016, or any combination thereof.

In certain embodiments, a modified immune cell or bind-ing protein is used in combination with an inhibitor of CTLA4. In particular embodiments, a modified immune cell or binding protein is used in combination with a CTLA4 specific antibody or binding fragment thereof, such as ipilimumab, tremelimumab, CTLA4-Ig fusion proteins (e.g., abatacept, belatacept), or any combination thereof.

In certain embodiments, a modified immune cell or bind-ing protein is used in combination with a B7-H3 specific antibody or binding fragment thereof, such as enoblituzumab (MGA271), 376.96, or both. A B7-H4 anti-body binding fragment may be a scFv or fusion protein thereof, as described in, for example, Dangaj et al., Cancer Res. 73:4820, 2013, as well as those described in U.S. Pat. No. 9,574,000 and PCT Patent Publication Nos. WO/201640724A1 and WO 2013/025779A1.

In certain embodiments, a modified immune cell or bind-ing protein is used in combination with an inhibitor of CD244.

In certain embodiments, a modified immune cell or bind-ing protein is used in combination with an inhibitor of BLTA, HVEM, CD160, or any combination thereof Anti CD-160 antibodies are described in, for example, PCT Publication No. WO 2010/084158.

In certain embodiments, a modified immune cell or bind-ing protein is used in combination with an inhibitor of TIM3.

In certain embodiments, a modified immune cell or bind-ing protein is used in combination with an inhibitor of Gal9.

In certain embodiments, a modified immune cell or bind-ing protein is used in combination with an inhibitor of adenosine signaling, such as a decoy adenosine receptor.

In certain embodiments, a modified immune cell or bind-ing protein is used in combination with an inhibitor of A2aR.

In certain embodiments, a modified immune cell or bind-ing protein is used in combination with an inhibitor of KIR, such as lirilumab (BMS-986015).

In certain embodiments, a modified immune cell is used in combination with an inhibitor of an inhibitory cytokine (typically, a cytokine other than TGFβ) or Treg development or activity.

In certain embodiments, a modified immune cell or bind-ing protein is used in combination with an IDO inhibitor, such as levo-1-methyl tryptophan, epacadostat (INCB024360; Liu et al., Blood 115:3520-30, 2010), ebselen (Terentis et al., Biochem. 49:591-600, 2010), indoximod, NLG919 (Mautino et al., American Association for Cancer Research 104th Annual Meeting 2013; Apr. 6-10, 2013), 1-methyl-tryptophan (1-MT)-tira-pazamine, or any combination thereof.

In certain embodiments, a modified immune cell or bind-ing protein is used in combination with an arginase inhibitor, such as N(omega)-Nitro-L-arginine methyl ester (L-NAME), N-omega-hydroxy-nor-1-arginine (nor-NOHA), L-NOHA, 2(S)-amino-6-boronohexanoic acid (ABH), S-(2-boronoethyl)-L-cysteine (BEC), or any com-bination thereof.

In certain embodiments, a modified immune cell or bind-ing protein is used in combination with an inhibitor of VISTA, such as CA-170 (Curis, Lexington, Mass.).

In certain embodiments, a modified immune cell is used in combination with an inhibitor of TIGIT such as, for example, COM902 (Compugen, Toronto, Ontario Canada), an inhibitor of CD155, such as, for example, COM701 (Compugen), or both.

In certain embodiments, a modified immune cell or bind-ing protein is used in combination with an inhibitor of PVRIG, PVRL2, or both. Anti-PVRIG antibodies are described in, for example, PCT Publication No. WO 2016/ 134333. Anti-PVRL2 antibodies are described in, for example, PCT Publication No. WO 2017/021526.

In certain embodiments, an modified immune cell or binding protein is used in combination with a LAIR1 inhibitor.

In certain embodiments, a modified immune cell or binding protein is used in combination with an inhibitor of CEACAM-1, CEACAM-3, CEACAM-5, or any combination thereof.

In certain embodiments, a modified immune cell or binding protein is used in combination with an agent that increases the activity (i.e., is an agonist) of a stimulatory immune checkpoint molecule. For example an modified immune cell or binding protein can be used in combination with a CD137 (4-1BB) agonist (such as, for example, urelumab), a CD134 (OX-40) agonist (such as, for example, MEDI6469, MEDI6383, or MEDI0562), lenalidomide, pomalidomide, a CD27 agonist (such as, for example, CDX-1127), a CD28 agonist (such as, for example, TGN1412, CD80, or CD86), a CD40 agonist (such as, for example, CP-870,893, rhuCD40L, or SGN-40), a CD122 agonist (such as, for example, IL-2) an agonist of GITR (such as, for example, humanized monoclonal antibodies described in PCT Patent Publication No. WO 2016/054638), an agonist of ICOS (CD278) (such as, for example, GSK3359609, mAb 88.2, JTX-2011, Icos 145-1, Icos 314-8, or any combination thereof). In any of the embodiments disclosed herein, a method may comprise administering a modified immune cell or binding protein with one or more agonist of a stimulatory immune checkpoint molecule, including any of the foregoing, singly or in any combination.

In certain embodiments, a combination therapy comprises a modified immune cell or binding protein and a secondary therapy comprising one or more of: an antibody or antigen binding-fragment thereof that is specific for a cancer antigen expressed by the non-inflamed solid tumor, a radiation treatment, a surgery, a chemotherapeutic agent, a cytokine, RNAi, or any combination thereof.

In certain embodiments, a combination therapy method comprises administering a modified immune cell or binding protein and further administering a radiation treatment or a surgery. Radiation therapy is well-known in the art and includes X-ray therapies, such as gamma-irradiation, and radiopharmaceutical therapies. Surgeries and surgical techniques appropriate to treating a given cancer in a subject are well-known to those of ordinary skill in the art.

In certain embodiments, a combination therapy method comprises administering a modified immune cell or binding protein and further administering a chemotherapeutic agent. A chemotherapeutic agent includes, but is not limited to, an inhibitor of chromatin function, a topoisomerase inhibitor, a microtubule inhibiting drug, a DNA damaging agent, an antimetabolite (such as folate antagonists, pyrimidine analogs, purine analogs, and sugar-modified analogs), a DNA synthesis inhibitor, a DNA interactive agent (such as an intercalating agent), and a DNA repair inhibitor. Illustrative chemotherapeutic agents include, without limitation, the following groups: anti-metabolites/anti-cancer agents, such as pyrimidine analogs (5-fluorouracil, floxuridine, capecitabine, gemcitabine and cytarabine) and purine analogs, folate antagonists and related inhibitors (mercaptopurine, thioguanine, pentostatin and 2-chlorodeoxyadenosine (cladribine)); antiproliferative/antimitotic agents including natural products such as vinca alkaloids (vinblastine, vincristine, and vinorelbine), microtubule disruptors such as taxane (paclitaxel, docetaxel), vincristin, vinblastin, nocodazole, epothilones and navelbine, epidipodophyllotoxins (etoposide, teniposide), DNA damaging agents (actinomycin, amsacrine, anthracyclines, bleomycin, busulfan, camptothecin, carboplatin, chlorambucil, cisplatin, cyclophosphamide, Cytoxan, dactinomycin, daunorubicin, doxorubicin, epirubicin, hexamethylmelamineoxaliplatin, iphosphamide, melphalan, mechlorethamine, mitomycin, mitoxantrone, nitrosourea, plicamycin, procarbazine, taxol, taxotere, temozolamide, teniposide, triethylenethiophosphoramide and etoposide (VP 16)); antibiotics such as dactinomycin (actinomycin D), daunorubicin, doxorubicin (adriamycin), idarubicin, anthracyclines, mitoxantrone, bleomycins, plicamycin (mithramycin) and mitomycin; enzymes (L-asparaginase which systemically metabolizes L-asparagine and deprives cells which do not have the capacity to synthesize their own asparagine); antiplatelet agents; antiproliferative/antimitotic alkylating agents such as nitrogen mustards (mechlorethamine, cyclophosphamide and analogs, melphalan, chlorambucil), ethylenimines and methylmelamines (hexamethylmelamine and thiotepa), alkyl sulfonates-busulfan, nitrosoureas (carmustine (BCNU) and analogs, streptozocin), trazenes-dacarbazinine (DTIC); antiproliferative/antimitotic antimetabolites such as folic acid analogs (methotrexate); platinum coordination complexes (cisplatin, carboplatin), procarbazine, hydroxyurea, mitotane, aminoglutethimide; hormones, hormone analogs (estrogen, tamoxifen, goserelin, bicalutamide, nilutamide) and aromatase inhibitors (letrozole, anastrozole); anticoagulants (heparin, synthetic heparin salts and other inhibitors of thrombin); fibrinolytic agents (such as tissue plasminogen activator, streptokinase and urokinase), aspirin, dipyridamole, ticlopidine, clopidogrel, abciximab; antimigratory agents; antisecretory agents (breveldin); immunosuppressives (cyclosporine, tacrolimus (FK-506), sirolimus (rapamycin), azathioprine, mycophenolate mofetil); anti-angiogenic compounds (TNP470, genistein) and growth factor inhibitors (vascular endothelial growth factor (VEGF) inhibitors, fibroblast growth factor (FGF) inhibitors); angiotensin receptor blocker; nitric oxide donors; anti-sense oligonucleotides; antibodies (trastuzumab, rituximab); chimeric antigen receptors; cell cycle inhibitors and differentiation inducers (tretinoin); mTOR inhibitors, topoisomerase inhibitors (doxorubicin (adriamycin), amsacrine, camptothecin, daunorubicin, dactinomycin, eniposide, epirubicin, etoposide, idarubicin, irinotecan (CPT-11) and mitoxantrone, topotecan, irinotecan), corticosteroids (cortisone, dexamethasone, hydrocortisone, methylpednisolone, prednisone, and prenisolone); growth factor signal transduction kinase inhibitors; mitochondrial dysfunction inducers, toxins such as Cholera toxin, ricin, *Pseudomonas* exotoxin, *Bordetella pertussis* adenylate cyclase toxin, or diphtheria toxin, and caspase activators; and chromatin disruptors.

Cytokines may be used to manipulate host immune response towards anticancer activity. See, e.g., Floros & Tarhini, Semin. Oncol. 42(4):539-548, 2015. Cytokines useful for promoting immune anticancer or antitumor response include, for example, IFN-α, IL-2, IL-3, IL-4, IL-10, IL-12, IL-13, IL-15, IL-16, IL-17, IL-18, IL-21, IL-24, and GM-CSF, singly or in any combination with a modified immune cell or binding protein of this disclosure.

In still further aspects, methods are provided for manufacturing a composition of the present disclosure. In certain embodiments, the methods comprise combining (i) an aliquot of a host cell transduced with a vector of the present disclosure with (ii) a pharmaceutically acceptable carrier. In certain embodiments, vectors of the present disclosure are used to transfect/transduce a host cell (e.g., a T cell) for use in adoptive transfer therapy (e.g., targeting a cancer antigen).

In some embodiments, the methods further comprise, prior to the aliquotting, culturing the transduced host cell and selecting the transduced cell as having incorporated (i.e., expressing) the vector. In further embodiments, the methods comprise, following the culturing and selection and prior to the aliquotting, expanding the transduced host cell. In any of the embodiments of the instant methods, the manufactured composition or unit dose may be frozen for later use. Any appropriate host cell can be used for manufacturing a composition or unit dose according to the instant methods, including, for example, a hematopoietic stem cell, a T cell, a primary T cell, a T cell line, a NK cell, or a NK-T cell. In specific embodiments, the methods comprise a host cell which is a CD8+ T cell, a CD4+ T cell, or both.

The present disclosure also includes the following exemplary embodiments.

Embodiment 1. A modified immune cell, comprising a heterologous polynucleotide that encodes a binding protein, wherein the encoded binding protein comprises: (a) a T cell receptor (TCR) a chain variable (Vα) domain comprising the CDR3 amino acid sequence (CDR3α) according to any one of SEQ ID NOs.:28, 19, 22, or 25, or a variant thereof, and a TCR β-chain variable (Vβ) domain; or (b) a TCR Vβ domain comprising the CDR3 amino acid sequence (CDR3β) according to any one of SEQ ID NOs.:40, 31, 34, or 37, or a variant thereof, and a TCR Vα domain; or (c) a TCR Vα domain of (a), and a TCR Vβ domain of (b), wherein the encoded binding protein is capable of binding to a RMFPNAPYL (SEQ ID NO.:94):human leukocyte antigen (HLA), wherein, optionally, the HLA comprises HLA-A*0201.

Embodiment 2. The modified immune cell of embodiment 1, wherein the encoded binding protein is capable of binding to the RMFPNAPYL (SEQ ID NO.:94):HLA complex with an IFNγ production $pEC_{50}$ of 4.0 or higher, or 4.5 or higher.

Embodiment 3. The modified immune cell of embodiment 1 or 2, wherein the encoded binding protein is capable of binding to the RMFPNAPYL (SEQ ID NO.:94): HLA complex with an IFNγ production $pEC_{50}$ of 5.0 or higher.

Embodiment 4. The modified immune cell of any one of embodiments 1-3, wherein the encoded binding protein is capable of binding to the RMFPNAPYL (SEQ ID NO.:94): HLA complex with an IFNγ production $pEC_{50}$ of 5.5 or higher.

Embodiment 5. The modified immune cell of any one of embodiments 1-4, wherein the encoded binding protein is capable of binding to the RMFPNAPYL (SEQ ID NO.:94): HLA complex with an IFNγ production $pEC_{50}$ of 6.0 or higher.

Embodiment 6. The modified immune cell of any one of embodiments 1-5, wherein the encoded binding protein is capable of binding to the RMFPNAPYL (SEQ ID NO.:94): HLA complex with an IFNγ production $pEC_{50}$ of 6.5 or higher.

Embodiment 7. The modified immune cell of any one of embodiments 1-6, wherein the HLA comprises HLA-A*201.

Embodiment 8. The modified immune cell of any one of embodiments 1-7, wherein 50% or more of the modified immune cells in a population produce IFN-γ when the population of the modified immune cells is co-cultured for 4 hours with antigen-presenting cells (e.g., HLA-A*0201+) pulsed with a peptide comprising or consisting of the amino acid sequence RMFPNAPYL (SEQ ID NO.:94) at a peptide concentration of $10^{-4}$ μM, $10^{-5}$ μM, or $10^{-6}$ μM in the co-culture, wherein the antigen-presenting cells optionally comprise T2 cells.

Embodiment 9. The modified immune cell of any one of embodiments 1-8, wherein 10% or more of the modified immune cells in a population are Nur77+ when the population of the modified immune cells is co-cultured (e.g., for about 24 hours) with antigen-presenting cells pulsed with a peptide comprising or consisting of the amino acid sequence RMFPNAPYL (SEQ ID NO.:94) at a peptide concentration of $10^{-2}$ μM in the co-culture, wherein the antigen-presenting cells optionally comprise T2 cells, Jurkat cells, or both.

Embodiment 10. The modified immune cell of embodiment 9, wherein 15% or more of the modified immune cells in the population are Nur77+ when the population of the modified immune cells is co-cultured (e.g., for about 24 hours) with antigen-presenting cells pulsed with a peptide comprising or consisting of the amino acid sequence RMFPNAPYL (SEQ ID NO.:94) at a peptide concentration of $10^{-2}$ μM in the co-culture.

Embodiment 11. The modified immune cell of embodiment 9 or 10, wherein 20% or more of the modified immune cells in the population are Nur77+ when the population of the modified immune cells is co-cultured (e.g., for about 24 hours) with antigen-presenting cells pulsed with a peptide comprising or consisting of the amino acid sequence RMFPNAPYL (SEQ ID NO.:94) at a peptide concentration of $10^{-2}$ μM in the co-culture.

Embodiment 12. The modified immune cell of any one of embodiments 9-11, wherein 40% or more of the modified immune cells in the population are Nur77+ when the population of the modified immune cells is co-cultured (e.g., for about 24 hours) with antigen-presenting cells pulsed with a peptide comprising or consisting of the amino acid sequence RMFPNAPYL (SEQ ID NO.:94) at a peptide concentration of $10^{-2}$ μM in the co-culture.

Embodiment 13. The modified immune cell of any one of embodiments 9-12, wherein 50% or more of the modified immune cells in the population are Nur77+ when the population of the modified immune cells is co-cultured (e.g., for about 24 hours) with antigen-presenting cells pulsed with a peptide comprising or consisting of the amino acid sequence RMFPNAPYL (SEQ ID NO.:94) at a peptide concentration of $10^{-2}$ μM in the co-culture.

Embodiment 14. The modified immune cell of any one of embodiments 1-13, wherein 10% or more of the modified immune cells in the population are Nur77+ when the population of the modified immune cells is co-cultured (e.g., for about 24 hours) with antigen-presenting cells pulsed with a peptide comprising or consisting of the amino acid sequence RMFPNAPYL (SEQ ID NO.:94) at a peptide concentration of $10^{-3}$ μM in the co-culture.

Embodiment 15. The modified immune cell of embodiment 14, wherein 15% or more of the modified immune cells in the population are Nur77+ when the population of the modified immune cells is co-cultured (e.g., for about 24 hours) with antigen-presenting cells pulsed with a peptide comprising or consisting of the amino acid sequence RMFPNAPYL (SEQ ID NO.:94) at a peptide concentration of $10^{-3}$ μM in the co-culture.

Embodiment 16. The modified immune cell of embodiment 14 or 15, wherein 20% or more of the modified immune cells in the population are Nur77+ when the population of the modified immune cells is co-cultured (e.g., for about 24 hours) with antigen-presenting cells pulsed with a peptide comprising or consisting of the amino acid sequence RMFPNAPYL (SEQ ID NO: 94) at a peptide concentration of about $10^{-3}$ μM in the co-culture.

Embodiment 17. The modified immune cell of any one of embodiments 1-16, wherein the modified immune cell is capable of killing 11% or more of HLA-A*0201⁺ MDA-MB-468 cells in a sample when the modified immune cell and the MDA-MB-468 cells are present in the sample at a ratio of 30:1.

Embodiment 18. The modified immune cell of embodiment 17, wherein the modified immune cell is capable of killing 12% or more of HLA-A*0201⁺ MDA-MB-468 cells in a sample when the modified immune cell and the MDA-MB-468 cells are present in the sample at a ratio of 30:1.

Embodiment 19. The modified immune cell of embodiment 17 or 18, wherein the modified immune cell is capable of killing 14% or more of HLA-A*0201⁺ MDA-MB-468 cells in a sample when the modified immune cell and the MDA-MB-468 cells are present in the sample at a ratio of 30:1.

Embodiment 20. The modified immune cell of any one of embodiments 17-19, wherein the modified immune cell is capable of killing 15% or more of HLA-A*0201⁺ MDA-MB-468 cells in a sample when the modified immune cell and the MDA-MB-468 cells are present in the sample at a ratio of 30:1.

Embodiment 21. The modified immune cell of any one of embodiments 17-20, wherein the modified immune cell is capable of killing 20% or more of HLA-A*0201⁺ MDA-MB-468 cells in a sample when the modified immune cell and the MDA-MB-468 cells are present in the sample at a ratio of 30:1.

Embodiment 22. The modified immune cell of any one of embodiments 17-21, wherein the modified immune cell is capable of killing 25% or more of HLA-A*0201⁺ MDA-MB-468 cells in a sample when the modified immune cell and the MDA-MB-468 cells are present in the sample at a ratio of 30:1.

Embodiment 23. The modified immune cell of any one of embodiments 1-22, wherein the modified immune cell is capable of killing 10% or more of HLA-A*0201⁺ MDA-MB-468 cells in a sample when the modified immune cell and the MDA-MB-468 cells are present in the sample at a ratio of 10:1.

Embodiment 24. The modified immune cell of any one of embodiments 1-23, wherein the modified immune cell is capable of killing about 5% or more of HLA-A*0201⁺ MDA-MB-468 cells in a sample when the modified immune cell and the MDA-MB-468 cells are present in the sample at a ratio of 1:1.

Embodiment 25. The modified immune cell of any one of embodiments 1-24, wherein the modified immune cell is capable of killing 21% or more of Panc1 cells in a sample when the modified immune cell and the Panc1 cells are present at a ratio of 30:1.

Embodiment 26. The modified immune cell of embodiment 25, wherein the modified immune cell is capable of killing 22% or more of Panc1 cells in a sample when the modified immune cell and the Panc1 cells are present at a ratio of 30:1.

Embodiment 27. The modified immune cell of embodiment 25 or 26, wherein the modified immune cell is capable of killing 23% or more of Panc1 cells in a sample when the modified immune cell and the Panc1 cells are present at a ratio of 30:1.

Embodiment 28. The modified immune cell of any one of embodiments 25-27, wherein the modified immune cell is capable of killing 24% or more of Panc1 cells in a sample when the modified immune cell and the Panc1 cells are present at a ratio of 30:1.

Embodiment 29. The modified immune cell of any one of embodiments 25-28, wherein the modified immune cell is capable of killing 25% or more of Panc1 cells in a sample when the modified immune cell and the Panc1 cells are present at a ratio of 30:1.

Embodiment 30. The modified immune cell of any one of embodiments 1-29, wherein the modified immune cell has increased killing activity against HLA-A*0201⁺ MDA-MB-468 cells and/or against Panc1 cells in a 4-hour co-culture as compared to a reference immune cell comprising a polynucleotide that encodes a T cell receptor comprising a TCRα chain having the amino acid sequence set forth in SEQ ID NO.:82 and a TCRβ chain having the amino acid sequence set forth in SEQ ID NO.:83.

Embodiment 31. The modified immune cell of any one of embodiments 1-30, wherein the encoded binding protein is capable of binding to a WT-1 peptide:HLA complex on a cell surface independent of CD8 or in the absence of CD8.

Embodiment 32. The modified immune cell of any one of embodiments 1-31, wherein: (i) the encoded Vβ domain comprises or consists of an amino acid sequence having at least 90% identity to the amino acid sequence of any one of SEQ ID NOs.:16, 5, 6, 7, 8, 13, 14, or 15; and/or (ii) the encoded Vα domain comprises or consists of an amino acid sequence having at least 90% identity to the amino acid sequence of any one of SEQ ID NOs.:12, 1, 2, 3, 4, 9, 10, or 11.

Embodiment 33. The modified immune cell of any one of embodiments 1-32, wherein the encoded Vβ domain comprises or consists of an amino acid sequence having at least 90% identity to any one of SEQ ID NOs.: 16, 5, 6, 7, 8, 13, 14, or 15, and/or the encoded Vα domain comprises or consists of an amino acid sequence having at least 90% identity to any one of SEQ ID NOs.:12, 1, 2, 3, 4, 9, 10, or 11, provided that: (i) at least three or four of the CDRs have no mutations; (ii) the CDRs that do have mutations have only up to two amino acid substitutions, up to a contiguous five amino acid deletion, or a combination thereof; and (iii) the encoded binding protein retains its ability to bind to a RMFPNAPYL (SEQ ID NO.:94):HLA complex, optionally with an interferon-gamma (IFNγ) production pEC50 of 4.0, 4.5, 5.0, 5.1, 5.2, 5.3, 5.4, 5.5, 5.6, 5.7, 5.8, 5.9, 6.0, 6.1, 6.2, 6.3, 6.4, 6.5, or higher.

Embodiment 34. The modified immune cell of any one of embodiments 1-33, wherein: (i) the encoded CDR3β comprises or consists of the amino acid sequence set forth in SEQ ID NO.:40, and the encoded CDR3α comprises or consists of the amino acid sequence set forth in SEQ ID NO.:28; (ii) the encoded CDR3β comprises or consists of the amino acid sequence set forth in SEQ ID NO: 31, and the encoded CDR3α comprises or consists of the amino acid sequence set forth in SEQ ID NO: 19; (iii) the encoded CDR3β comprises or consists of the amino acid sequence set forth in SEQ ID NO: 34, and the encoded CDR3α comprises or consists of the amino acid sequence set forth in SEQ ID NO: 22; or (iv) the encoded CDR3β comprises or consists of the amino acid sequence set forth in SEQ ID NO: 37, and the encoded CDR3α comprises or consists of the amino acid sequence set forth in SEQ ID NO: 25.

Embodiment 35. The modified immune cell of any one of embodiments 1-34, wherein: (i) the encoded Vβ domain comprises the CDR1β amino acid sequence of any one of SEQ ID NOs.:38, 29, 32, or 35 and/or the CDR2β amino acid sequence of any one of SEQ ID NOs.: 39, 30, 33, or 36; and/or (ii) the encoded Vα domain comprises the CDR1α amino acid sequence of any one of SEQ ID NOs.:26, 17, 20, or 23, and/or the CDR2α amino acid sequence of any one of SEQ ID NOs.:27, 18, 21, or 24.

Embodiment 36. The modified immune cell of any one of embodiments 1-35, wherein the encoded TCR Vα and Vβ domains comprise CDR1α, CDR2α, CDR3α, CDR1β, CDR2β, and CDR3β amino acid sequences of: (i) SEQ ID NOs.:26-28 and 38-40, respectively; (ii) SEQ ID NOs.:23, 27, 28, and 38-40, respectively; (iii) SEQ ID NOs.: 17-19 and 29-31, respectively; (iv) SEQ ID NOs.: 20-22 and 32-34, respectively; or (v) SEQ ID NOs.: 23-25 and 35-37, respectively.

Embodiment 37. The modified immune cell of any one of embodiments 1-36, wherein the encoded TCR Vβ domain comprises: (i) an amino acid sequence according to a TRBJ02-03 gene segment; and/or (ii) an amino acid sequence according to a TRBV06-05 gene segment, an amino acid sequence according to a TRBV07-09 gene segment, or an amino acid sequence according to a TRBV20-01 gene segment.

Embodiment 38. The modified immune cell of any one of embodiments 1-37, wherein the encoded TCR Vα domain comprises: (i) an amino acid sequence according to a TRAJ43 gene segment; and/or (ii) an amino acid sequence according to a TRAV20-02 gene segment; an amino acid sequence according to a TRAV38DV08 gene segment; or an amino acid sequence according to a TRAV38-01 gene segment.

Embodiment 39. The modified immune cell of embodiment 38, wherein: (i) the encoded TCR Vβ domain comprises an amino acid sequence according to a TRBJ02-03 gene segment; and (ii) the encoded TCR Vα domain comprises an amino acid sequence according to a TRAJ43 gene segment.

Embodiment 40. The modified immune cell of embodiment 38, wherein: (i) the encoded TCR Vβ domain comprises an amino acid sequence according to a TRBV06-05 gene segment; and (ii) the encoded TCR Vα domain comprises an amino acid sequence according to a TRAV20 gene segment.

Embodiment 41. The modified immune cell of embodiment 38, wherein: (i) the encoded TCR Vβ domain comprises an amino acid sequence according to a TRBV07-09 gene segment; and (ii) the encoded TCR Vα domain comprises an amino acid sequence according to a TRAV38DV08 gene segment.

Embodiment 42. The modified immune cell of embodiment 38, wherein: (i) the encoded TCR Vβ domain comprises an amino acid sequence according to a TRBV20-01 gene segment; and (ii) the encoded TCR Vα domain comprises an amino acid sequence according to a TRAV38-01 gene segment.

Embodiment 43. The modified immune cell of any one of embodiments 1-42, wherein: (i) the encoded Vβ domain comprises or consists of the amino acid sequence set forth in SEQ ID NO.:16 or 8, and the encoded Vα domain comprises or consists of the amino acid sequence set forth in SEQ ID NO.:12 or 4; (ii) the encoded Vβ domain comprises or consists of the amino acid sequence set forth in SEQ ID NO.:13 or 5, and the encoded Vα domain comprises or consists of the amino acid sequence set forth in SEQ ID NO.:9 or 1; (iii) the encoded Vβ domain comprises or consists of the amino acid sequence set forth in SEQ ID NO.:14 or 6, and the encoded Vα domain comprises or consists of the amino acid sequence set forth in SEQ ID NO.:10 or 2; or (iv) the encoded Vβ domain comprises or consists of the amino acid sequence set forth in SEQ ID NO.:15 or 7, and the encoded Vα domain comprises or consists of the amino acid sequence set forth in SEQ ID NO.:11 or 3.

Embodiment 44. The modified immune cell of any one of embodiments 1-43, wherein the encoded binding protein further comprises: (i) a TCR α chain constant domain (Cα), or a fragment thereof; and/or (ii) a TCR β chain constant domain (Cβ), or a fragment thereof.

Embodiment 45. The modified immune cell of embodiment 44, wherein the encoded Cα comprises or consists of an amino acid sequence having at least 90% identity to any one of SEQ ID NOs.:41-44.

Embodiment 46. The modified immune cell of embodiment 44 or 45, wherein the encoded Cβ comprises or consists of an amino acid sequence having at least 90% identity to SEQ ID NO.:45.

Embodiment 47. The modified immune cell of any one of embodiments 44-46, wherein the encoded binding protein comprises: (i) a TCR β chain having at least 90% identity to, comprising, or consisting of the amino acid sequence set forth in SEQ ID NO.:61 or 57, and a TCR α chain having at least 90% identity to, comprising, or consisting of the amino acid sequence set forth in SEQ ID NO.:53 or 49; (ii) a TCR β chain having at least 90% identity to, comprising, or consisting of the amino acid sequence set forth in SEQ ID NO.:58 or 54, and a TCR α chain having at least 90% identity to, comprising, or consisting of the amino acid sequence set forth in SEQ ID NO.:50 or 46; (iii) a TCR β chain having at least 90% identity to, comprising, or consisting of the amino acid sequence set forth in SEQ ID NO.:59 or 55, and a TCR α chain having at least 90% identity to, comprising, or consisting of the amino acid sequence set forth in SEQ ID NO.:51 or 52; or (iv) a TCR β chain having at least 90% identity to, comprising, or consisting of the amino acid sequence set forth in SEQ ID NO.:60 or 56, and a TCR α chain having at least 90% identity to, comprising, or consisting of the amino acid sequence set forth in SEQ ID NO.:52 or 48.

Embodiment 48. The modified immune cell of any one of embodiments 1-47, wherein the encoded binding protein is a TCR, a chimeric antigen receptor (CAR), or a single-chain TCR (scTCR).

Embodiment 49. The modified immune cell of any one of embodiments 1-48, wherein the immune cell is a human immune system cell.

Embodiment 50. The modified immune cell of any one of embodiments 1-49, wherein the immune cell is a T cell, optionally a CD4$^+$ T cell, a CD8$^+$ T cell, a CD4$^-$ CD8$^-$ double negative T cell, or a γδ T cell, a natural killer cell, a NK-T cell, a dendritic cell, or any combination thereof.

Embodiment 51. The modified immune cell of embodiment 50, wherein the T cell is a naïve T cell, a central memory T cell, an effector memory T cell, a stem cell memory T cell, or any combination thereof.

Embodiment 52. The modified immune cell of any one of embodiments 1-51, wherein the polynucleotide encoding the binding protein is codon-optimized for expression in the immune cell.

Embodiment 53. The modified immune cell of any one of embodiments 1-52, wherein the polynucleotide encoding the binding protein comprises a polynucleotide having at least 75% identity to the polynucleotide sequence set forth in any one of SEQ ID NOs.:62-77.

Embodiment 54. The modified immune cell of embodiment 53, wherein the polynucleotide encoding the binding protein comprises: (i) a polynucleotide having at least 75% identity to the polynucleotide sequence set forth in SEQ ID NO.:77, and a polynucleotide having at least 75% identity to the polynucleotide sequence set forth in SEQ ID NO.:69; (ii) a polynucleotide having at least 75% identity to the polynucleotide sequence set forth in SEQ ID NO.:74, and a polynucleotide having at least 75% identity to the polynucleotide sequence set forth in SEQ ID NO.:66; (iii) a polynucleotide having at least 75% identity to the polynucleotide sequence set forth in SEQ ID NO.:75, and a polynucleotide having at least 75% identity to the polynucleotide sequence set forth in SEQ ID NO.:67; or (iv) a polynucleotide having at least 75% identity to the polynucleotide sequence set forth in SEQ ID NO.:76, and a polynucleotide having at least 75% identity to the polynucleotide sequence set forth in SEQ ID NO.:68.

Embodiment 55. The modified immune cell of any one of embodiments 1-54, wherein the polynucleotide encoding a binding protein further comprises a polynucleotide encoding a self-cleaving peptide disposed between the Vβ-encoding polynucleotide and the Vα-encoding polynucleotide.

Embodiment 56. The modified immune cell of embodiment 55, wherein the encoded self-cleaving peptide comprises or consists of an amino acid sequence having at least 90% identity to the amino acid sequence set forth in any one of SEQ ID NOs.:84-88.

Embodiment 57. The modified immune cell of embodiment 55 or 56, wherein the polynucleotide encoding a self-cleaving peptide comprises or consists of a polynucleotide sequence having at least 75% identity to the polynucleotide sequence set forth in any one of SEQ ID NOs.: 89-93.

Embodiment 58. The modified immune cell of any one of embodiments 55-57, wherein the polynucleotide encoding a binding protein has a structure from 5'-end to 3'-end of (TCRβ chain-encoding polynucleotide)-(self-cleaving peptide-encoding polynucleotide)-(TCRα chain-encoding polynucleotide).

Embodiment 59. The modified immune cell any one of embodiments 55-58, wherein the polynucleotide encoding a binding protein comprises a polynucleotide having at least 75% identity to the polynucleotide sequence set forth in any one of SEQ ID NOs.:78-81.

Embodiment 60. The modified immune cell of embodiment 53, wherein the polynucleotide encoding a binding protein comprises a polynucleotide comprising or consisting of the polynucleotide sequence set forth in any one of SEQ ID NOs.:78-81.

Embodiment 61. The modified immune cell of any one of embodiments 1-60, further comprising: (i) a heterologous polynucleotide encoding a polypeptide that comprises an extracellular portion of a CD8 co-receptor α chain, wherein, optionally, the encoded polypeptide is or comprises a CD8 co-receptor α chain; (ii) a heterologous polynucleotide encoding a polypeptide that comprises an extracellular portion of a CD8 co-receptor β chain, wherein, optionally, the encoded polypeptide is or comprises a CD8 co-receptor β chain; or (iii) the polynucleotide of (i) and the polynucleotide of (ii), wherein, optionally, the host cell comprises a CD4+ T cell.

Embodiment 62. The host cell of embodiment 61, comprising:
(a) the heterologous polynucleotide encoding a polypeptide comprising an extracellular portion of a CD8 co-receptor α chain wherein, optionally, the encoded polypeptide is or comprises a CD8 co-receptor α chain; (b) the heterologous polynucleotide encoding a polypeptide comprising an extracellular portion of a CD8 co-receptor β chain, wherein, optionally, the encoded polypeptide is or comprises a CD8 co-receptor β chain; and (c) a polynucleotide encoding a self-cleaving peptide disposed between the polynucleotide of (a) and the polynucleotide of (b).

Embodiment 63. The modified immune cell of any one of embodiments 1-62, wherein the immune cell comprises a chromosomal gene knockout of a PD-1 gene; a LAG3 gene; a TIM3 gene; a CTLA4 gene; an HLA component gene; a TCR component gene; or any combination thereof.

Embodiment 64. The modified immune cell of embodiment 63, wherein the chromosomal gene knockout comprises a knockout of an HLA component gene selected from an α1 macroglobulin gene; an α2 macroglobulin gene; an α3 macroglobulin gene; a β1 microglobulin gene; or a β2 microglobulin gene; or any combination thereof.

Embodiment 65. The modified immune cell of embodiment 63 or 64, wherein the chromosomal gene knockout comprises a knockout of a TCR component gene selected from a TCR α variable region gene; a TCR β variable region gene; a TCR constant region gene; or any combination thereof.

Embodiment 66. An isolated polynucleotide encoding a binding protein, wherein the encoded binding protein comprises a TCR Vα domain and a TCR domain and is capable of binding to a RMFPNAPYL (SEQ ID NO.:94):HLA complex, wherein: (i) the encoded Vα domain comprises the CDR3 amino acid sequence set forth in any one of SEQ ID NOs.:28, 19, 22, or 25; (ii) the encoded Vβ domain comprises the CDR3 amino acid sequence set forth in any one of SEQ ID NOs.:40, 31, 34, or 37; (iii) the encoded Vα domain comprises the CDR1 amino acid sequence set forth in any one of SEQ ID NOs.:26, 17, 20, or 23; (iv) the encoded Vβ domain comprises the CDR1 amino acid sequence set forth in any one of SEQ ID NOs.:38, 32, or 35; (v) the encoded Vα domain comprises the CDR2 amino acid sequence set forth in any one of SEQ ID NOs.:27, 18, 21, or 24; (vi) the encoded Vβ domain comprises the CDR2 amino acid sequence set forth in any one of SEQ ID NO.:39, 30, 33, or 36; (vii) the encoded Vα domain comprises or consists of an amino acid sequence having at least 90% identity to the amino acid sequence set forth in any one of SEQ ID NOs.:4, 1-3, 12, or 9-11; (viii) the encoded Vβ domain comprises or consists of an amino acid sequence having at least 90% identity to the amino acid sequence set forth in any one of SEQ ID NOs.:8, 5-7, 16, or 13-15; (ix) the encoded TCR Vα is comprised in a TCRα chain, wherein the TCRα chain comprises or consists of an amino acid sequence having at least 90% identity to the amino acid sequence set forth in any one of SEQ ID NOs.:53 and 46-52; (x) the encoded TCR Vβ is comprised in a TCRβ chain, wherein the TCRβ chain an amino acid sequence comprising, consisting of, or having at least 90% identity to the amino acid sequence set forth in any one of SEQ ID NOs.:61 and 54-60; or (xi) any combination of (i)-(x).

Embodiment 67. The isolated polynucleotide of embodiment 66, wherein the polynucleotide is codon-optimized for expression in a host cell, wherein, optionally, the host cell is a human T cell, NK cell, or NK-T cell.

Embodiment 68. The isolated polynucleotide of embodiment 66 or 67, wherein the polynucleotide comprises a polynucleotide having at least 75% identity to the polynucleotide sequence set forth in any one of SEQ ID NOs: 62-81.

Embodiment 69. A vector, comprising the polynucleotide of any one of embodiments 66-68.

Embodiment 70. The vector of embodiment 69, wherein the vector is a lentiviral vector or a retroviral vector.

Embodiment 71. A host cell, comprising the polynucleotide of any one of embodiments 66-68 and capable of expressing the encoded binding protein.

Embodiment 72. A composition, comprising: (i) the modified immune cell of any one of embodiments 1-65; (ii) the polynucleotide of any one of embodiments 66-68; (iii) the vector of embodiment 69 or 70; and/or (iv) the host cell of embodiment 71; and a pharmaceutically acceptable carrier, excipient, or diluent.

Embodiment 73. The composition of embodiment 72, comprising:
(i) the modified immune cell of any one of embodiments 1-65; and (ii) an immune cell comprising a polynucleotide that encodes a binding protein that comprises a TCR Vα and a TCR Vβ and is capable of specifically binding to a VLDFAPPGA (SEQ ID NO.:100):HLA complex, wherein, optionally, the HLA comprises HLA-A*0201, and wherein, optionally, the modified immune cell of (i) and the immune cell of (ii) are each independently selected from a T cell, a NK cell, and NK-T cell.

Embodiment 74. The composition of embodiment 73, wherein the binding protein of the immune cell in (ii) comprises: (a) CDR1α, CDR2α, CDR3α, CDR1β, CDR2β, and CDR3β amino acid sequences of SEQ ID NOs.:101-103 and 105-107, respectively, and wherein, optionally, (1) the Vα has at least 90% identity to, comprises, or consists of the amino acid sequence set forth in SEQ ID NO.:104 and/or (2) the Vβ has at least 90% identity to, comprises, or consists of the amino acid sequence set forth in SEQ ID NO.:108; (b) CDR1α, CDR2α, CDR3α, CDR1β, CDR2β, and CDR3β amino acid sequences of SEQ ID NOs.:109-110 and 113-115, respectively, and wherein, optionally, (1) the Vα has at least 90% identity to, comprises, or consists of the amino acid sequence set forth in SEQ ID NO.:112 and/or (2) the Vβ has at least 90% identity to, comprises, or consists of the amino acid sequence set forth in SEQ ID NO.:116; or (c) CDR1α, CDR2α, CDR3α, CDR1β, CDR2β, and CDR3β amino acid sequences of SEQ ID NOs.:117-119 and 121-123, respectively, and wherein, optionally, (1) the Vα has at least 90% identity to, comprises, or consists of the amino acid sequence set forth in SEQ ID NO.:120 and/or (2) the Vβ has at least 90% identity to, comprises, or consists of the amino acid sequence set forth in SEQ ID NO.:124.

Embodiment 75. A method for treating a subject having a disease or disorder associated with WT-1 expression, comprising administering to the subject an effective amount of:
(i) the modified immune cell of any one of embodiments 1-65; (ii) the polynucleotide of any one of embodiments 66-68; (iii) the vector of embodiment 69 or 70; (iv) the host cell of embodiment 71; and/or (v) the composition of any one of embodiments 72-74.

Embodiment 76. The method of embodiment 75, comprising administering the modified immune cell of any one of embodiments 1-65 to a subject who has received, is receiving, or will receive an immune cell comprising a polynucleotide that encodes a binding protein that comprises a TCR Vα and a TCR Vβ and is capable of specifically binding to a VLDFAPPGA (SEQ ID NO.:100):HLA complex, wherein, optionally, the HLA comprises HLA-A*0201, and wherein, optionally, the modified immune cell and the immune cell are each independently selected from a T cell, a NK cell, and NK-T cell.

Embodiment 77. The method of embodiment 76, wherein the binding protein that is capable of specifically binding to the VLDFAPPGA (SEQ ID NO.:100):HLA complex comprises: (a) CDR1α, CDR2α, CDR3α, CDR1β, CDR2β, and CDR3β amino acid sequences of SEQ ID NOs.:101-103 and 105-107, respectively, and wherein, optionally, (1) the Vα has at least 90% identity to, comprises, or consists of the amino acid sequence set forth in SEQ ID NO.:104 and/or (2) the Vβ has at least 90% identity to, comprises, or consists of the amino acid sequence set forth in SEQ ID NO.:108; (b)

CDR1α, CDR2α, CDR3α, CDR1β, CDR2β, and CDR3β amino acid sequences of SEQ ID NOs.:109-110 and 113-115, respectively, and wherein, optionally, (1) the Vα has at least 90% identity to, comprises, or consists of the amino acid sequence set forth in SEQ ID NO.:112 and/or (2) the Vβ has at least 90% identity to, comprises, or consists of the amino acid sequence set forth in SEQ ID NO.:116; or (c) CDR1α, CDR2α, CDR3α, CDR1β, CDR2β, and CDR3β amino acid sequences of SEQ ID NOs.:117-119 and 121-123, respectively, and wherein, optionally, (1) the Vα has at least 90% identity to, comprises, or consists of the amino acid sequence set forth in SEQ ID NO.:120 and/or (2) the Vβ has at least 90% identity to, comprises, or consists of the amino acid sequence set forth in SEQ ID NO.:124.

Embodiment 78. The method of any one of embodiments 75-77, wherein the disease or disorder is a hematological malignancy or a solid cancer.

Embodiment 79. The method of embodiment 78, wherein the hematological malignancy is selected from acute lymphoblastic leukemia (ALL), acute lymphocytic leukemia, acute myelocytic leukemia, acute myeloid leukemia (AML, including refractory and relapsed AML, and including acute myeloblastic leukemia, acute promyelocitic leukemia, acute myelocytic leukemia, acute myelomonocytic leukemia (e.g., with or without eosinophilia), acute monocytic leukemia, acute erythroid leukemia, and acute megakaryoblastic leukemia), chronic myelogenous leukemia (CIVIL), chronic myelocytic leukemia, chronic eosinophilic leukemia (CEL), myelodysplastic syndrome (MDS), non-Hodgkin's lymphoma (NHL), or multiple myeloma (MM, including refractory and relapsed MM).

Embodiment 80. The method of embodiment 78, wherein the solid cancer is selected from biliary cancer, bladder cancer, bone and soft tissue carcinoma, brain tumor, breast cancer, breast carcinoma, cervical cancer, colon cancer, colorectal adenocarcinoma, colorectal cancer, desmoid tumor, embryonal cancer, endometrial cancer, esophageal cancer, gastric cancer, gastric adenocarcinoma, glioblastoma multiforme, glioblastoma, melanoma, diffuse peritoneal mesothelioma, malignant pleural mesothelioma, glioma, astrocytoma, gynecological tumor, head and neck squamous cell carcinoma, hepatic cancer, hepatocellular carcinoma, lung cancer, non small-cell lung cancer, malignant melanoma, osteosarcoma, ovarian cancer (e.g., epithelial ovarian cancer, ovarian carcinoma), fallopian tube cancer, endometrial carcinoma, pancreatic cancer, pancreatic ductal adenocarcinoma, primary astrocytic tumor, primary thyroid cancer, prostate cancer, renal cancer, renal cell carcinoma, rhabdomyosarcoma, skin cancer, soft tissue sarcoma, osteogenic sarcoma, testicular germ-cell tumor, urothelial cancer, uterine sarcoma, uterine carcinosarcoma, or uterine cancer.

Embodiment 81. The method according to any one of embodiments 75-80, wherein the modified immune cell is modified ex vivo to comprise the heterologous polynucleotide.

Embodiment 82. The method according to any one of embodiments 75-81, wherein the modified immune cell is allogeneic, syngeneic, or autologous to the subject.

Embodiment 83. The method according to any one of embodiments 75-82, wherein the modified immune cell is a hematopoietic progenitor cell or a human immune system cell.

Embodiment 84. The method according to embodiment 83, wherein the immune system cell is a CD4+ T cell, a CD8+ T cell, a CD4− CD8− double negative T cell, a γδ T cell, a natural killer cell, a dendritic cell, or any combination thereof.

Embodiment 85. The method according to embodiment 84, wherein the T cell is a naïve T cell, a central memory T cell, an effector memory T cell, or any combination thereof.

Embodiment 86. The method according to any one of embodiments 75-85, wherein the method comprises administering a plurality of doses of the modified immune cell to the subject.

Embodiment 87. The method according to embodiment 86, wherein the plurality of doses are administered at intervals between administrations of about two to about four weeks.

Embodiment 88. The method according to any one of embodiments 75-87, wherein the modified immune cell is administered to the subject at a dose of about $10^4$ cells/kg to about $10^{11}$ cells/kg.

Embodiment 89. The method according to any one of embodiments 75-88, wherein the method further comprises administering a cytokine to the subject.

Embodiment 90. The method according to embodiment 89, wherein the cytokine is IL-2, IL-15, IL-21 or any combination thereof.

Embodiment 91. The method according to embodiment 90, wherein the cytokine is IL-2 and is administered concurrently or sequentially with the modified immune cell.

Embodiment 92. The method according to embodiment 91, wherein the cytokine is administered sequentially, provided that the subject was administered the modified immune cell at least three or four times before cytokine administration.

Embodiment 93. The method according to any one of embodiments 89-92, wherein the cytokine is IL-2 and is administered subcutaneously.

Embodiment 94. The method according to any one of embodiments 75-93, wherein the subject is further receiving immunosuppressive therapy.

Embodiment 95. The method according to embodiment 94, wherein the immunosuppressive therapy is selected from calcineurin inhibitors, corticosteroids, microtubule inhibitors, low dose of a mycophenolic acid prodrug, or any combination thereof.

Embodiment 96. The method according to any one of embodiments 75-95, wherein the subject has received a non-myeloablative or a myeloablative hematopoietic cell transplant.

Embodiment 97. The method according to embodiment 96, wherein the subject is administered the modified immune cell at least three months after the non-myeloablative hematopoietic cell transplant.

Embodiment 98. The method according to embodiment 97, wherein the subject is administered the modified immune cell at least two months after the myeloablative hematopoietic cell transplant.

Embodiment 99. The method of any one of embodiments 75-98, wherein the subject has previously received therapy for AML.

Embodiment 100. A composition, comprising: (i) the modified immune cell of any one of embodiments 1-65; (ii) the polynucleotide of any one of embodiments 66-68; (iii) the vector of embodiment 69 or 70; and/or (iv) the host cell of embodiment 71, for use in the treatment of a disease or disorder associated with WT-1 expression.

Embodiment 101. A composition, comprising: (i) the modified immune cell of any one of embodiments 1-65; (ii) the polynucleotide of any one of embodiments 66-68; (iii) the vector of embodiment 69 or 70; and/or (iv) the host cell of embodiment 71, for use in the manufacture of a medicament for the treatment of a disease or disorder associated with WT-1 expression.

Embodiment 102. The composition for use according to embodiment 100 or 101, wherein the disease or disorder is a hematological malignancy or a solid cancer.

Embodiment 103. The composition for use according to embodiment 102, wherein the hematological malignancy is selected from acute lymphoblastic leukemia (ALL), acute lymphocytic leukemia, acute myelocytic leukemia, acute myeloid leukemia (AML, including refractory and relapsed AML, and including acute myeloblastic leukemia, acute promyelocitic leukemia, acute myelocytic leukemia, acute myelomonocytic leukemia (e.g., with or without eosinophilia), acute monocytic leukemia, acute erythroid leukemia, and acute megakaryoblastic leukemia), chronic myelogenous leukemia (CML), chronic myelocytic leukemia, chronic eosinophilic leukemia (CEL), myelodysplastic syndrome (MDS), non-Hodgkin's lymphoma (NHL), or multiple myeloma (MM, including refractory and relapsed MM).

Embodiment 104. The composition for use according to embodiment 102, wherein the solid cancer is selected from biliary cancer, bladder cancer, bone and soft tissue carcinoma, brain tumor, breast cancer, breast carcinoma, cervical cancer, colon cancer, colorectal adenocarcinoma, colorectal cancer, desmoid tumor, embryonal cancer, endometrial cancer, esophageal cancer, gastric cancer, gastric adenocarcinoma, glioblastoma multiforme, glioblastoma, melanoma, diffuse peritoneal mesothelioma, malignant pleural mesothelioma, glioma, astrocytoma, gynecological tumor, head and neck squamous cell carcinoma, hepatic cancer, hepatocellular carcinoma, lung cancer, non small-cell lung cancer, malignant melanoma, osteosarcoma, ovarian cancer (e.g., epithelial ovarian cancer, ovarian carcinoma), fallopian tube cancer, endometrial carcinoma, pancreatic cancer, pancreatic ductal adenocarcinoma, primary astrocytic tumor, primary thyroid cancer, prostate cancer, renal cancer, renal cell carcinoma, rhabdomyosarcoma, skin cancer, soft tissue sarcoma, osteogenic sarcoma, testicular germ-cell tumor, urothelial cancer, uterine sarcoma, uterine carcinosarcoma, or uterine cancer.

Embodiment 105. A binding protein comprising a T cell receptor (TCR) a chain variable (Vα) domain and a TCR β chain variable (Vβ) domain, wherein: the Vα domain comprises: (i) the CDR3 amino acid sequence (CDR3α) according to any one of SEQ ID NOs.:28, 19, 22, or 25, or 28, or a variant thereof; (ii) the CDR1 amino acid sequence (CDR1α) of any one of SEQ ID NOs.:26, 17, 20, or 23; (iii) the CDR2 amino acid sequence (CDR2α) of any one of SEQ ID NOs.: 27, 18, 21, or 24; (iv) an amino acid sequence having at least 90% identity to the amino acid sequence set forth in any one of SEQ ID NOs:1-4 or 9-12; or (v) any combination of (i)-(iv); and the Vβ domain comprises: (vi) the CDR3 amino acid sequence (CDR3β) according to any one of SEQ ID NOs: 40, 31, 34, or 37, or a variant thereof; (vii) the CDR1 amino acid sequence (CDR1β) of any one of SEQ ID NOs.:38, 29, 32, or 35; (viii) the CDR2 amino acid sequence (CDR2β) of any one of SEQ ID NOs.:39, 30, 33, or 36; (ix) an amino acid sequence having at least 90% identity to the amino acid sequence set forth in any one of SEQ ID NOs:5-8 or 13-16; or (x) any combination of (vi)-(x), and wherein the binding protein of embodiment 105, which is capable of binding to a RMFPNAPYL (SEQ ID NO:94):HLA complex, wherein, optionally, the HLA comprises HLA-A*0201.

Embodiment 106. The binding protein of embodiment 105, further comprising: (1) a TCR α chain constant domain (Cα), or a fragment thereof; and/or (2) a TCR β chain constant domain (Cβ), or a fragment thereof.

Embodiment 107. The binding protein of embodiment 106, wherein the Ca comprises or consists of the amino acid sequence of any one of SEQ ID NOs.:41-44.

Embodiment 108. The binding protein of embodiment 106 or 107, wherein the Cβ comprises or consists of the amino acid sequence of SEQ ID NO.:45.

Embodiment 109. An isolated polynucleotide encoding the binding protein of any one of embodiments 105-108.

Embodiment 110. The polynucleotide of embodiment 109, which is codon-optimized for expression in a host cell.

Embodiment 111. A modified immune cell, comprising the polynucleotide of any one of embodiments 109-110, wherein the polynucleotide is heterologous to the immune cell.

---

SEQUENCES

SEQ ID NO: 1 (#4 α chain variable domain with leader sequence)
MKSLRVLLVILWLQLSWVWSQQKEVEQNSGPLSVPEGAIASLNCTYSDRGSQS
FFWYRQYSGKSPELIMFIYSNGDKEDGRFTAQLNKASQYVSLLIRDSQPSDSAT
YLCAVNIGNHDMRFGAGTRLTVKPN SEQ ID NO: 2 (#6 α chain variable domain with leader sequence)
MEKMLECAFIVLWLQLGWLSGEDQVTQSPEALRLQEGESSSLNCSYTVSGLRG
LFWYRQDPGKGPEFLFTLYSAGEEKEKERLKATLTKKESFLHITAPKPEDSATY
LCAVQTMDGNQFYFGTGTSLTVIPN SEQ ID NO: 3 (#7 α chain variable domain with leader sequence)
MACPGFLWALVISTCLEFSMAQTVTQSQPEMSVQEAETVTLSCTYDTSESDYY
LFWYKQPPSRQMILVIRQEAYKQQNATENRFSVNFQKAAKSFSLKISDSQLGDA
AMYFCASSPGTYKYIFGTGTRLKVLAN SEQ ID NO: 4 (#10 α chain variable domain with leader sequence)
MTRVSLLWAVVVSTCLESGMAQTVTQSQPEMSVQEAETVTLSCTYDTSESNY
YLFWYKQPPSRQMILVIRQEAYKQQNATENRFSVNFQKAAKSFSLKISDSQLGD
TAMYFCAFNPWENYGQNFVFGPGTRLSVLPY SEQ ID NO: 5 (#4 β chain variable domain with leader sequence)
MGCRLLCCAVLCLLGAVPIDTEVTQTPKHLVMGMTNKKSLKCEQHMGHRAM
YWYKQKAKKPPELMFVYSYEKLSINESVPSRFSPECPNSSLLNLHLHALQPEDS
ALYLCASSQGTSGADTQYFGPGTRLTVLE SEQ ID NO: 6 (#6 β chain variable domain with leader sequence)
MSIGLLCCAALSLLWAGPVNAGVTQTPKFQVLKTGQSMTLQCAQDMNHEYM
SWYRQDPGMGLRLIHYSVGAGITDQGEVPNGYNVSRSTTEDFPLRLLSAAPSQT
SVYFCASSYSLWDLQETQYFGPGTRLLVLE SEQ ID NO: 7 (#7 β chain variable domain with leader sequence)
MGTSLLCWMALCLLGADHADTGVSQDPRHKITKRGQNVTFRCDPISEHNRLY
WYRQTLGQGPEFLTYFQNEAQLEKSRLLSDRFSAERPKGSFSTLEIQRTEQGDS
AMYLCASSFSDGGATDTQYFGPGTRLTVLE SEQ ID NO: 8 (#10 β chain variable domain with leader sequence)
MLLLLLLLGPAGSGLGAVVSQHPSWVICKSGTSVKIECRSLDFQATTMFWYRQ
FPKQSLMLMATSNEGSKATYEQGVEKDKFLINHASLTLSTLTVTSAHPEDSSFYI
CSARPHSLTDTQYFGPGTRLTVLE SEQ ID NO: 9 (#4 α chain variable domain, leader sequence removed)
QKEVEQNSGPLSVPEGAIASLNCTYSDRGSQSFFWYRQYSGKSPELIMFIYSNG
DKEDGRFTAQLNKASQYVSLLIRDSQPSDSATYLCAVNIGNHDMRFGAGTRLT
VKPN SEQ ID NO: 10 (#6 α chain variable domain, leader sequence removed)
EDQVTQSPEALRLQEGESSSLNCSYTVSGLRGLFWYRQDPGKGPEFLFTLYSAG
EEKEKERLKATLTKKESFLHITAPKPEDSATYLCAVQTMDGNQFYFGTGTSLTV
IPN SEQ ID NO: 11 (#7 α chain variable domain, leader sequence removed)
AQTVTQSQPEMSVQEAETVTLSCTYDTSESDYYLFWYKQPPSRQMILVIRQEA
YKQQNATENRFSVNFQKAAKSFSLKISDSQLGDAAMYFCASSPGTYKYIFGTGT
RLKVLAN SEQ ID NO: 12 (#10 α chain variable domain, leader sequence removed)
AQTVTQSQPEMSVQEAETVTLSCTYDTSESNYYLFWYKQPPSRQMILVIRQEA
YKQQNATENRFSVNFQKAAKSFSLKISDSQLGDTAMYFCAFNPWENYGQNFVF
GPGTRLSVLPY SEQ ID NO: 13 (#4 β chain variable domain, leader sequence removed)
DTEVTQTPKHLVMGMTNKKSLKCEQHMGHRAMYWYKQKAKKPPELMFVYS
YEKLSINESVPSRFSPECPNSSLLNLHLHALQPEDSALYLCASSQGTSGADTQYF
GPGTRLTVLE -continued

---

SEQUENCES

---

SEQ ID NO: 14 (#6 β chain variable domain, leader sequence removed)
NAGVTQTPKFQVLKTGQSMTLQCAQDMNHEYMSWYRQDPGMGLRLIHYSVG
AGITDQGEVPNGYNVSRSTTEDFPLRLLSAAPSQTSVYFCASSYSLWDLQETQY
FGPGTRLLVLE SEQ ID NO: 15 (#7 β chain variable domain, leader sequence removed)
DTGVSQDPRHKITKRGQNVTFRCDPISEHNRLYWYRQTLGQGPEFLTYFQNEA
QLEKSRLLSDRFSAERPKGSFSTLEIQRTEQGDSAMYLCASSFSDGGATDTQYF
GPGTRLTVLE SEQ ID NO: 16 (#10 β chain variable domain, leader sequence removed)
GAVVSQHPSWVICKSGTSVKIECRSLDFQATTMFWYRQFPKQSLMLMATSNEG
SKATYEQGVEKDKFLINHASLTLSTLTVTSAHPEDSSFYICSARPHSLTDTQYFG
PGTRLTVLE

SEQ ID NO: 17 (#4 CDR1α)
DRGSQS

SEQ ID NO: 18 (#4 CDR2α)
IYSNGD

SEQ ID NO: 19 (#4 CDR3α)
CAVNIGNHDMRF

SEQ ID NO: 20 (#6 CDR1α)
VSGLRG

SEQ ID NO: 21 (#6 CDR2α)
LYSAGEE

SEQ ID NO: 22 (#6 CDR3α)
CAVQTMDGNQFYF

SEQ ID NO: 23 (#7 CDR1α)
TSESDYY

SEQ ID NO: 24 (#7 CDR2α)
QEAYKQQN

SEQ ID NO: 25 (#7 CDR3α)
CASSPGTYKYIF

SEQ ID NO: 26 (#10 CDR1α)
TSESNYY

SEQ ID NO: 27 (#10 CDR2α)
QEAYKQQN

SEQ ID NO: 28 (#10 CDR3α)
CAFNPWENYGQNFVF

SEQ ID NO: 29 (#4 CDR1β)
MGHRA

SEQ ID NO: 30 (#4 CDR2β)
YSYEKL

SEQ ID NO: 31 (#4 CDR3β)
CASSQGTSGADTQYF

SEQ ID NO: 32 (#6 CDR1β)
MNHEY

SEQ ID NO: 33 (#6 CDR2β)
SVGAGI

SEQ ID NO: 34 (#6 CDR3β)
CASSYSLWDLQETQYF

SEQ ID NO: 35 (#7 CDR1β)
SEHNR

SEQ ID NO: 36 (#7 CDR2β)
FQNEAQ

SEQ ID NO: 37 (#7 CDR3β)
CASSFSDGGATDTQYF

-continued

| SEQUENCES |
| --- |

SEQ ID NO: 38 (#10 CDR1β)
DFQATT

SEQ ID NO: 39 (#10 CDR2β)
SNEGSKA

SEQ ID NO: 40 (#10 CDR3β)
CSARPHSLTDTQYF

SEQ ID NO: 41 (#4 TCR α constant domain)
IQNPDPAVYQLRDSKSSDKSVCLFTDFDSQTNVSQSKDSDVYITDKCVLDMRS
MDFKSNSAVAWSNKSDFACANAFNNSIIPEDTFFPSPESSCDVKLVEKSFETDTN
LNFQNLSVIGFRILLLKVAGFNLLMTLRLWSS SEQ ID NO: 42 (#6 TCR α constant domain)
IQNPDPAVYQLRDSKSSDKSVCLFTDFDSQTNVSQSKDSDVYITDKCVLDMRS
MDFKSNSAVAWSNKSDFACANAFNNSIIPEDTFFPSPESSCDVKLVEKSFETDTN
LNFQNLSVIGFRILLLKVAGFNLLMTLRLWSS SEQ ID NO: 43 (#7 TCR α constant domain)
IQNPDPAVYQLRDSKSSDKSVCLFTDFDSQTNVSQSKDSDVYITDKCVLDMRS
MDFKSNSAVAWSNKSDFACANAFNNSIIPEDTFFPSPESSCDVKLVEKSFETDTN
LNFQNLSVIGFRILLLKVAGFNLLMTLRLWSS SEQ ID NO: 44 (#10 TCR α constant domain)
IQNPDPAVYQLRDSKSSDKSVCLFTDFDSQTNVSQSKDSDVYITDKCVLDMRS
MDFKSNSAVAWSNKSDFACANAFNNSIIPEDTFFPSPESSCDVKLVEKSFETDTN
LNFQNLSVIGFRILLLKVAGFNLLMTLRLWSS SEQ ID NO: 45 (TCR β constant domain)
DLKNVFPPEVAVFEPSEAEISHTQKATLVCLATGFYPDHVELSWWVNGKEVHS
GVCTDPQPLKEQPALNDSRYCLSSRLRVSATFWQNPRNHFRCQVQFYGLSEND
EWTQDRAKPVTQIVSAEAWGRADCGFTSESYQQGVLSATILYEILLGKATLYA
VLVSALVLMAMVKRKDSRG SEQ ID NO: 46 (#4 α chain with leader sequence)
MKSLRVLLVILWLQLSWVWSQQKEVEQNSGPLSVPEGAIASLNCTYSDRGSQS
FFWYRQYSGKSPELIMFIYSNGDKEDGRFTAQLNKASQYVSLLIRDSQPSDSAT
YLCAVNIGNHDMRFGAGTRLTVKPNIQNPDPAVYQLRDSKSSDKSVCLFTDFD
SQTNVSQSKDSDVYITDKCVLDMRSMDFKSNSAVAWSNKSDFACANAFNNSII
PEDTFFPSPESSCDVKLVEKSFETDTNLNFQNLSVIGFRILLLKVAGFNLLMTLRL
WSS SEQ ID NO: 47 (#6 α chain with leader sequence)
MEKMLECAFIVLWLQLGWLSGEDQVTQSPEALRLQEGESSSLNCSYTVSGLRG
LFWYRQDPGKGPEFLFTLYSAGEEKEKERLKATLTKKESFLHITAPKPEDSATY
LCAVQTMDGNQFYFGTGTSLTVIPNIQNPDPAVYQLRDSKSSDKSVCLFTDFDS
QTNVSQSKDSDVYITDKCVLDMRSMDFKSNSAVAWSNKSDFACANAFNNSIIP
EDTFFPSPESSCDVKLVEKSFETDTNLNFQNLSVIGFRILLLKVAGFNLLMTLRL
WSS SEQ ID NO: 48 (#7 α chain with leader sequence)
MACPGFLWALVISTCLEFSMAQTVTQSQPEMSVQEAETVTLSCTYDTSESDYY
LFWYKQPPSRQMILVIRQEAYKQQNATENRFSVNFQKAAKSFSLKISDSQLGDA
AMYFCASSPGTYKYIFGTGTRLKVLANIQNPDPAVYQLRDSKSSDKSVCLFTDF
DSQTNVSQSKDSDVYITDKCVLDMRSMDFKSNSAVAWSNKSDFACANAFNNS
IIPEDTFFPSPESSCDVKLVEKSFETDTNLNFQNLSVIGFRILLLKVAGFNLLMTL
RLWSS SEQ ID NO: 49 (#10 α chain with leader sequence)
MTRVSLLWAVVVSTCLESGMAQTVTQSQPEMSVQEAETVTLSCTYDTSESNY
YLFWYKQPPSRQMILVIRQEAYKQQNATENRFSVNFQKAAKSFSLKISDSQLGD
TAMYFCAFNPWENYGQNFVFGPGTRLSVLPYIQNPDPAVYQLRDSKSSDKSVC
LFTDFDSQTNVSQSKDSDVYITDKCVLDMRSMDFKSNSAVAWSNKSDFACAN
AFNNSIIPEDTFFPSPESSCDVKLVEKSFETDTNLNFQNLSVIGFRILLLKVAGFNL
LMTLRLWSS SEQ ID NO: 50 (#4 α chain, leader sequence removed)
QKEVEQNSGPLSVPEGAIASLNCTYSDRGSQSFFWYRQYSGKSPELIMFIYSNG
DKEDGRFTAQLNKASQYVSLLIRDSQPSDSATYLCAVNIGNHDMRFGAGTRLT
VKPNIQNPDPAVYQLRDSKSSDKSVCLFTDFDSQTNVSQSKDSDVYITDKCVLD
MRSMDFKSNSAVAWSNKSDFACANAFNNSIIPEDTFFPSPESSCDVKLVEKSFE
TDTNLNFQNLSVIGFRILLLKVAGFNLLMTLRLWSS -continued

SEQUENCES

SEQ ID NO: 51 (#6 α chain, leader sequence removed)
EDQVTQSPEALRLQEGESSSLNCSYTVSGLRGLFWYRQDPGKGPEFLFTLYSAG
EEKEKERLKATLTKKESFLHITAPKPEDSATYLCAVQTMDGNQFYFGTGTSLTV
IPNIQNPDPAVYQLRDSKSSDKSVCLFTDFDSQTNVSQSKDSDVYITDKCVLDM
RSMDFKSNSAVAWSNKSDFACANAFNNSIIPEDTFFPSPESSCDVKLVEKSFETD
TNLNFQNLSVIGFRILLLKVAGFNLLMTLRLWSS SEQ ID NO: 52 (#7 α chain, leader sequence removed)
AQTVTQSQPEMSVQEAETVTLSCTYDTSESDYYLFWYKQPPSRQMILVIRQEA
YKQQNATENRFSVNFQKAAKSFSLKISDSQLGDAAMYFCASSPGTYKYIFGTGT
RLKVLANIQNPDPAVYQLRDSKSSDKSVCLFTDFDSQTNVSQSKDSDVYITDKC
VLDMRSMDFKSNSAVAWSNKSDFACANAFNNSIIPEDTFFPSPESSCDVKLVEK
SFETDTNLNFQNLSVIGFRILLLKVAGFNLLMTLRLWSS SEQ ID NO: 53 (#10 α chain, leader sequence removed)
AQTVTQSQPEMSVQEAETVTLSCTYDTSESNYYLFWYKQPPSRQMILVIRQEA
YKQQNATENRFSVNFQKAAKSFSLKISDSQLGDTAMYFCAFNPWENYGQNFVF
GPGTRLSVLPYIQNPDPAVYQLRDSKSSDKSVCLFTDFDSQTNVSQSKDSDVYI
TDKCVLDMRSMDFKSNSAVAWSNKSDFACANAFNNSIIPEDTFFPSPESSCDVK
LVEKSFETDTNLNFQNLSVIGFRILLLKVAGFNLLMTLRLWSS SEQ ID NO: 54 (#4 β chain with leader sequence)
MGCRLLCCAVLCLLGAVPIDTEVTQTPKHLVMGMTNKKSLKCEQHMGHRAM
YWYKQKAKKPPELMFVYSYEKLSINESVPSRFSPECPNSSLLNLHLHALQPEDS
ALYLCASSQGTSGADTQYFGPGTRLTVLEDLKNVFPPEVAVFEPSEAEISHTQK
ATLVCLATGFYPDHVELSWWVNGKEVHSGVCTDPQPLKEQPALNDSRYCLSS
RLRVSATFWQNPRNHFRCQVQFYGLSENDEWTQDRAKPVTQIVSAEAWGRAD
CGFTSESYQQGVLSATILYEILLGKATLYAVLVSALVLMAMVKRKDSRG SEQ ID NO: 55 (#6 β chain with leader sequence)
MSIGLLCCAALSLLWAGPVNAGVTQTPKFQVLKTGQSMTLQCAQDMNHEYM
SWYRQDPGMGLRLIHYSVGAGITDQGEVPNGYNVSRTTEDFPLRLLSAAPSQT
SVYFCASSYSLWDLQETQYFGPGTRLLVLEDLKNVFPPEVAVFEPSEAEISHTQ
KATLVCLATGFYPDHVELSWWVNGKEVHSGVCTDPQPLKEQPALNDSRYCLS
SRLRVSATFWQNPRNHFRCQVQFYGLSENDEWTQDRAKPVTQIVSAEAWGRA
DCGFTSESYQQGVLSATILYEILLGKATLYAVLVSALVLMAMVKRKDSRG SEQ ID NO: 56 (#7 β chain with leader sequence)
MGTSLLCWMALCLLGADHADTGVSQDPRHKITKRGQNVTFRCDPISEHNRLY
WYRQTLGQGPEFLTYFQNEAQLEKSRLLSDRFSAERPKGSFSTLEIQRTEQGDS
AMYLCASSFSDGGATDTQYFGPGTRLTVLEDLKNVFPPEVAVFEPSEAEISHTQ
KATLVCLATGFYPDHVELSWWVNGKEVHSGVCTDPQPLKEQPALNDSRYCLS
SRLRVSATFWQNPRNHFRCQVQFYGLSENDEWTQDRAKPVTQIVSAEAWGRA
DCGFTSESYQQGVLSATILYEILLGKATLYAVLVSALVLMAMVKRKDSRG SEQ ID NO: 57 (#10 β chain with leader sequence)
MLLLLLLLGPAGSGLGAVVSQHPSWVICKSGTSVKIECRSLDFQATTMFWYRQ
FPKQSLMLMATSNEGSKATYEQGVEKDKFLINHASLTLSTLTVTSAHPEDSSFYI
CSARPHSLTDTQYFGPGTRLTVLEDLKNVFPPEVAVFEPSEAEISHTQKATLVCL
ATGFYPDHVELSWWVNGKEVHSGVCTDPQPLKEQPALNDSRYCLSSRLRVSA
TFWQNPRNHFRCQVQFYGLSENDEWTQDRAKPVTQIVSAEAWGRADCGFTSE
SYQQGVLSATILYEILLGKATLYAVLVSALVLMAMVKRKDSRG SEQ ID NO: 58 (#4 β chain, leader sequence removed)
DTEVTQTPKHLVMGMTNKKSLKCEQHMGHRAMYWYKQKAKKPPELMFVYS
YEKLSINESVPSRFSPECPNSSLLNLHLHALQPEDSALYLCASSQGTSGADTQYF
GPGTRLTVLEDLKNVFPPEVAVFEPSEAEISHTQKATLVCLATGFYPDHVELSW
WVNGKEVHSGVCTDPQPLKEQPALNDSRYCLSSRLRVSATFWQNPRNHFRCQ
VQFYGLSENDEWTQDRAKPVTQIVSAEAWGRADCGFTSESYQQGVLSATILYE
ILLGKATLYAVLVSALVLMAMVKRKDSRG SEQ ID NO: 59 (#6 β chain, leader sequence removed)
NAGVTQTPKFQVLKTGQSMTLQCAQDMNHEYMSWYRQDPGMGLRLIHYSVG
AGITDQGEVPNGYNVSRTTEDFPLRLLSAAPSQTSVYFCASSYSLWDLQETQY
FGPGTRLLVLEDLKNVFPPEVAVFEPSEAEISHTQKATLVCLATGFYPDHVELS
WWVNGKEVHSGVCTDPQPLKEQPALNDSRYCLSSRLRVSATFWQNPRNHFRC
QVQFYGLSENDEWTQDRAKPVTQIVSAEAWGRADCGFTSESYQQGVLSATILY
EILLGKATLYAVLVSALVLMAMVKRKDSRG SEQ ID NO: 60 (#7 β chain, leader sequence removed)
DTGVSQDPRHKITKRGQNVTFRCDPISEHNRLYWYRQTLGQGPEFLTYFQNEA
QLEKSRLLSDRFSAERPKGSFSTLEIQRTEQGDSAMYLCASSFSDGGATDTQYF
GPGTRLTVLEDLKNVFPPEVAVFEPSEAEISHTQKATLVCLATGFYPDHVELSW
WVNGKEVHSGVCTDPQPLKEQPALNDSRYCLSSRLRVSATFWQNPRNHFRCQ
VQFYGLSENDEWTQDRAKPVTQIVSAEAWGRADCGFTSESYQQGVLSATILYE
ILLGKATLYAVLVSALVLMAMVKRKDSRG

SEQUENCES

SEQ ID NO: 61 (#10 β chain, leader sequence removed)
GAVVSQHPSWVICKSGTSVKIECRSLDFQATTMFWYRQFPKQSLMLMATSNEG
SKATYEQGVEKDKFLINHASLTLSTLTVTSAHPEDSSFYICSARPHSLTDTQYFG
PGTRLTVLEDLKNVFPPEVAVFEPSEAEISHTQKATLVCLATGFYPDHVELSWW
VNGKEVHSGVCTDPQPLKEQPALNDSRYCLSSRLRVSATFWQNPRNHFRCQVQ
FYGLSENDEWTQDRAKPVTQIVSAEAWGRADCGFTSESYQQGVLSATILYEILL
GKATLYAVLVSALVLMAMVKRKDSRG SEQ ID NO: 62 (#4 α gene fragment)
ATGAAATCCTTGAGAGTTTTACTAGTGATCCTGTGGCTTCAGTTGAGCTGGG
TTTGGAGCCAACAGAAGGAGGTGGAGCAGAATTCTGGACCCCTCAGTGTTC
CAGAGGGAGCCATTGCCTCTCTCAACTGCACTTACAGTGACCGAGGTTCCC
AGTCCTTCTTCTGGTACAGACAATATTCTGGGAAAAGCCCTGAGTTGATAAT
GTTCATATACTCCAATGGTGACAAAGAAGATGGAAGGTTTACAGCACAGCT
CAATAAAGCCAGCCAGTATGTTTCTCTGCTCATCAGAGACTCCCAGCCCAGT
GATTCAGCCACCTACCTCTGTGCCGTGAACATAGGAAACCATGACATGCGC
TTTGGAGCAGGGACCAGACTGACAGTAAAACCAAATATCCAGAACCCTGAC
CCTGCCGTGTACCAGCTGAGAGACTCTAAATCCAGTGACAAGTCTGTCTGCC
TATTCACCGATTTTGATTCTCAAACAAATGTGTCACAAAGTAAGGATTCTGA
TGTGTATATCACAGACAAAACTGTGCTAGACATGAGGTCTATGGACTTCAA
GAGCAACAGTGCTGTGGCCTGGAGCAACAAATCTGACTTTGCATGTGCAAA
CGCCTTCAACAACAGCATTATTCCAGAAGACACCTTCTTCCCCAGCCCAGAA
AGTTCCTGTGATGTCAAGCTGGTCGAGAAAAGCTTTGAAACAGATACGAAC
CTAAACTTTCAAAACCTGTCAGTGATTGGGTTCCGAATCCTCCTCCTGAAAG
TGGCCGGGTTTAATCTGCTCATGACGCTGCGGCTGTGGTCCAGCTGA SEQ ID NO: 63 (#6 α gene fragment)
ATGGAGAAAATGTTGGAGTGTGCATTCATAGTCTTGTGGCTTCAGCTTGGCT
GGTTGAGTGGAGAAGACCAGGTGACGCAGAGTCCCGAGGCCCTGAGACTCC
AGGAGGGAGAGAGTAGCAGTCTCAACTGCAGTTACACAGTCAGCGGTTTAA
GAGGGCTGTTCTGGTATAGGCAAGATCCTGGGAAAGGCCCTGAATTCCTCT
TCACCCTGTATTCAGCTGGGGAAGAAAAGGAGAAAGAAAGGCTAAAAGCC
ACATTAACAAAGAAGGAAAGCTTTCTGCACATCACAGCCCCTAAACCTGAA
GACTCAGCCACTTATCTCTGTGCTGTGCAGACCATGGACGGTAACCAGTTCT
ATTTTGGGACAGGGACAAGTTTGACGGTCATTCCAAATATCCAGAACCCTG
ACCCTGCCGTGTACCAGCTGAGAGACTCTAAATCCAGTGACAAGTCTGTCT
GCCTATTCACCGATTTTGATTCTCAAACAAATGTGTCACAAAGTAAGGATTC
TGATGTGTATATCACAGACAAAACTGTGCTAGACATGAGGTCTATGGACTT
CAAGAGCAACAGTGCTGTGGCCTGGAGCAACAAATCTGACTTTGCATGTGC
AAACGCCTTCAACAACAGCATTATTCCAGAAGACACCTTCTTCCCCAGCCCA
GAAAGTTCCTGTGATGTCAAGCTGGTCGAGAAAAGCTTTGAAACAGATACG
AACCTAAACTTTCAAAACCTGTCAGTGATTGGGTTCCGAATCCTCCTCCTGA
AAGTGGCCGGGTTTAATCTGCTCATGACGCTGCGGCTGTGGTCCAGCTGA SEQ ID NO: 64 (#7 α gene fragment)
ATGGCATGCCCTGGCTTCCTGTGGGCACTTGTGATCTCCACCTGTCTTGAAT
TTAGCATGGCTCAGACAGTCACTCAGTCTCAACCAGAGATGTCTGTGCAGG
AGGCAGAGACCGTGACCCTGAGCTGCACATATGACACCAGTGAGAGTGATT
ATTATTTATTCTGGTACAAGCAGCCTCCCAGCAGGCAGATGATTCTCGTTAT
TCGCCAAGAAGCTTATAAGCAACAGAATGCAACAGAGAATCGTTTCTCTGT
GAACTTCCAGAAAGCAGCCAAATCCTTCAGTCTCAAGATCTCAGACTCACA
GCTGGGGGATGCCGCGATGTATTTCTGTGCTTCCAGTCCAGGAACCTACAA
ATACATCTTTGGAACAGGCACCAGGCTGAAGGTTTTAGCAAATATCCAGAA
CCCTGACCCTGCCGTGTACCAGCTGAGAGACTCTAAATCCAGTGACAAGTC
TGTCTGCCTATTCACCGATTTTGATTCTCAAACAAATGTGTCACAAAGTAAG
GATTCTGATGTGTATATCACAGACAAAACTGTGCTAGACATGAGGTCTATG
GACTTCAAGAGCAACAGTGCTGTGGCCTGGAGCAACAAATCTGACTTTGCA
TGTGCAAACGCCTTCAACAACAGCATTATTCCAGAAGACACCTTCTTCCCCA
GCCCAGAAAGTTCCTGTGATGTCAAGCTGGTCGAGAAAAGCTTTGAAACAG
ATACGAACCTAAACTTTCAAAACCTGTCAGTGATTGGGTTCCGAATCCTCCT
CCTGAAAGTGGCCGGGTTTAATCTGCTCATGACGCTGCGGCTGTGGTCCAGC
TGA SEQ ID NO: 65 (#10 α gene fragment)
ATGACACGAGTTAGCTTGCTGTGGGCAGTCGTGGTCTCCACCTGTCTTGAAT
CCGGCATGGCCCAGACAGTCACTCAGTCTCAACCAGAGATGTCTGTGCAGG
AGGCAGAGACTGTGACCCTGAGTTGCACATATGACACCAGTGAGAGTAATT
ATTATTTGTTCTGGTACAAACAGCCTCCCAGCAGGCAGATGATTCTCGTTAT
TCGCCAAGAAGCTTATAAGCAACAGAATGCAACGGAGAATCGTTTCTCTGT
GAACTTCCAGAAAGCAGCCAAATCCTTCAGTCTCAAGATCTCAGACTCACA
GCTGGGGGACACTGCGATGTATTTCTGTGCTTTCAACCCTTGGGAGAACTAT
GGTCAGAATTTTGTCTTTGGTCCCGGAACCAGATTGTCCGTGCTGCCCTATA
TCCAGAACCCTGACCCTGCCGTGTACCAGCTGAGAGACTCTAAATCCAGTG
ACAAGTCTGTCTGCCTATTCACCGATTTTGATTCTCAAACAAATGTGTCACA
AAGTAAGGATTCTGATGTGTATATCACAGACAAAACTGTGCTAGACATGAG
GTCTATGGACTTCAAGAGCAACAGTGCTGTGGCCTGGAGCAACAAATCTGA
CTTTGCATGTGCAAACGCCTTCAACAACAGCATTATTCCAGAAGACACCTTC -continued

SEQUENCES

TTCCCCAGCCCAGAAAGTTCCTGTGATGTCAAGCTGGTCGAGAAAAGCTTT
GAAACAGATACGAACCTAAACTTTCAAAACCTGTCAGTGATTGGGTTCCGA
ATCCTCCTCCTGAAAGTGGCCGGGTTTAATCTGCTCATGACGCTGCGGCTGT
GGTCCAGCTGA

SEQ ID NO: 66 (#4 α gene fragment, codon-optimized)
ATGAAGAGCCTGAGAGTCCTGCTGGTGATTTTGTGGCTGCAGCTGTCTTGGG
TTTGGTCTCAGCAGAAAGAAGTGGAGCAGAATAGCGGCCCTCTGTCTGTTC
CTGAAGGCGCTATTGCTAGCCTGAATTGCACATACAGCGATAGAGGATCTC
AGAGCTTCTTCTGGTACCGGCAGTACAGCGGCAAGAGCCCAGAACTGATCA
TGTTCATCTACAGCAATGGCGACAAGGAGGATGGCAGGTTTACAGCCCAGC
TGAACAAGGCCAGCCAGTATGTTTCTCTGCTGATCAGAGATAGCCAGCCTA
GCGATTCTGCCACCTACCTGTGTGCCGTGAACATCGGAAATCACGACATGA
GATTTGGAGCCGGCACAAGACTGACCGTGAAGCCCAATATCCAGAACCCTG
ATCCTGCTGTGTACCAGCTGCGGGACAGCAAGAGCAGCGACAAGAGCGTGT
GCCTGTTCACCGACTTCGACAGCCAGACCAACGTGTCCCAGAGCAAGGACA
GCGACGTGTACATCACCGATAAGTGCGTGCTGGACATGCGGAGCATGGACT
TCAAGAGCAACAGCGCCGTGGCCTGGTCCAACAAGAGCGACTTCGCCTGCG
CCAACGCCTTCAACAACAGCATTATCCCCGAGGACACATTCTTCCCAAGCCC
CGAGAGCAGCTGCGACGTGAAGCTGGTGGAAAAGAGCTTCGAGACAGACA
CCAACCTGAACTTCCAGAACCTCAGCGTGATCGGCTTCCGGATCCTGCTGCT
GAAGGTGGCCGGCTTCAACCTGCTGATGACCCTGCGGCTGTGGTCCAGCTG
A SEQ ID NO: 67 (#6 α gene fragment, codon-optimized)
ATGGAGAAGATGCTGGAGTGTGCGTTCATCGTTCTGTGGCTGCAACTTGGAT
GGCTGTCTGGAGAGGATCAGGTTACACAGTCTCCTGAAGCCCTGAGACTGC
AAGAAGGAGAAAGCTCTAGCCTGAACTGCAGCTACACAGTGTCTGGACTGA
GAGGCCTGTTCTGGTACAGACAGGATCCTGGAAAAGGCCCAGAGTTCCTGT
TTACCCTGTATTCTGCCGGCGAGGAGAAGGAGAAAGAGAGACTGAAAGCTA
CCCTGACCAAGAAGGAGAGCTTCCTGCACATTACCGCCCCCAAACCTGAGG
ATTCTGCCACATATCTGTGTGCTGTGCAGACCATGGATGGCAACCAGTTCTA
CTTCGGCACAGGCACATCTCTGACCGTTATCCCCAATATCCAGAACCCTGAT
CCTGCCGTGTACCAGCTGCGGGACAGCAAGAGCAGCGACAAGAGCGTGTGC
CTGTTCACCGACTTCGACAGCCAGACCAACGTGTCCCAGAGCAAGGACAGC
GACGTGTACATCACCGATAAGTGCGTGCTGGACATGCGGAGCATGGACTTC
AAGAGCAACAGCGCCGTGGCCTGGTCCAACAAGAGCGACTTCGCCTGCGCC
AACGCCTTCAACAACAGCATTATCCCCGAGGACACATTCTTCCCAAGCCCC
GAGAGCAGCTGCGACGTGAAGCTGGTGGAAAAGAGCTTCGAGACAGACAC
CAACCTGAACTTCCAGAACCTCAGCGTGATCGGCTTCCGGATCCTGCTGCTG
AAGGTGGCCGGCTTCAACCTGCTGATGACCCTGCGGCTGTGGTCCAGCTGA SEQ ID NO: 68 (#7 α gene fragment, codon-optimized)
ATGGCTTGTCCTGGATTCTTATGGGCTCTGGTGATCAGCACCTGTCTGGAGT
TCTCTATGGCCCAGACAGTGACACAGTCTCAGCCTGAAATGTCTGTGCAGG
AAGCCGAAACCGTGACACTGTCTTGCACCTACGATACAAGCGAGAGCGACT
ACTACCTGTTCTGGTACAAGCAGCCTCCCTCTAGGCAGATGATCCTGGTGAT
TAGACAGGAGGCCTACAAACAGCAGAATGCCACCGAGAACCGGTTTAGCGT
GAACTTCCAGAAAGCCGCCAAGAGCTTCAGCCTGAAAATCTCTGACAGCCA
GCTGGGAGATGCTGCCATGTACTTTTGTGCCAGCTCTCCAGGCACCTACAAG
TACATTTTTGGCACCGGCACCAGACTGAAGGTGCTGGCCAATATCCAGAAT
CCCGATCCTGCCGTGTACCAGCTGCGGGACAGCAAGAGCAGCGACAAGAGC
GTGTGCCTGTTCACCGACTTCGACAGCCAGACCAACGTGTCCCAGAGCAAG
GACAGCGACGTGTACATCACCGATAAGTGCGTGCTGGACATGCGGAGCATG
GACTTCAAGAGCAACAGCGCCGTGGCCTGGTCCAACAAGAGCGACTTCGCC
TGCGCCAACGCCTTCAACAACAGCATTATCCCCGAGGACACATTCTTCCCAA
GCCCCGAGAGCAGCTGCGACGTGAAGCTGGTGGAAAAGAGCTTCGAGACA
GACACCAACCTGAACTTCCAGAACCTCAGCGTGATCGGCTTCCGGATCCTG
CTGCTGAAGGTGGCCGGCTTCAACCTGCTGATGACCCTGCGGCTGTGGTCCA
GCTGA SEQ ID NO: 69 (#10 α gene fragment, codon-optimized)
ATGACCAGAGTTAGCCTGTTATGGGCTGTGGTGGTGAGCACATGTCTGGAA
TCTGGAATGGCCCAGACAGTGACACAGTCTCAGCCTGAAATGTCTGTGCAG
GAAGCCGAAACCGTTACACTGAGCTGCACCTACGATACAAGCGAGAGCAAC
TACTACCTGTTCTGGTACAAGCAGCCCCCCTTCTAGGCAGATGATCCTGGTGA
TCAGACAGGAGGCCTATAAACAGCAGAATGCCACCGAGAACCGGTTTAGCG
TGAACTTCCAGAAAGCCGCCAAGAGCTTCAGCCTGAAAATCTCTGACAGCC
AGCTGGGCGATACAGCCATGTACTTTTGTGCCTTCAACCCCTGGGAGAACTA
TGGCCAGAATTTCGTGTTCGGCCCTGGCACCAGACTGTCTGTTCTGCCTTAT
ATCCAGAACCCCGATCCTGCTGTGTACCAGCTGCGGGACAGCAAGAGCAGC
GACAAGAGCGTGTGCCTGTTCACCGACTTCGACAGCCAGACCAACGTGTCC
CAGAGCAAGGACAGCGACGTGTACATCACCGATAAGTGCGTGCTGGACATG
CGGAGCATGGACTTCAAGAGCAACAGCGCCGTGGCCTGGTCCAACAAGAGC

| SEQUENCES |
| --- |

```
GACTTCGCCTGCGCCAACGCCTTCAACAACAGCATTATCCCCGAGGACACA
TTCTTCCCAAGCCCCGAGAGCAGCTGCGACGTGAAGCTGGTGGAAAAGAGC
TTCGAGACAGACACCAACCTGAACTTCCAGAACCTCAGCGTGATCGGCTTC
CGGATCCTGCTGCTGAAGGTGGCCGGCTTCAACCTGCTGATGACCCTGCGG
CTGTGGTCCAGCTGA

SEQ ID NO: 70 (#4 β gene fragment)
ATGGGCTGCAGGCTGCTCTGCTGTGCGGTTCTCTGTCTCCTGGGAGCAGTTC
CCATAGACACTGAAGTTACCCAGACACCAAAACACCTGGTCATGGGAATGA
CAAATAAGAAGTCTTTGAAATGTGAACAACATATGGGGCACAGGGCTATGT
ATTGGTACAAGCAGAAAGCTAAGAAGCCACCGGAGCTCATGTTTGTCTACA
GCTATGAGAAACTCTCTATAAATGAAAGTGTGCCAAGTCGCTTCTCACCTGA
ATGCCCCAACAGCTCTCTCTTAAACCTTCACCTACACGCCCTGCAGCCAGAA
GACTCAGCCCTGTATCTCTGCGCCAGCAGCCAAGGGACTAGCGGGGCAGAT
ACGCAGTATTTTGGCCCAGGCACCCGGCTGACAGTGCTCGAGGACCTGAAA
AACGTGTTCCCACCCGAGGTCGCTGTGTTTGAGCCATCAGAAGCAGAGATC
TCCCACACCCAAAAGGCCACACTGGTGTGCCTGGCCACAGGCTTCTACCCC
GACCACGTGGAGCTGAGCTGGTGGGTGAATGGGAAGGAGGTGCACAGTGG
GGTCAGCACAGACCCGCAGCCCCTCAAGGAGCAGCCCGCCCTCAATGACTC
CAGATACTGCCTGAGCAGCCGCCTGAGGGTCTCGGCCACCTTCTGGCAGAA
CCCCCGCAACCACTTCCGCTGTCAAGTCCAGTTCTACGGGCTCTCGGAGAAT
GACGAGTGGACCCAGGATAGGGCCAAACCTGTCACCCAGATCGTCAGCGCC
GAGGCCTGGGGTAGAGCAGACTGTGGCTTCACCTCCGAGTCTTACCAGCAA
GGGGTCCTGTCTGCCACCATCCTCTATGAGATCTTGCTAGGGAAGGCCACCT
TGTATGCCGTGCTGGTCAGTGCCCTCGTGCTGATGGCCATGGTCAAGAGAA
AGGATTCCAGAGGCTAG SEQ ID NO: 71 (#6 β gene fragment)
ATGAGCATCGGCCTCCTGTGCTGTGCAGCCTTGTCTCTCCTGTGGGCAGGTC
CAGTGAATGCTGGTGTCACTCAGACCCCAAAATTCCAGGTCCTGAAGACAG
GACAGAGCATGACACTGCAGTGTGCCCAGGATATGAACCATGAATACATGT
CCTGGTATCGACAAGACCCAGGCATGGGGCTGAGGCTGATTCATTACTCAG
TTGGTGCTGGTATCACTGACCAAGGAGAAGTCCCCAATGGCTACAATGTCT
CCAGATCAACCACAGAGGATTTCCCGCTCAGGCTGCTGTCGGCTGCTCCCTC
CCAGACATCTGTGTACTTCTGTGCCAGCAGTTACTCTCTTTGGGACCTTCAA
GAGACCCAGTACTTCGGGCCAGGCACGCGGCTCCTGGTGCTCGAGGACCTG
AAAAACGTGTTCCCACCCGAGGTCGCTGTGTTTGAGCCATCAGAAGCAGAG
ATCTCCCACACCCAAAAGGCCACACTGGTGTGCCTGGCCACAGGCTTCTAC
CCCGACCACGTGGAGCTGAGCTGGTGGGTGAATGGGAAGGAGGTGCACAG
TGGGGTCAGCACAGACCCGCAGCCCCTCAAGGAGCAGCCCGCCCTCAATGA
CTCCAGATACTGCCTGAGCAGCCGCCTGAGGGTCTCGGCCACCTTCTGGCA
GAACCCCCGCAACCACTTCCGCTGTCAAGTCCAGTTCTACGGGCTCTCGGAG
AATGACGAGTGGACCCAGGATAGGGCCAAACCTGTCACCCAGATCGTCAGC
GCCGAGGCCTGGGGTAGAGCAGACTGTGGCTTCACCTCCGAGTCTTACCAG
CAAGGGGTCCTGTCTGCCACCATCCTCTATGAGATCTTGCTAGGGAAGGCC
ACCTTGTATGCCGTGCTGGTCAGTGCCCTCGTGCTGATGGCCATGGTCAAGA
GAAAGGATTCCAGAGGCTAG SEQ ID NO: 72 (#7 β gene fragment)
ATGGGCACCAGCCTCCTCTGCTGGATGGCCCTGTGTCTCCTGGGGGCAGATC
ACGCAGATACTGGAGTCTCCCAGGACCCCAGACACAAGATCACAAAGAGG
GGACAGAATGTAACTTTCAGGTGTGATCCAATTTCTGAACACAACCGCCTTT
ATTGGTACCGACAGACCCTGGGGCAGGGCCCAGAGTTTCTGACTTACTTCC
AGAATGAAGCTCAACTAGAAAAATCAAGGCTGCTCAGTGATCGGTTCTCTG
CAGAGAGGCCTAAGGGATCTTTCTCCACCTTGGAGATCCAGCGCACAGAGC
AGGGGGACTCGGCCATGTATCTCTGTGCCAGCAGCTTTTCAGACGGGGGGG
CTACAGATACGCAGTATTTTGGCCCAGGCACCCGGCTGACAGTGCTCGAGG
ACCTGAAAAACGTGTTCCCACCCGAGGTCGCTGTGTTTGAGCCATCAGAAG
CAGAGATCTCCCACACCCAAAAGGCCACACTGGTGTGCCTGGCCACAGGCT
TCTACCCCGACCACGTGGAGCTGAGCTGGTGGGTGAATGGGAAGGAGGTGC
ACAGTGGGGTCAGCACAGACCCGCAGCCCCTCAAGGAGCAGCCCGCCCTCA
ATGACTCCAGATACTGCCTGAGCAGCCGCCTGAGGGTCTCGGCCACCTTCTG
GCAGAACCCCCGCAACCACTTCCGCTGTCAAGTCCAGTTCTACGGGCTCTCG
GAGAATGACGAGTGGACCCAGGATAGGGCCAAACCTGTCACCCAGATCGTC
AGCGCCGAGGCCTGGGGTAGAGCAGACTGTGGCTTCACCTCCGAGTCTTAC
CAGCAAGGGGTCCTGTCTGCCACCATCCTCTATGAGATCTTGCTAGGGAAG
GCCACCTTGTATGCCGTGCTGGTCAGTGCCCTCGTGCTGATGGCCATGGTCA
AGAGAAAGGATTCCAGAGGCTAG SEQ ID NO: 73 (#10 β gene fragment)
ATGCTGCTGCTTCTGCTGCTTCTGGGGCCAGCAGGCTCCGGGCTTGGTGCTG
TCGTCTCTCAACATCCGAGCTGGGTTATCTGTAAGAGTGGAACCTCTGTGAA
GATCGAGTGCCGTTCCCTGGACTTTCAGGCCACAACTATGTTTTGGTATCGT
CAGTTCCCGAAACAGAGTCTCATGCTGATGGCAACTTCCAATGAGGGCTCC
AAGGCCACATACGAGCAAGGCGTCGAGAAGGACAAGTTTCTCATCAACCAT
GCAAGCCTGACCTTGTCCACTCTGACAGTGACCAGTGCCCATCCTGAAGAC
AGCAGCTTCTACATCTGCAGTGCTAGACCCCATTCTCTCACAGATACGCAGT
```

| SEQUENCES |
| --- |

```
ATTTTGGCCCAGGCACCCGGCTGACAGTGCTCGAGGACCTGAAAAACGTGT
TCCCACCCGAGGTCGCTGTGTGTTTGAGCCATCAGAAGCAGAGATCTCCCACA
CCCAAAAGGCCACACTGGTGTGCCTGGCCACAGGCTTCTACCCCGACCACG
TGGAGCTGAGCTGGTGGGTGAATGGGAAGGAGGTGCACAGTGGGGTCAGC
ACAGACCCGCAGCCCCTCAAGGAGCAGCCCGCCCTCAATGACTCCAGATAC
TGCCTGAGCAGCCGCCTGAGGGTCTCGGCCACCTTCTGGCAGAACCCCCGC
AACCACTTCCGCTGTCAAGTCCAGTTCTACGGGCTCTCGGAGAATGACGAG
TGGACCCAGGATAGGGCCAAACCTGTCACCCAGATCGTCAGCGCCGAGGCC
TGGGGTAGAGCAGACTGTGGCTTCACCTCCGAGTCTTACCAGCAAGGGGTC
CTGTCTGCCACCATCCTCTATGAGATCTTGCTAGGGAAGGCCACCTTGTATG
CCGTGCTGGTCAGTGCCCTCGTGCTGATGGCCATGGTCAAGAGAAAGGATT
CCAGAGGCTAG

SEQ ID NO: 74 (#4 β gene fragment, codon-optimized)
ATGGGCTGTAGACTGTTGTGTTGTGCTGTGCTGTGTCTGTTGGGAGCTGTGC
CTATCGATACAGAGGTGACCCAGACCCCTAAACATCTGGTTATGGGCATGA
CCAACAAGAAGAGCCTGAAGTGCGAGCAGCACATGGGCCATAGGGCCATG
TATTGGTATAAGCAGAAGGCCAAGAAACCTCCTGAGCTGATGTTCGTGTAC
AGCTACGAGAAGCTGAGCATCAACGAGAGCGTGCCCAGCAGATTTTCTCCT
GAGTGCCCTAATTCTAGCCTGCTGAATCTGCACCTGCATGCTCTGCAGCCTG
AGGATTCTGCTCTGTACCTGTGTGCTTCTTCTCAGGGCACATCTGGAGCTGA
TACACAGTACTTCGGACCTGGCACAAGACTGACAGTGCTGGAAGACCTGAA
GAACGTGTTCCCCCCAGAGGTGGCCGTGTTCGAGCCTAGCGAGGCCGAGAT
CAGCCACACCCAGAAAGCCACCCTCGTGTGCCTGGCCACCGGCTTTTACCCC
GACCACGTGGAACTGTCTTGGTGGGTCAACGGCAAAGAGGTGCACAGCGGC
GTCTGCACCGACCCCCAGCCCTGAAAGAGCAGCCCGCCCTGAACGACAGC
CGGTACTGTCTGAGCAGCAGACTGAGAGTGTCCGCCACCTTCTGGCAGAAC
CCCCGGAACCACTTCAGATGCCAGGTGCAGTTCTACGGCCTGAGCGAGAAC
GACGAGTGGACCCAGGACCGGGCCAAGCCCGTGACCCAGATCGTGTCTGCT
GAGGCCTGGGGCAGAGCCGATTGCGGCTTCACCAGCGAGAGCTACCAGCAG
GGCGTGCTGAGCGCCACCATCCTGTACGAGATCCTGCTGGGCAAGGCCACC
CTGTACGCCGTGCTGGTGTCCGCCCTGGTGCTGATGGCCATGGTCAAGCGG
AAGGACAGCCGGGGC SEQ ID NO: 75 (#6 β gene fragment, codon-optimized)
ATGTCTATCGGTCTGCTGTGCTGTGCTGCTCTTTCTCTGCTTTGGGCTGGACC
TGTGAATGCTGGAGTTACACAAACCCCCAAGTTCCAAGTGCTGAAGACAGG
ACAGAGCATGACCCTGCAGTGTGCTCAGGACATGAATCACGAGTACATGAG
CTGGTACAGACAGGATCCTGGAATGGGCCTGAGGCTGATCCACTACTCTGT
TGGAGCCGGAATTACAGATCAGGGAGAAGTGCCAAATGGCTACAACGTGA
GCAGGAGCACAACCGAGGACTTCCCCTTAAGACTGTTGTCTGCTGCTCCATC
TCAGACAAGCGTGTACTTTTGCGCCAGCTCCTACTCTCTGTGGGATCTGCAG
GAAACCCAGTACTTTGGACCAGGCACAAGACTGTTAGTGCTGGAGGACCTG
AAGAACGTGTTCCCCCCAGAGGTGGCCGTGTTCGAGCCTAGCGAGGCCGAG
ATCAGCCACACCCAGAAAGCCACCCTCGTGTGCCTGGCCACCGGCTTTTACC
CCGACCACGTGGAACTGTCTTGGTGGGTCAACGGCAAAGAGGTGCACAGCG
GCGTCTGCACCGACCCCCAGCCCTGAAAGAGCAGCCCGCCCTGAACGACA
GCCGGTACTGTCTGAGCAGCAGACTGAGAGTGTCCGCCACCTTCTGGCAGA
ACCCCCGGAACCACTTCAGATGCCAGGTGCAGTTCTACGGCCTGAGCGAGA
ACGACGAGTGGACCCAGGACCGGGCCAAGCCCGTGACCCAGATCGTGTCTG
CTGAGGCCTGGGGCAGAGCCGATTGCGGCTTCACCAGCGAGAGCTACCAGC
AGGGCGTGCTGAGCGCCACCATCCTGTACGAGATCCTGCTGGGCAAGGCCA
CCCTGTACGCCGTGCTGGTGTCCGCCCTGGTGCTGATGGCCATGGTCAAGCG
GAAGGACAGCCGGGGC SEQ ID NO: 76 (#7 β gene fragment, codon-optimized)
ATGGGCACATCTCTTCTCTGCTGGATGGCTCTTTGTCTGCTTGGAGCCGATC
ATGCCGATACAGGAGTTAGCCAGGATCCTAGACACAAGATCACCAAGAGA
GGCCAGAATGTGACCTTCCGGTGCGATCCTATCTCTGAGCACAACAGGCTG
TACTGGTACAGACAAACACTGGGACAAGGACCTGAGTTCCTGACCTACTTC
CAGAACGAAGCCCAGCTGGAGAAGTCTAGACTTCTGAGCGACAGATTTAGC
GCCGAGAGACCTAAAGGCAGCTTTAGCACCCTGGAGATCCAGAGAACAGA
ACAGGGCGATTCTGCCATGTACCTGTGTGCTAGCAGCTTTTCTGATGGAGGC
GCCACCGATACACAGTATTTCGGACCTGGCACAAGACTGACAGTGCTGGAG
GACCTGAAGAACGTGTTCCCCCCAGAGGTGGCCGTGTTCGAGCCTAGCGAG
GCCGAGATCAGCCACACCCAGAAAGCCACCCTCGTGTGCCTGGCCACCGGC
TTTTACCCCGACCACGTGGAACTGTCTTGGTGGGTCAACGGCAAAGAGGTG
CACAGCGGCGTCTGCACCGACCCCCAGCCCTGAAAGAGCAGCCCGCCCTG
AACGACAGCCGGTACTGTCTGAGCAGCAGACTGAGAGTGTCCGCCACCTTC
TGGCAGAACCCCCGGAACCACTTCAGATGCCAGGTGCAGTTCTACGGCCTG
AGCGAGAACGACGAGTGGACCCAGGACCGGGCCAAGCCCGTGACCCAGAT
CGTGTCTGCTGAGGCCTGGGGCAGAGCCGATTGCGGCTTCACCAGCGAGAG
CTACCAGCAGGGCGTGCTGAGCGCCACCATCCTGTACGAGATCCTGCTGGG
CAAGGCCACCCTGTACGCCGTGCTGGTGTCCGCCCTGGTGCTGATGGCCATG
GTCAAGCGGAAGGACAGCCGGGGC
```

-continued

| SEQUENCES |
| --- |

SEQ ID NO: 77 (#10 β gene fragment, codon-optimized)
ATGCTGCTTCTTCTCCTCCTTCTCGGACCTGCTGGATCTGGATTAGGAGCTGT
TGTGTCTCAGCACCCTTCTTGGGTGATCTGTAAAAGCGGCACAAGCGTGAA
GATCGAGTGCAGAAGCCTGGACTTTCAGGCCACAACCATGTTCTGGTATAG
GCAGTTCCCCAAGCAGTCTCTGATGCTGATGGCCACCTCTAATGAGGGCTCT
AAGGCCACATATGAACAGGGAGTGGAGAAGGACAAGTTCCTGATCAACCA
CGCCTCTCTGACCCTGTCTACCCTGACAGTTACATCTGCCCACCCTGAGGAT
AGCAGCTTTTACATCTGTAGCGCCAGACCTCACAGCCTGACCGATACACAG
TACTTTGGCCCTGGCACAAGACTGACAGTGTTAGAAGACCTGAAGAACGTG
TTCCCCCCAGAGGTGGCCGTGTTCGAGCCTAGCGAGGCCGAGATCAGCCAC
ACCCAGAAAGCCCACCCTCGTGTGCCTGGCCACCGGCTTTTACCCCGACCAC
GTGGAACTGTCTTGGTGGGTCAACGGCAAAGAGGTGCACAGCGGCGTCTGC
ACCGACCCCCAGCCCCTGAAAGAGCAGCCCGCCCTGAACGACAGCCGGTAC
TGTCTGAGCAGCAGACTGAGAGTGTCCGCCCACCTTCTGGCAGAACCCCCGG
AACCACTTCAGATGCCAGGTGCAGTTCTACGGCCTGAGCGAGAACGACGAG
TGGACCCAGGACCGGGCCAAGCCCGTGACCCAGATCGTGTCTGAGGCC
TGGGGCAGAGCCGATTGCGGCTTCACCAGCGAGAGCTACCAGCAGGGCGTG
CTGAGCGCCACCATCCTGTACGAGATCCTGCTGGGCAAGGCCACCCTGTAC
GCCGTGCTGGTGTCCGCCCTGGTGCTGATGGCCATGGTCAAGCGGAAGGAC
AGCCGGGGC SEQ ID NO: 78 (#4 β-P2A-#4 α, codon-optimized)
ATGGGCTGTAGACTGTTGTGTTGTGCTGTGCTGTGTCTGTTGGGAGCTGTGC
CTATCGATACAGAGGTGACCCAGACCCCTAAACATCTGGTTATGGGCATGA
CCAACAAGAAGAGCCTGAAGTGCGAGCAGCACATGGGCCATAGGGCCATG
TATTGGTATAAGCAGAAGGCCAAGAAACCTCCTGAGCTGATGTTCGTGTAC
AGCTACGAGAAGCTGAGCATCAACGAGAGCGTGCCCAGCAGATTTTCTCCT
GAGTGCCCTAATTCTAGCCTGCTGAATCTGCACCTGCATGCTCTGCAGCCTG
AGGATTCTGCTCTGTACCTGTGTGCTTCTTCTCAGGGCACATCTGGAGCTGA
TACACAGTACTTCGGACCTGGCACAAGACTGACAGTGCTGGAAGACCTGAA
GAACGTGTTCCCCCCAGAGGTGGCCGTGTTCGAGCCTAGCGAGGCCGAGAT
CAGCCACACCCAGAAAGCCCACCCTCGTGTGCCTGGCCACCGGCTTTTACCCC
GACCACGTGGAACTGTCTTGGTGGGTCAACGGCAAAGAGGTGCACAGCGGC
GTCTGCACCGACCCCCAGCCCCTGAAAGAGCAGCCCGCCCTGAACGACAGC
CGGTACTGTCTGAGCAGCAGACTGAGAGTGTCCGCCCACCTTCTGGCAGAAC
CCCCGGAACCACTTCAGATGCCAGGTGCAGTTCTACGGCCTGAGCGAGAAC
GACGAGTGGACCCAGGACCGGGCCAAGCCCGTGACCCAGATCGTGTCTGCT
GAGGCCTGGGGCAGAGCCGATTGCGGCTTCACCAGCGAGAGCTACCAGCAG
GGCGTGCTGAGCGCCACCATCCTGTACGAGATCCTGCTGGGCAAGGCCACC
CTGTACGCCGTGCTGGTGTCCGCCCTGGTGCTGATGGCCATGGTCAAGCGG
AAGGACAGCCGGGGCGGTTCCGGAGCCACGAACTTCTCTCTGTTAAAGCAA
GCAGGAGACGTGGAAGAAAACCCCGGTCCCATGAAGAGCCTGAGAGTCCT
GCTGGTGATTTTGTGGCTGCAGCTGTCTTGGGTTTGGTCTCAGCAGAAAGAA
GTGGAGCAGAATAGCGGCCCTCTGTCTGTTCCTGAAGGCGCTATTGCTAGCC
TGAATTGCACATACAGCGATAGAGGATCTCAGAGCTTCTTCTGGTACCGGC
AGTACAGCGGCAAGAGCCCAGAACTGATCATGTTCATCTACAGCAATGGCG
ACAAGGAGGATGGCAGGTTTACAGCCCAGCTGAACAAGGCCAGCCAGTAT
GTTTCTCTGCTGATCAGAGATAGCCAGCCTAGCGATTCTGCCACCTACCTGT
GTGCCGTGAACATCGGGAAATCACGACATGAGATTTGGAGCCGGCACAAGAC
TGACCGTGAAGCCCAATATCCAGAACCCTGATCCTGCTGTGTACCAGCTGC
GGGACAGCAAGAGCAGCGACAAGAGCGTGTGCCTGTTCACCGACTTCGACA
GCCAGACCAACGTGTCCCAGAGCAAGGACAGCGACGTGTACATCACCGATA
AGTGCGTGCTGGACATGCGGAGCATGGACTTCAAGAGCAACAGCGCCGTGG
CCTGGTCCAACAAGAGCGACTTCGCCTGCGCCAACGCCTTCAACAACAGCA
TTATCCCCGAGGACACATTCTTCCCCAAGCCCCGAGAGCAGCTGCGACGTGA
AGCTGGTGGAAAAGAGCTTCGAGACAGACACCAACCTGAACTTCCAGAACC
TCAGCGTGATCGGCTTCCGGATCCTGCTGCTGAAGGTGGCCGGCTTCAACCT
GCTGATGACCCTGCGGCTGTGGTCCAGCTGA SEQ ID NO: 79 (#6 β-P2A-#6 α, codon-optimized)
ATGTCTATCGGTCTGCTGTGCTGTGCTGCTCTTTCTCTGCTTTGGGCTGGACC
TGTGAATGCTGGAGTTACACAAACCCCCAAGTTCCAAGTGCTGAAGACAGG
ACAGAGCATGACCCTGCAGTGTGCTCAGGACATGAATCACGAGTACATGAG
CTGGTACAGACAGGATCCTGGAATGGGCCTGAGGCTGATCCACTACTCTGT
TGGAGCCGGAATTACAGATCAGGGAGAAGTGCCAAATGGCTACAACGTGA
GCAGGAGCACAACCGAGGACTTCCCCTTAAGACTGTTGTCTGCTGCTCCATC
TCAGACAAGCGTGTACTTTTGCGCCAGCTCCTACTCTCTGTGGGATCTGCAG
GAAACCCAGTACTTTGGACCAGGCACAAGACTGTTAGTGCTGGAGGACCTG
AAGAACGTGTTCCCCCCAGAGGTGGCCGTGTTCGAGCCTAGCGAGGCCGAG
ATCAGCCACACCCAGAAAGCCCACCCTCGTGTGCCTGGCCACCGGCTTTTACC
CCGACCACGTGGAACTGTCTTGGTGGGTCAACGGCAAAGAGGTGCACAGC
GCGTCTGCACCGACCCCCAGCCCCTGAAAGAGCAGCCCGCCCTGAACGACA
GCCGGTACTGTCTGAGCAGCAGACTGAGAGTGTCCGCCCACCTTCTGGCAGA
ACCCCCGGAACCACTTCAGATGCCAGGTGCAGTTCTACGGCCTGAGCGAGA
ACGACGAGTGGACCCAGGACCGGGCCAAGCCCGTGACCCAGATCGTGTCTG
CTGAGGCCTGGGGCAGAGCCGATTGCGGCTTCACCAGCGAGAGCTACCAGC
AGGGCGTGCTGAGCGCCACCATCCTGTACGAGATCCTGCTGGGCAAGGCCA -continued

---
SEQUENCES
---

CCCTGTACGCCGTGCTGGTGTCCGCCCTGGTGCTGATGGCCATGGTCAAGCG
GAAGGACAGCCGGGGCGGTTCCGGAGCCACGAACTTCTCTCTGTTAAAGCA
AGCAGGAGACGTGGAAGAAAACCCCGGTCCCATGGAGAAGATGCTGGAGT
GTGCGTTCATCGTTCTGTGGCTGCAACTTGGATGGCTGTCTGGAGAGGATCA
GGTTACACAGTCTCCTGAAGCCCTGAGACTGCAAGAAGGAGAAAGCTCTAG
CCTGAACTGCAGCTACACAGTGTCTGGACTGAGAGGCCTGTTCTGGTACAG
ACAGGATCCTGGAAAAGGCCCAGAGTTCCTGTTTACCCTGTATTCTGCCGGC
GAGGAGAAGGAGAAAGAGAGACTGAAAGCTACCCTGACCAAGAAGGAGA
GCTTCCTGCACATTACCGCCCCCAAACCTGAGGATTCTGCCACATATCTGTG
TGCTGTGCAGACCATGGATGGCAACCAGTTCTACTTCGGCACAGGCACATC
TCTGACCGTTATCCCCAATATCCAGAACCCTGATCCTGCCGTGTACCAGCTG
CGGGACAGCAAGAGCAGCGACAAGAGCGTGTGCCTGTTCACCGACTTCGAC
AGCCAGACCAACGTGTCCCAGAGCAAGGACAGCGACGTGTACATCACCGAT
AAGTGCGTGCTGGACATGCGGAGCATGGACTTCAAGAGCAACAGCGCCGTG
GCCTGGTCCAACAAGAGCGACTTCGCCTGCGCCAACGCCTTCAACAACAGC
ATTATCCCCGAGGACACATTCTTCCCAAGCCCCGAGAGCAGCTGCGACGTG
AAGCTGGTGGAAAAGAGCTTCGAGACAGACACCAACCTGAACTTCCAGAAC
CTCAGCGTGATCGGCTTCCGGATCCTGCTGCTGAAGGTGGCCGGCTTCAACC
TGCTGATGACCCTGCGGCTGTGGTCCAGCTGA

SEQ ID NO: 80 (#7 β-P2A-#7 α, codon-optimized)
ATGGGCACATCTCTTCTCTGCTGGATGGCTCTTTGTCTGCTTGGAGCCGATC
ATGCCGATACAGGAGTTAGCCAGGATCCTAGACACAAGATCACCAAGAGA
GGCCAGAATGTGACCTTCCGGTGCGATCCTATCTCTGAGCACAACAGGCTG
TACTGGTACAGACAAACACTGGGACAAGGACCTGAGTTCCTGACCTACTTC
CAGAACGAAGCCCAGCTGGAGAAGTCTAGACTTCTGAGCGACAGATTTAGC
GCCGAGAGACCTAAAGGCAGCTTTAGCACCCTGGAGATCCAGAGAACAGA
ACAGGGCGATTCTGCCATGTACCTGTGTGCTAGCAGCTTTTCTGATGGAGGC
GCCACCGATACACAGTATTTCGGACCTGGCACAAGACTGACAGTGCTGGAG
GACCTGAAGAACGTGTTCCCCCCAGAGGTGGCCGTGTTCGAGCCTAGCGAG
GCCGAGATCAGCCACACCCAGAAAGCCACCCTCGTGTGCCTGGCCACCGGC
TTTTACCCCGACCACGTGGAACTGTCTTGGTGGGTCAACGGCAAAGAGGTG
CACAGCGGCGTCTGCACCGACCCCCAGCCCCTGAAAGAGCAGCCCGCCCTG
AACGACAGCCGGTACTGTCTGAGCAGCAGACTGAGAGTGTCCGCCACCTTC
TGGCAGAACCCCCGGAACCACTTCAGATGCCAGGTGCAGTTCTACGGCCTG
AGCGAGAACGACGAGTGGACCCAGGACCGGGCCAAGCCCGTGACCCAGAT
CGTGTCTGCTGAGGCCTGGGGCAGAGCCGATTGCGGCTTCACCAGCGAGAG
CTACCAGCAGGGCGTGCTGAGCGCCACCATCCTGTACGAGATCCTGCTGGG
CAAGGCCACCCTGTACGCCGTGCTGGTGTCCGCCCTGGTGCTGATGGCCATG
GTCAAGCGGAAGGACAGCCGGGGCGGTTCCGGAGCCACGAACTTCTCTCTG
TTAAAGCAAGCAGGAGACGTGGAAGAAAACCCCGGTCCCATGGCTTGTCCT
GGATTCTTATGGGCTCTGGTGATCAGCACCTGTCTGGAGTTCTCTATGGCCC
AGACAGTGACACAGTCTCAGCCTGAAATGTCTGTGCAGGAAGCCGAAACCG
TGACACTGTCTTGCACCTACGATACAAGCGAGAGCGACTACTACCTGTTCTG
GTACAAGCAGCCTCCCTCTAGGCAGATGATCCTGGTGATTAGACAGGAGGC
CTACAAACAGCAGAATGCCACCGAGAACCGGTTTAGCGTGAACTTCCAGAA
AGCCGCCAAGAGCTTCAGCCTGAAAATCTCTGACAGCCAGCTGGGAGATGC
TGCCATGTACTTTTGTGCCAGCTCTCCAGGCACCTACAAGTACATTTTTGGC
ACCGGCACCAGACTGAAGGTGCTGGCCAATATCCAGAATCCCGATCCTGCC
GTGTACCAGCTGCGGGACAGCAAGAGCAGCGACAAGAGCGTGTGCCTGTTC
ACCGACTTCGACAGCCAGACCAACGTGTCCCAGAGCAAGGACAGCGACGTG
TACATCACCGATAAGTGCGTGCTGGACATGCGGAGCATGGACTTCAAGAGC
AACAGCGCCGTGGCCTGGTCCAACAAGAGCGACTTCGCCTGCGCCAACGCC
TTCAACAACAGCATTATCCCCGAGGACACATTCTTCCCAAGCCCCGAGAGC
AGCTGCGACGTGAAGCTGGTGGAAAAGAGCTTCGAGACAGACACCAACCT
GAACTTCCAGAACCTCAGCGTGATCGGCTTCCGGATCCTGCTGCTGAAGGT
GGCCGGCTTCAACCTGCTGATGACCCTGCGGCTGTGGTCCAGCTGA SEQ ID NO: 81 (#10 β-P2A-#10 α, codon-optimized)
ATGCTGCTTCTTCTCCTCCTTCTCGGACCTGCTGGATCTGGATTAGGAGCTGT
TGTGTCTCAGCACCCTTCTTGGGTGATCTGTAAAAGCGGCACAAGCGTGAA
GATCGAGTGCAGAAGCCTGGACTTTCAGGCCACAACCATGTTCTGGTATAG
GCAGTTCCCCAAGCAGTCTCTGATGCTGATGGCCACCTCTAATGAGGGCTCT
AAGGCCACATATGAACAGGGAGTGGAGAAGGACAAGTTCCTGATCAACCA
CGCCTCTCTGACCCTGTCTACCCTGACAGTTACATCTGCCCACCCTGAGGAT
AGCAGCTTTTACATCTGTAGCGCCAGACCTCACAGCCTGACCGATACACAG
TACTTTGGCCCTGGCACAAGACTGACAGTGTTAGAAGACCTGAAGAACGTG
TTCCCCCCAGAGGTGGCCGTGTTCGAGCCTAGCGAGGCCGAGATCAGCCAC
ACCCAGAAAGCCACCCTCGTGTGCCTGGCCACCGGCTTTTACCCCGACCAC
GTGGAACTGTCTTGGTGGGTCAACGGCAAAGAGGTGCACAGCGGCGTCTGC
ACCGACCCCCAGCCCCTGAAAGAGCAGCCCGCCCTGAACGACAGCCGGTAC
TGTCTGAGCAGCAGACTGAGAGTGTCCGCCACCTTCTGGCAGAACCCCCGG
AACCACTTCAGATGCCAGGTGCAGTTCTACGGCCTGAGCGAGAACGACGAG
TGGACCCAGGACCGGGCCAAGCCCGTGACCCAGATCGTGTCTGCTGAGGCC
TGGGGCAGAGCCGATTGCGGCTTCACCAGCGAGAGCTACCAGCAGGGCGTG
CTGAGCGCCACCATCCTGTACGAGATCCTGCTGGGCAAGGCCACCCTGTAC
GCCGTGCTGGTGTCCGCCCTGGTGCTGATGGCCATGGTCAAGCGGAAGGAC -continued

| SEQUENCES |
| --- |

```
AGCCGGGGCGGTTCCGGAGCCACGAACTTCTCTCTGTTAAAGCAAGCAGGA
GACGTGGAAGAAAACCCCGGTCCCATGACCAGAGTTAGCCTGTTATGGGCT
GTGGTGGTGAGCACATGTCTGGAATCTGGAATGGCCCAGACAGTGACACAG
TCTCAGCCTGAAATGTCTGTGCAGGAAGCCGAAACCGTTACACTGAGCTGC
ACCTACGATACAAGCGAGAGCAACTACTACCTGTTCTGGTACAAGCAGCCC
CCTTCTAGGCAGATGATCCTGGTGATCAGACAGGAGGCCTATAAACAGCAG
AATGCCACCGAGAACCGGTTTAGCGTGAACTTCCAGAAAGCCGCCAAGAGC
TTCAGCCTGAAAATCTCTGACAGCCAGCTGGGCGATACAGCCATGTACTTTT
GTGCCTTCAACCCCTGGGAGAACTATGGCCAGAATTTCGTGTTCGGCCCTGG
CACCAGACTGTCTGTTCTGCCTTATATCCAGAACCCCGATCCTGCTGTGTAC
CAGCTGCGGGACAGCAAGAGCAGCGACAAGAGCGTGTGCCTGTTCACCGAC
TTCGACAGCCAGACCAACGTGTCCCAGAGCAAGGACAGCGACGTGTACATC
ACCGATAAGTGCGTGCTGGACATGCGGAGCATGGACTTCAAGAGCAACAGC
GCCGTGGCCTGGTCCAACAAGAGCGACTTCGCCTGCGCCAACGCCTTCAAC
AACAGCATTATCCCCGAGGACACATTCTTCCCAAGCCCCGAGAGCAGCTGC
GACGTGAAGCTGGTGGAAAAGAGCTTCGAGACAGACACCAACCTGAACTTC
CAGAACCTCAGCGTGATCGGCTTCCGGATCCTGCTGCTGAAGGTGGCCGGC
TTCAACCTGCTGATGACCCTGCGGCTGTGGTCCAGCTGA
```

SEQ ID NO: 82 (Reference TCR α chain)
```
MTSIRAVFIFLWLQLDLVNGENVEQHPSTLSVQEGDSAVIKCTYSDSASNYFPW
YKQELGKRPQLIIDIRSNVGEKKDQRIAVTLNKTAKHFSLHITETQPEDSAVYFC
AATEDYQLIWGAGTKLIIKPDIQNPDPAVYQLRDSKSSDKSVCLFTDFDSQTNV
SQSKDSDVYITDKTVLDMRSMDFKSNSAVAWSNKSDFACANAFNNSIIPEDTFF
PSPESSCDVKLVEKSFETDTNLNFQNLSVIGFRILLLKVAGFNLLMTLRLWSS
```

SEQ ID NO: 83 (Reference TCR β chain)
```
MSNQVLCCVVLCFLGANTVDGGITQSPKYLFRKEGQNVTLSCEQNLNHDAMY
WYRQDPGQGLRLIYYSQIVNDFQKGDIAEGYSVSREKKESFPLTVTSAQKNPTA
FYLCASSPGALYEQYFGPGTRLTVTEDLKNVFPPEVAVFEPSEAEISHTQKATLV
CLATGFYPDHVELSWWVNGKEVHSGVSTDPQPLKEQPALNDSRYCLSSRLRVS
ATFWQNPRNHFRCQVQFYGLSENDEWTQDRAKPVTQIVSAEAWGRADCGFTS
ESYQQGVLSATILYEILLGKATLYAVLVSALVLMAMVKRKDSRG
```

SEQ ID NO: 84 (*Porcine teschovirus*-1 2A (P2A-1) peptide)
```
GSGATNFSLLKQAGDVEENPGP
```

SEQ ID NO: 85 (*Porcine teschovirus*-2 2A (P2A-2) peptide)
```
SGATNFSLLKQAGDVEENPGP
```

SEQ ID NO: 86 (*Thosea asigna* virus 2A (T2A) peptide)
```
GSGEGRGSLLTCGDVEENPGP
```

SEQ ID NO: 87 (*Equine rhinitis* A virus (ERAV) 2A (E2A) peptide)
```
GSGQCTNYALLKLAGDVESNPGP
```

SEQ ID NO: 88 (Foot-and-mouth disease virus 2A (F2A) peptide)
```
GSGVKQTLNFDLLKLAGDVESNPGP
```

SEQ ID NO: 89 (*Porcine teschovirus*-1 2A (P2A-1) peptide-nt sequence)
```
GGAAGTGGAGCTACGAATTTTTCTTTATTAAAACAAGCAGGAGATGTTGAG
GAGAATCCCGGTCCA
```

SEQ ID NO: 90 (*Porcine teschovirus*-2 2A (P2A-2) peptide-nt sequence)
```
AGCGGCGCCACCAACTTCAGCCTGCTGAAACAGGCCGGCGACGTGGAAGA
GAACCCTGGCCCT
```

SEQ ID NO: 91 (*Thosea asigna* virus 2A (T2A) peptide-nt sequence)
```
GGAAGCGGAGAGGGCAGAGGAAGTCTGCTAACATGCGGTGACGTCGAGGA
GAATCCTGGACCT
```

SEQ ID NO: 92 (*Equine rhinitis* A virus (ERAV) 2A (E2A) peptide-nt sequence)
```
GGAAGCGGACAGTGTACTAATTATGCTCTCTTGAAATTGGCTGGAGATGTT
GAGAGCAACCCTGGACCT
```

SEQ ID NO: 93 (Foot-and-mouth disease virus 2A (F2A) peptide-nt sequence)
```
GGAAGCGGAGTGAAACAGACTTTGAATTTTGACCTTCTCAAGTTGGCGGGA
GACGTGGAGTCCAACCCTGGACCT
```

SEQ ID NO: 94 (WT-1 peptide antigen)
```
RMFPNAPYL
```

SEQ ID NO: 95 (G-S linker)
```
GGGGS
```

-continued

| SEQUENCES |
| --- |

SEQ ID NO: 96
GlyxSery, wherein X and Y are each independently a non-zero integer SEQ ID NO: 97-meganuclease recognition site
LAGLIDADG SEQ ID NO: 98-meganuclease recognition site
GIY-YIG SEQ ID NO: 99-meganuclease recognition site
PD-(D/E)XK SEQ ID NO.: 100 (WT-1 aa 37-45)
VLDFAPPGA

SEQ ID NO.: 101 (TCR 10.1 CDR1α)
DSAIYN

SEQ ID NO.: 102 (TCR 10.1 CDR2α)
IQSSQRE

SEQ ID NO.: 103 (TCR 10.1 CDR3α)
CAVKETSGSRLTF

SEQ ID NO.: 104 (TCR 10.1 Vα)
KQEVTQIPAALSVPEGENLVLNCSFTDSAIYNLQWFRQDPGKGLTSLLLIQSSQR
EQTSGRLNASLDKSSGRSTLYIAASQPGDSATYLCAVKETSGSRLTFGEGTQLT
VNP

SEQ ID NO.: 105 (TCR 10.1 CDR1β)
SGHVS

SEQ ID NO.: 106 (TCR 10.1 CDR2β)
FNYEAQ

SEQ ID NO.: 107 (TCR 10.1 CDR3β)
CASSLTGSYEQYF

SEQ ID NO.: 108 (TCR 10.1 Vβ)
GAGVSQSPRYKVTKRGQDVALRCDPISGHVSLYWYRQALGQGPEFLTYFNYE
AQQDKSGLPNDRFSAERPEGSISTLTIQRTEQRDSAMYRCASSLTGSYEQYFGP
GTRLTVTE

SEQ ID NO.: 109 (TCR 13.1 CDR1α)
NSMFDY

SEQ ID NO.: 110 (TCR 13.1 CDR2α)
ISSIKDK

SEQ ID NO.: 111 (TCR 13.1 CDR3α)
CAASGIGDYKLSF

SEQ ID NO.: 112 (TCR 13.1 Vα)
DQQVKQNSPSLSVQEGRISILNCDYTNSMFDYFLWYKKYPAEGPTFLISISSIKD
KNEDGRFTVFLNKSAKHLSLHIVPSQPGDSAVYFCAASGIGDYKLSFGAGTTVT
VRAN

SEQ ID NO.: 113 (TCR 13.1 CDR1β)
PRHDT

SEQ ID NO.: 114 (TCR 13.1 CDR2β)
FYEKMQ

SEQ ID NO.: 115 (TCR 13.1 CDR3β)
CASSLRLGRETQYF

SEQ ID NO.: 116 (TCR 13.1 Vβ)
AAGVIQSPRHLIKEKRETATLKCYPIPRHDTVYWYQQGPGQDPQFLISFYEKMQ
SDKGSIPDRFSAQQFSDYHSELNMSSLELGDSALYFCASSLRLGRETQYFGPGTR
LLVLE

SEQ ID NO.: 117 (TCR 16.1 CDR1α)
VSGLRG

SEQ ID NO.: 118 (TCR 16.1 CDR2α)
LYSAGEE

-continued

SEQUENCES

SEQ ID NO.: 119 (TCR 16.1 CDR3α)
CAVITGFQKLVF

SEQ ID NO.: 120 (TCR 16.1 Vα)
EDQVTQSPEALRLQEGESSSLNCSYTVSGLRGLFWYRQDPGKGPEFLFTLYSAG
EEKEKERLKATLTKKESFLHITAPKPEDSATYLCAVITGFQKLVFGTGTRLLVSP
N

SEQ ID NO.: 121 (TCR 16.1 CDR1β)
MNHEY

SEQ ID NO.: 122 (TCR 16.1 CDR2β)
SMNVEV

SEQ ID NO.: 123 (TCR 16.1 CDR3β)
CASSFSGGTYEQYF

SEQ ID NO.: 124 (TCR 16.1 Vβ)
EAQVTQNPRYLITVTGKKLTVTCSQNMNHEYMSWYRQDPGLGLRQIYYSMNV
EVTDKGDVPEGYKVSRKEKRNFPLILESPSPNQTSLYFCASSFSGGTYEQYFGPG
TRLTVTE

EXAMPLES

Example 1

Identification and Characterization of TCRs Specific for a WT-1 Peptide

Figure 2A:
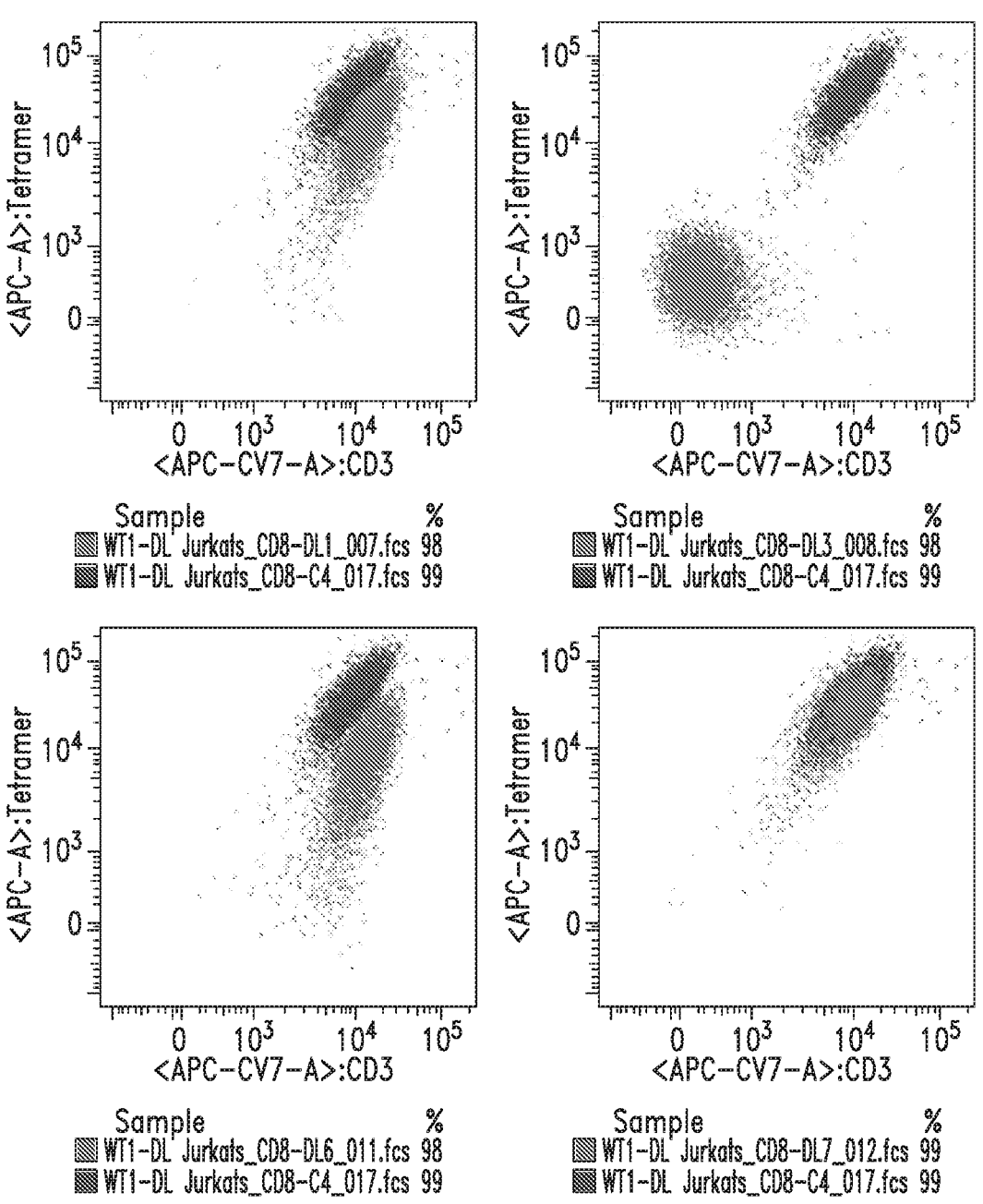
FIGS. 2A-2C show that exemplary WT-1-specific binding proteins are expressed in transduced host cells. Ten (10) WT-1 specific TCRs from the 24 clonotypes shown in FIG. 1 were used to transduce TCRα/TCRβ-deficient J76 Jurkat T cells. WT-1:HLA-A tetramer binding and CD3 expression of the transduced cells (shown in light grey) was compared to cells transduced with a reference WT-1-specific TCR (shown in dark grey) having an α chain according to SEQ ID NO.:82 and a β chain according to SEQ ID NO.:83 and described by Schmitt et al. (*Nat. Biotechnol.* 35:1188, 2017).
Figure 2B:
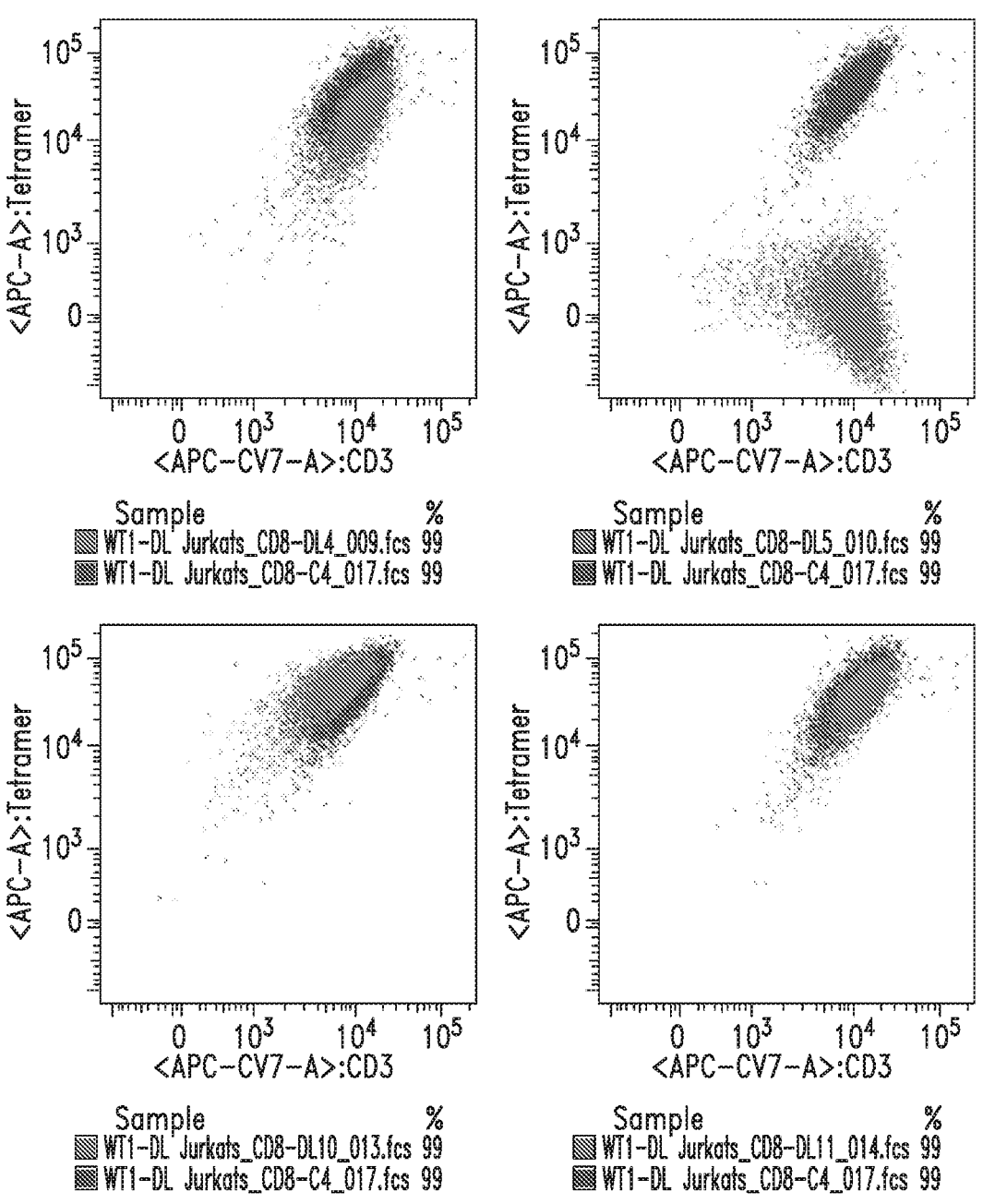
Figure 2C:
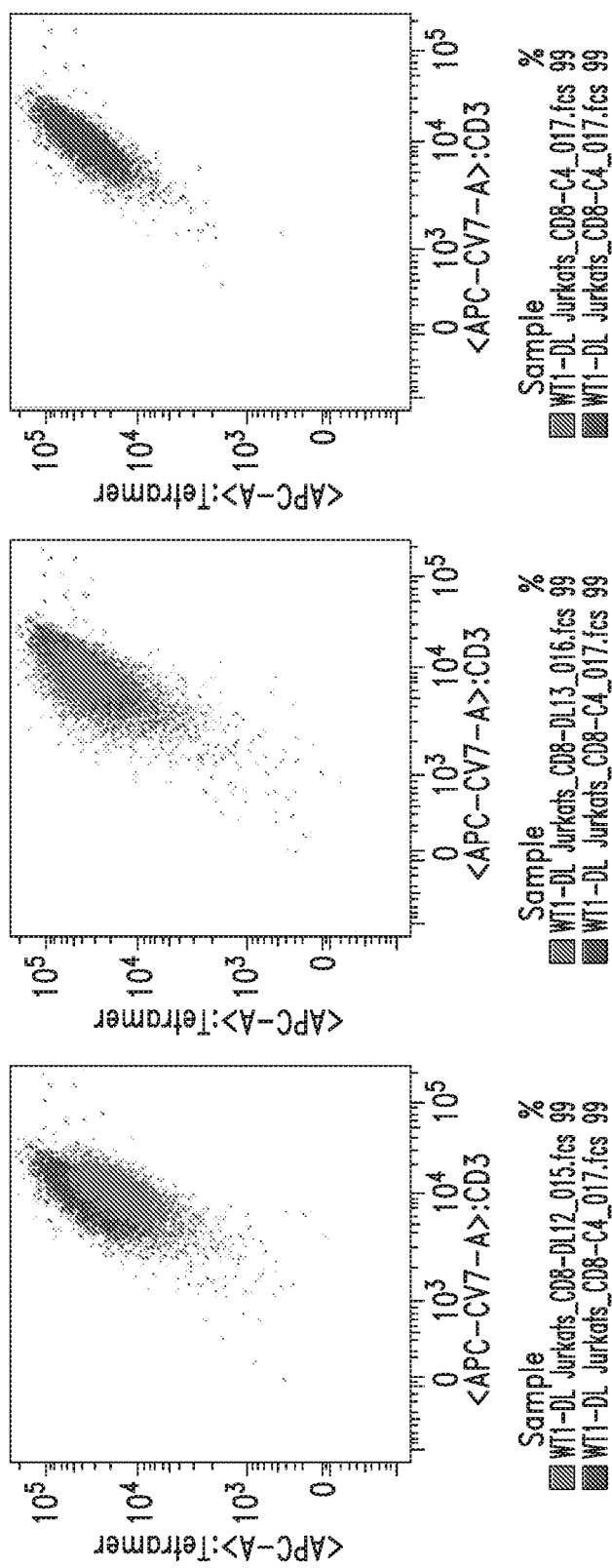

CD8⁺ T cells from four donors were cultured with autologous dendritic cells (DCs) pulsed with the WT-1 peptide RMFPNAPYL (SEQ ID NO:94) (Ho, Greenberg et al., 2006). The T cell lines were combined, stained with CD8-independent (CD8i) WT-1 peptide:HLA tetramer and sorted for high tetramer staining cells. A total of 40 polyclonal T cell lines with high tetramer staining were identified. The sorted T cell samples and a fraction of the total unsorted sample were both analyzed by TCR repertoire analysis (Adaptive Biotechnologies) to quantitate each TCR clonotype. A fraction of high tetramer-staining cells was also analyzed by single-cell RNA sequencing and TCR pairing (10x genomics). 24 TCR clonotypes were identified as WT-1-specific by comparison of the fold-enrichment of each clonotype within the sorted versus unsorted population and the CD3 surface expression of each clonotype (FIG. 1). Of these, 10 were selected for synthesis. TCRα/TCRβ-deficient J76 Jurkat T cells were transduced to express the candidate TCRs. The affinity of each candidate for WT-1 was assessed by measuring the relative WT-1 peptide:HLA tetramer staining as compared to CD3 expression, which is a marker of total transgenic TCR surface expression. The results were compared to those of cells expressing the WT-1 peptide:HLA-specific TCR having an α chain according to SEQ ID NO:82 and a chain according to SEQ ID NO:83. Data are shown in FIGS. 2A-2C.

Figure 3A:
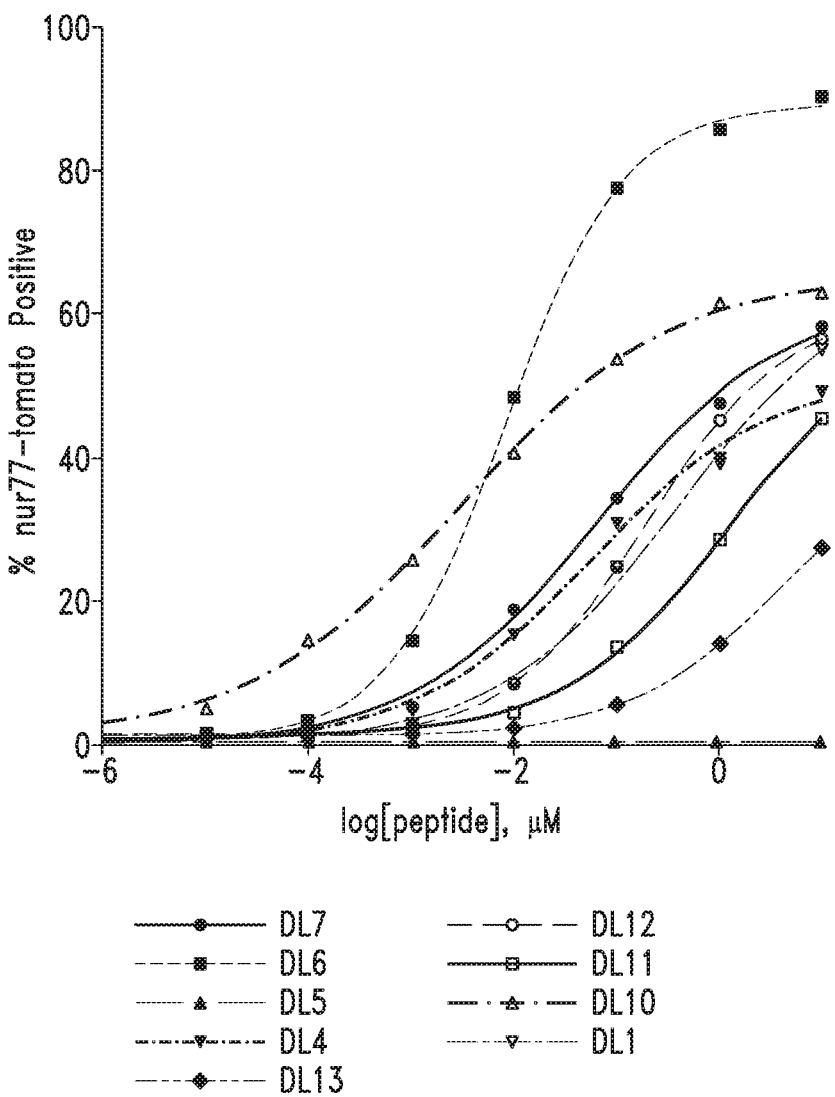
FIGS. 3A and 3B show that binding proteins of the present disclosure are functional in transduced host cells. (A) Jurkat cells expressing Nur77-dtTomato reporter (reporting antigen-specific signaling in human T cells; see Ahsouri and Weiss, *J Immunol* 198(2):657-668 (2017)) were transduced with WT-1-specific TCR and incubated for 24 h with APCs loaded with WT-1 peptide at the indicated concentrations. (B) Nur77 activation peptide $EC_{50}$ values of the indicated TCRs.
Figure 3B:
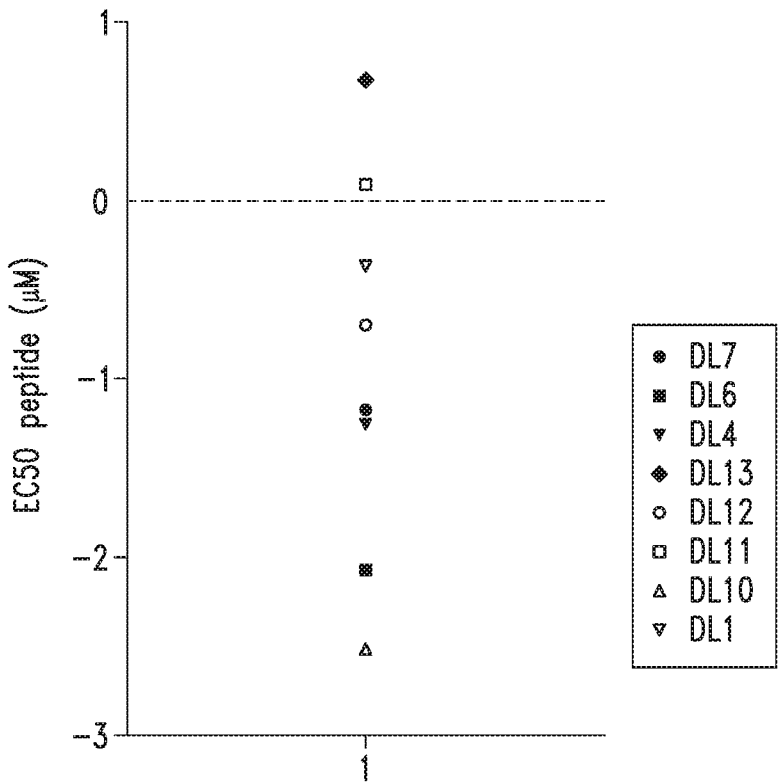

TCR-transduced Jurkat cells expressing the Nur77-tomato activation marker were assessed for activation in the presence of peptide. Data are shown in FIG. 3A.

Figure 4A:
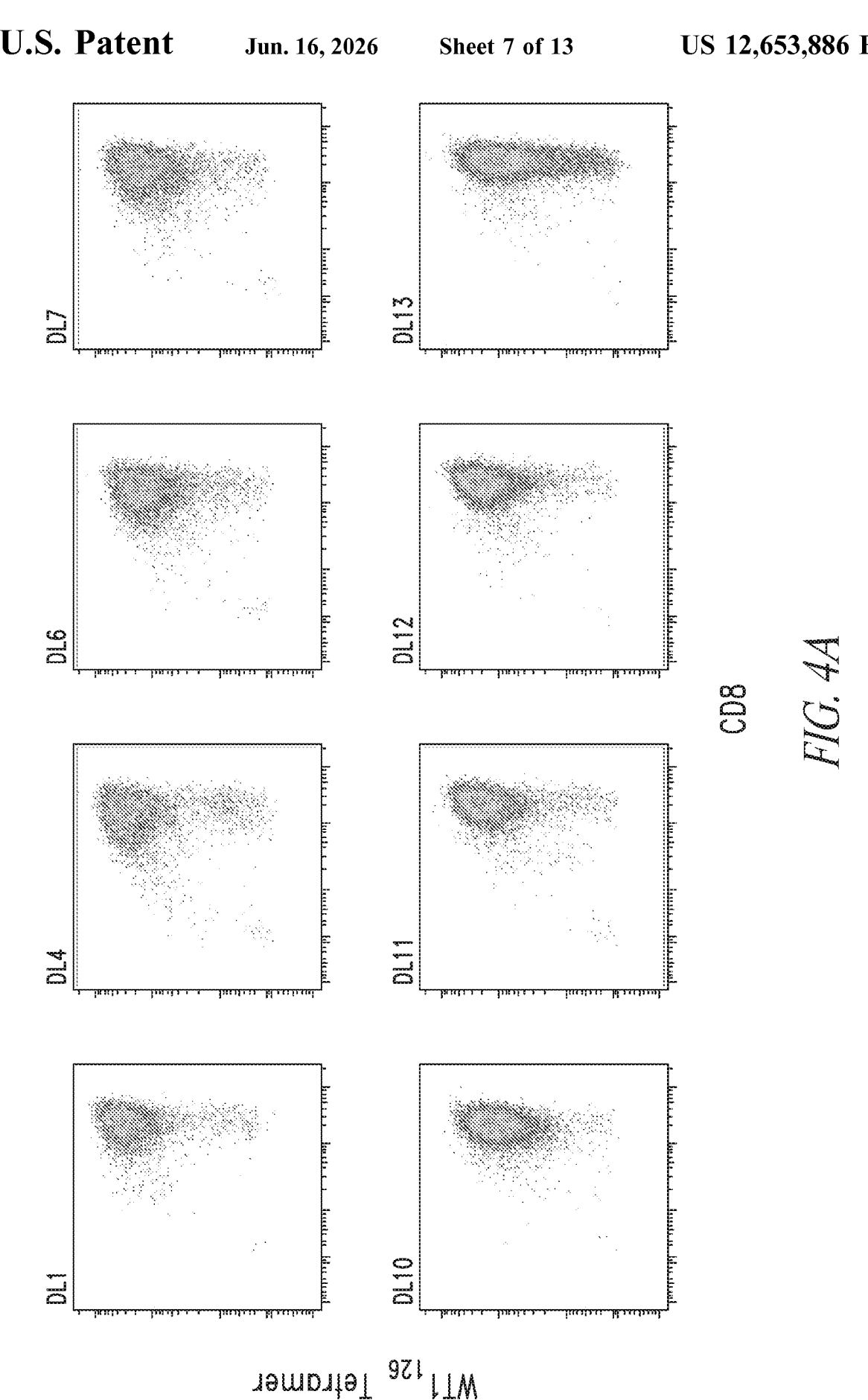
FIGS. 4A-4C show further functional characterization of exemplary binding proteins of the present disclosure. (A) Peptide/MHC tetramer binding by CD8+ T cells that were transduced to express a WT-1-specific TCR as indicated. (B) IFNγ production (as determined by flow cytometry) by expanded antigen-specific CD8+ T cells in a 4 hour co-culture with T2 target cells pulsed with titrated concentrations of peptide. Shown is the percentage of IFN-γ+ T cells. (C) IFNγ peptide $EC_{50}$ for each TCR was determined by fitting the percentage of IFNγ-producing cells to dose-response curves by linear regression.
Figure 4B:
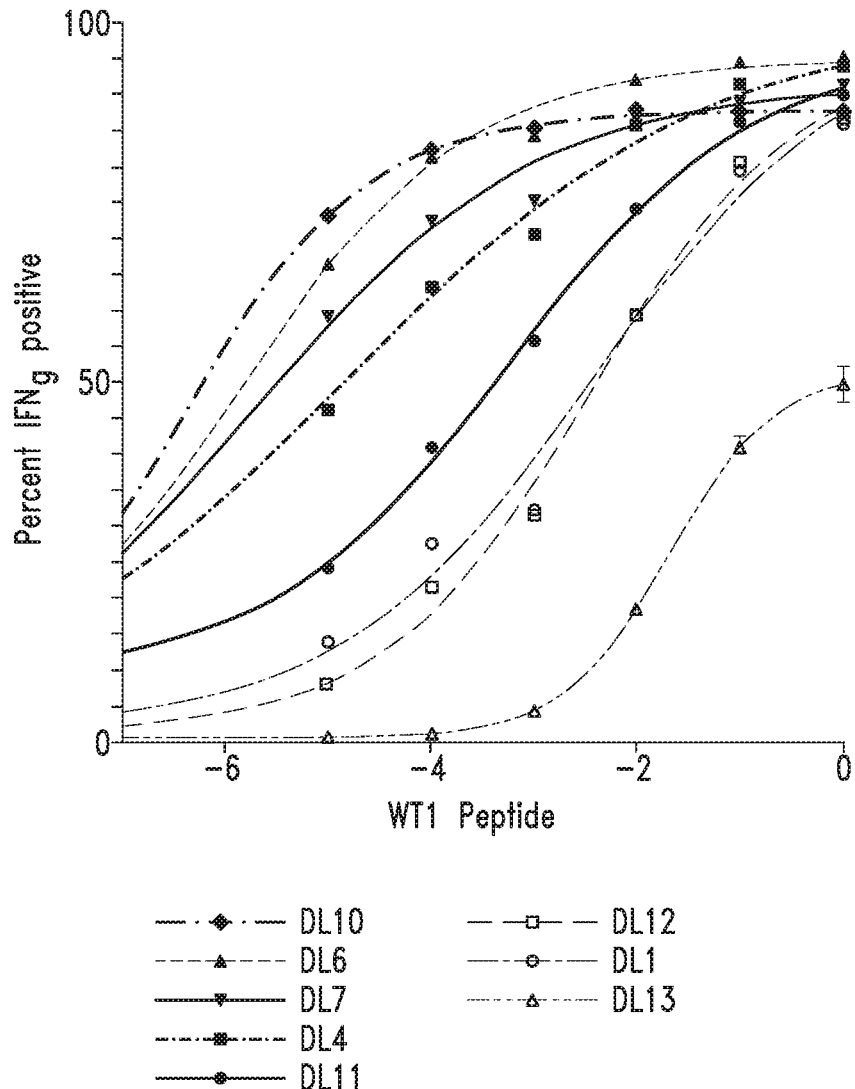
Figure 4C:
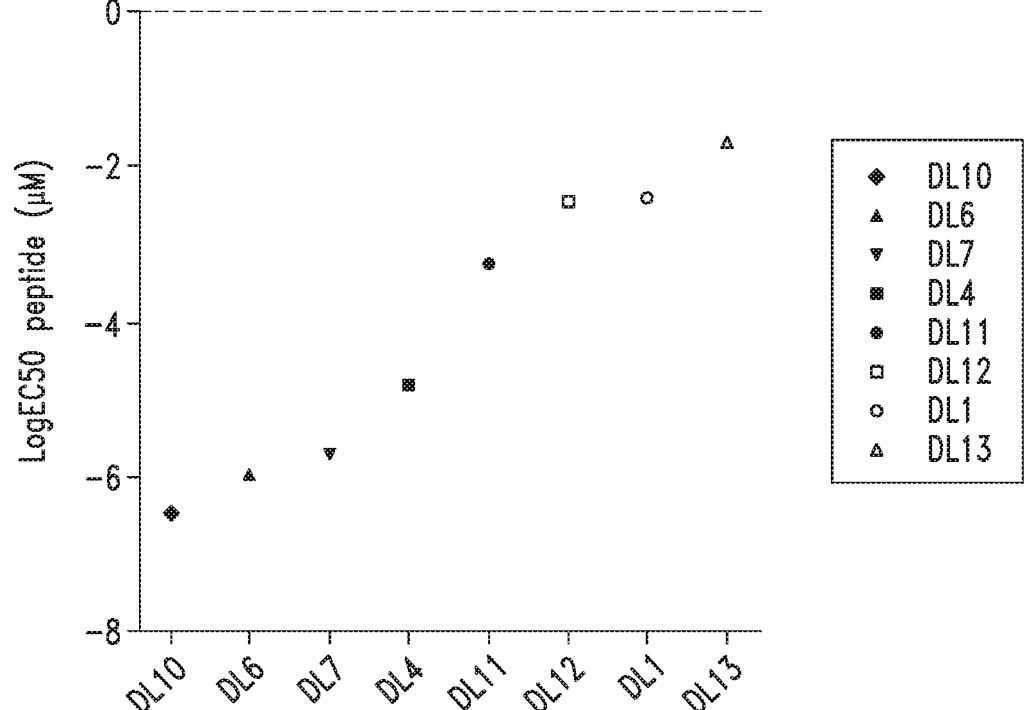

CD8+ T cells isolated from donor PMBCs were transduced to express one of eight TCRs selected for further study. After one week, the transduced cells were sorted for WT-1 peptide:HLA tetramer staining and CD8 expression (FIG. 4A). Tetramer⁺ CD8⁺ T cells were expanded and assayed for IFNγ production. The expanded antigen-specific cells were cultured for four hours with T2 target cells pulsed with titrated concentrations of WT-1 peptide, and IFNγ production was determined by flow cytometry (FIG. 4B). The percentage of IFNγ-producing cells was fit to dose-response curves by non-linear regression to calculate the peptide $EC_{50}$ for each TCR (FIG. 4C).

Figure 5A:
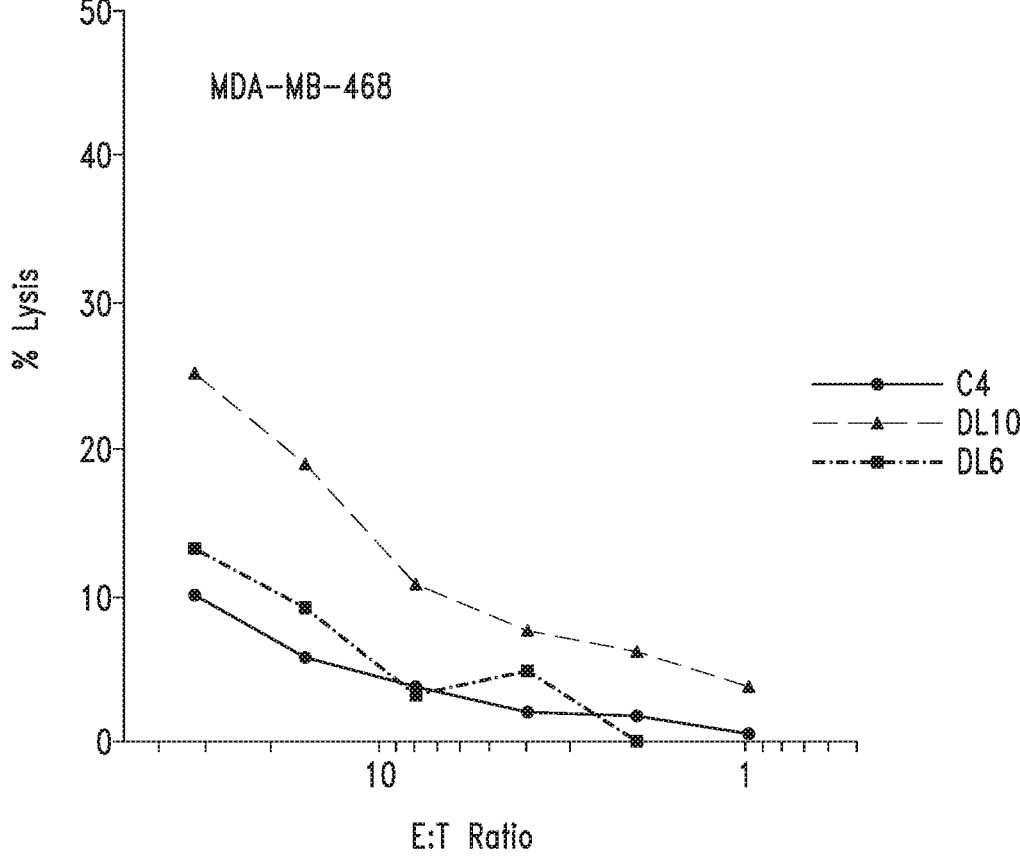
FIGS. 5A and 5B show lysis of tumor cells by T cells expressing an exemplary binding protein of the present disclosure (TCR DL6 or DL10), as compared to lysis by T cells expressing a reference TCR (a chain according to SEQ ID NO.:82; β chain according to SEQ ID NO.:83). (A) Lysis of HLA-A2-transduced tumor cell line MDA-MB-468 cells. (B) Lysis of naturally HLA-A2+ tumor line Panc-1 cells. Both (A) and (B) show results from 4 h assays in which target cells were loaded with $^{51}Cr$ and TCR-transduced T cell-mediated killing was calculated by measuring Cr-release in response to decreasing doses of effector T cells relative to tumor cell targets (E:T; x-axis).
Figure 5B:
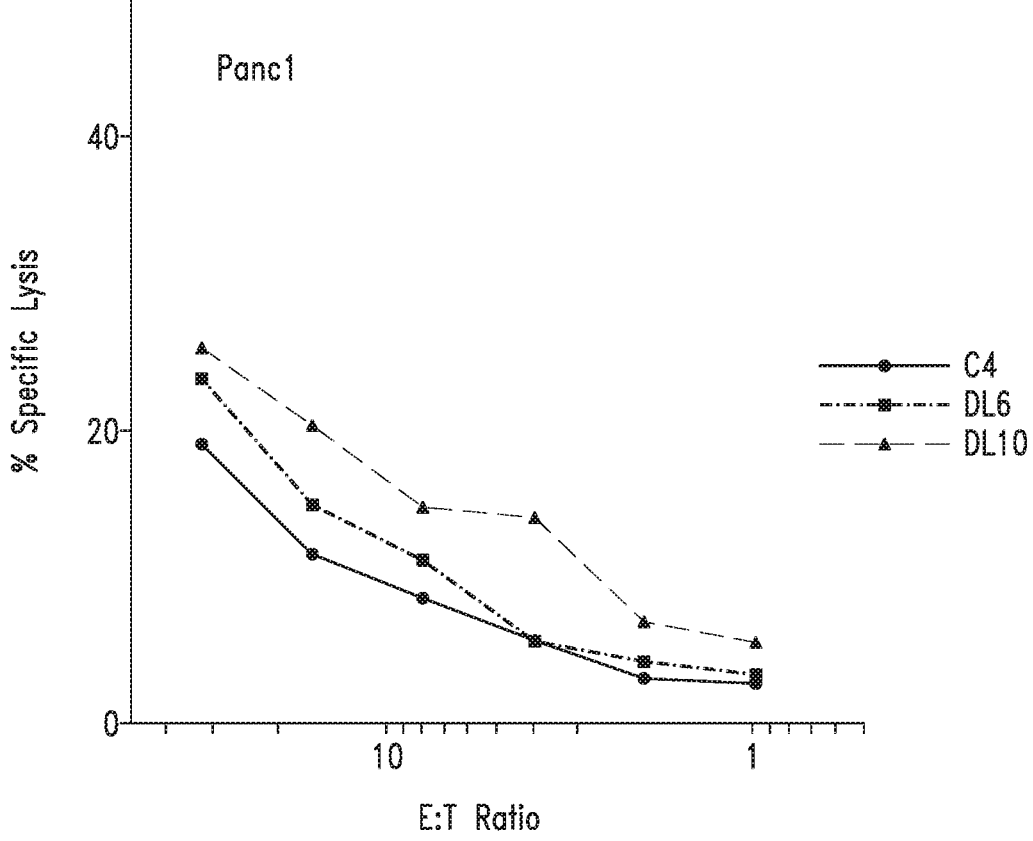

T cells expressing the two TCRs with the lowest $EC_{50}$ values were compared to T cells expressing the reference WT-1 specific TCR for the ability to induce tumor cell lysis. Tumor cell line MDA-MB-468, which was transduced to express HLA-A2, and the naturally HLA_A2⁺ tumor cell line Panc-1 were loaded with ⁵¹Cr. TCR-transduced T cell-mediated killing was calculated by measuring Cr release in response to decreasing doses of effector T cells relative to tumor cell targets (FIGS. 5A and 5B).

Figure 6:
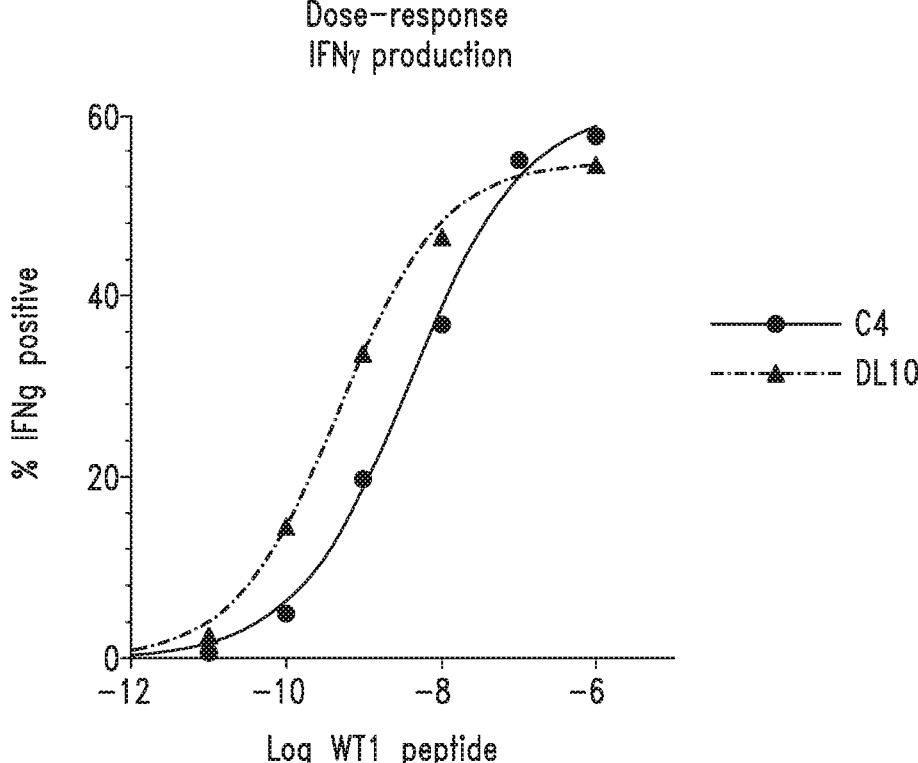
FIG. 6 shows IFN-γ production by exemplary TCR DL10 of the present disclosure, as compared to the reference TCR (a chain according to SEQ ID NO.:82; β chain according to SEQ ID NO.:83), in the presence of T2 target cells pulsed with peptide.
Figure 7:
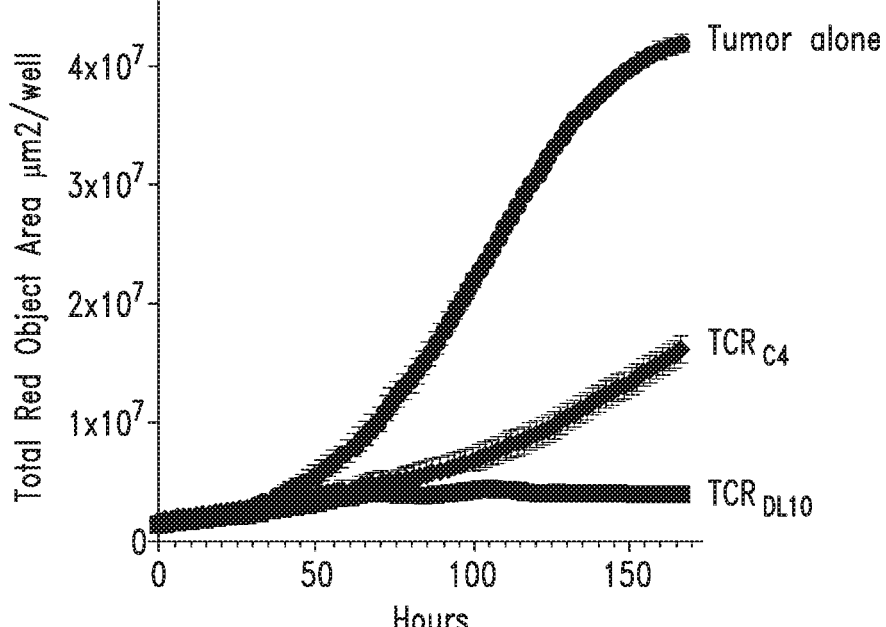
FIG. 7 shows reduced growth of Panc-1 tumor cells in the presence of T cells expressing exemplary TCR DL10 of the present disclosure, as compared to tumor cells alone or in the presence of T cells expressing the reference TCR (α chain according to SEQ ID NO.:82; β chain according to SEQ ID NO.:83). Cell proliferation/survival was monitored over 7 days in an IncuCyte assay. Error bars indicate standard error of the mean.

T cells expressing exemplary TCR DL10 were further investigated for IFN-γ production (FIG. 6) and the ability to reduce growth of tumor cell line cells (FIG. 7). For IFN-γ production, primary CD8+ T cells were transduced with a reference TCR or with TCRDL10 and cultured with the peptide-pulsed T2 target cells as indicated in FIG. 6. After 4 hours, IFNγ production was assessed by intracellular flow cytometry and percent IFNγ positivity was fit to a dose response curve by nonlinear regression in Graphpad Prism. To assess the ability to control tumor growth, primary CD8+ T cells were transduced with a reference TCR (comprising a TCRα chain having the amino acid sequence set forth in SEQ ID NO: 82 and a TCRβ chain having the amino acid sequence set forth in SEQ ID NO: 83) or with TCRDL10 and cultured in triplicate with the HLA-A2+ WT1+ pancreatic tumor cell line Panc-1 (transduced to express a red fluorescence protein) at a ratio of 8:1 in an IncuCyte assay, and cell proliferation/survival was monitored over 7 days. Error bars indicate standard error of the mean.

The various embodiments described above can be combined to provide further embodiments. All of the U.S. patents, U.S. patent application publications, U.S. patent applications, foreign patents, foreign patent applications and non-patent publications referred to in this specification and/or listed in the Application Data Sheet, including U.S. Patent Application No. 62/889,519, filed Aug. 20, 2019, are incorporated herein by reference, in their entirety. Aspects of the embodiments can be modified, if necessary to employ concepts of the various patents, applications and publications to provide yet further embodiments.

These and other changes can be made to the embodiments in light of the above-detailed description. In general, in the following claims, the terms used should not be construed to limit the claims to the specific embodiments disclosed in the specification and the claims, but should be construed to include all possible embodiments along with the full scope of equivalents to which such claims are entitled. Accordingly, the claims are not limited by the disclosure.

---

What is claimed is:

1. A host cell, comprising a heterologous polynucleotide that encodes a binding protein comprising a T cell receptor (TCR) α chain variable (Vα) domain and a TCR β-chain variable (Vβ) domain,
   wherein the encoded TCR Vα and Vβ domains comprise CDR1α, CDR2α, CDR3α, CDR1β, CDR2β, and CDR3β amino acid sequences of:
   (i) SEQ ID NOs.: 26-28 and 38-40, respectively; or
   (ii) SEQ ID NOs.: 23, 27, 28, and 38-40, respectively,
   and wherein the encoded binding protein is capable of binding to a RMFPNAPYL (SEQ ID NO.: 94): human leukocyte antigen (HLA) complex.

2. The host cell of claim 1, wherein the HLA comprises HLA-A*201.

3. The host cell of claim 1, wherein:
   (i) the encoded Vβ domain comprises an amino acid sequence having at least 90% identity to the amino acid sequence of any one of SEQ ID NOs.: 16 and 8; and/or
   (ii) the encoded Vα domain comprises an amino acid sequence having at least 90% identity to the amino acid sequence of any one of SEQ ID NOs.: 12 and 4.

4. The host cell of claim 1, wherein the encoded TCR Vα and Vβ domains comprise CDR1α, CDR2α, CDR3α, CDR1β, CDR2β, and CDR3β amino acid sequences of SEQ ID NOs.: 26-28 and 38-40, respectively.

5. The host cell of claim 1, wherein:
   the encoded Vβ domain comprises the amino acid sequence of SEQ ID NO.: 16, and the encoded Vα domain comprises of the amino acid sequence of SEQ ID NO.: 12.

6. The host cell of claim 1, wherein the encoded VB domain comprises the amino acid sequence of SEQ ID NO.: 8, and the encoded Va domain comprises the amino acid sequence of SEQ ID NO.: 4.

7. The host cell of claim 1, wherein:
   (i) the encoded TCR Vβ domain comprises an amino acid sequence according to a TRBJ02-03 gene segment; and/or
   (ii) the encoded TCR Vα domain comprises an amino acid sequence according to a TRAJ43 gene segment.

8. The host cell of claim 1, wherein the encoded Vβ domain comprises the amino acid sequence of SEQ ID NO.: 16 or 8, and the encoded Vα domain comprises the amino acid sequence of SEQ ID NO.: 12 or 4.

9. The host cell of claim 1, wherein the encoded binding protein further comprises:
   (i) a TCR α chain constant domain (Cα), or a fragment thereof; and/or
   (ii) a TCR β chain constant domain (Cβ), or a fragment thereof.

10. The host cell of claim 9, wherein: (i) the encoded Cα comprises an amino acid sequence having at least 90% identity to SEQ ID NO.: 44; and/or (ii) the encoded Cβ comprises an amino acid sequence having at least 90% identity to SEQ ID NO.: 45.

11. The host cell of claim 1, wherein the encoded binding protein comprises a TCR β chain having at least 90% identity to the amino acid sequence of SEQ ID NO.: 61 or 57, and a TCR α chain having at least 90% identity to the amino acid sequence of SEQ ID NO.: 53 or 49.

12. The host cell of claim 1, wherein the encoded binding protein is a TCR, a chimeric antigen receptor (CAR), or a single-chain TCR (scTCR).

13. The host cell of claim 1, wherein the host cell is an immune system cell.

14. The host cell of claim 1, wherein the host cell is a human T cell.

15. The host cell of claim 14, wherein the T cell is a naïve T cell, a central memory T cell, an effector memory T cell, a stem cell memory T cell, or any combination thereof.

16. The host cell of claim 1, wherein the polynucleotide encoding the binding protein comprises a polynucleotide having at least 75% identity to the polynucleotide sequence set forth in any one of SEQ ID NOs.: 65, 69, 73, and 77.

17. The host cell of claim 1, further comprising:
  (i) a heterologous polynucleotide encoding a polypeptide that comprises an extracellular portion of a CD8 co-receptor α chain, wherein, optionally, the encoded polypeptide comprises a CD8 co-receptor α chain;
  (ii) a heterologous polynucleotide encoding a polypeptide that comprises an extracellular portion of a CD8 co-receptor β chain, wherein, optionally, the encoded polypeptide comprises a CD8 co-receptor β chain; or
  (iii) the polynucleotide of (i) and the polynucleotide of (ii),
wherein, optionally, the host cell comprises a CD4+ T cell.

18. An isolated polynucleotide encoding a binding protein, wherein the encoded binding protein comprises a TCR Vα domain and a TCR Vβ domain and is capable of binding to a RMFPNAPYL (SEQ ID NO.: 94): HLA complex, wherein the HLA optionally comprises HLA-A*0201, and wherein the encoded TCR Vα and Vβ domains comprise CDR1α, CDR2α, CDR3α, CDR1β, CDR2β, and CDR3β amino acid sequences of:
  (i) SEQ ID NOs.: 26-28 and 38-40, respectively; or
  (ii) SEQ ID NOs.: 23, 27, 28, and 38-40, respectively.

19. The isolated polynucleotide of claim 18, wherein the polynucleotide comprises a polynucleotide having at least 75% identity to the polynucleotide sequence set forth in any one of SEQ ID Nos.: 65, 69, 73, 77 and 81.

20. A vector, comprising the polynucleotide of claim 18.

21. A composition, comprising:
  the host cell of claim 1; and
  a pharmaceutically acceptable carrier, excipient, or diluent.

22. A method for treating a HLA-A*201-positive subject having a hyperproliferative disorder associated with WT-1 expression, comprising administering to the subject an effective amount of the host cell of claim 1, wherein the host cell comprises a CD4+ T cell, a CD8+ T cell, or both.

23. The method of claim 22, wherein the hyperproliferative disorder is a hematological malignancy or a solid cancer.

24. The method of claim 23, wherein the hematological malignancy is selected from acute lymphoblastic leukemia (ALL), acute lymphocytic leukemia, acute myelocytic leukemia, acute myeloid leukemia (AML, including refractory and relapsed AML, and including acute myeloblastic leukemia, acute promyelocytic leukemia, acute myelocytic leukemia, acute myelomonocytic leukemia (e.g., with or without eosinophilia), acute monocytic leukemia, acute erythroid leukemia, and acute megakaryoblastic leukemia), chronic myelogenous leukemia (CML), chronic myelocytic leukemia, chronic eosinophilic leukemia (CEL), myelodysplastic syndrome (MDS), non-Hodgkin's lymphoma (NHL), or multiple myeloma (MM, including refractory and relapsed MM).

25. The method of claim 23, wherein the solid cancer is selected from biliary cancer, bladder cancer, bone and soft tissue carcinoma, brain tumor, breast cancer, breast carcinoma, cervical cancer, colon cancer, colorectal adenocarcinoma, colorectal cancer, desmoid tumor, embryonal cancer, endometrial cancer, esophageal cancer, gastric cancer, gastric adenocarcinoma, glioblastoma multiforme, glioblastoma, melanoma, diffuse peritoneal mesothelioma, malignant pleural mesothelioma, glioma, astrocytoma, gynecological tumor, head and neck squamous cell carcinoma, hepatic cancer, hepatocellular carcinoma, lung cancer, non small-cell lung cancer, malignant melanoma, osteosarcoma, ovarian cancer (e.g., epithelial ovarian cancer, ovarian carcinoma), fallopian tube cancer, endometrial carcinoma, pancreatic cancer, pancreatic ductal adenocarcinoma, primary astrocytic tumor, primary thyroid cancer, prostate cancer, renal cancer, renal cell carcinoma, rhabdomyosarcoma, skin cancer, soft tissue sarcoma, osteogenic sarcoma, testicular germ-cell tumor, urothelial cancer, uterine sarcoma, uterine carcinosarcoma, or uterine cancer.

26. A binding protein comprising a T cell receptor (TCR) α chain variable (Vα) domain and a TCR β chain variable (Vβ) domain, wherein the encoded TCR Vα and Vβ domains comprise CDR1α, CDR2α, CDR3α, CDR1β, CDR2β, and CDR3β amino acid sequences of:
  (i) SEQ ID NOs.: 26-28 and 38-40, respectively; or
  (ii) SEQ ID NOs.: 23, 27, 28, and 38-40, respectively.

27. The binding protein of claim 26, which is a TCR comprising a TCR Cα and a TCR Cβ, wherein the TCR Cα and the TCR Cβ each comprise a cysteine amino acid in place of a native amino acid.

28. A method comprising introducing the polynucleotide of claim 18 into a host cell.

29. The method of claim 22, wherein the encoded binding protein is a TCR and wherein:
  (i) the encoded Vβ domain comprises the amino acid sequence of SEQ ID NO.: 16, and the encoded Vα domain comprises the amino acid sequence of SEQ ID NO.: 12; or
  (ii) the encoded Vβ domain comprises or consists of the amino acid sequence of SEQ ID NO.: 8, and the encoded Vα domain comprises or consists of the amino acid sequence of SEQ ID NO.: 4.

30. The isolated polynucleotide of claim 18, wherein:
  the encoded binding protein is a TCR comprising a TCR α chain constant domain (Cα) and a TCR β chain constant domain (Cβ), and wherein the TCR Cα and the TCR Cβ each comprise a cysteine amino acid in place of a native amino acid; and/or
  the encoded binding protein is a TCR comprising a TCR α chain and a TCR β chain, and wherein the polynucleotide comprises: a sequence encoding a self-cleaving peptide, wherein the sequence encoding a self-cleaving peptide is disposed between (i) a sequence encoding the TCR β chain and (ii) a sequence encoding the TCR α chain.

31. The vector of claim 20, which is a lentiviral, retroviral, or adenoviral expression vector.

32. The host cell of claim 14, wherein:

the host cell is a human CD8+ T cell; and/or (i) the encoded Vβ domain consists of the amino acid sequence of SEQ ID NO.: 8, and the encoded Vα domain consists of the amino acid sequence of SEQ ID NO.: 4; or (ii) the encoded Vβ domain consists of the amino acid sequence of SEQ ID NO.: 16, and the encoded Vα domain consists of the amino acid sequence of SEQ ID NO.: 12.

\* \* \* \* \*

```
                        SEQUENCE LISTING

<160> NUMBER OF SEQ ID NOS: 124

<210> SEQ ID NO 1
<211> LENGTH: 132
<212> TYPE: PRT
<213> ORGANISM: Artificial Sequence
<220> FEATURE:
<223> OTHER INFORMATION: Synthetic sequence No. 4 alpha chain variable
      domain with leader sequence

<400> SEQUENCE: 1

Met Lys Ser Leu Arg Val Leu Leu Val Ile Leu Trp Leu Gln Leu Ser
1               5                   10                  15

Trp Val Trp Ser Gln Gln Lys Glu Val Glu Gln Asn Ser Gly Pro Leu
                20                  25                  30

Ser Val Pro Glu Gly Ala Ile Ala Ser Leu Asn Cys Thr Tyr Ser Asp
            35                  40                  45

Arg Gly Ser Gln Ser Phe Phe Trp Tyr Arg Gln Tyr Ser Gly Lys Ser
        50                  55                  60

Pro Glu Leu Ile Met Phe Ile Tyr Ser Asn Gly Asp Lys Glu Asp Gly
65                  70                  75                  80

Arg Phe Thr Ala Gln Leu Asn Lys Ala Ser Gln Tyr Val Ser Leu Leu
                85                  90                  95

Ile Arg Asp Ser Gln Pro Ser Asp Ser Ala Thr Tyr Leu Cys Ala Val
                100                 105                 110

Asn Ile Gly Asn His Asp Met Arg Phe Gly Ala Gly Thr Arg Leu Thr
            115                 120                 125

Val Lys Pro Asn
    130

<210> SEQ ID NO 2
<211> LENGTH: 132
<212> TYPE: PRT
<213> ORGANISM: Artificial Sequence
<220> FEATURE:
<223> OTHER INFORMATION: Synthetic sequence No. 6 alpha chain variable
      domain with leader sequence

<400> SEQUENCE: 2

Met Glu Lys Met Leu Glu Cys Ala Phe Ile Val Leu Trp Leu Gln Leu
1               5                   10                  15

Gly Trp Leu Ser Gly Glu Asp Gln Val Thr Gln Ser Pro Glu Ala Leu
                20                  25                  30

Arg Leu Gln Glu Gly Glu Ser Ser Ser Leu Asn Cys Ser Tyr Thr Val
            35                  40                  45

Ser Gly Leu Arg Gly Leu Phe Trp Tyr Arg Gln Asp Pro Gly Lys Gly
        50                  55                  60

Pro Glu Phe Leu Phe Thr Leu Tyr Ser Ala Gly Glu Glu Lys Glu Lys
65                  70                  75                  80

Glu Arg Leu Lys Ala Thr Leu Thr Lys Lys Glu Ser Phe Leu His Ile
                85                  90                  95

Thr Ala Pro Lys Pro Glu Asp Ser Ala Thr Tyr Leu Cys Ala Val Gln
            100                 105                 110

Thr Met Asp Gly Asn Gln Phe Tyr Phe Gly Thr Gly Thr Ser Leu Thr
```

-continued

```
            115              120              125

Val Ile Pro Asn
    130

<210> SEQ ID NO 3
<211> LENGTH: 134
<212> TYPE: PRT
<213> ORGANISM: Artificial Sequence
<220> FEATURE:
<223> OTHER INFORMATION: Synthetic sequence No. 7 alpha chain variable
      domain with leader sequence

<400> SEQUENCE: 3

Met Ala Cys Pro Gly Phe Leu Trp Ala Leu Val Ile Ser Thr Cys Leu
1               5                   10                  15

Glu Phe Ser Met Ala Gln Thr Val Thr Gln Ser Gln Pro Glu Met Ser
            20                  25                  30

Val Gln Glu Ala Glu Thr Val Thr Leu Ser Cys Thr Tyr Asp Thr Ser
        35                  40                  45

Glu Ser Asp Tyr Tyr Leu Phe Trp Tyr Lys Gln Pro Pro Ser Arg Gln
    50                  55                  60

Met Ile Leu Val Ile Arg Gln Glu Ala Tyr Lys Gln Gln Asn Ala Thr
65                  70                  75                  80

Glu Asn Arg Phe Ser Val Asn Phe Gln Lys Ala Ala Lys Ser Phe Ser
                85                  90                  95

Leu Lys Ile Ser Asp Ser Gln Leu Gly Asp Ala Ala Met Tyr Phe Cys
            100                 105                 110

Ala Ser Ser Pro Gly Thr Tyr Lys Tyr Ile Phe Gly Thr Gly Thr Arg
            115                 120                 125

Leu Lys Val Leu Ala Asn
    130

<210> SEQ ID NO 4
<211> LENGTH: 137
<212> TYPE: PRT
<213> ORGANISM: Artificial Sequence
<220> FEATURE:
<223> OTHER INFORMATION: Synthetic sequence No. 10 alpha chain variable
      domain with leader sequence

<400> SEQUENCE: 4

Met Thr Arg Val Ser Leu Leu Trp Ala Val Val Val Ser Thr Cys Leu
1               5                   10                  15

Glu Ser Gly Met Ala Gln Thr Val Thr Gln Ser Gln Pro Glu Met Ser
            20                  25                  30

Val Gln Glu Ala Glu Thr Val Thr Leu Ser Cys Thr Tyr Asp Thr Ser
        35                  40                  45

Glu Ser Asn Tyr Tyr Leu Phe Trp Tyr Lys Gln Pro Pro Ser Arg Gln
    50                  55                  60

Met Ile Leu Val Ile Arg Gln Glu Ala Tyr Lys Gln Gln Asn Ala Thr
65                  70                  75                  80

Glu Asn Arg Phe Ser Val Asn Phe Gln Lys Ala Ala Lys Ser Phe Ser
                85                  90                  95

Leu Lys Ile Ser Asp Ser Gln Leu Gly Asp Thr Ala Met Tyr Phe Cys
            100                 105                 110

Ala Phe Asn Pro Trp Glu Asn Tyr Gly Gln Asn Phe Val Phe Gly Pro
            115                 120                 125

Gly Thr Arg Leu Ser Val Leu Pro Tyr
```

```
    130                 135

<210> SEQ ID NO 5
<211> LENGTH: 134
<212> TYPE: PRT
<213> ORGANISM: Artificial Sequence
<220> FEATURE:
<223> OTHER INFORMATION: Synthetic sequence No. 4 beta chain variable
      domain with leader sequence

<400> SEQUENCE: 5

Met Gly Cys Arg Leu Leu Cys Cys Ala Val Leu Cys Leu Leu Gly Ala
1               5                   10                  15

Val Pro Ile Asp Thr Glu Val Thr Gln Thr Pro Lys His Leu Val Met
            20                  25                  30

Gly Met Thr Asn Lys Lys Ser Leu Lys Cys Glu Gln His Met Gly His
        35                  40                  45

Arg Ala Met Tyr Trp Tyr Lys Gln Lys Ala Lys Lys Pro Pro Glu Leu
    50                  55                  60

Met Phe Val Tyr Ser Tyr Glu Lys Leu Ser Ile Asn Glu Ser Val Pro
65                  70                  75                  80

Ser Arg Phe Ser Pro Glu Cys Pro Asn Ser Ser Leu Leu Asn Leu His
                85                  90                  95

Leu His Ala Leu Gln Pro Glu Asp Ser Ala Leu Tyr Leu Cys Ala Ser
            100                 105                 110

Ser Gln Gly Thr Ser Gly Ala Asp Thr Gln Tyr Phe Gly Pro Gly Thr
        115                 120                 125

Arg Leu Thr Val Leu Glu
    130

<210> SEQ ID NO 6
<211> LENGTH: 135
<212> TYPE: PRT
<213> ORGANISM: Artificial Sequence
<220> FEATURE:
<223> OTHER INFORMATION: Synthetic sequence No. 6 beta chain variable
      domain with leader sequence

<400> SEQUENCE: 6

Met Ser Ile Gly Leu Leu Cys Cys Ala Ala Leu Ser Leu Leu Trp Ala
1               5                   10                  15

Gly Pro Val Asn Ala Gly Val Thr Gln Thr Pro Lys Phe Gln Val Leu
            20                  25                  30

Lys Thr Gly Gln Ser Met Thr Leu Gln Cys Ala Gln Asp Met Asn His
        35                  40                  45

Glu Tyr Met Ser Trp Tyr Arg Gln Asp Pro Gly Met Gly Leu Arg Leu
    50                  55                  60

Ile His Tyr Ser Val Gly Ala Gly Ile Thr Asp Gln Gly Glu Val Pro
65                  70                  75                  80

Asn Gly Tyr Asn Val Ser Arg Ser Thr Thr Glu Asp Phe Pro Leu Arg
                85                  90                  95

Leu Leu Ser Ala Ala Pro Ser Gln Thr Ser Val Tyr Phe Cys Ala Ser
            100                 105                 110

Ser Tyr Ser Leu Trp Asp Leu Gln Glu Thr Gln Tyr Phe Gly Pro Gly
        115                 120                 125

Thr Arg Leu Leu Val Leu Glu
    130                 135
```

-continued

```
<210> SEQ ID NO 7
<211> LENGTH: 136
<212> TYPE: PRT
<213> ORGANISM: Artificial Sequence
<220> FEATURE:
<223> OTHER INFORMATION: Synthetic sequence No. 7 beta chain variable
      domain with leader sequence

<400> SEQUENCE: 7

Met Gly Thr Ser Leu Leu Cys Trp Met Ala Leu Cys Leu Leu Gly Ala
1               5                   10                  15

Asp His Ala Asp Thr Gly Val Ser Gln Asp Pro Arg His Lys Ile Thr
                20                  25                  30

Lys Arg Gly Gln Asn Val Thr Phe Arg Cys Asp Pro Ile Ser Glu His
            35                  40                  45

Asn Arg Leu Tyr Trp Tyr Arg Gln Thr Leu Gly Gln Gly Pro Glu Phe
        50                  55                  60

Leu Thr Tyr Phe Gln Asn Glu Ala Gln Leu Glu Lys Ser Arg Leu Leu
65                  70                  75                  80

Ser Asp Arg Phe Ser Ala Glu Arg Pro Lys Gly Ser Phe Ser Thr Leu
                85                  90                  95

Glu Ile Gln Arg Thr Glu Gln Gly Asp Ser Ala Met Tyr Leu Cys Ala
            100                 105                 110

Ser Ser Phe Ser Asp Gly Gly Ala Thr Asp Thr Gln Tyr Phe Gly Pro
        115                 120                 125

Gly Thr Arg Leu Thr Val Leu Glu
    130                 135

<210> SEQ ID NO 8
<211> LENGTH: 132
<212> TYPE: PRT
<213> ORGANISM: Artificial Sequence
<220> FEATURE:
<223> OTHER INFORMATION: Synthetic sequence No. 10 beta chain variable
      domain with leader sequence

<400> SEQUENCE: 8

Met Leu Leu Leu Leu Leu Leu Leu Gly Pro Ala Gly Ser Gly Leu Gly
1               5                   10                  15

Ala Val Val Ser Gln His Pro Ser Trp Val Ile Cys Lys Ser Gly Thr
                20                  25                  30

Ser Val Lys Ile Glu Cys Arg Ser Leu Asp Phe Gln Ala Thr Thr Met
            35                  40                  45

Phe Trp Tyr Arg Gln Phe Pro Lys Gln Ser Leu Met Leu Met Ala Thr
        50                  55                  60

Ser Asn Glu Gly Ser Lys Ala Thr Tyr Glu Gln Gly Val Glu Lys Asp
65                  70                  75                  80

Lys Phe Leu Ile Asn His Ala Ser Leu Thr Leu Ser Thr Leu Thr Val
                85                  90                  95

Thr Ser Ala His Pro Glu Asp Ser Ser Phe Tyr Ile Cys Ser Ala Arg
            100                 105                 110

Pro His Ser Leu Thr Asp Thr Gln Tyr Phe Gly Pro Gly Thr Arg Leu
        115                 120                 125

Thr Val Leu Glu
    130

<210> SEQ ID NO 9
<211> LENGTH: 111
<212> TYPE: PRT
```

<213> ORGANISM: Artificial Sequence
<220> FEATURE:
<223> OTHER INFORMATION: Synthetic sequence No. 4 alpha chain variable
      domain, leader sequence removed

<400> SEQUENCE: 9

Gln Lys Glu Val Glu Gln Asn Ser Gly Pro Leu Ser Val Pro Glu Gly
1               5                   10                  15

Ala Ile Ala Ser Leu Asn Cys Thr Tyr Ser Asp Arg Gly Ser Gln Ser
            20                  25                  30

Phe Phe Trp Tyr Arg Gln Tyr Ser Gly Lys Ser Pro Glu Leu Ile Met
        35                  40                  45

Phe Ile Tyr Ser Asn Gly Asp Lys Glu Asp Gly Arg Phe Thr Ala Gln
        50                  55                  60

Leu Asn Lys Ala Ser Gln Tyr Val Ser Leu Leu Ile Arg Asp Ser Gln
65                  70                  75                  80

Pro Ser Asp Ser Ala Thr Tyr Leu Cys Ala Val Asn Ile Gly Asn His
                85                  90                  95

Asp Met Arg Phe Gly Ala Gly Thr Arg Leu Thr Val Lys Pro Asn
                100                 105                 110

<210> SEQ ID NO 10
<211> LENGTH: 111
<212> TYPE: PRT
<213> ORGANISM: Artificial Sequence
<220> FEATURE:
<223> OTHER INFORMATION: Synthetic sequence No. 6 alpha chain variable
      domain, leader sequence removed

<400> SEQUENCE: 10

Glu Asp Gln Val Thr Gln Ser Pro Glu Ala Leu Arg Leu Gln Glu Gly
1               5                   10                  15

Glu Ser Ser Ser Leu Asn Cys Ser Tyr Thr Val Ser Gly Leu Arg Gly
            20                  25                  30

Leu Phe Trp Tyr Arg Gln Asp Pro Gly Lys Gly Pro Glu Phe Leu Phe
        35                  40                  45

Thr Leu Tyr Ser Ala Gly Glu Glu Lys Glu Lys Glu Arg Leu Lys Ala
    50                  55                  60

Thr Leu Thr Lys Lys Glu Ser Phe Leu His Ile Thr Ala Pro Lys Pro
65                  70                  75                  80

Glu Asp Ser Ala Thr Tyr Leu Cys Ala Val Gln Thr Met Asp Gly Asn
                85                  90                  95

Gln Phe Tyr Phe Gly Thr Gly Thr Ser Leu Thr Val Ile Pro Asn
                100                 105                 110

<210> SEQ ID NO 11
<211> LENGTH: 114
<212> TYPE: PRT
<213> ORGANISM: Artificial Sequence
<220> FEATURE:
<223> OTHER INFORMATION: Synthetic sequence No. 7 alpha chain variable
      domain, leader sequence removed

<400> SEQUENCE: 11

Ala Gln Thr Val Thr Gln Ser Gln Pro Glu Met Ser Val Gln Glu Ala
1               5                   10                  15

Glu Thr Val Thr Leu Ser Cys Thr Tyr Asp Thr Ser Glu Ser Asp Tyr
            20                  25                  30

Tyr Leu Phe Trp Tyr Lys Gln Pro Pro Ser Arg Gln Met Ile Leu Val
        35                  40                  45

-continued

Ile Arg Gln Glu Ala Tyr Lys Gln Gln Asn Ala Thr Glu Asn Arg Phe
    50                  55                  60

Ser Val Asn Phe Gln Lys Ala Ala Lys Ser Phe Ser Leu Lys Ile Ser
65                  70                  75                  80

Asp Ser Gln Leu Gly Asp Ala Ala Met Tyr Phe Cys Ala Ser Ser Pro
                85                  90                  95

Gly Thr Tyr Lys Tyr Ile Phe Gly Thr Gly Thr Arg Leu Lys Val Leu
            100                 105                 110

Ala Asn

<210> SEQ ID NO 12
<211> LENGTH: 117
<212> TYPE: PRT
<213> ORGANISM: Artificial Sequence
<220> FEATURE:
<223> OTHER INFORMATION: Synthetic sequence No. 10 alpha chain variable
      domain, leader sequence removed

<400> SEQUENCE: 12

Ala Gln Thr Val Thr Gln Ser Gln Pro Glu Met Ser Val Gln Glu Ala
1               5                   10                  15

Glu Thr Val Thr Leu Ser Cys Thr Tyr Asp Thr Ser Glu Ser Asn Tyr
                20                  25                  30

Tyr Leu Phe Trp Tyr Lys Gln Pro Pro Ser Arg Gln Met Ile Leu Val
            35                  40                  45

Ile Arg Gln Glu Ala Tyr Lys Gln Gln Asn Ala Thr Glu Asn Arg Phe
    50                  55                  60

Ser Val Asn Phe Gln Lys Ala Ala Lys Ser Phe Ser Leu Lys Ile Ser
65                  70                  75                  80

Asp Ser Gln Leu Gly Asp Thr Ala Met Tyr Phe Cys Ala Phe Asn Pro
                85                  90                  95

Trp Glu Asn Tyr Gly Gln Asn Phe Val Phe Gly Pro Gly Thr Arg Leu
            100                 105                 110

Ser Val Leu Pro Tyr
        115

<210> SEQ ID NO 13
<211> LENGTH: 115
<212> TYPE: PRT
<213> ORGANISM: Artificial Sequence
<220> FEATURE:
<223> OTHER INFORMATION: Synthetic sequence No. 4 beta chain variable
      domain, leader sequence removed

<400> SEQUENCE: 13

Asp Thr Glu Val Thr Gln Thr Pro Lys His Leu Val Met Gly Met Thr
1               5                   10                  15

Asn Lys Lys Ser Leu Lys Cys Glu Gln His Met Gly His Arg Ala Met
                20                  25                  30

Tyr Trp Tyr Lys Gln Lys Ala Lys Lys Pro Pro Glu Leu Met Phe Val
            35                  40                  45

Tyr Ser Tyr Glu Lys Leu Ser Ile Asn Glu Ser Val Pro Ser Arg Phe
    50                  55                  60

Ser Pro Glu Cys Pro Asn Ser Ser Leu Leu Asn Leu His Leu His Ala
65                  70                  75                  80

Leu Gln Pro Glu Asp Ser Ala Leu Tyr Leu Cys Ala Ser Ser Gln Gly
                85                  90                  95

-continued

```
Thr Ser Gly Ala Asp Thr Gln Tyr Phe Gly Pro Gly Thr Arg Leu Thr
            100             105             110

Val Leu Glu
        115

<210> SEQ ID NO 14
<211> LENGTH: 116
<212> TYPE: PRT
<213> ORGANISM: Artificial Sequence
<220> FEATURE:
<223> OTHER INFORMATION: Synthetic sequence No. 6 beta chain variable
      domain, leader sequence removed

<400> SEQUENCE: 14

Asn Ala Gly Val Thr Gln Thr Pro Lys Phe Gln Val Leu Lys Thr Gly
1               5               10              15

Gln Ser Met Thr Leu Gln Cys Ala Gln Asp Met Asn His Glu Tyr Met
            20              25              30

Ser Trp Tyr Arg Gln Asp Pro Gly Met Gly Leu Arg Leu Ile His Tyr
        35              40              45

Ser Val Gly Ala Gly Ile Thr Asp Gln Gly Glu Val Pro Asn Gly Tyr
    50              55              60

Asn Val Ser Arg Ser Thr Thr Glu Asp Phe Pro Leu Arg Leu Leu Ser
65              70              75              80

Ala Ala Pro Ser Gln Thr Ser Val Tyr Phe Cys Ala Ser Ser Tyr Ser
            85              90              95

Leu Trp Asp Leu Gln Glu Thr Gln Tyr Phe Gly Pro Gly Thr Arg Leu
            100             105             110

Leu Val Leu Glu
        115

<210> SEQ ID NO 15
<211> LENGTH: 117
<212> TYPE: PRT
<213> ORGANISM: Artificial Sequence
<220> FEATURE:
<223> OTHER INFORMATION: Synthetic sequence No. 7 beta chain variable
      domain, leader sequence removed

<400> SEQUENCE: 15

Asp Thr Gly Val Ser Gln Asp Pro Arg His Lys Ile Thr Lys Arg Gly
1               5               10              15

Gln Asn Val Thr Phe Arg Cys Asp Pro Ile Ser Glu His Asn Arg Leu
            20              25              30

Tyr Trp Tyr Arg Gln Thr Leu Gly Gln Gly Pro Glu Phe Leu Thr Tyr
        35              40              45

Phe Gln Asn Glu Ala Gln Leu Glu Lys Ser Arg Leu Leu Ser Asp Arg
    50              55              60

Phe Ser Ala Glu Arg Pro Lys Gly Ser Phe Ser Thr Leu Glu Ile Gln
65              70              75              80

Arg Thr Glu Gln Gly Asp Ser Ala Met Tyr Leu Cys Ala Ser Ser Phe
            85              90              95

Ser Asp Gly Gly Ala Thr Asp Thr Gln Tyr Phe Gly Pro Gly Thr Arg
            100             105             110

Leu Thr Val Leu Glu
        115

<210> SEQ ID NO 16
<211> LENGTH: 117
```

-continued

```
<212> TYPE: PRT
<213> ORGANISM: Artificial Sequence
<220> FEATURE:
<223> OTHER INFORMATION: Synthetic sequence No. 10 beta chain variable
      domain, leader sequence removed

<400> SEQUENCE: 16

Gly Ala Val Val Ser Gln His Pro Ser Trp Val Ile Cys Lys Ser Gly
1               5                   10                  15

Thr Ser Val Lys Ile Glu Cys Arg Ser Leu Asp Phe Gln Ala Thr Thr
            20                  25                  30

Met Phe Trp Tyr Arg Gln Phe Pro Lys Gln Ser Leu Met Leu Met Ala
        35                  40                  45

Thr Ser Asn Glu Gly Ser Lys Ala Thr Tyr Glu Gln Gly Val Glu Lys
    50                  55                  60

Asp Lys Phe Leu Ile Asn His Ala Ser Leu Thr Leu Ser Thr Leu Thr
65                  70                  75                  80

Val Thr Ser Ala His Pro Glu Asp Ser Ser Phe Tyr Ile Cys Ser Ala
                85                  90                  95

Arg Pro His Ser Leu Thr Asp Thr Gln Tyr Phe Gly Pro Gly Thr Arg
            100                 105                 110

Leu Thr Val Leu Glu
        115

<210> SEQ ID NO 17
<211> LENGTH: 6
<212> TYPE: PRT
<213> ORGANISM: Artificial Sequence
<220> FEATURE:
<223> OTHER INFORMATION: Synthetic sequence  No. 4 CDR1alpha

<400> SEQUENCE: 17

Asp Arg Gly Ser Gln Ser
1               5

<210> SEQ ID NO 18
<211> LENGTH: 6
<212> TYPE: PRT
<213> ORGANISM: Artificial Sequence
<220> FEATURE:
<223> OTHER INFORMATION: Synthetic sequence  No. 4 CDR2alpha

<400> SEQUENCE: 18

Ile Tyr Ser Asn Gly Asp
1               5

<210> SEQ ID NO 19
<211> LENGTH: 12
<212> TYPE: PRT
<213> ORGANISM: Artificial Sequence
<220> FEATURE:
<223> OTHER INFORMATION: Synthetic sequence  No. 4 CDR3alpha

<400> SEQUENCE: 19

Cys Ala Val Asn Ile Gly Asn His Asp Met Arg Phe
1               5                   10

<210> SEQ ID NO 20
<211> LENGTH: 6
<212> TYPE: PRT
<213> ORGANISM: Artificial Sequence
<220> FEATURE:
<223> OTHER INFORMATION: Synthetic sequence  No. 6 CDR1alpha
```

-continued

```
<400> SEQUENCE: 20

Val Ser Gly Leu Arg Gly
1               5

<210> SEQ ID NO 21
<211> LENGTH: 7
<212> TYPE: PRT
<213> ORGANISM: Artificial Sequence
<220> FEATURE:
<223> OTHER INFORMATION: Synthetic sequence  No. 6 CDR2alpha

<400> SEQUENCE: 21

Leu Tyr Ser Ala Gly Glu Glu
1               5

<210> SEQ ID NO 22
<211> LENGTH: 13
<212> TYPE: PRT
<213> ORGANISM: Artificial Sequence
<220> FEATURE:
<223> OTHER INFORMATION: Synthetic sequence  No. 6 CDR3alpha

<400> SEQUENCE: 22

Cys Ala Val Gln Thr Met Asp Gly Asn Gln Phe Tyr Phe
1               5                   10

<210> SEQ ID NO 23
<211> LENGTH: 7
<212> TYPE: PRT
<213> ORGANISM: Artificial Sequence
<220> FEATURE:
<223> OTHER INFORMATION: Synthetic sequence  No. 7 CDR1alpha

<400> SEQUENCE: 23

Thr Ser Glu Ser Asp Tyr Tyr
1               5

<210> SEQ ID NO 24
<211> LENGTH: 8
<212> TYPE: PRT
<213> ORGANISM: Artificial Sequence
<220> FEATURE:
<223> OTHER INFORMATION: Synthetic sequence No. 7 CDR2alpha

<400> SEQUENCE: 24

Gln Glu Ala Tyr Lys Gln Gln Asn
1               5

<210> SEQ ID NO 25
<211> LENGTH: 12
<212> TYPE: PRT
<213> ORGANISM: Artificial Sequence
<220> FEATURE:
<223> OTHER INFORMATION: Synthetic sequence No. 7 CDR3alpha

<400> SEQUENCE: 25

Cys Ala Ser Ser Pro Gly Thr Tyr Lys Tyr Ile Phe
1               5                   10

<210> SEQ ID NO 26
<211> LENGTH: 7
<212> TYPE: PRT
<213> ORGANISM: Artificial Sequence
<220> FEATURE:
<223> OTHER INFORMATION: Synthetic sequence No. 10 CDR1alpha

<400> SEQUENCE: 26
```

```
Thr Ser Glu Ser Asn Tyr Tyr
1               5

<210> SEQ ID NO 27
<211> LENGTH: 8
<212> TYPE: PRT
<213> ORGANISM: Artificial Sequence
<220> FEATURE:
<223> OTHER INFORMATION: Synthetic sequence No. 10 CDR2alpha

<400> SEQUENCE: 27

Gln Glu Ala Tyr Lys Gln Gln Asn
1               5

<210> SEQ ID NO 28
<211> LENGTH: 15
<212> TYPE: PRT
<213> ORGANISM: Artificial Sequence
<220> FEATURE:
<223> OTHER INFORMATION: Synthetic sequenceNo. 10 CDR3alpha

<400> SEQUENCE: 28

Cys Ala Phe Asn Pro Trp Glu Asn Tyr Gly Gln Asn Phe Val Phe
1               5                   10                  15

<210> SEQ ID NO 29
<211> LENGTH: 5
<212> TYPE: PRT
<213> ORGANISM: Artificial Sequence
<220> FEATURE:
<223> OTHER INFORMATION: Synthetic sequence No. 4 CDR1beta

<400> SEQUENCE: 29

Met Gly His Arg Ala
1               5

<210> SEQ ID NO 30
<211> LENGTH: 6
<212> TYPE: PRT
<213> ORGANISM: Artificial Sequence
<220> FEATURE:
<223> OTHER INFORMATION: Synthetic sequence No. 4 CDR2beta

<400> SEQUENCE: 30

Tyr Ser Tyr Glu Lys Leu
1               5

<210> SEQ ID NO 31
<211> LENGTH: 15
<212> TYPE: PRT
<213> ORGANISM: Artificial Sequence
<220> FEATURE:
<223> OTHER INFORMATION: Synthetic sequence No. 4 CDR3beta

<400> SEQUENCE: 31

Cys Ala Ser Ser Gln Gly Thr Ser Gly Ala Asp Thr Gln Tyr Phe
1               5                   10                  15

<210> SEQ ID NO 32
<211> LENGTH: 5
<212> TYPE: PRT
<213> ORGANISM: Artificial Sequence
<220> FEATURE:
<223> OTHER INFORMATION: Synthetic sequence No. 6 CDR1beta

<400> SEQUENCE: 32
```

-continued

```
Met Asn His Glu Tyr
1               5

<210> SEQ ID NO 33
<211> LENGTH: 6
<212> TYPE: PRT
<213> ORGANISM: Artificial Sequence
<220> FEATURE:
<223> OTHER INFORMATION: Synthetic sequence No. 6 CDR2beta

<400> SEQUENCE: 33

Ser Val Gly Ala Gly Ile
1               5

<210> SEQ ID NO 34
<211> LENGTH: 16
<212> TYPE: PRT
<213> ORGANISM: Artificial Sequence
<220> FEATURE:
<223> OTHER INFORMATION: Synthetic sequence No. 6 CDR3beta

<400> SEQUENCE: 34

Cys Ala Ser Ser Tyr Ser Leu Trp Asp Leu Gln Glu Thr Gln Tyr Phe
1               5                   10                  15

<210> SEQ ID NO 35
<211> LENGTH: 5
<212> TYPE: PRT
<213> ORGANISM: Artificial Sequence
<220> FEATURE:
<223> OTHER INFORMATION: Synthetic sequence No. 7 CDR1beta

<400> SEQUENCE: 35

Ser Glu His Asn Arg
1               5

<210> SEQ ID NO 36
<211> LENGTH: 6
<212> TYPE: PRT
<213> ORGANISM: Artificial Sequence
<220> FEATURE:
<223> OTHER INFORMATION: Synthetic sequence No. 7 CDR2beta

<400> SEQUENCE: 36

Phe Gln Asn Glu Ala Gln
1               5

<210> SEQ ID NO 37
<211> LENGTH: 16
<212> TYPE: PRT
<213> ORGANISM: Artificial Sequence
<220> FEATURE:
<223> OTHER INFORMATION: Synthetic sequence No. 7 CDR3beta

<400> SEQUENCE: 37

Cys Ala Ser Ser Phe Ser Asp Gly Gly Ala Thr Asp Thr Gln Tyr Phe
1               5                   10                  15

<210> SEQ ID NO 38
<211> LENGTH: 6
<212> TYPE: PRT
<213> ORGANISM: Artificial Sequence
<220> FEATURE:
<223> OTHER INFORMATION: Synthetic sequence No. 10 CDR1beta

<400> SEQUENCE: 38

Asp Phe Gln Ala Thr Thr
```

-continued

```
1               5

<210> SEQ ID NO 39
<211> LENGTH: 7
<212> TYPE: PRT
<213> ORGANISM: Artificial Sequence
<220> FEATURE:
<223> OTHER INFORMATION: Synthetic sequence No. 10 CDR2beta

<400> SEQUENCE: 39

Ser Asn Glu Gly Ser Lys Ala
1               5

<210> SEQ ID NO 40
<211> LENGTH: 14
<212> TYPE: PRT
<213> ORGANISM: Artificial Sequence
<220> FEATURE:
<223> OTHER INFORMATION: Synthetic sequence No. 10 CDR3beta

<400> SEQUENCE: 40

Cys Ser Ala Arg Pro His Ser Leu Thr Asp Thr Gln Tyr Phe
1               5                   10

<210> SEQ ID NO 41
<211> LENGTH: 140
<212> TYPE: PRT
<213> ORGANISM: Artificial Sequence
<220> FEATURE:
<223> OTHER INFORMATION: Synthetic sequence No. 4 TCR alpha constant
      domain

<400> SEQUENCE: 41

Ile Gln Asn Pro Asp Pro Ala Val Tyr Gln Leu Arg Asp Ser Lys Ser
1               5                   10                  15

Ser Asp Lys Ser Val Cys Leu Phe Thr Asp Phe Asp Ser Gln Thr Asn
            20                  25                  30

Val Ser Gln Ser Lys Asp Ser Asp Val Tyr Ile Thr Asp Lys Cys Val
        35                  40                  45

Leu Asp Met Arg Ser Met Asp Phe Lys Ser Asn Ser Ala Val Ala Trp
    50                  55                  60

Ser Asn Lys Ser Asp Phe Ala Cys Ala Asn Ala Phe Asn Asn Ser Ile
65                  70                  75                  80

Ile Pro Glu Asp Thr Phe Phe Pro Ser Pro Glu Ser Ser Cys Asp Val
                85                  90                  95

Lys Leu Val Glu Lys Ser Phe Glu Thr Asp Thr Asn Leu Asn Phe Gln
            100                 105                 110

Asn Leu Ser Val Ile Gly Phe Arg Ile Leu Leu Leu Lys Val Ala Gly
        115                 120                 125

Phe Asn Leu Leu Met Thr Leu Arg Leu Trp Ser Ser
        130                 135                 140

<210> SEQ ID NO 42
<211> LENGTH: 140
<212> TYPE: PRT
<213> ORGANISM: Artificial Sequence
<220> FEATURE:
<223> OTHER INFORMATION: Synthetic sequence No. 6 TCR alpha constant
      domain

<400> SEQUENCE: 42

Ile Gln Asn Pro Asp Pro Ala Val Tyr Gln Leu Arg Asp Ser Lys Ser
1               5                   10                  15
```

-continued

```
Ser Asp Lys Ser Val Cys Leu Phe Thr Asp Phe Asp Ser Gln Thr Asn
            20                  25                  30

Val Ser Gln Ser Lys Asp Ser Asp Val Tyr Ile Thr Asp Lys Cys Val
            35                  40                  45

Leu Asp Met Arg Ser Met Asp Phe Lys Ser Asn Ser Ala Val Ala Trp
            50                  55                  60

Ser Asn Lys Ser Asp Phe Ala Cys Ala Asn Ala Phe Asn Asn Ser Ile
65                  70                  75                  80

Ile Pro Glu Asp Thr Phe Phe Pro Ser Pro Glu Ser Ser Cys Asp Val
                85                  90                  95

Lys Leu Val Glu Lys Ser Phe Glu Thr Asp Thr Asn Leu Asn Phe Gln
            100                 105                 110

Asn Leu Ser Val Ile Gly Phe Arg Ile Leu Leu Leu Lys Val Ala Gly
            115                 120                 125

Phe Asn Leu Leu Met Thr Leu Arg Leu Trp Ser Ser
        130                 135                 140
```

<210> SEQ ID NO 43
<211> LENGTH: 140
<212> TYPE: PRT
<213> ORGANISM: Artificial Sequence
<220> FEATURE:
<223> OTHER INFORMATION: Synthetic sequence No. 7 TCR alpha constant
    domain

<400> SEQUENCE: 43

```
Ile Gln Asn Pro Asp Pro Ala Val Tyr Gln Leu Arg Asp Ser Lys Ser
1               5                   10                  15

Ser Asp Lys Ser Val Cys Leu Phe Thr Asp Phe Asp Ser Gln Thr Asn
            20                  25                  30

Val Ser Gln Ser Lys Asp Ser Asp Val Tyr Ile Thr Asp Lys Cys Val
            35                  40                  45

Leu Asp Met Arg Ser Met Asp Phe Lys Ser Asn Ser Ala Val Ala Trp
            50                  55                  60

Ser Asn Lys Ser Asp Phe Ala Cys Ala Asn Ala Phe Asn Asn Ser Ile
65                  70                  75                  80

Ile Pro Glu Asp Thr Phe Phe Pro Ser Pro Glu Ser Ser Cys Asp Val
                85                  90                  95

Lys Leu Val Glu Lys Ser Phe Glu Thr Asp Thr Asn Leu Asn Phe Gln
            100                 105                 110

Asn Leu Ser Val Ile Gly Phe Arg Ile Leu Leu Leu Lys Val Ala Gly
            115                 120                 125

Phe Asn Leu Leu Met Thr Leu Arg Leu Trp Ser Ser
        130                 135                 140
```

<210> SEQ ID NO 44
<211> LENGTH: 140
<212> TYPE: PRT
<213> ORGANISM: Artificial Sequence
<220> FEATURE:
<223> OTHER INFORMATION: Synthetic sequence No. 10 TCR alpha constant
    domain

<400> SEQUENCE: 44

```
Ile Gln Asn Pro Asp Pro Ala Val Tyr Gln Leu Arg Asp Ser Lys Ser
1               5                   10                  15

Ser Asp Lys Ser Val Cys Leu Phe Thr Asp Phe Asp Ser Gln Thr Asn
            20                  25                  30
```

Val Ser Gln Ser Lys Asp Ser Asp Val Tyr Ile Thr Asp Lys Cys Val
        35              40              45

Leu Asp Met Arg Ser Met Asp Phe Lys Ser Asn Ser Ala Val Ala Trp
    50              55              60

Ser Asn Lys Ser Asp Phe Ala Cys Ala Asn Ala Phe Asn Asn Ser Ile
65              70              75              80

Ile Pro Glu Asp Thr Phe Phe Pro Ser Pro Glu Ser Ser Cys Asp Val
                85              90              95

Lys Leu Val Glu Lys Ser Phe Glu Thr Asp Thr Asn Leu Asn Phe Gln
        100             105             110

Asn Leu Ser Val Ile Gly Phe Arg Ile Leu Leu Leu Lys Val Ala Gly
        115             120             125

Phe Asn Leu Leu Met Thr Leu Arg Leu Trp Ser Ser
    130             135             140

<210> SEQ ID NO 45
<211> LENGTH: 178
<212> TYPE: PRT
<213> ORGANISM: Artificial Sequence
<220> FEATURE:
<223> OTHER INFORMATION: Synthetic sequence TCR beta constant domain

<400> SEQUENCE: 45

Asp Leu Lys Asn Val Phe Pro Pro Glu Val Ala Val Phe Glu Pro Ser
1               5               10              15

Glu Ala Glu Ile Ser His Thr Gln Lys Ala Thr Leu Val Cys Leu Ala
            20              25              30

Thr Gly Phe Tyr Pro Asp His Val Glu Leu Ser Trp Trp Val Asn Gly
        35              40              45

Lys Glu Val His Ser Gly Val Cys Thr Asp Pro Gln Pro Leu Lys Glu
    50              55              60

Gln Pro Ala Leu Asn Asp Ser Arg Tyr Cys Leu Ser Ser Arg Leu Arg
65              70              75              80

Val Ser Ala Thr Phe Trp Gln Asn Pro Arg Asn His Phe Arg Cys Gln
                85              90              95

Val Gln Phe Tyr Gly Leu Ser Glu Asn Asp Glu Trp Thr Gln Asp Arg
        100             105             110

Ala Lys Pro Val Thr Gln Ile Val Ser Ala Glu Ala Trp Gly Arg Ala
        115             120             125

Asp Cys Gly Phe Thr Ser Glu Ser Tyr Gln Gln Gly Val Leu Ser Ala
    130             135             140

Thr Ile Leu Tyr Glu Ile Leu Leu Gly Lys Ala Thr Leu Tyr Ala Val
145             150             155             160

Leu Val Ser Ala Leu Val Leu Met Ala Met Val Lys Arg Lys Asp Ser
            165             170             175

Arg Gly

<210> SEQ ID NO 46
<211> LENGTH: 272
<212> TYPE: PRT
<213> ORGANISM: Artificial Sequence
<220> FEATURE:
<223> OTHER INFORMATION: Synthetic sequence No. 4 alpha chain with
      leader sequence

<400> SEQUENCE: 46

Met Lys Ser Leu Arg Val Leu Leu Val Ile Leu Trp Leu Gln Leu Ser

-continued

```
1              5                    10                   15

Trp Val Trp Ser Gln Gln Lys Glu Val Glu Gln Asn Ser Gly Pro Leu
            20                   25                   30

Ser Val Pro Glu Gly Ala Ile Ala Ser Leu Asn Cys Thr Tyr Ser Asp
            35                   40                   45

Arg Gly Ser Gln Ser Phe Phe Trp Tyr Arg Gln Tyr Ser Gly Lys Ser
    50                   55                   60

Pro Glu Leu Ile Met Phe Ile Tyr Ser Asn Gly Asp Lys Glu Asp Gly
65                   70                   75                   80

Arg Phe Thr Ala Gln Leu Asn Lys Ala Ser Gln Tyr Val Ser Leu Leu
                85                   90                   95

Ile Arg Asp Ser Gln Pro Ser Asp Ser Ala Thr Tyr Leu Cys Ala Val
            100                  105                  110

Asn Ile Gly Asn His Asp Met Arg Phe Gly Ala Gly Thr Arg Leu Thr
            115                  120                  125

Val Lys Pro Asn Ile Gln Asn Pro Asp Pro Ala Val Tyr Gln Leu Arg
    130                  135                  140

Asp Ser Lys Ser Ser Asp Lys Ser Val Cys Leu Phe Thr Asp Phe Asp
145                  150                  155                  160

Ser Gln Thr Asn Val Ser Gln Ser Lys Asp Ser Asp Val Tyr Ile Thr
                165                  170                  175

Asp Lys Cys Val Leu Asp Met Arg Ser Met Asp Phe Lys Ser Asn Ser
            180                  185                  190

Ala Val Ala Trp Ser Asn Lys Ser Asp Phe Ala Cys Ala Asn Ala Phe
            195                  200                  205

Asn Asn Ser Ile Ile Pro Glu Asp Thr Phe Phe Pro Ser Pro Glu Ser
    210                  215                  220

Ser Cys Asp Val Lys Leu Val Glu Lys Ser Phe Glu Thr Asp Thr Asn
225                  230                  235                  240

Leu Asn Phe Gln Asn Leu Ser Val Ile Gly Phe Arg Ile Leu Leu Leu
                245                  250                  255

Lys Val Ala Gly Phe Asn Leu Leu Met Thr Leu Arg Leu Trp Ser Ser
            260                  265                  270
```

```
<210> SEQ ID NO 47
<211> LENGTH: 272
<212> TYPE: PRT
<213> ORGANISM: Artificial Sequence
<220> FEATURE:
<223> OTHER INFORMATION: Synthetic sequence No. 6 alpha chain with
      leader sequence

<400> SEQUENCE: 47
```

```
Met Glu Lys Met Leu Glu Cys Ala Phe Ile Val Leu Trp Leu Gln Leu
1              5                    10                   15

Gly Trp Leu Ser Gly Glu Asp Gln Val Thr Gln Ser Pro Glu Ala Leu
            20                   25                   30

Arg Leu Gln Glu Gly Glu Ser Ser Ser Leu Asn Cys Ser Tyr Thr Val
            35                   40                   45

Ser Gly Leu Arg Gly Leu Phe Trp Tyr Arg Gln Asp Pro Gly Lys Gly
    50                   55                   60

Pro Glu Phe Leu Phe Thr Leu Tyr Ser Ala Gly Glu Glu Lys Glu Lys
65                   70                   75                   80

Glu Arg Leu Lys Ala Thr Leu Thr Lys Lys Glu Ser Phe Leu His Ile
                85                   90                   95
```

-continued

Thr Ala Pro Lys Pro Glu Asp Ser Ala Thr Tyr Leu Cys Ala Val Gln
            100                 105                 110

Thr Met Asp Gly Asn Gln Phe Tyr Phe Gly Thr Gly Thr Ser Leu Thr
            115                 120                 125

Val Ile Pro Asn Ile Gln Asn Pro Asp Pro Ala Val Tyr Gln Leu Arg
            130                 135                 140

Asp Ser Lys Ser Ser Asp Lys Ser Val Cys Leu Phe Thr Asp Phe Asp
145                 150                 155                 160

Ser Gln Thr Asn Val Ser Gln Ser Lys Asp Ser Asp Val Tyr Ile Thr
                    165                 170                 175

Asp Lys Cys Val Leu Asp Met Arg Ser Met Asp Phe Lys Ser Asn Ser
            180                 185                 190

Ala Val Ala Trp Ser Asn Lys Ser Asp Phe Ala Cys Ala Asn Ala Phe
            195                 200                 205

Asn Asn Ser Ile Ile Pro Glu Asp Thr Phe Phe Pro Ser Pro Glu Ser
            210                 215                 220

Ser Cys Asp Val Lys Leu Val Glu Lys Ser Phe Glu Thr Asp Thr Asn
225                 230                 235                 240

Leu Asn Phe Gln Asn Leu Ser Val Ile Gly Phe Arg Ile Leu Leu Leu
                    245                 250                 255

Lys Val Ala Gly Phe Asn Leu Leu Met Thr Leu Arg Leu Trp Ser Ser
            260                 265                 270

<210> SEQ ID NO 48
<211> LENGTH: 274
<212> TYPE: PRT
<213> ORGANISM: Artificial Sequence
<220> FEATURE:
<223> OTHER INFORMATION: Synthetic sequence No. 7 alpha chain with
      leader sequence

<400> SEQUENCE: 48

Met Ala Cys Pro Gly Phe Leu Trp Ala Leu Val Ile Ser Thr Cys Leu
1               5                   10                  15

Glu Phe Ser Met Ala Gln Thr Val Thr Gln Ser Gln Pro Glu Met Ser
            20                  25                  30

Val Gln Glu Ala Glu Thr Val Thr Leu Ser Cys Thr Tyr Asp Thr Ser
            35                  40                  45

Glu Ser Asp Tyr Tyr Leu Phe Trp Tyr Lys Gln Pro Pro Ser Arg Gln
            50                  55                  60

Met Ile Leu Val Ile Arg Gln Glu Ala Tyr Lys Gln Gln Asn Ala Thr
65                  70                  75                  80

Glu Asn Arg Phe Ser Val Asn Phe Gln Lys Ala Ala Lys Ser Phe Ser
                    85                  90                  95

Leu Lys Ile Ser Asp Ser Gln Leu Gly Asp Ala Ala Met Tyr Phe Cys
            100                 105                 110

Ala Ser Ser Pro Gly Thr Tyr Lys Tyr Ile Phe Gly Thr Gly Thr Arg
            115                 120                 125

Leu Lys Val Leu Ala Asn Ile Gln Asn Pro Asp Pro Ala Val Tyr Gln
            130                 135                 140

Leu Arg Asp Ser Lys Ser Ser Asp Lys Ser Val Cys Leu Phe Thr Asp
145                 150                 155                 160

Phe Asp Ser Gln Thr Asn Val Ser Gln Ser Lys Asp Ser Asp Val Tyr
                    165                 170                 175

Ile Thr Asp Lys Cys Val Leu Asp Met Arg Ser Met Asp Phe Lys Ser
            180                 185                 190

-continued

```
Asn Ser Ala Val Ala Trp Ser Asn Lys Ser Asp Phe Ala Cys Ala Asn
        195                 200                 205

Ala Phe Asn Asn Ser Ile Ile Pro Glu Asp Thr Phe Phe Pro Ser Pro
    210                 215                 220

Glu Ser Ser Cys Asp Val Lys Leu Val Glu Lys Ser Phe Glu Thr Asp
225                 230                 235                 240

Thr Asn Leu Asn Phe Gln Asn Leu Ser Val Ile Gly Phe Arg Ile Leu
                245                 250                 255

Leu Leu Lys Val Ala Gly Phe Asn Leu Leu Met Thr Leu Arg Leu Trp
                260                 265                 270

Ser Ser

<210> SEQ ID NO 49
<211> LENGTH: 277
<212> TYPE: PRT
<213> ORGANISM: Artificial Sequence
<220> FEATURE:
<223> OTHER INFORMATION: Synthetic sequence No. 10 alpha chain with
      leader sequence

<400> SEQUENCE: 49

Met Thr Arg Val Ser Leu Leu Trp Ala Val Val Val Ser Thr Cys Leu
1               5                   10                  15

Glu Ser Gly Met Ala Gln Thr Val Thr Gln Ser Gln Pro Glu Met Ser
            20                  25                  30

Val Gln Glu Ala Glu Thr Val Thr Leu Ser Cys Thr Tyr Asp Thr Ser
        35                  40                  45

Glu Ser Asn Tyr Tyr Leu Phe Trp Tyr Lys Gln Pro Pro Ser Arg Gln
    50                  55                  60

Met Ile Leu Val Ile Arg Gln Glu Ala Tyr Lys Gln Gln Asn Ala Thr
65                  70                  75                  80

Glu Asn Arg Phe Ser Val Asn Phe Gln Lys Ala Ala Lys Ser Phe Ser
                85                  90                  95

Leu Lys Ile Ser Asp Ser Gln Leu Gly Asp Thr Ala Met Tyr Phe Cys
                100                 105                 110

Ala Phe Asn Pro Trp Glu Asn Tyr Gly Gln Asn Phe Val Phe Gly Pro
            115                 120                 125

Gly Thr Arg Leu Ser Val Leu Pro Tyr Ile Gln Asn Pro Asp Pro Ala
        130                 135                 140

Val Tyr Gln Leu Arg Asp Ser Lys Ser Ser Asp Lys Ser Val Cys Leu
145                 150                 155                 160

Phe Thr Asp Phe Asp Ser Gln Thr Asn Val Ser Gln Ser Lys Asp Ser
                165                 170                 175

Asp Val Tyr Ile Thr Asp Lys Cys Val Leu Asp Met Arg Ser Met Asp
                180                 185                 190

Phe Lys Ser Asn Ser Ala Val Ala Trp Ser Asn Lys Ser Asp Phe Ala
            195                 200                 205

Cys Ala Asn Ala Phe Asn Asn Ser Ile Ile Pro Glu Asp Thr Phe Phe
    210                 215                 220

Pro Ser Pro Glu Ser Ser Cys Asp Val Lys Leu Val Glu Lys Ser Phe
225                 230                 235                 240

Glu Thr Asp Thr Asn Leu Asn Phe Gln Asn Leu Ser Val Ile Gly Phe
                245                 250                 255

Arg Ile Leu Leu Leu Lys Val Ala Gly Phe Asn Leu Leu Met Thr Leu
                260                 265                 270
```

```
Arg Leu Trp Ser Ser
        275

<210> SEQ ID NO 50
<211> LENGTH: 251
<212> TYPE: PRT
<213> ORGANISM: Artificial Sequence
<220> FEATURE:
<223> OTHER INFORMATION: Synthetic sequence No. 4 alpha chain, leader
      sequence removed

<400> SEQUENCE: 50

Gln Lys Glu Val Glu Gln Asn Ser Gly Pro Leu Ser Val Pro Glu Gly
1               5                   10                  15

Ala Ile Ala Ser Leu Asn Cys Thr Tyr Ser Asp Arg Gly Ser Gln Ser
            20                  25                  30

Phe Phe Trp Tyr Arg Gln Tyr Ser Gly Lys Ser Pro Glu Leu Ile Met
        35                  40                  45

Phe Ile Tyr Ser Asn Gly Asp Lys Glu Asp Gly Arg Phe Thr Ala Gln
    50                  55                  60

Leu Asn Lys Ala Ser Gln Tyr Val Ser Leu Leu Ile Arg Asp Ser Gln
65                  70                  75                  80

Pro Ser Asp Ser Ala Thr Tyr Leu Cys Ala Val Asn Ile Gly Asn His
            85                  90                  95

Asp Met Arg Phe Gly Ala Gly Thr Arg Leu Thr Val Lys Pro Asn Ile
            100                 105                 110

Gln Asn Pro Asp Pro Ala Val Tyr Gln Leu Arg Asp Ser Lys Ser Ser
        115                 120                 125

Asp Lys Ser Val Cys Leu Phe Thr Asp Phe Asp Ser Gln Thr Asn Val
    130                 135                 140

Ser Gln Ser Lys Asp Ser Asp Val Tyr Ile Thr Asp Lys Cys Val Leu
145                 150                 155                 160

Asp Met Arg Ser Met Asp Phe Lys Ser Asn Ser Ala Val Ala Trp Ser
            165                 170                 175

Asn Lys Ser Asp Phe Ala Cys Ala Asn Ala Phe Asn Asn Ser Ile Ile
            180                 185                 190

Pro Glu Asp Thr Phe Phe Pro Ser Pro Glu Ser Ser Cys Asp Val Lys
        195                 200                 205

Leu Val Glu Lys Ser Phe Glu Thr Asp Thr Asn Leu Asn Phe Gln Asn
    210                 215                 220

Leu Ser Val Ile Gly Phe Arg Ile Leu Leu Leu Lys Val Ala Gly Phe
225                 230                 235                 240

Asn Leu Leu Met Thr Leu Arg Leu Trp Ser Ser
                245                 250

<210> SEQ ID NO 51
<211> LENGTH: 251
<212> TYPE: PRT
<213> ORGANISM: Artificial Sequence
<220> FEATURE:
<223> OTHER INFORMATION: Synthetic sequence No. 6 alpha chain, leader
      sequence removed

<400> SEQUENCE: 51

Glu Asp Gln Val Thr Gln Ser Pro Glu Ala Leu Arg Leu Gln Glu Gly
1               5                   10                  15

Glu Ser Ser Ser Leu Asn Cys Ser Tyr Thr Val Ser Gly Leu Arg Gly
            20                  25                  30
```

```
Leu Phe Trp Tyr Arg Gln Asp Pro Gly Lys Gly Pro Glu Phe Leu Phe
        35                  40                  45

Thr Leu Tyr Ser Ala Gly Glu Glu Lys Glu Lys Glu Arg Leu Lys Ala
    50                  55                  60

Thr Leu Thr Lys Lys Glu Ser Phe Leu His Ile Thr Ala Pro Lys Pro
65                  70                  75                  80

Glu Asp Ser Ala Thr Tyr Leu Cys Ala Val Gln Thr Met Asp Gly Asn
                85                  90                  95

Gln Phe Tyr Phe Gly Thr Gly Thr Ser Leu Thr Val Ile Pro Asn Ile
                100                 105                 110

Gln Asn Pro Asp Pro Ala Val Tyr Gln Leu Arg Asp Ser Lys Ser Ser
            115                 120                 125

Asp Lys Ser Val Cys Leu Phe Thr Asp Phe Asp Ser Gln Thr Asn Val
    130                 135                 140

Ser Gln Ser Lys Asp Ser Asp Val Tyr Ile Thr Asp Lys Cys Val Leu
145                 150                 155                 160

Asp Met Arg Ser Met Asp Phe Lys Ser Asn Ser Ala Val Ala Trp Ser
                165                 170                 175

Asn Lys Ser Asp Phe Ala Cys Ala Asn Ala Phe Asn Asn Ser Ile Ile
                180                 185                 190

Pro Glu Asp Thr Phe Phe Pro Ser Pro Glu Ser Ser Cys Asp Val Lys
            195                 200                 205

Leu Val Glu Lys Ser Phe Glu Thr Asp Thr Asn Leu Asn Phe Gln Asn
    210                 215                 220

Leu Ser Val Ile Gly Phe Arg Ile Leu Leu Leu Lys Val Ala Gly Phe
225                 230                 235                 240

Asn Leu Leu Met Thr Leu Arg Leu Trp Ser Ser
                245                 250

<210> SEQ ID NO 52
<211> LENGTH: 254
<212> TYPE: PRT
<213> ORGANISM: Artificial Sequence
<220> FEATURE:
<223> OTHER INFORMATION: Synthetic sequence No. 7 alpha chain, leader
      sequence removed

<400> SEQUENCE: 52

Ala Gln Thr Val Thr Gln Ser Gln Pro Glu Met Ser Val Gln Glu Ala
1               5                   10                  15

Glu Thr Val Thr Leu Ser Cys Thr Tyr Asp Thr Ser Glu Ser Asp Tyr
            20                  25                  30

Tyr Leu Phe Trp Tyr Lys Gln Pro Pro Ser Arg Gln Met Ile Leu Val
        35                  40                  45

Ile Arg Gln Glu Ala Tyr Lys Gln Gln Asn Ala Thr Glu Asn Arg Phe
    50                  55                  60

Ser Val Asn Phe Gln Lys Ala Ala Lys Ser Phe Ser Leu Lys Ile Ser
65                  70                  75                  80

Asp Ser Gln Leu Gly Asp Ala Ala Met Tyr Phe Cys Ala Ser Ser Pro
                85                  90                  95

Gly Thr Tyr Lys Tyr Ile Phe Gly Thr Gly Thr Arg Leu Lys Val Leu
                100                 105                 110

Ala Asn Ile Gln Asn Pro Asp Pro Ala Val Tyr Gln Leu Arg Asp Ser
            115                 120                 125

Lys Ser Ser Asp Lys Ser Val Cys Leu Phe Thr Asp Phe Asp Ser Gln
```

-continued

```
        130                 135                 140

Thr Asn Val Ser Gln Ser Lys Asp Ser Asp Val Tyr Ile Thr Asp Lys
145                 150                 155                 160

Cys Val Leu Asp Met Arg Ser Met Asp Phe Lys Ser Asn Ser Ala Val
                165                 170                 175

Ala Trp Ser Asn Lys Ser Asp Phe Ala Cys Ala Asn Ala Phe Asn Asn
                180                 185                 190

Ser Ile Ile Pro Glu Asp Thr Phe Phe Pro Ser Pro Glu Ser Ser Cys
                195                 200                 205

Asp Val Lys Leu Val Glu Lys Ser Phe Glu Thr Asp Thr Asn Leu Asn
            210                 215                 220

Phe Gln Asn Leu Ser Val Ile Gly Phe Arg Ile Leu Leu Leu Lys Val
225                 230                 235                 240

Ala Gly Phe Asn Leu Leu Met Thr Leu Arg Leu Trp Ser Ser
                245                 250

<210> SEQ ID NO 53
<211> LENGTH: 257
<212> TYPE: PRT
<213> ORGANISM: Artificial Sequence
<220> FEATURE:
<223> OTHER INFORMATION: Synthetic sequence No. 10 alpha chain, leader
      sequence removed

<400> SEQUENCE: 53

Ala Gln Thr Val Thr Gln Ser Gln Pro Glu Met Ser Val Gln Glu Ala
1               5                   10                  15

Glu Thr Val Thr Leu Ser Cys Thr Tyr Asp Thr Ser Glu Ser Asn Tyr
                20                  25                  30

Tyr Leu Phe Trp Tyr Lys Gln Pro Pro Ser Arg Gln Met Ile Leu Val
            35                  40                  45

Ile Arg Gln Glu Ala Tyr Lys Gln Gln Asn Ala Thr Glu Asn Arg Phe
        50                  55                  60

Ser Val Asn Phe Gln Lys Ala Ala Lys Ser Phe Ser Leu Lys Ile Ser
65                  70                  75                  80

Asp Ser Gln Leu Gly Asp Thr Ala Met Tyr Phe Cys Ala Phe Asn Pro
                85                  90                  95

Trp Glu Asn Tyr Gly Gln Asn Phe Val Phe Gly Pro Gly Thr Arg Leu
                100                 105                 110

Ser Val Leu Pro Tyr Ile Gln Asn Pro Asp Pro Ala Val Tyr Gln Leu
            115                 120                 125

Arg Asp Ser Lys Ser Ser Asp Lys Ser Val Cys Leu Phe Thr Asp Phe
            130                 135                 140

Asp Ser Gln Thr Asn Val Ser Gln Ser Lys Asp Ser Asp Val Tyr Ile
145                 150                 155                 160

Thr Asp Lys Cys Val Leu Asp Met Arg Ser Met Asp Phe Lys Ser Asn
                165                 170                 175

Ser Ala Val Ala Trp Ser Asn Lys Ser Asp Phe Ala Cys Ala Asn Ala
                180                 185                 190

Phe Asn Asn Ser Ile Ile Pro Glu Asp Thr Phe Phe Pro Ser Pro Glu
            195                 200                 205

Ser Ser Cys Asp Val Lys Leu Val Glu Lys Ser Phe Glu Thr Asp Thr
            210                 215                 220

Asn Leu Asn Phe Gln Asn Leu Ser Val Ile Gly Phe Arg Ile Leu Leu
225                 230                 235                 240
```

-continued

```
Leu Lys Val Ala Gly Phe Asn Leu Leu Met Thr Leu Arg Leu Trp Ser
            245                 250                 255

Ser

<210> SEQ ID NO 54
<211> LENGTH: 312
<212> TYPE: PRT
<213> ORGANISM: Artificial Sequence
<220> FEATURE:
<223> OTHER INFORMATION: Synthetic sequence No. 4 beta chain with leader
      sequence

<400> SEQUENCE: 54

Met Gly Cys Arg Leu Leu Cys Cys Ala Val Leu Cys Leu Leu Gly Ala
1               5                   10                  15

Val Pro Ile Asp Thr Glu Val Thr Gln Thr Pro Lys His Leu Val Met
            20                  25                  30

Gly Met Thr Asn Lys Lys Ser Leu Lys Cys Glu Gln His Met Gly His
        35                  40                  45

Arg Ala Met Tyr Trp Tyr Lys Gln Lys Ala Lys Lys Pro Pro Glu Leu
    50                  55                  60

Met Phe Val Tyr Ser Tyr Glu Lys Leu Ser Ile Asn Glu Ser Val Pro
65                  70                  75                  80

Ser Arg Phe Ser Pro Glu Cys Pro Asn Ser Ser Leu Leu Asn Leu His
            85                  90                  95

Leu His Ala Leu Gln Pro Glu Asp Ser Ala Leu Tyr Leu Cys Ala Ser
            100                 105                 110

Ser Gln Gly Thr Ser Gly Ala Asp Thr Gln Tyr Phe Gly Pro Gly Thr
            115                 120                 125

Arg Leu Thr Val Leu Glu Asp Leu Lys Asn Val Phe Pro Pro Glu Val
    130                 135                 140

Ala Val Phe Glu Pro Ser Glu Ala Glu Ile Ser His Thr Gln Lys Ala
145                 150                 155                 160

Thr Leu Val Cys Leu Ala Thr Gly Phe Tyr Pro Asp His Val Glu Leu
            165                 170                 175

Ser Trp Trp Val Asn Gly Lys Glu Val His Ser Gly Val Cys Thr Asp
            180                 185                 190

Pro Gln Pro Leu Lys Glu Gln Pro Ala Leu Asn Asp Ser Arg Tyr Cys
            195                 200                 205

Leu Ser Ser Arg Leu Arg Val Ser Ala Thr Phe Trp Gln Asn Pro Arg
    210                 215                 220

Asn His Phe Arg Cys Gln Val Gln Phe Tyr Gly Leu Ser Glu Asn Asp
225                 230                 235                 240

Glu Trp Thr Gln Asp Arg Ala Lys Pro Val Thr Gln Ile Val Ser Ala
            245                 250                 255

Glu Ala Trp Gly Arg Ala Asp Cys Gly Phe Thr Ser Glu Ser Tyr Gln
            260                 265                 270

Gln Gly Val Leu Ser Ala Thr Ile Leu Tyr Glu Ile Leu Leu Gly Lys
            275                 280                 285

Ala Thr Leu Tyr Ala Val Leu Val Ser Ala Leu Val Leu Met Ala Met
    290                 295                 300

Val Lys Arg Lys Asp Ser Arg Gly
305                 310

<210> SEQ ID NO 55
<211> LENGTH: 313
```

<212> TYPE: PRT
<213> ORGANISM: Artificial Sequence
<220> FEATURE:
<223> OTHER INFORMATION: Synthetic sequence No. 6 beta chain with leader
      sequence

<400> SEQUENCE: 55

Met Ser Ile Gly Leu Leu Cys Cys Ala Ala Leu Ser Leu Leu Trp Ala
1               5                   10                  15

Gly Pro Val Asn Ala Gly Val Thr Gln Thr Pro Lys Phe Gln Val Leu
            20                  25                  30

Lys Thr Gly Gln Ser Met Thr Leu Gln Cys Ala Gln Asp Met Asn His
        35                  40                  45

Glu Tyr Met Ser Trp Tyr Arg Gln Asp Pro Gly Met Gly Leu Arg Leu
    50                  55                  60

Ile His Tyr Ser Val Gly Ala Gly Ile Thr Asp Gln Gly Glu Val Pro
65                  70                  75                  80

Asn Gly Tyr Asn Val Ser Arg Ser Thr Thr Glu Asp Phe Pro Leu Arg
            85                  90                  95

Leu Leu Ser Ala Ala Pro Ser Gln Thr Ser Val Tyr Phe Cys Ala Ser
            100                 105                 110

Ser Tyr Ser Leu Trp Asp Leu Gln Glu Thr Gln Tyr Phe Gly Pro Gly
        115                 120                 125

Thr Arg Leu Leu Val Leu Glu Asp Leu Lys Asn Val Phe Pro Pro Glu
        130                 135                 140

Val Ala Val Phe Glu Pro Ser Glu Ala Glu Ile Ser His Thr Gln Lys
145                 150                 155                 160

Ala Thr Leu Val Cys Leu Ala Thr Gly Phe Tyr Pro Asp His Val Glu
            165                 170                 175

Leu Ser Trp Trp Val Asn Gly Lys Glu Val His Ser Gly Val Cys Thr
            180                 185                 190

Asp Pro Gln Pro Leu Lys Glu Gln Pro Ala Leu Asn Asp Ser Arg Tyr
            195                 200                 205

Cys Leu Ser Ser Arg Leu Arg Val Ser Ala Thr Phe Trp Gln Asn Pro
    210                 215                 220

Arg Asn His Phe Arg Cys Gln Val Gln Phe Tyr Gly Leu Ser Glu Asn
225                 230                 235                 240

Asp Glu Trp Thr Gln Asp Arg Ala Lys Pro Val Thr Gln Ile Val Ser
            245                 250                 255

Ala Glu Ala Trp Gly Arg Ala Asp Cys Gly Phe Thr Ser Glu Ser Tyr
            260                 265                 270

Gln Gln Gly Val Leu Ser Ala Thr Ile Leu Tyr Glu Ile Leu Leu Gly
        275                 280                 285

Lys Ala Thr Leu Tyr Ala Val Leu Val Ser Ala Leu Val Leu Met Ala
    290                 295                 300

Met Val Lys Arg Lys Asp Ser Arg Gly
305                 310

<210> SEQ ID NO 56
<211> LENGTH: 314
<212> TYPE: PRT
<213> ORGANISM: Artificial Sequence
<220> FEATURE:
<223> OTHER INFORMATION: Synthetic sequence No. 7 beta chain with leader
      sequence

<400> SEQUENCE: 56

-continued

```
Met Gly Thr Ser Leu Leu Cys Trp Met Ala Leu Cys Leu Leu Gly Ala
1               5                   10                  15

Asp His Ala Asp Thr Gly Val Ser Gln Asp Pro Arg His Lys Ile Thr
                20                  25                  30

Lys Arg Gly Gln Asn Val Thr Phe Arg Cys Asp Pro Ile Ser Glu His
            35                  40                  45

Asn Arg Leu Tyr Trp Tyr Arg Gln Thr Leu Gly Gln Gly Pro Glu Phe
        50                  55                  60

Leu Thr Tyr Phe Gln Asn Glu Ala Gln Leu Glu Lys Ser Arg Leu Leu
65                  70                  75                  80

Ser Asp Arg Phe Ser Ala Glu Arg Pro Lys Gly Ser Phe Ser Thr Leu
                85                  90                  95

Glu Ile Gln Arg Thr Glu Gln Gly Asp Ser Ala Met Tyr Leu Cys Ala
            100                 105                 110

Ser Ser Phe Ser Asp Gly Gly Ala Thr Asp Thr Gln Tyr Phe Gly Pro
        115                 120                 125

Gly Thr Arg Leu Thr Val Leu Glu Asp Leu Lys Asn Val Phe Pro Pro
        130                 135                 140

Glu Val Ala Val Phe Glu Pro Ser Glu Ala Glu Ile Ser His Thr Gln
145                 150                 155                 160

Lys Ala Thr Leu Val Cys Leu Ala Thr Gly Phe Tyr Pro Asp His Val
                165                 170                 175

Glu Leu Ser Trp Trp Val Asn Gly Lys Glu Val His Ser Gly Val Cys
                180                 185                 190

Thr Asp Pro Gln Pro Leu Lys Glu Gln Pro Ala Leu Asn Asp Ser Arg
                195                 200                 205

Tyr Cys Leu Ser Ser Arg Leu Arg Val Ser Ala Thr Phe Trp Gln Asn
        210                 215                 220

Pro Arg Asn His Phe Arg Cys Gln Val Gln Phe Tyr Gly Leu Ser Glu
225                 230                 235                 240

Asn Asp Glu Trp Thr Gln Asp Arg Ala Lys Pro Val Thr Gln Ile Val
                245                 250                 255

Ser Ala Glu Ala Trp Gly Arg Ala Asp Cys Gly Phe Thr Ser Glu Ser
                260                 265                 270

Tyr Gln Gln Gly Val Leu Ser Ala Thr Ile Leu Tyr Glu Ile Leu Leu
        275                 280                 285

Gly Lys Ala Thr Leu Tyr Ala Val Leu Val Ser Ala Leu Val Leu Met
        290                 295                 300

Ala Met Val Lys Arg Lys Asp Ser Arg Gly
305                 310
```

```
<210> SEQ ID NO 57
<211> LENGTH: 310
<212> TYPE: PRT
<213> ORGANISM: Artificial Sequence
<220> FEATURE:
<223> OTHER INFORMATION: Synthetic sequence No. 10 beta chain with
      leader sequence

<400> SEQUENCE: 57
```

```
Met Leu Leu Leu Leu Leu Leu Leu Gly Pro Ala Gly Ser Gly Leu Gly
1               5                   10                  15

Ala Val Val Ser Gln His Pro Ser Trp Val Ile Cys Lys Ser Gly Thr
                20                  25                  30

Ser Val Lys Ile Glu Cys Arg Ser Leu Asp Phe Gln Ala Thr Thr Met
            35                  40                  45
```

-continued

```
Phe Trp Tyr Arg Gln Phe Pro Lys Gln Ser Leu Met Leu Met Ala Thr
    50                  55                  60

Ser Asn Glu Gly Ser Lys Ala Thr Tyr Glu Gln Gly Val Glu Lys Asp
65                  70                  75                  80

Lys Phe Leu Ile Asn His Ala Ser Leu Thr Leu Ser Thr Leu Thr Val
                85                  90                  95

Thr Ser Ala His Pro Glu Asp Ser Ser Phe Tyr Ile Cys Ser Ala Arg
            100                 105                 110

Pro His Ser Leu Thr Asp Thr Gln Tyr Phe Gly Pro Gly Thr Arg Leu
            115                 120                 125

Thr Val Leu Glu Asp Leu Lys Asn Val Phe Pro Pro Glu Val Ala Val
            130                 135                 140

Phe Glu Pro Ser Glu Ala Glu Ile Ser His Thr Gln Lys Ala Thr Leu
145                 150                 155                 160

Val Cys Leu Ala Thr Gly Phe Tyr Pro Asp His Val Glu Leu Ser Trp
                165                 170                 175

Trp Val Asn Gly Lys Glu Val His Ser Gly Val Cys Thr Asp Pro Gln
                180                 185                 190

Pro Leu Lys Glu Gln Pro Ala Leu Asn Asp Ser Arg Tyr Cys Leu Ser
            195                 200                 205

Ser Arg Leu Arg Val Ser Ala Thr Phe Trp Gln Asn Pro Arg Asn His
            210                 215                 220

Phe Arg Cys Gln Val Gln Phe Tyr Gly Leu Ser Glu Asn Asp Glu Trp
225                 230                 235                 240

Thr Gln Asp Arg Ala Lys Pro Val Thr Gln Ile Val Ser Ala Glu Ala
                245                 250                 255

Trp Gly Arg Ala Asp Cys Gly Phe Thr Ser Glu Ser Tyr Gln Gln Gly
                260                 265                 270

Val Leu Ser Ala Thr Ile Leu Tyr Glu Ile Leu Leu Gly Lys Ala Thr
            275                 280                 285

Leu Tyr Ala Val Leu Val Ser Ala Leu Val Leu Met Ala Met Val Lys
    290                 295                 300

Arg Lys Asp Ser Arg Gly
305                 310
```

```
<210> SEQ ID NO 58
<211> LENGTH: 293
<212> TYPE: PRT
<213> ORGANISM: Artificial Sequence
<220> FEATURE:
<223> OTHER INFORMATION: Synthetic sequence No. 4 beta chain, leader
      sequence removed

<400> SEQUENCE: 58
```

```
Asp Thr Glu Val Thr Gln Thr Pro Lys His Leu Val Met Gly Met Thr
1               5                   10                  15

Asn Lys Lys Ser Leu Lys Cys Glu Gln His Met Gly His Arg Ala Met
                20                  25                  30

Tyr Trp Tyr Lys Gln Lys Ala Lys Lys Pro Pro Glu Leu Met Phe Val
            35                  40                  45

Tyr Ser Tyr Glu Lys Leu Ser Ile Asn Glu Ser Val Pro Ser Arg Phe
    50                  55                  60

Ser Pro Glu Cys Pro Asn Ser Ser Leu Leu Asn Leu His Leu His Ala
65                  70                  75                  80

Leu Gln Pro Glu Asp Ser Ala Leu Tyr Leu Cys Ala Ser Ser Gln Gly
```

-continued

```
                     85                  90                  95

Thr Ser Gly Ala Asp Thr Gln Tyr Phe Gly Pro Gly Thr Arg Leu Thr
            100                 105                 110

Val Leu Glu Asp Leu Lys Asn Val Phe Pro Pro Glu Val Ala Val Phe
        115                 120                 125

Glu Pro Ser Glu Ala Glu Ile Ser His Thr Gln Lys Ala Thr Leu Val
    130                 135                 140

Cys Leu Ala Thr Gly Phe Tyr Pro Asp His Val Glu Leu Ser Trp Trp
145                 150                 155                 160

Val Asn Gly Lys Glu Val His Ser Gly Val Cys Thr Asp Pro Gln Pro
                165                 170                 175

Leu Lys Glu Gln Pro Ala Leu Asn Asp Ser Arg Tyr Cys Leu Ser Ser
            180                 185                 190

Arg Leu Arg Val Ser Ala Thr Phe Trp Gln Asn Pro Arg Asn His Phe
        195                 200                 205

Arg Cys Gln Val Gln Phe Tyr Gly Leu Ser Glu Asn Asp Glu Trp Thr
    210                 215                 220

Gln Asp Arg Ala Lys Pro Val Thr Gln Ile Val Ser Ala Glu Ala Trp
225                 230                 235                 240

Gly Arg Ala Asp Cys Gly Phe Thr Ser Glu Ser Tyr Gln Gln Gly Val
                245                 250                 255

Leu Ser Ala Thr Ile Leu Tyr Glu Ile Leu Leu Gly Lys Ala Thr Leu
            260                 265                 270

Tyr Ala Val Leu Val Ser Ala Leu Val Leu Met Ala Met Val Lys Arg
        275                 280                 285

Lys Asp Ser Arg Gly
    290

<210> SEQ ID NO 59
<211> LENGTH: 294
<212> TYPE: PRT
<213> ORGANISM: Artificial Sequence
<220> FEATURE:
<223> OTHER INFORMATION: Synthetic sequence No. 6 beta chain, leader
      sequence removed

<400> SEQUENCE: 59

Asn Ala Gly Val Thr Gln Thr Pro Lys Phe Gln Val Leu Lys Thr Gly
1               5                   10                  15

Gln Ser Met Thr Leu Gln Cys Ala Gln Asp Met Asn His Glu Tyr Met
            20                  25                  30

Ser Trp Tyr Arg Gln Asp Pro Gly Met Gly Leu Arg Leu Ile His Tyr
        35                  40                  45

Ser Val Gly Ala Gly Ile Thr Asp Gln Gly Glu Val Pro Asn Gly Tyr
    50                  55                  60

Asn Val Ser Arg Ser Thr Thr Glu Asp Phe Pro Leu Arg Leu Leu Ser
65                  70                  75                  80

Ala Ala Pro Ser Gln Thr Ser Val Tyr Phe Cys Ala Ser Ser Tyr Ser
                85                  90                  95

Leu Trp Asp Leu Gln Glu Thr Gln Tyr Phe Gly Pro Gly Thr Arg Leu
            100                 105                 110

Leu Val Leu Glu Asp Leu Lys Asn Val Phe Pro Pro Glu Val Ala Val
        115                 120                 125

Phe Glu Pro Ser Glu Ala Glu Ile Ser His Thr Gln Lys Ala Thr Leu
    130                 135                 140
```

-continued

```
Val Cys Leu Ala Thr Gly Phe Tyr Pro Asp His Val Glu Leu Ser Trp
145                 150                 155                 160

Trp Val Asn Gly Lys Glu Val His Ser Gly Val Cys Thr Asp Pro Gln
                165                 170                 175

Pro Leu Lys Glu Gln Pro Ala Leu Asn Asp Ser Arg Tyr Cys Leu Ser
            180                 185                 190

Ser Arg Leu Arg Val Ser Ala Thr Phe Trp Gln Asn Pro Arg Asn His
            195                 200                 205

Phe Arg Cys Gln Val Gln Phe Tyr Gly Leu Ser Glu Asn Asp Glu Trp
    210                 215                 220

Thr Gln Asp Arg Ala Lys Pro Val Thr Gln Ile Val Ser Ala Glu Ala
225                 230                 235                 240

Trp Gly Arg Ala Asp Cys Gly Phe Thr Ser Glu Ser Tyr Gln Gln Gly
                245                 250                 255

Val Leu Ser Ala Thr Ile Leu Tyr Glu Ile Leu Leu Gly Lys Ala Thr
                260                 265                 270

Leu Tyr Ala Val Leu Val Ser Ala Leu Val Leu Met Ala Met Val Lys
            275                 280                 285

Arg Lys Asp Ser Arg Gly
            290
```

```
<210> SEQ ID NO 60
<211> LENGTH: 295
<212> TYPE: PRT
<213> ORGANISM: Artificial Sequence
<220> FEATURE:
<223> OTHER INFORMATION: Synthetic sequence No. 7 beta chain, leader
      sequence removed

<400> SEQUENCE: 60
```

```
Asp Thr Gly Val Ser Gln Asp Pro Arg His Lys Ile Thr Lys Arg Gly
1               5                   10                  15

Gln Asn Val Thr Phe Arg Cys Asp Pro Ile Ser Glu His Asn Arg Leu
                20                  25                  30

Tyr Trp Tyr Arg Gln Thr Leu Gly Gln Gly Pro Glu Phe Leu Thr Tyr
            35                  40                  45

Phe Gln Asn Glu Ala Gln Leu Glu Lys Ser Arg Leu Leu Ser Asp Arg
    50                  55                  60

Phe Ser Ala Glu Arg Pro Lys Gly Ser Phe Ser Thr Leu Glu Ile Gln
65                  70                  75                  80

Arg Thr Glu Gln Gly Asp Ser Ala Met Tyr Leu Cys Ala Ser Ser Phe
                85                  90                  95

Ser Asp Gly Gly Ala Thr Asp Thr Gln Tyr Phe Gly Pro Gly Thr Arg
            100                 105                 110

Leu Thr Val Leu Glu Asp Leu Lys Asn Val Phe Pro Pro Glu Val Ala
            115                 120                 125

Val Phe Glu Pro Ser Glu Ala Glu Ile Ser His Thr Gln Lys Ala Thr
    130                 135                 140

Leu Val Cys Leu Ala Thr Gly Phe Tyr Pro Asp His Val Glu Leu Ser
145                 150                 155                 160

Trp Trp Val Asn Gly Lys Glu Val His Ser Gly Val Cys Thr Asp Pro
                165                 170                 175

Gln Pro Leu Lys Glu Gln Pro Ala Leu Asn Asp Ser Arg Tyr Cys Leu
            180                 185                 190

Ser Ser Arg Leu Arg Val Ser Ala Thr Phe Trp Gln Asn Pro Arg Asn
            195                 200                 205
```

```
His Phe Arg Cys Gln Val Gln Phe Tyr Gly Leu Ser Glu Asn Asp Glu
    210             215             220

Trp Thr Gln Asp Arg Ala Lys Pro Val Thr Gln Ile Val Ser Ala Glu
225             230             235             240

Ala Trp Gly Arg Ala Asp Cys Gly Phe Thr Ser Glu Ser Tyr Gln Gln
            245             250             255

Gly Val Leu Ser Ala Thr Ile Leu Tyr Glu Ile Leu Leu Gly Lys Ala
            260             265             270

Thr Leu Tyr Ala Val Leu Val Ser Ala Leu Val Leu Met Ala Met Val
        275             280             285

Lys Arg Lys Asp Ser Arg Gly
    290             295
```

```
<210> SEQ ID NO 61
<211> LENGTH: 295
<212> TYPE: PRT
<213> ORGANISM: Artificial Sequence
<220> FEATURE:
<223> OTHER INFORMATION: Synthetic sequence No. 10 beta chain, leader
      sequence removed

<400> SEQUENCE: 61
```

```
Gly Ala Val Val Ser Gln His Pro Ser Trp Val Ile Cys Lys Ser Gly
1           5               10              15

Thr Ser Val Lys Ile Glu Cys Arg Ser Leu Asp Phe Gln Ala Thr Thr
            20              25              30

Met Phe Trp Tyr Arg Gln Phe Pro Lys Gln Ser Leu Met Leu Met Ala
            35              40              45

Thr Ser Asn Glu Gly Ser Lys Ala Thr Tyr Glu Gln Gly Val Glu Lys
    50              55              60

Asp Lys Phe Leu Ile Asn His Ala Ser Leu Thr Leu Ser Thr Leu Thr
65              70              75              80

Val Thr Ser Ala His Pro Glu Asp Ser Ser Phe Tyr Ile Cys Ser Ala
            85              90              95

Arg Pro His Ser Leu Thr Asp Thr Gln Tyr Phe Gly Pro Gly Thr Arg
            100             105             110

Leu Thr Val Leu Glu Asp Leu Lys Asn Val Phe Pro Pro Glu Val Ala
            115             120             125

Val Phe Glu Pro Ser Glu Ala Glu Ile Ser His Thr Gln Lys Ala Thr
    130             135             140

Leu Val Cys Leu Ala Thr Gly Phe Tyr Pro Asp His Val Glu Leu Ser
145             150             155             160

Trp Trp Val Asn Gly Lys Glu Val His Ser Gly Val Cys Thr Asp Pro
            165             170             175

Gln Pro Leu Lys Glu Gln Pro Ala Leu Asn Asp Ser Arg Tyr Cys Leu
            180             185             190

Ser Ser Arg Leu Arg Val Ser Ala Thr Phe Trp Gln Asn Pro Arg Asn
            195             200             205

His Phe Arg Cys Gln Val Gln Phe Tyr Gly Leu Ser Glu Asn Asp Glu
    210             215             220

Trp Thr Gln Asp Arg Ala Lys Pro Val Thr Gln Ile Val Ser Ala Glu
225             230             235             240

Ala Trp Gly Arg Ala Asp Cys Gly Phe Thr Ser Glu Ser Tyr Gln Gln
            245             250             255

Gly Val Leu Ser Ala Thr Ile Leu Tyr Glu Ile Leu Leu Gly Lys Ala
```

```
            260              265               270
Thr Leu Tyr Ala Val Leu Val Ser Ala Leu Val Leu Met Ala Met Val
        275              280               285

Lys Arg Lys Asp Ser Arg Gly
    290              295
```

```
<210> SEQ ID NO 62
<211> LENGTH: 819
<212> TYPE: DNA
<213> ORGANISM: Artificial Sequence
<220> FEATURE:
<223> OTHER INFORMATION: Synthetic sequence No. 4 alpha gene fragment

<400> SEQUENCE: 62
atgaaatcct tgagagtttt actagtgatc ctgtggcttc agttgagctg ggtttggagc    60
caacagaagg aggtggagca gaattctgga cccctcagtg ttccagaggg agccattgcc   120
tctctcaact gcacttacag tgaccgaggt tcccagtcct tcttctggta cagacaatat   180
tctgggaaaa gccctgagtt gataatgttc atatactcca atggtgacaa agaagatgga   240
aggtttacag cacagctcaa taaagccagc cagtatgttt ctctgctcat cagagactcc   300
cagcccagtg attcagccac ctacctctgt gccgtgaaca taggaaacca tgacatgcgc   360
tttggagcag ggaccagact gacagtaaaa ccaaatatcc agaaccctga ccctgccgtg   420
taccagctga gagactctaa atccagtgac aagtctgtct gcctattcac cgattttgat   480
tctcaaacaa atgtgtcaca aagtaaggat tctgatgtgt atatcacaga caaaactgtg   540
ctagacatga ggtctatgga cttcaagagc aacagtgctg tggcctggag caacaaatct   600
gactttgcat gtgcaaacgc cttcaacaac agcattattc agaagacac cttcttcccc    660 agcccagaaa gttcctgtga tgtcaagctg gtcgagaaaa gctttgaaac agatacgaac   720
ctaaactttc aaaacctgtc agtgattggg ttccgaatcc tcctcctgaa agtggccggg   780
tttaatctgc tcatgacgct gcggctgtgg tccagctga                          819
```

```
<210> SEQ ID NO 63
<211> LENGTH: 819
<212> TYPE: DNA
<213> ORGANISM: Artificial Sequence
<220> FEATURE:
<223> OTHER INFORMATION: Synthetic sequence No. 6 alpha gene fragment

<400> SEQUENCE: 63
atggagaaaa tgttggagtg tgcattcata gtcttgtggc ttcagcttgg ctggttgagt    60
ggagaagacc aggtgacgca gagtcccgag gccctgagac tccaggaggg agagagtagc   120
agtctcaact gcagttacac agtcagcggt ttaagagggc tgttctggta taggcaagat   180
cctgggaaag gccctgaatt cctcttcacc ctgtattcag ctgggaaga aaaggagaaa    240 gaaaggctaa agccacatt aacaaagaag gaaagctttc tgcacatcac agcccctaaa   300
cctgaagact cagccactta tctctgtgct gtgcagacca tggacggtaa ccagttctat   360
tttgggacag ggacaagttt gacggtcatt ccaaatatcc agaaccctga ccctgccgtg   420
taccagctga gagactctaa atccagtgac aagtctgtct gcctattcac cgattttgat   480
tctcaaacaa atgtgtcaca aagtaaggat tctgatgtgt atatcacaga caaaactgtg   540
ctagacatga ggtctatgga cttcaagagc aacagtgctg tggcctggag caacaaatct   600
gactttgcat gtgcaaacgc cttcaacaac agcattattc agaagacac cttcttcccc    660 agcccagaaa gttcctgtga tgtcaagctg gtcgagaaaa gctttgaaac agatacgaac   720
```
ctaaactttc aaaacctgtc agtgattggg ttccgaatcc tcctcctgaa agtggccggg        780
tttaatctgc tcatgacgct gcggctgtgg tccagctga                              819

<210> SEQ ID NO 64
<211> LENGTH: 825
<212> TYPE: DNA
<213> ORGANISM: Artificial Sequence
<220> FEATURE:
<223> OTHER INFORMATION: Synthetic sequence No. 7 alpha gene fragment

<400> SEQUENCE: 64
atggcatgcc ctggcttcct gtgggcactt gtgatctcca cctgtcttga atttagcatg         60
gctcagacag tcactcagtc tcaaccagag atgtctgtgc aggaggcaga gaccgtgacc        120
ctgagctgca catatgacac cagtgagagt gattattatt tattctggta caagcagcct        180
cccagcaggc agatgattct cgttattcgc caagaagctt ataagcaaca gaatgcaaca        240
gagaatcgtt tctctgtgaa cttccagaaa gcagccaaat ccttcagtct caagatctca        300
gactcacagc tgggggatgc cgcgatgtat ttctgtgctt ccagtccagg aacctacaaa        360
tacatctttg gaacaggcac caggctgaag gttttagcaa atatccagaa ccctgaccct        420
gccgtgtacc agctgagaga ctctaaatcc agtgacaagt ctgtctgcct attcaccgat        480
tttgattctc aaacaaatgt gtcacaaagt aaggattctg atgtgtatat cacagacaaa        540
actgtgctag acatgaggtc tatggacttc aagagcaaca gtgctgtggc ctggagcaac        600
aaatctgact ttgcatgtgc aaacgccttc aacaacagca ttattccaga agacaccttc        660
ttccccagcc cagaaagttc ctgtgatgtc aagctggtcg agaaaagctt tgaaacagat        720
acgaacctaa actttcaaaa cctgtcagtg attgggttcc gaatcctcct cctgaaagtg        780
gccgggttta atctgctcat gacgctgcgg ctgtggtcca gctga                       825

<210> SEQ ID NO 65
<211> LENGTH: 834
<212> TYPE: DNA
<213> ORGANISM: Artificial Sequence
<220> FEATURE:
<223> OTHER INFORMATION: Synthetic sequence No. 10 alpha gene fragment

<400> SEQUENCE: 65
atgacacgag ttagcttgct gtgggcagtc gtggtctcca cctgtcttga atccggcatg         60
gcccagacag tcactcagtc tcaaccagag atgtctgtgc aggaggcaga gactgtgacc        120
ctgagttgca catatgacac cagtgagagt aattattatt tgttctggta caaacagcct        180
cccagcaggc agatgattct cgttattcgc caagaagctt ataagcaaca gaatgcaacg        240
gagaatcgtt tctctgtgaa cttccagaaa gcagccaaat ccttcagtct caagatctca        300
gactcacagc tgggggacac tgcgatgtat ttctgtgctt caacccttg ggagaactat        360 ggtcagaatt ttgtctttgg tcccggaacc agattgtccg tgctgcccta tatccagaac        420
cctgaccctg ccgtgtacca gctgagagac tctaaatcca gtgacaagtc tgtctgccta        480
ttcaccgatt ttgattctca aacaaatgtg tcacaaagta aggattctga tgtgtatatc        540
acagacaaaa ctgtgctaga catgaggtct atggacttca agagcaacag tgctgtggcc        600
tggagcaaca aatctgactt tgcatgtgca aacgccttca acaacagcat tattccagaa        660
gacaccttct tccccagccc agaaagttcc tgtgatgtca agctggtcga gaaaagcttt        720
gaaacagata cgaacctaaa ctttcaaaac ctgtcagtga ttgggttccg aatcctcctc        780

-continued

```
ctgaaagtgg ccgggtttaa tctgctcatg acgctgcggc tgtggtccag ctga          834
```

```
<210> SEQ ID NO 66
<211> LENGTH: 819
<212> TYPE: DNA
<213> ORGANISM: Artificial Sequence
<220> FEATURE:
<223> OTHER INFORMATION: Synthetic sequence No. 4 alpha gene fragment,
      codon-optimized

<400> SEQUENCE: 66
atgaagagcc tgagagtcct gctggtgatt ttgtggctgc agctgtcttg ggtttggtct          60
cagcagaaag aagtggagca gaatagcggc cctctgtctg ttcctgaagg cgctattgct         120
agcctgaatt gcacatacag cgatagagga tctcagagct tcttctggta ccggcagtac         180
agcggcaaga gcccagaact gatcatgttc atctacagca atggcgacaa ggaggatggc         240
aggtttacag cccagctgaa caaggccagc cagtatgttt ctctgctgat cagagatagc         300
cagcctagcg attctgccac ctacctgtgt gccgtgaaca tcggaaatca cgacatgaga         360
tttggagccg gcacaagact gaccgtgaag cccaatatcc agaaccctga tcctgctgtg         420
taccagctgc gggacagcaa gagcagcgac aagagcgtgt gcctgttcac cgacttcgac         480
agccagacca acgtgtccca gagcaaggac agcgacgtgt acatcaccga taagtgcgtg         540
ctggacatgc ggagcatgga cttcaagagc aacagcgccg tggcctggtc caacaagagc         600
gacttcgcct gcgccaacgc cttcaacaac agcattatcc ccgaggacac attcttccca         660
agccccgaga gcagctgcga cgtgaagctg gtggaaaaga gcttcgagac agacaccaac         720
ctgaacttcc agaacctcag cgtgatcggc ttccggatcc tgctgctgaa ggtggccggc         780
ttcaacctgc tgatgaccct gcggctgtgg tccagctga                                819
```

```
<210> SEQ ID NO 67
<211> LENGTH: 819
<212> TYPE: DNA
<213> ORGANISM: Artificial Sequence
<220> FEATURE:
<223> OTHER INFORMATION: Synthetic sequence No. 6 alpha gene fragment,
      codon-optimized

<400> SEQUENCE: 67
atggagaaga tgctggagtg tgcgttcatc gttctgtggc tgcaacttgg atggctgtct          60
ggagaggatc aggttacaca gtctcctgaa gccctgagac tgcaagaagg agaaagctct         120
agcctgaact gcagctacac agtgtctgga ctgagaggcc tgttctggta cagacaggat         180
cctggaaaag gcccagagtt cctgtttacc ctgtattctg ccggcgagga gaaggagaaa         240
gagagactga aagctaccct gaccaagaag gagagcttcc tgcacattac cgcccccaaa         300
cctgaggatt ctgccacata tctgtgtgct gtgcagacca tggatggcaa ccagttctac         360
ttcggcacag gcacatctct gaccgttatc cccaatatcc agaaccctga tcctgccgtg         420
taccagctgc gggacagcaa gagcagcgac aagagcgtgt gcctgttcac cgacttcgac         480
agccagacca acgtgtccca gagcaaggac agcgacgtgt acatcaccga taagtgcgtg         540
ctggacatgc ggagcatgga cttcaagagc aacagcgccg tggcctggtc caacaagagc         600
gacttcgcct gcgccaacgc cttcaacaac agcattatcc ccgaggacac attcttccca         660
agccccgaga gcagctgcga cgtgaagctg gtggaaaaga gcttcgagac agacaccaac         720
ctgaacttcc agaacctcag cgtgatcggc ttccggatcc tgctgctgaa ggtggccggc         780
ttcaacctgc tgatgaccct gcggctgtgg tccagctga                                819
```

```
<210> SEQ ID NO 68
<211> LENGTH: 825
<212> TYPE: DNA
<213> ORGANISM: Artificial Sequence
<220> FEATURE:
<223> OTHER INFORMATION: Synthetic sequence No. 7 alpha gene fragment,
      codon-optimized

<400> SEQUENCE: 68
atggcttgtc ctggattctt atgggctctg gtgatcagca cctgtctgga gttctctatg        60
gcccagacag tgacacagtc tcagcctgaa atgtctgtgc aggaagccga aaccgtgaca       120
ctgtcttgca cctacgatac aagcgagagc gactactacc tgttctggta caagcagcct       180
ccctctaggc agatgatcct ggtgattaga caggaggcct acaaacagca gaatgccacc       240
gagaaccggt ttagcgtgaa cttccagaaa gccgccaaga gcttcagcct gaaaatctct       300
gacagccagc tgggagatgc tgccatgtac ttttgtgcca gctctccagg cacctacaag       360
tacatttttg gcaccggcac cagactgaag gtgctggcca atatccagaa tcccgatcct       420
gccgtgtacc agctgcggga cagcaagagc agcgacaaga gcgtgtgcct gttcaccgac       480
ttcgacagcc agaccaacgt gtcccagagc aaggacagcg acgtgtacat caccgataag       540
tgcgtgctgg acatgcggag catggacttc aagagcaaca gcgccgtggc ctggtccaac       600
aagagcgact tcgcctgcgc caacgccttc aacaacagca ttatccccga ggacacattc       660
ttcccaagcc ccgagagcag ctgcgacgtg aagctggtgg aaaagagctt cgagacagac       720
accaacctga acttccagaa cctcagcgtg atcggcttcc ggatcctgct gctgaaggtg       780
gccggcttca acctgctgat gaccctgcgg ctgtggtcca gctga                       825

<210> SEQ ID NO 69
<211> LENGTH: 834
<212> TYPE: DNA
<213> ORGANISM: Artificial Sequence
<220> FEATURE:
<223> OTHER INFORMATION: Synthetic sequence No. 10 alpha gene fragment,
      codon-optimized

<400> SEQUENCE: 69
atgaccagag ttagcctgtt atgggctgtg gtggtgagca catgtctgga atctggaatg        60
gcccagacag tgacacagtc tcagcctgaa atgtctgtgc aggaagccga aaccgttaca       120
ctgagctgca cctacgatac aagcgagagc aactactacc tgttctggta caagcagccc       180
ccttctaggc agatgatcct ggtgatcaga caggaggcct ataaacagca gaatgccacc       240
gagaaccggt ttagcgtgaa cttccagaaa gccgccaaga gcttcagcct gaaaatctct       300
gacagccagc tgggcgatac agccatgtac ttttgtgcct caaacccctg ggagaactat       360
ggccagaatt cgtgttcgg ccctggcacc agactgtctg ttctgcctta tatccagaac        420
cccgatcctg ctgtgtacca gctgcgggac agcaagagc gcgacaagag cgtgtgcctg        480
ttcaccgact tcgacagcca gaccaacgtg tcccagagca aggacagcga cgtgtacatc       540
accgataagt gcgtgctgga catgcggagc atggacttca gagcaacag cgccgtggcc        600 tggtccaaca gagcgactt cgcctgcgcc aacgccttca caacagcat tatccccgag        660 gacacattct tcccaagccc cgagagcagc tgcgacgtga agctggtgga aaagagcttc       720
gagacagaca ccaacctgaa cttccagaac ctcagcgtga tcggcttccg gatcctgctg       780
ctgaaggtgg ccggcttcaa cctgctgatg accctgcggc tgtggtccag ctga             834
```

<210> SEQ ID NO 70
<211> LENGTH: 939
<212> TYPE: DNA
<213> ORGANISM: Artificial Sequence
<220> FEATURE:
<223> OTHER INFORMATION: Synthetic sequence No. 4 beta gene fragment

<400> SEQUENCE: 70

```
atgggctgca ggctgctctg ctgtgcggtt ctctgtctcc tgggagcagt tcccatagac      60
actgaagtta cccagacacc aaaacacctg gtcatgggaa tgacaaataa gaagtctttg     120
aaatgtgaac aacatatggg gcacagggct atgtattggt acaagcagaa agctaagaag     180
ccaccggagc tcatgtttgt ctacagctat gagaaactct ctataaatga aagtgtgcca     240
agtcgcttct cacctgaatg ccccaacagc tctctcttaa accttcacct acacgccctg     300
cagccagaag actcagccct gtatctctgc gccagcagcc aagggactag cggggcagat     360
acgcagtatt ttggcccagg cacccggctg acagtgctcg aggacctgaa aaacgtgttc     420 ccaccccgagg tcgctgtgtt tgagccatca gaagcagaga tctcccacac ccaaaaggcc     480
acactggtgt gcctggccac aggcttctac cccgaccacg tggagctgag ctggtgggtg     540
aatgggaagg aggtgcacag tggggtcagc acagacccgc agcccctcaa ggagcagccc     600
gccctcaatg actccagata ctgcctgagc agccgcctga gggtctcggc caccttctgg     660 cagaacccccc gcaaccactt ccgctgtcaa gtccagttct acgggctctc ggagaatgac     720
gagtggaccc aggatagggc caaacctgtc acccagatcg tcagcgccga ggcctggggt     780
agagcagact gtggcttcac ctccgagtct taccagcaag gggtcctgtc tgccaccatc     840
ctctatgaga tcttgctagg gaaggccacc ttgtatgccg tgctggtcag tgccctcgtg     900
ctgatggcca tggtcaagag aaaggattcc agaggctag                             939
```

<210> SEQ ID NO 71
<211> LENGTH: 942
<212> TYPE: DNA
<213> ORGANISM: Artificial Sequence
<220> FEATURE:
<223> OTHER INFORMATION: Synthetic sequence No. 6 beta gene fragment

<400> SEQUENCE: 71

```
atgagcatcg gcctcctgtg ctgtgcagcc ttgtctctcc tgtgggcagg tccagtgaat      60
gctggtgtca ctcagacccc aaaattccag gtcctgaaga caggacagag catgacactg     120
cagtgtgccc aggatatgaa ccatgaatac atgtcctggt atcgacaaga cccaggcatg     180
gggctgaggc tgattcatta ctcagttggt gctggtatca ctgaccaagg agaagtcccc     240
aatggctaca atgtctccag atcaaccaca gaggatttcc cgctcaggct gctgtcggct     300
gctccctccc agacatctgt gtacttctgt gccagcagtt actctctttg ggaccttcaa     360
gagacccagt acttcgggcc aggcacgcgg ctcctggtgc tcgaggacct gaaaaacgtg     420
ttcccacccg aggtcgctgt gtttgagcca tcagaagcag agatctccca cacccaaaag     480
gccacactgg tgtgcctggc acaggcttc tacccccgacc acgtggagct gagctggtgg     540
gtgaatggga aggaggtgca cagtggggtc agcacagacc cgcagcccct caaggagcag     600
cccgccctca atgactccag atactgcctg agcagccgcc tgagggtctc ggccaccttc     660
tggcagaacc cccgcaacca cttccgctgt caagtccagt tctacgggct ctcggagaat     720
gacgagtgga cccaggatag ggccaaacct gtcacccaga tcgtcagcgc cgaggcctgg     780
ggtagagcag actgtggctt cacctccgag tcttaccagc aaggggtcct gtctgccacc     840
```
atcctctatg agatcttgct agggaaggcc accttgtatg ccgtgctggt cagtgccctc        900
gtgctgatgg ccatggtcaa gagaaaggat tccagaggct ag                          942

<210> SEQ ID NO 72
<211> LENGTH: 945
<212> TYPE: DNA
<213> ORGANISM: Artificial Sequence
<220> FEATURE:
<223> OTHER INFORMATION: Synthetic sequence No. 7 beta gene fragment

<400> SEQUENCE: 72
atgggcacca gcctcctctg ctggatggcc ctgtgtctcc tgggggcaga tcacgcagat         60
actggagtct cccaggaccc cagacacaag atcacaaaga ggggacagaa tgtaactttc        120
aggtgtgatc caatttctga acacaaccgc ctttattggt accgacgac cctggggcag        180 ggcccagagt ttctgactta cttccagaat gaagctcaac tagaaaaatc aaggctgctc        240
agtgatcggt ctctgcaga gaggcctaag ggatctttct ccaccttgga gatccagcgc        300
acagagcagg gggactcggc catgtatctc tgtgccagca gcttttcaga cggggggggct       360 acagatacgc agtattttgg cccaggcacc cggctgacag tgctcgagga cctgaaaaac        420
gtgttcccac ccgaggtcgc tgtgtttgag ccatcagaag cagagatctc ccacacccaa        480
aaggccacac tggtgtgcct ggccacaggc ttctaccccg accacgtgga gctgagctgg        540
tgggtgaatg ggaaggaggt gcacagtggg gtcagcacag acccgcagcc cctcaaggag        600
cagcccgccc tcaatgactc cagatactgc ctgagcagcc gcctgagggt ctcggccacc        660
ttctggcaga accccgcaa ccacttccgc tgtcaagtcc agttctacgg gctctcggag          720
aatgacgagt ggacccagga tagggccaaa cctgtcaccc agatcgtcag cgccgaggcc        780
tggggtagag cagactgtgg cttcacctcc gagtcttacc agcaaggggt cctgtctgcc        840
accatcctct atgagatctt gctagggaag gccaccttgt atgccgtgct ggtcagtgcc        900
ctcgtgctga tggccatggt caagagaaag gattccagag gctag                        945

<210> SEQ ID NO 73
<211> LENGTH: 933
<212> TYPE: DNA
<213> ORGANISM: Artificial Sequence
<220> FEATURE:
<223> OTHER INFORMATION: Synthetic sequence No. 10 beta gene fragment

<400> SEQUENCE: 73
atgctgctgc ttctgctgct tctggggcca gcaggctccg ggcttggtgc tgtcgtctct         60
caacatccga gctgggttat ctgtaagagt ggaacctctg tgaagatcga gtgccgttcc        120
ctggactttc aggccacaac tatgttttgg tatcgtcagt ccccgaaaca gagtctcatg        180
ctgatggcaa cttccaatga gggctccaag gccacatacg agcaaggcgt cgagaaggac        240
aagtttctca tcaaccatgc aagcctgacc ttgtccactc tgacagtgac cagtgcccat        300
cctgaagaca gcagcttcta catctgcagt gctagacccc attctctcac agatacgcag        360
tattttggcc caggcacccg gctgacagtg ctcgaggacc tgaaaaacgt gttcccaccc        420
gaggtcgctg tgtttgagcc atcagaagca gagatctccc acacccaaaa ggccacactg        480
gtgtgcctgg ccacaggctt ctaccccgac cacgtggagc tgagctggtg ggtgaatggg        540
aaggaggtgc acagtggggt cagcacagac ccgcagcccc tcaaggagca gcccgccctc        600
aatgactcca gatactgcct gagcagccgc ctgagggtct cggccacctt ctggcagaac        660

-continued

```
cccgcaacc acttccgctg tcaagtccag ttctacgggc tctcggagaa tgacgagtgg    720
acccaggata gggccaaacc tgtcacccag atcgtcagcg ccgaggcctg gggtagagca    780
gactgtggct tcacctccga gtcttaccag caaggggtcc tgtctgccac catcctctat    840
gagatcttgc tagggaaggc caccttgtat gccgtgctgg tcagtgccct cgtgctgatg    900
gccatggtca agagaaagga ttccagaggc tag                                 933
```

<210> SEQ ID NO 74
<211> LENGTH: 936
<212> TYPE: DNA
<213> ORGANISM: Artificial Sequence
<220> FEATURE:
<223> OTHER INFORMATION: Synthetic sequence No. 4 beta gene fragment,
      codon-optimized

<400> SEQUENCE: 74

```
atgggctgta gactgttgtg ttgtgctgtg ctgtgtctgt tgggagctgt gcctatcgat     60
acagaggtga cccagacccc taaacatctg gttatgggca tgaccaacaa gaagagcctg    120
aagtgcgagc agcacatggg ccatagggcc atgtattggt ataagcagaa ggccaagaaa    180
cctcctgagc tgatgttcgt gtacagctac gagaagctga gcatcaacga gagcgtgccc    240
agcagatttt ctcctgagtg ccctaattct agcctgctga atctgcacct gcatgctctg    300
cagcctgagg attctgctct gtacctgtgt gcttcttctc agggcacatc tggagctgat    360
acacagtact tcggacctgg cacaagactg acagtgctgg aagacctgaa gaacgtgttc    420
cccccagagg tggccgtgtt cgagcctagc gaggccgaga tcagccacac ccagaaagcc    480
accctcgtgt gcctggccac cggctttttac cccgaccacg tggaactgtc ttggtgggtc    540
aacggcaaag aggtgcacag cggcgtctgc accgaccccc agcccctgaa agagcagccc    600
gccctgaacg acagccggta ctgtctgagc agcagactga gagtgtccgc caccttctgg    660
cagaaccccc ggaaccactt cagatgccag gtgcagttct acggcctgag cgagaacgac    720
gagtggaccc aggaccgggc caagcccgtg acccagatcg tgtctgctga ggcctggggc    780
agagccgatt gcggcttcac cagcgagagc taccagcagg gcgtgctgag cgccaccatc    840
ctgtacgaga tcctgctggg caaggccacc ctgtacgccg tgctggtgtc cgccctggtg    900
ctgatggcca tggtcaagcg gaaggacagc cggggc                              936
```

<210> SEQ ID NO 75
<211> LENGTH: 939
<212> TYPE: DNA
<213> ORGANISM: Artificial Sequence
<220> FEATURE:
<223> OTHER INFORMATION: Synthetic sequence No. 6 beta gene fragment,
      codon-optimized

<400> SEQUENCE: 75

```
atgtctatcg gtctgctgtg ctgtgctgct ctttctctgc tttgggctgg acctgtgaat     60
gctggagtta cacaaacccc caagttccaa gtgctgaaga caggacagag catgaccctg    120
cagtgtgctc aggacatgaa tcacgagtac atgagctggt acagacagga tcctggaatg    180
ggcctgaggc tgatccacta ctctgttgga gccggaatta cagatcaggg agaagtgcca    240
aatggctaca cgtgagcag gagcacaacc gaggacttcc ccttaagact gttgtctgct    300
gctccatctc agacaagcgt gtactttttgc gccagctcct actctctgtg ggatctgcag    360
gaaacccagt actttggacc aggcacaaga ctgttagtgc tggaggacct gaagaacgtg    420 ttcccccccag aggtggccgt gttcgagcct agcgaggccg agatcagcca cacccagaaa    480
```

-continued

```
gccaccctcg tgtgcctggc caccggcttt taccccgacc acgtggaact gtcttggtgg        540
gtcaacggca aagaggtgca cagcggcgtc tgcaccgacc cccagcccct gaaagagcag        600
cccgccctga cgacagccg gtactgtctg agcagcagac tgagagtgtc cgccaccttc         660
tggcagaacc cccggaacca cttcagatgc caggtgcagt tctacggcct gagcgagaac        720
gacgagtgga cccaggaccg ggccaagccc gtgacccaga tcgtgtctgc tgaggcctgg        780
ggcagagccg attgcggctt caccagcgag agctaccagc agggcgtgct gagcgccacc        840
atcctgtacg agatcctgct gggcaaggcc accctgtacg ccgtgctggt gtccgccctg        900
gtgctgatgg ccatggtcaa gcggaaggac agccggggc                               939
```

```
<210> SEQ ID NO 76
<211> LENGTH: 942
<212> TYPE: DNA
<213> ORGANISM: Artificial Sequence
<220> FEATURE:
<223> OTHER INFORMATION: Synthetic sequence No. 7 beta gene fragment,
      codon-optimized

<400> SEQUENCE: 76
atgggcacat ctcttctctg ctggatggct ctttgtctgc ttggagccga tcatgccgat         60
acaggagtta gccaggatcc tagacacaag atcaccaaga gaggccagaa tgtgaccttc        120
cggtgcgatc ctatctctga gcacaacagg ctgtactggt acagacaaac actgggacaa        180
ggacctgagt tcctgaccta cttccagaac gaagcccagc tggagaagtc tagacttctg        240
agcgacagat ttagcgccga gagacctaaa ggcagcttta gcaccctgga gatccagaga        300
acagaacagg gcgattctgc catgtacctg tgtgctagca gcttttctga tggaggcgcc        360
accgatacac agtatttcgg acctggcaca agactgacag tgctggagga cctgaagaac        420
gtgttccccc cagaggtggc cgtgttcgag cctagcgagg ccgagatcag ccacacccag        480
aaagccaccc tcgtgtgcct ggccaccggc ttttaccccg accacgtgga actgtcttgg       540
tgggtcaacg gcaaagaggt gcacagcggc gtctgcaccg acccccagcc cctgaaagag       600
cagcccgccc tgaacgacag ccggtactgt ctgagcagca gactgagagt gtccgccacc       660
ttctggcaga accccggaa ccacttcaga tgccaggtgc agttctacgg cctgagcgag       720
aacgacgagt ggacccagga ccgggccaag cccgtgaccc agatcgtgtc tgctgaggcc       780
tggggcagag ccgattgcgg cttcaccagc gagagctacc agcagggcgt gctgagcgcc       840
accatcctgt acgagatcct gctgggcaag gccaccctgt acgccgtgct ggtgtccgcc       900
ctggtgctga tggccatggt caagcggaag gacagccggg gc                          942
```

```
<210> SEQ ID NO 77
<211> LENGTH: 930
<212> TYPE: DNA
<213> ORGANISM: Artificial Sequence
<220> FEATURE:
<223> OTHER INFORMATION: Synthetic sequence No. 10 beta gene fragment,
      codon-optimized

<400> SEQUENCE: 77
atgctgcttc ttctcctcct tctcggacct gctggatctg gattaggagc tgttgtgtct         60 cagcacccctt cttgggtgat ctgtaaaagc ggcacaagcg tgaagatcga gtgcagaagc       120
ctggactttc aggccacaac catgttctgg tataggcagt tccccaagca gtctctgatg        180
ctgatggcca cctctaatga gggctctaag gccacatatg aacagggagt ggagaaggac        240
```

-continued

```
aagttcctga tcaaccacgc ctctctgacc ctgtctaccc tgacagttac atctgcccac      300
cctgaggata gcagctttta catctgtagc gccagacctc acagcctgac cgatacacag      360
tactttggcc ctggcacaag actgacagtg ttagaagacc tgaagaacgt gttcccccca      420
gaggtggccg tgttcgagcc tagcgaggcc gagatcagcc acacccagaa agccaccctc      480
gtgtgcctgg ccaccggctt ttaccccgac cacgtggaac tgtcttggtg ggtcaacggc      540
aaagaggtgc acagcggcgt ctgcaccgac ccccagcccc tgaaagagca gcccgccctg      600
aacgacagcc ggtactgtct gagcagcaga ctgagagtgt ccgccacctt ctggcagaac      660 cccccggaacc acttcagatg ccaggtgcag ttctacggcc tgagcgagaa cgacgagtgg      720
acccaggacc gggccaagcc cgtgacccag atcgtgtctg ctgaggcctg gggcagagcc      780
gattgcggct tcaccagcga gagctaccag caggcgtgc tgagcgccac catcctgtac      840
gagatcctgc tgggcaaggc caccctgtac gccgtgctgg tgtccgccct ggtgctgatg      900
gccatggtca agcggaagga cagccggggc                                       930
```

```
<210> SEQ ID NO 78
<211> LENGTH: 1821
<212> TYPE: DNA
<213> ORGANISM: Artificial Sequence
<220> FEATURE:
<223> OTHER INFORMATION: Synthetic sequence No. 4 beta-P2A-No. 4 alpha,
      codon-optimized

<400> SEQUENCE: 78
```

```
atgggctgta gactgttgtg ttgtgctgtg ctgtgtctgt tgggagctgt gcctatcgat       60
acagaggtga cccagacccc taaacatctg gttatgggca tgaccaacaa gaagagcctg      120
aagtgcgagc agcacatggg ccataggggc atgtattggt ataagcagaa ggccaagaaa      180
cctcctgagc tgatgttcgt gtacagctac gagaagctga gcatcaacga gagcgtgccc      240
agcagatttt ctcctgagtg ccctaattct agcctgctga atctgcacct gcatgctctg      300
cagcctgagg attctgctct gtacctgtgt gcttcttctc agggcacatc tggagctgat      360
acacagtact tcggacctgg cacaagactg acagtgctgg aagacctgaa gaacgtgttc      420 ccccagagg tggccgtgtt cgagcctagc gaggccgaga tcagccacac ccagaaagcc      480
accctcgtgt gcctggccac cggctttttac cccgaccacg tggaactgtc ttggtgggtc      540
aacggcaaag aggtgcacag cggcgtctgc accgacccccc agcccctgaa agagcagccc      600
gccctgaacg acagccggta ctgtctgagc agcagactga gagtgtccgc caccttctgg      660
cagaaccccc ggaaccactt cagatgccag gtgcagttct acggcctgag cgagaacgac      720
gagtggaccc aggaccgggc caagcccgtg acccagatcg tgtctgctga ggcctggggc      780
agagccgatt gcggcttcac cagcgagagc taccagcagg cgtgctgag cgccaccatc      840 ctgtacgaga tcctgctggg caaggccacc ctgtacgccg tgctggtgtc cgccctggtg      900
ctgatggcca tggtcaagcg gaaggacagc cggggcggtt ccggagccac gaacttctct      960
ctgttaaagc aagcaggaga cgtggaagaa aaccccggtc ccatgaagag cctgagagtc     1020
ctgctggtgt ttttgtggct gcagctgtct tgggtttggt ctcagcagaa agaagtggag     1080
cagaatagcg ccctctgtc tgttcctgaa ggcgctattg ctagcctgaa ttgcacatac     1140
agcgatagag gatctcagag cttcttctgg taccggcagt acagcggcaa gagcccagaa     1200
ctgatcatgt tcatctacag caatggcgac aaggaggatg caggtttac agcccagctg     1260 aacaaggcca gccagtatgt ttctctgctg atcagagata gccagcctag cgattctgcc     1320
```

-continued

```
acctacctgt gtgccgtgaa catcggaaat cacgacatga gatttggagc cggcacaaga     1380
ctgaccgtga agcccaatat ccagaaccct gatcctgctg tgtaccagct gcgggacagc     1440
aagagcagcg acaagagcgt gtgcctgttc accgacttcg acagccagac caacgtgtcc     1500
cagagcaagg acacgcgacgt gtacatcacc gataagtgcg tgctggacat gcggagcatg     1560
gacttcaaga gcaacagcgc cgtggcctgg tccaacaaga gcgacttcgc ctgcgccaac     1620
gccttcaaca acagcattat ccccgaggac acattcttcc caagccccga gagcagctgc     1680
gacgtgaagc tggtggaaaa gagcttcgag acagacacca acctgaactt ccagaacctc     1740
agcgtgatcg gcttccggat cctgctgctg aaggtggccg gcttcaacct gctgatgacc     1800
ctgcggctgt ggtccagctg a                                              1821
```

<210> SEQ ID NO 79
<211> LENGTH: 1824
<212> TYPE: DNA
<213> ORGANISM: Artificial Sequence
<220> FEATURE:
<223> OTHER INFORMATION: Synthetic sequence No. 6 beta-P2A-No. 6 alpha,
      codon-optimized

<400> SEQUENCE: 79

```
atgtctatcg gtctgctgtg ctgtgctgct ctttctctgc tttgggctgg acctgtgaat      60
gctggagtta cacaaacccc caagttccaa gtgctgaaga caggacagag catgaccctg     120
cagtgtgctc aggacatgaa tcacgagtac atgagctggt acagacagga tcctggaatg     180
ggcctgaggc tgatccacta ctctgttgga gccggaatta cagatcaggg agaagtgcca     240
aatggctaca cgtgagcag gagcacaacc gaggacttcc ccttaagact gttgtctgct     300
gctccatctc agacaagcgt gtacttttgc gccagctcct actctctgtg ggatctgcag     360
gaaacccagt actttggacc aggcacaaga ctgttagtgc tggaggacct gaagaacgtg     420
ttccccccag aggtggccgt gttcgagcct agcgaggccg agatcagcca cacccagaaa     480
gccaccctcg tgtgcctggc caccggcttt taccccgacc acgtggaact gtcttggtgg     540
gtcaacggca agaggtgca cagcggcgtc tgcaccgacc cccagcccct gaaagagcag     600
cccgccctga cgacagccg gtactgtctg agcagcagac tgagagtgtc cgccaccttc     660
tggcagaacc cccggaacca cttcagatgc caggtgcagt tctacggcct gagcgagaac     720
gacgagtgga cccaggaccg ggccaagccc gtgacccaga tcgtgtctgc tgaggcctgg     780
ggcagagccg attgcggctt caccagcgag agctaccagc agggcgtgct gagcgccacc     840
atcctgtacg agatcctgct gggcaaggcc accctgtacg ccgtgctggt tccgccctg     900 gtgctgatgg ccatggtcaa gcggaaggac agccggggcg gttccggagc cacgaacttc     960
tctctgttaa agcaagcagg agacgtgaa gaaaaccccg gtcccatgga gaagatgctg    1020
gagtgtgcgt tcatcgttct gtggctgcaa cttggatggc tgtctggaga ggatcaggtt    1080
acacagtctc ctgaagccct gagactgcaa gaaggagaaa gctctagcct gaactgcagc    1140
tacacagtgt ctggactgag aggcctgttc tggtacagac aggatcctgg aaaaggccca    1200
gagttcctgt ttaccctgta ttctgccggc gaggagaagg agaaagagag actgaaagct    1260
accctgacca agaaggagag cttcctgcac attaccgccc ccaaacctga ggattctgcc    1320
acatatctgt gtgctgtgca gaccatggat ggcaaccagt tctacttcgg cacaggcaca    1380
tctctgaccg ttatcccaa tatccagaac cctgatcctg ccgtgtacca gctgcgggac    1440
agcaagagca gcgacaagag cgtgtgcctg ttcaccgact cgacagcca gaccaacgtg    1500
```

-continued

```
tcccagagca aggacagcga cgtgtacatc accgataagt gcgtgctgga catgcggagc      1560
atggacttca agagcaacag cgccgtggcc tggtccaaca agagcgactt cgcctgcgcc      1620
aacgccttca acaacagcat tatccccgag gacacattct tcccaagccc cgagagcagc      1680
tgcgacgtga agctggtgga aaagagcttc gagacagaca ccaacctgaa cttccagaac      1740
ctcagcgtga tcggcttccg gatcctgctg ctgaaggtgg ccggcttcaa cctgctgatg      1800
accctgcggc tgtggtccag ctga                                              1824
```

<210> SEQ ID NO 80

<400> SEQUENCE: 80

000

<210> SEQ ID NO 81
<211> LENGTH: 1830
<212> TYPE: DNA
<213> ORGANISM: Artificial Sequence
<220> FEATURE:
<223> OTHER INFORMATION: Synthetic sequence No. 10 beta-P2A-No. 10
      alpha, codon-optimized

<400> SEQUENCE: 81

```
atgctgcttc ttctcctcct tctcggacct gctggatctg gattaggagc tgttgtgtct       60
cagcaccctt cttgggtgat ctgtaaaagc ggcacaagcg tgaagatcga gtgcagaagc      120
ctggactttc aggccacaac catgttctgg tataggcagt tccccaagca gtctctgatg      180
ctgatggcca cctctaatga gggctctaag gccacatatg aacagggagt ggagaaggac      240
aagttcctga tcaaccacgc ctctctgacc ctgtctaccc tgacagttac atctgcccac      300
cctgaggata gcagctttta catctgtagc gccagacctc acagcctgac cgatacacag      360
tactttggcc ctggcacaag actgacagtg ttagaagacc tgaagaacgt gttccccca       420 gaggtggccg tgttcgagcc tagcgaggcc gagatcagcc acacccagaa agccaccctc      480
gtgtgcctgg ccaccggctt ttaccccgac cacgtggaac tgtcttggtg ggtcaacggc      540
aaagaggtgc acagcggcgt ctgcaccgac ccccagcccc tgaaagagca gcccgccctg      600
aacgacagcc ggtactgtct gagcagcaga ctgagagtgt ccgccacctt ctggcagaac      660
ccccggaacc acttcagatg ccaggtgcag ttctacggcc tgagcgagaa cgacgagtgg      720
acccaggacc gggccaagcc cgtgacccag atcgtgtctg ctgaggcctg gggcagagcc      780
gattgcggct tcaccagcga gagctaccag cagggcgtgc tgagcgccac catcctgtac      840
gagatcctgc tgggcaaggc cacctgtac gccgtgctgg tgtccgccct ggtgctgatg       900
gccatggtca gcggaagga cagccggggc ggttccggag ccacgaactt ctctctgtta       960
aagcaagcag gagacgtgga agaaaacccc ggtcccatga ccagagttag cctgttatgg      1020
gctgtggtgg tgagcacatg tctggaatct ggaatggccc agacagtgac acagtctcag      1080
cctgaaatgt ctgtgcagga agccgaaacc gttacactga gctgcaccta cgatacaagc      1140
gagagcaact actacctgtt ctggtacaag cagcccccctt ctaggcagat gatcctggtg      1200
atcagacagg aggcctataa acagcagaat gccaccgaga accggtttag cgtgaacttc      1260
cagaaagccg ccaagagctt cagcctgaaa atctctgaca gccagctggg cgatacagcc      1320
atgtactttt gtgccttcaa cccctgggag aactatggcc agaatttcgt gttcggccct      1380 ggcaccgac tgtctgttct gcctttatatc cagaaccccg atcctgctgt gtaccagctg      1440
cgggacagca agagcagcga caagagcgtg tgcctgttca ccgacttcga cagccagacc      1500
```

```
aacgtgtccc agagcaagga cagcgacgtg tacatcaccg ataagtgcgt gctggacatg      1560
cggagcatgg acttcaagag caacagcgcc gtggcctggt ccaacaagag cgacttcgcc      1620
tgcgccaacg ccttcaacaa cagcattatc cccgaggaca cattcttccc aagccccgag      1680
agcagctgcg acgtgaagct ggtggaaaag agcttcgaga cagacaccaa cctgaacttc      1740
cagaacctca gcgtgatcgg cttccggatc ctgctgctga aggtggccgg cttcaacctg      1800
ctgatgaccc tgcggctgtg gtccagctga                                      1830
```

```
<210> SEQ ID NO 82
<211> LENGTH: 270
<212> TYPE: PRT
<213> ORGANISM: Artificial Sequence
<220> FEATURE:
<223> OTHER INFORMATION: Synthetic sequence Reference TCR alpha chain

<400> SEQUENCE: 82

Met Thr Ser Ile Arg Ala Val Phe Ile Phe Leu Trp Leu Gln Leu Asp
1               5                   10                  15

Leu Val Asn Gly Glu Asn Val Glu Gln His Pro Ser Thr Leu Ser Val
            20                  25                  30

Gln Glu Gly Asp Ser Ala Val Ile Lys Cys Thr Tyr Ser Asp Ser Ala
        35                  40                  45

Ser Asn Tyr Phe Pro Trp Tyr Lys Gln Glu Leu Gly Lys Arg Pro Gln
    50                  55                  60

Leu Ile Ile Asp Ile Arg Ser Asn Val Gly Glu Lys Lys Asp Gln Arg
65                  70                  75                  80

Ile Ala Val Thr Leu Asn Lys Thr Ala Lys His Phe Ser Leu His Ile
                85                  90                  95

Thr Glu Thr Gln Pro Glu Asp Ser Ala Val Tyr Phe Cys Ala Ala Thr
            100                 105                 110

Glu Asp Tyr Gln Leu Ile Trp Gly Ala Gly Thr Lys Leu Ile Ile Lys
        115                 120                 125

Pro Asp Ile Gln Asn Pro Asp Pro Ala Val Tyr Gln Leu Arg Asp Ser
    130                 135                 140

Lys Ser Ser Asp Lys Ser Val Cys Leu Phe Thr Asp Phe Asp Ser Gln
145                 150                 155                 160

Thr Asn Val Ser Gln Ser Lys Asp Ser Asp Val Tyr Ile Thr Asp Lys
                165                 170                 175

Thr Val Leu Asp Met Arg Ser Met Asp Phe Lys Ser Asn Ser Ala Val
            180                 185                 190

Ala Trp Ser Asn Lys Ser Asp Phe Ala Cys Ala Asn Ala Phe Asn Asn
        195                 200                 205

Ser Ile Ile Pro Glu Asp Thr Phe Phe Pro Ser Pro Glu Ser Ser Cys
    210                 215                 220

Asp Val Lys Leu Val Glu Lys Ser Phe Glu Thr Asp Thr Asn Leu Asn
225                 230                 235                 240

Phe Gln Asn Leu Ser Val Ile Gly Phe Arg Ile Leu Leu Leu Lys Val
                245                 250                 255

Ala Gly Phe Asn Leu Leu Met Thr Leu Arg Leu Trp Ser Ser
            260                 265                 270

<210> SEQ ID NO 83
<211> LENGTH: 310
<212> TYPE: PRT
<213> ORGANISM: Artificial Sequence
```

<220> FEATURE:
<223> OTHER INFORMATION: Synthetic sequence Reference TCR beta chain

<400> SEQUENCE: 83

Met Ser Asn Gln Val Leu Cys Cys Val Val Leu Cys Phe Leu Gly Ala
1               5                   10                  15

Asn Thr Val Asp Gly Gly Ile Thr Gln Ser Pro Lys Tyr Leu Phe Arg
            20                  25                  30

Lys Glu Gly Gln Asn Val Thr Leu Ser Cys Glu Gln Asn Leu Asn His
        35                  40                  45

Asp Ala Met Tyr Trp Tyr Arg Gln Asp Pro Gly Gln Gly Leu Arg Leu
    50                  55                  60

Ile Tyr Tyr Ser Gln Ile Val Asn Asp Phe Gln Lys Gly Asp Ile Ala
65                  70                  75                  80

Glu Gly Tyr Ser Val Ser Arg Glu Lys Lys Glu Ser Phe Pro Leu Thr
                85                  90                  95

Val Thr Ser Ala Gln Lys Asn Pro Thr Ala Phe Tyr Leu Cys Ala Ser
            100                 105                 110

Ser Pro Gly Ala Leu Tyr Glu Gln Tyr Phe Gly Pro Gly Thr Arg Leu
        115                 120                 125

Thr Val Thr Glu Asp Leu Lys Asn Val Phe Pro Pro Glu Val Ala Val
        130                 135                 140

Phe Glu Pro Ser Glu Ala Glu Ile Ser His Thr Gln Lys Ala Thr Leu
145                 150                 155                 160

Val Cys Leu Ala Thr Gly Phe Tyr Pro Asp His Val Glu Leu Ser Trp
                165                 170                 175

Trp Val Asn Gly Lys Glu Val His Ser Gly Val Ser Thr Asp Pro Gln
            180                 185                 190

Pro Leu Lys Glu Gln Pro Ala Leu Asn Asp Ser Arg Tyr Cys Leu Ser
        195                 200                 205

Ser Arg Leu Arg Val Ser Ala Thr Phe Trp Gln Asn Pro Arg Asn His
    210                 215                 220

Phe Arg Cys Gln Val Gln Phe Tyr Gly Leu Ser Glu Asn Asp Glu Trp
225                 230                 235                 240

Thr Gln Asp Arg Ala Lys Pro Val Thr Gln Ile Val Ser Ala Glu Ala
            245                 250                 255

Trp Gly Arg Ala Asp Cys Gly Phe Thr Ser Glu Ser Tyr Gln Gln Gly
            260                 265                 270

Val Leu Ser Ala Thr Ile Leu Tyr Glu Ile Leu Leu Gly Lys Ala Thr
        275                 280                 285

Leu Tyr Ala Val Leu Val Ser Ala Leu Val Leu Met Ala Met Val Lys
    290                 295                 300

Arg Lys Asp Ser Arg Gly
305                 310

<210> SEQ ID NO 84
<211> LENGTH: 22
<212> TYPE: PRT
<213> ORGANISM: Artificial Sequence
<220> FEATURE:
<223> OTHER INFORMATION: Synthetic sequence Porcine teschovirus-1 2A
      (P2A-1) peptide

<400> SEQUENCE: 84

Gly Ser Gly Ala Thr Asn Phe Ser Leu Leu Lys Gln Ala Gly Asp Val
1               5                   10                  15

```
Glu Glu Asn Pro Gly Pro
          20

<210> SEQ ID NO 85
<211> LENGTH: 21
<212> TYPE: PRT
<213> ORGANISM: Artificial Sequence
<220> FEATURE:
<223> OTHER INFORMATION: Synthetic sequence Porcine teschovirus-2 2A
      (P2A-2) peptide

<400> SEQUENCE: 85

Ser Gly Ala Thr Asn Phe Ser Leu Leu Lys Gln Ala Gly Asp Val Glu
1               5                   10                  15

Glu Asn Pro Gly Pro
          20

<210> SEQ ID NO 86
<211> LENGTH: 21
<212> TYPE: PRT
<213> ORGANISM: Artificial Sequence
<220> FEATURE:
<223> OTHER INFORMATION: Synthetic sequence Thosea asigna virus 2A (T2A)
      peptide

<400> SEQUENCE: 86

Gly Ser Gly Glu Gly Arg Gly Ser Leu Leu Thr Cys Gly Asp Val Glu
1               5                   10                  15

Glu Asn Pro Gly Pro
          20

<210> SEQ ID NO 87
<211> LENGTH: 23
<212> TYPE: PRT
<213> ORGANISM: Artificial Sequence
<220> FEATURE:
<223> OTHER INFORMATION: Synthetic sequence Equine rhinitis A virus
      (ERAV) 2A (E2A) peptide

<400> SEQUENCE: 87

Gly Ser Gly Gln Cys Thr Asn Tyr Ala Leu Leu Lys Leu Ala Gly Asp
1               5                   10                  15

Val Glu Ser Asn Pro Gly Pro
          20

<210> SEQ ID NO 88
<211> LENGTH: 25
<212> TYPE: PRT
<213> ORGANISM: Artificial Sequence
<220> FEATURE:
<223> OTHER INFORMATION: Synthetic sequence Foot-and-mouth disease virus
      2A (F2A) peptide

<400> SEQUENCE: 88

Gly Ser Gly Val Lys Gln Thr Leu Asn Phe Asp Leu Leu Lys Leu Ala
1               5                   10                  15

Gly Asp Val Glu Ser Asn Pro Gly Pro
          20                  25

<210> SEQ ID NO 89
<211> LENGTH: 66
<212> TYPE: DNA
<213> ORGANISM: Artificial Sequence
<220> FEATURE:
<223> OTHER INFORMATION: Synthetic sequence Porcine teschovirus-1 2A
      (P2A-1) peptide - nt sequence
```

-continued

<400> SEQUENCE: 89
ggaagtggag ctacgaattt ttctttatta aaacaagcag gagatgttga ggagaatccc      60
ggtcca                                                                66

<210> SEQ ID NO 90
<211> LENGTH: 63
<212> TYPE: DNA
<213> ORGANISM: Artificial Sequence
<220> FEATURE:
<223> OTHER INFORMATION: Synthetic sequence Porcine teschovirus-2 2A
      (P2A-2) peptide - nt sequence

<400> SEQUENCE: 90
agcggcgcca ccaacttcag cctgctgaaa caggccggcg acgtggaaga gaaccctggc      60
cct                                                                   63

<210> SEQ ID NO 91
<211> LENGTH: 63
<212> TYPE: DNA
<213> ORGANISM: Artificial Sequence
<220> FEATURE:
<223> OTHER INFORMATION: Synthetic sequence Thosea asigna virus 2A (T2A)
      peptide - nt sequence

<400> SEQUENCE: 91
ggaagcggag agggcagagg aagtctgcta acatgcggtg acgtcgagga gaatcctgga      60
cct                                                                   63

<210> SEQ ID NO 92
<211> LENGTH: 69
<212> TYPE: DNA
<213> ORGANISM: Artificial Sequence
<220> FEATURE:
<223> OTHER INFORMATION: Synthetic sequence Equine rhinitis A virus
      (ERAV) 2A (E2A) peptide - nt sequence

<400> SEQUENCE: 92
ggaagcggac agtgtactaa ttatgctctc ttgaaattgg ctggagatgt tgagagcaac      60
cctggacct                                                             69

<210> SEQ ID NO 93
<211> LENGTH: 75
<212> TYPE: DNA
<213> ORGANISM: Artificial Sequence
<220> FEATURE:
<223> OTHER INFORMATION: Synthetic sequence Foot-and-mouth disease virus
      2A (F2A) peptide - nt sequence

<400> SEQUENCE: 93
ggaagcggag tgaaacagac tttgaatttt gaccttctca agttggcggg agacgtggag      60
tccaaccctg gacct                                                      75

<210> SEQ ID NO 94
<211> LENGTH: 9
<212> TYPE: PRT
<213> ORGANISM: Artificial Sequence
<220> FEATURE:
<223> OTHER INFORMATION: Synthetic sequence WT-1 peptide antigen

<400> SEQUENCE: 94

Arg Met Phe Pro Asn Ala Pro Tyr Leu
1               5

```
<210> SEQ ID NO 95
<211> LENGTH: 5
<212> TYPE: PRT
<213> ORGANISM: Artificial Sequence
<220> FEATURE:
<223> OTHER INFORMATION: Synthetic sequence G-S linker

<400> SEQUENCE: 95

Gly Gly Gly Gly Ser
1               5

<210> SEQ ID NO 96
<211> LENGTH: 20
<212> TYPE: PRT
<213> ORGANISM: Artificial Sequence
<220> FEATURE:
<223> OTHER INFORMATION: Synthetic sequence G-S linker

<400> SEQUENCE: 96

Gly Gly Gly Gly Gly Gly Gly Gly Gly Gly Ser Ser Ser Ser Ser Ser
1               5                   10                  15

Ser Ser Ser Ser
            20

<210> SEQ ID NO 97
<211> LENGTH: 9
<212> TYPE: PRT
<213> ORGANISM: Artificial Sequence
<220> FEATURE:
<223> OTHER INFORMATION: Synthetic sequence meganuclease recognition
      site

<400> SEQUENCE: 97

Leu Ala Gly Leu Ile Asp Ala Asp Gly
1               5

<210> SEQ ID NO 98
<211> LENGTH: 6
<212> TYPE: PRT
<213> ORGANISM: Artificial Sequence
<220> FEATURE:
<223> OTHER INFORMATION: Synthetic sequence meganuclease recognition
      site

<400> SEQUENCE: 98

Gly Ile Tyr Tyr Ile Gly
1               5

<210> SEQ ID NO 99
<211> LENGTH: 5
<212> TYPE: PRT
<213> ORGANISM: Artificial Sequence
<220> FEATURE:
<223> OTHER INFORMATION: Synthetic sequence meganuclease recognition
      site
<220> FEATURE:
<221> NAME/KEY: VARIANT
<222> LOCATION: 3
<223> OTHER INFORMATION: Xaa = Asp or Glu
<220> FEATURE:
<221> NAME/KEY: VARIANT
<222> LOCATION: 4
<223> OTHER INFORMATION: Xaa = any amino acid

<400> SEQUENCE: 99

Pro Asp Xaa Xaa Lys
1               5
```

```
<210> SEQ ID NO 100
<211> LENGTH: 9
<212> TYPE: PRT
<213> ORGANISM: Artificial Sequence
<220> FEATURE:
<223> OTHER INFORMATION: Synthetic sequence WT-1 aa 37-45

<400> SEQUENCE: 100

Val Leu Asp Phe Ala Pro Pro Gly Ala
1               5

<210> SEQ ID NO 101
<211> LENGTH: 6
<212> TYPE: PRT
<213> ORGANISM: Artificial Sequence
<220> FEATURE:
<223> OTHER INFORMATION: Synthetic sequence TCR 10.1 CDR1alpha

<400> SEQUENCE: 101

Asp Ser Ala Ile Tyr Asn
1               5

<210> SEQ ID NO 102
<211> LENGTH: 7
<212> TYPE: PRT
<213> ORGANISM: Artificial Sequence
<220> FEATURE:
<223> OTHER INFORMATION: Synthetic sequence TTCR 10.1 CDR2alpha

<400> SEQUENCE: 102

Ile Gln Ser Ser Gln Arg Glu
1               5

<210> SEQ ID NO 103
<211> LENGTH: 13
<212> TYPE: PRT
<213> ORGANISM: Artificial Sequence
<220> FEATURE:
<223> OTHER INFORMATION: Synthetic sequence TCR 10.1 CDR3alpha

<400> SEQUENCE: 103

Cys Ala Val Lys Glu Thr Ser Gly Ser Arg Leu Thr Phe
1               5                   10

<210> SEQ ID NO 104
<211> LENGTH: 112
<212> TYPE: PRT
<213> ORGANISM: Artificial Sequence
<220> FEATURE:
<223> OTHER INFORMATION: Synthetic sequence TCR 10.1 Valpha

<400> SEQUENCE: 104

Lys Gln Glu Val Thr Gln Ile Pro Ala Ala Leu Ser Val Pro Glu Gly
1               5                   10                  15

Glu Asn Leu Val Leu Asn Cys Ser Phe Thr Asp Ser Ala Ile Tyr Asn
            20                  25                  30

Leu Gln Trp Phe Arg Gln Asp Pro Gly Lys Gly Leu Thr Ser Leu Leu
        35                  40                  45

Leu Ile Gln Ser Ser Gln Arg Glu Gln Thr Ser Gly Arg Leu Asn Ala
    50                  55                  60

Ser Leu Asp Lys Ser Ser Gly Arg Ser Thr Leu Tyr Ile Ala Ala Ser
65                  70                  75                  80

Gln Pro Gly Asp Ser Ala Thr Tyr Leu Cys Ala Val Lys Glu Thr Ser
```

-continued

```
                85              90              95

Gly Ser Arg Leu Thr Phe Gly Glu Gly Thr Gln Leu Thr Val Asn Pro
            100             105             110

<210> SEQ ID NO 105
<211> LENGTH: 5
<212> TYPE: PRT
<213> ORGANISM: Artificial Sequence
<220> FEATURE:
<223> OTHER INFORMATION: Synthetic sequence TCR 10.1 CDR1beta

<400> SEQUENCE: 105

Ser Gly His Val Ser
1               5

<210> SEQ ID NO 106
<211> LENGTH: 6
<212> TYPE: PRT
<213> ORGANISM: Artificial Sequence
<220> FEATURE:
<223> OTHER INFORMATION: Synthetic sequence TCR 10.1 CDR2beta

<400> SEQUENCE: 106

Phe Asn Tyr Glu Ala Gln
1               5

<210> SEQ ID NO 107
<211> LENGTH: 13
<212> TYPE: PRT
<213> ORGANISM: Artificial Sequence
<220> FEATURE:
<223> OTHER INFORMATION: Synthetic sequence TCR 10.1 CDR3beta

<400> SEQUENCE: 107

Cys Ala Ser Ser Leu Thr Gly Ser Tyr Glu Gln Tyr Phe
1               5                   10

<210> SEQ ID NO 108
<211> LENGTH: 114
<212> TYPE: PRT
<213> ORGANISM: Artificial Sequence
<220> FEATURE:
<223> OTHER INFORMATION: Synthetic sequence TCR 10.1 Vbeta

<400> SEQUENCE: 108

Gly Ala Gly Val Ser Gln Ser Pro Arg Tyr Lys Val Thr Lys Arg Gly
1               5                   10                  15

Gln Asp Val Ala Leu Arg Cys Asp Pro Ile Ser Gly His Val Ser Leu
            20                  25                  30

Tyr Trp Tyr Arg Gln Ala Leu Gly Gln Gly Pro Glu Phe Leu Thr Tyr
        35                  40                  45

Phe Asn Tyr Glu Ala Gln Gln Asp Lys Ser Gly Leu Pro Asn Asp Arg
    50                  55                  60

Phe Ser Ala Glu Arg Pro Glu Gly Ser Ile Ser Thr Leu Thr Ile Gln
65                  70                  75                  80

Arg Thr Glu Gln Arg Asp Ser Ala Met Tyr Arg Cys Ala Ser Ser Leu
                85                  90                  95

Thr Gly Ser Tyr Glu Gln Tyr Phe Gly Pro Gly Thr Arg Leu Thr Val
            100                 105                 110

Thr Glu

<210> SEQ ID NO 109
```

<211> LENGTH: 6
<212> TYPE: PRT
<213> ORGANISM: Artificial Sequence
<220> FEATURE:
<223> OTHER INFORMATION: Synthetic sequence TCR 13.1 CDR1alpha

<400> SEQUENCE: 109

Asn Ser Met Phe Asp Tyr
1               5

<210> SEQ ID NO 110
<211> LENGTH: 7
<212> TYPE: PRT
<213> ORGANISM: Artificial Sequence
<220> FEATURE:
<223> OTHER INFORMATION: Synthetic sequence TCR 13.1 CDR2alpha

<400> SEQUENCE: 110

Ile Ser Ser Ile Lys Asp Lys
1               5

<210> SEQ ID NO 111
<211> LENGTH: 13
<212> TYPE: PRT
<213> ORGANISM: Artificial Sequence
<220> FEATURE:
<223> OTHER INFORMATION: Synthetic sequence TCR 13.1 CDR3alpha

<400> SEQUENCE: 111

Cys Ala Ala Ser Gly Ile Gly Asp Tyr Lys Leu Ser Phe
1               5                   10

<210> SEQ ID NO 112
<211> LENGTH: 113
<212> TYPE: PRT
<213> ORGANISM: Artificial Sequence
<220> FEATURE:
<223> OTHER INFORMATION: Synthetic sequence TCR 13.1 Valpha

<400> SEQUENCE: 112

Asp Gln Gln Val Lys Gln Asn Ser Pro Ser Leu Ser Val Gln Glu Gly
1               5                   10                  15

Arg Ile Ser Ile Leu Asn Cys Asp Tyr Thr Asn Ser Met Phe Asp Tyr
            20                  25                  30

Phe Leu Trp Tyr Lys Lys Tyr Pro Ala Glu Gly Pro Thr Phe Leu Ile
        35                  40                  45

Ser Ile Ser Ser Ile Lys Asp Lys Asn Glu Asp Gly Arg Phe Thr Val
    50                  55                  60

Phe Leu Asn Lys Ser Ala Lys His Leu Ser Leu His Ile Val Pro Ser
65                  70                  75                  80

Gln Pro Gly Asp Ser Ala Val Tyr Phe Cys Ala Ala Ser Gly Ile Gly
                85                  90                  95

Asp Tyr Lys Leu Ser Phe Gly Ala Gly Thr Thr Val Thr Val Arg Ala
            100                 105                 110

Asn

<210> SEQ ID NO 113
<211> LENGTH: 5
<212> TYPE: PRT
<213> ORGANISM: Artificial Sequence
<220> FEATURE:
<223> OTHER INFORMATION: Synthetic sequence TCR 13.1 CDR1beta

<400> SEQUENCE: 113

Pro Arg His Asp Thr
1               5

<210> SEQ ID NO 114
<211> LENGTH: 6
<212> TYPE: PRT
<213> ORGANISM: Artificial Sequence
<220> FEATURE:
<223> OTHER INFORMATION: Synthetic sequence TCR 13.1 CDR2beta

<400> SEQUENCE: 114

Phe Tyr Glu Lys Met Gln
1               5

<210> SEQ ID NO 115
<211> LENGTH: 14
<212> TYPE: PRT
<213> ORGANISM: Artificial Sequence
<220> FEATURE:
<223> OTHER INFORMATION: Synthetic sequence TCR 13.1 CDR3beta

<400> SEQUENCE: 115

Cys Ala Ser Ser Leu Arg Leu Gly Arg Glu Thr Gln Tyr Phe
1               5                   10

<210> SEQ ID NO 116
<211> LENGTH: 114
<212> TYPE: PRT
<213> ORGANISM: Artificial Sequence
<220> FEATURE:
<223> OTHER INFORMATION: Synthetic sequence TCR 13.1 Vbeta

<400> SEQUENCE: 116

Ala Ala Gly Val Ile Gln Ser Pro Arg His Leu Ile Lys Glu Lys Arg
1               5                   10                  15

Glu Thr Ala Thr Leu Lys Cys Tyr Pro Ile Pro Arg His Asp Thr Val
                20                  25                  30

Tyr Trp Tyr Gln Gln Gly Pro Gly Gln Asp Pro Gln Phe Leu Ile Ser
            35                  40                  45

Phe Tyr Glu Lys Met Gln Ser Asp Lys Gly Ser Ile Pro Asp Arg Phe
        50                  55                  60

Ser Ala Gln Gln Phe Ser Asp Tyr His Ser Glu Leu Asn Met Ser Ser
65                  70                  75                  80

Leu Glu Leu Gly Asp Ser Ala Leu Tyr Phe Cys Ala Ser Ser Leu Arg
                85                  90                  95

Leu Gly Arg Glu Thr Gln Tyr Phe Gly Pro Gly Thr Arg Leu Leu Val
            100                 105                 110

Leu Glu

<210> SEQ ID NO 117
<211> LENGTH: 6
<212> TYPE: PRT
<213> ORGANISM: Artificial Sequence
<220> FEATURE:
<223> OTHER INFORMATION: Synthetic sequence TCR 16.1 CDR1alpha

<400> SEQUENCE: 117

Val Ser Gly Leu Arg Gly
1               5

<210> SEQ ID NO 118
<211> LENGTH: 7

<212> TYPE: PRT
<213> ORGANISM: Artificial Sequence
<220> FEATURE:
<223> OTHER INFORMATION: Synthetic sequence TCR 16.1 CDR2alpha

<400> SEQUENCE: 118

Leu Tyr Ser Ala Gly Glu Glu
1               5

<210> SEQ ID NO 119
<211> LENGTH: 12
<212> TYPE: PRT
<213> ORGANISM: Artificial Sequence
<220> FEATURE:
<223> OTHER INFORMATION: Synthetic sequence TCR 16.1 CDR3alpha

<400> SEQUENCE: 119

Cys Ala Val Ile Thr Gly Phe Gln Lys Leu Val Phe
1               5                   10

<210> SEQ ID NO 120
<211> LENGTH: 110
<212> TYPE: PRT
<213> ORGANISM: Artificial Sequence
<220> FEATURE:
<223> OTHER INFORMATION: Synthetic sequence TCR 16.1 Valpha

<400> SEQUENCE: 120

Glu Asp Gln Val Thr Gln Ser Pro Glu Ala Leu Arg Leu Gln Glu Gly
1               5                   10                  15

Glu Ser Ser Ser Leu Asn Cys Ser Tyr Thr Val Ser Gly Leu Arg Gly
            20                  25                  30

Leu Phe Trp Tyr Arg Gln Asp Pro Gly Lys Gly Pro Glu Phe Leu Phe
        35                  40                  45

Thr Leu Tyr Ser Ala Gly Glu Glu Lys Glu Lys Glu Arg Leu Lys Ala
    50                  55                  60

Thr Leu Thr Lys Lys Glu Ser Phe Leu His Ile Thr Ala Pro Lys Pro
65                  70                  75                  80

Glu Asp Ser Ala Thr Tyr Leu Cys Ala Val Ile Thr Gly Phe Gln Lys
                85                  90                  95

Leu Val Phe Gly Thr Gly Thr Arg Leu Leu Val Ser Pro Asn
            100                 105                 110

<210> SEQ ID NO 121
<211> LENGTH: 5
<212> TYPE: PRT
<213> ORGANISM: Artificial Sequence
<220> FEATURE:
<223> OTHER INFORMATION: Synthetic sequence TCR 16.1 CDR1beta

<400> SEQUENCE: 121

Met Asn His Glu Tyr
1               5

<210> SEQ ID NO 122
<211> LENGTH: 6
<212> TYPE: PRT
<213> ORGANISM: Artificial Sequence
<220> FEATURE:
<223> OTHER INFORMATION: Synthetic sequence TCR 16.1 CDR2beta

<400> SEQUENCE: 122

Ser Met Asn Val Glu Val
1               5

```
<210> SEQ ID NO 123
<211> LENGTH: 14
<212> TYPE: PRT
<213> ORGANISM: Artificial Sequence
<220> FEATURE:
<223> OTHER INFORMATION: Synthetic sequence TCR 16.1 CDR3beta

<400> SEQUENCE: 123

Cys Ala Ser Ser Phe Ser Gly Gly Thr Tyr Glu Gln Tyr Phe
1               5                   10

<210> SEQ ID NO 124
<211> LENGTH: 114
<212> TYPE: PRT
<213> ORGANISM: Artificial Sequence
<220> FEATURE:
<223> OTHER INFORMATION: Synthetic sequence TCR 16.1 Vbeta

<400> SEQUENCE: 124

Glu Ala Gln Val Thr Gln Asn Pro Arg Tyr Leu Ile Thr Val Thr Gly
1               5                   10                  15

Lys Lys Leu Thr Val Thr Cys Ser Gln Asn Met Asn His Glu Tyr Met
            20                  25                  30

Ser Trp Tyr Arg Gln Asp Pro Gly Leu Gly Leu Arg Gln Ile Tyr Tyr
        35                  40                  45

Ser Met Asn Val Glu Val Thr Asp Lys Gly Asp Val Pro Glu Gly Tyr
    50                  55                  60

Lys Val Ser Arg Lys Glu Lys Arg Asn Phe Pro Leu Ile Leu Glu Ser
65                  70                  75                  80

Pro Ser Pro Asn Gln Thr Ser Leu Tyr Phe Cys Ala Ser Ser Phe Ser
            85                  90                  95

Gly Gly Thr Tyr Glu Gln Tyr Phe Gly Pro Gly Thr Arg Leu Thr Val
            100                 105                 110

Thr Glu
```